US005646123A

United States Patent [19]
Ippolito et al.

[11] Patent Number: 5,646,123
[45] Date of Patent: Jul. 8, 1997

[54] TIME DEPENDENT ADMINISTRATION OF OLIGOSACCHARIDE GLYCOSIDES RELATED TO BLOOD GROUP DETERMINANTS HAVING A TYPE I OR TYPE II CORE STRUCTURE IN REDUCING INFLAMMATION IN A SENSITIZED MAMMAL ARISING FORM EXPOSURE TO AN ANTIGEN

[75] Inventors: Robert M. Ippolito; Wasimul Haque, both of Edmonton, Canada; Cong Jiang, San Diego, Calif.; H. Rizk Hanna, Edmonton, Canada; Andre P. Venot, Agoura Hills, Calif.; Pandurang V. Nikrad, Edmonton, Canada; Mohammed A. Kashem, Thousand Oaks, Calif.; Richard Smith, Edmonton; Om P. Srivastava, Jackson Heights, both of Canada

[73] Assignee: Alberta Research Council, Alberta, Canada

[21] Appl. No.: 405,785

[22] Filed: Mar. 17, 1995

Related U.S. Application Data

[63] Continuation of Ser. No. 81,214, Jun. 25, 1993, abandoned, which is a continuation of Ser. No. 988,518, Dec. 10, 1992, abandoned, which is a continuation-in-part of Ser. No. 895,930, Jun. 9, 1992, abandoned, which is a continuation-in-part of Ser. No. 889,017, May 26, 1992, abandoned, which is a continuation-in-part of Ser. No. 714,161, Jun. 10, 1991, abandoned.

[51] Int. Cl.$^6$ ............................ A61K 31/70; C07H 15/00
[52] U.S. Cl. .......................... 514/25; 514/885; 536/17.2; 536/17.9
[58] Field of Search ............... 514/25, 885; 536/17.2, 536/17.9

[56] References Cited

U.S. PATENT DOCUMENTS

| | | | |
|---|---|---|---|
| 4,137,401 | 1/1979 | Lemieux et al. | 536/116 |
| 4,195,174 | 3/1980 | Lemieux et al. | 536/55 |
| 4,563,445 | 1/1986 | Feizi et al. | 514/25 |
| 4,612,132 | 9/1986 | Wollenberg et al. | 252/51.5 A |
| 4,675,392 | 6/1987 | Dahmen et al. | 536/17.6 |
| 4,766,150 | 8/1988 | Kiel | 514/567 |
| 4,767,845 | 8/1988 | Lemieux et al. | 536/18.2 |
| 5,059,535 | 10/1991 | Mazid et al. | 435/193 |
| 5,079,235 | 1/1992 | Purifoy et al. | 514/49 |
| 5,079,353 | 1/1992 | Ratcliffe et al. | 536/53 |
| 5,109,116 | 4/1992 | Arkwright et al. | 530/395 |
| 5,143,712 | 9/1992 | Brandley et al. | 424/1.73 |
| 5,211,936 | 5/1993 | Brandley et al. | 424/1.73 |
| 5,211,937 | 5/1993 | Brandley et al. | 424/1.73 |
| 5,344,870 | 9/1994 | Ratcliffe et al. | 525/54.2 |
| 5,374,655 | 12/1994 | Kashem et al. | 514/540 |
| 5,470,842 | 11/1995 | Brandley et al. | 514/61 |

FOREIGN PATENT DOCUMENTS

| | | |
|---|---|---|
| 0 166 442 | 6/1985 | European Pat. Off. |
| 0 315 113 | 10/1988 | European Pat. Off. |
| 0 380 084 | 1/1990 | European Pat. Off. |
| 0 395 217 | 3/1990 | European Pat. Off. |
| WO90/01938 | 3/1990 | WIPO |
| WO91/06632 | 5/1991 | WIPO |
| WO91/07993 | 6/1991 | WIPO |
| WO91/08231 | 6/1991 | WIPO |
| WO91/16449 | 10/1991 | WIPO |
| WO91/16900 | 11/1991 | WIPO |
| WO91/19501 | 12/1991 | WIPO |
| WO91/19502 | 12/1991 | WIPO |
| WO92/01718 | 2/1992 | WIPO |
| WO92/02527 | 2/1992 | WIPO |
| WO92/07572 | 5/1992 | WIPO |
| WO92/09293 | 6/1992 | WIPO |
| WO92/12729 | 8/1992 | WIPO |
| WO92/14757 | 9/1992 | WIPO |
| WO92/16612 | 10/1992 | WIPO |
| WO94/08051 | 4/1994 | WIPO |

OTHER PUBLICATIONS

Japanese Patent No. 1–180828, Jul. 18, 1989, Chemical Abstract only (CA 112:179707a (1990)).
Abbas et al., *Proc. Japanese–German Symp.* Berlin, pp. 20–21 (1988).
Alais and Veyrieres, *Carbohydr. Res.*, 207:11–31 (1990).
Amvam–Zollo et al., *Carbohydr. Res.*, 150:199–212 (1986).
Aplin and Hughes, *Biochem. Biophys. Acta,* 694:375–418 (1982).
Barondes, "Developmentally Regulated Lectins," in Cell Interactions and Development: *Molecular Mechanisms* (Yamada, D.M. Ed.) New York, John Wiley & Sons, pp. 185–202 (1983).
Berg, Ellen L. et al., "A Carbohydrate Domain Common to Both Sialyl Le$^a$ and Sialyl Le$^x$ Is Recognized by the Endothelial Cell Leukocyte Adhesion Molecule ELAM–1*," *The Journal of Biological Chemistry,* vol. 266, No. 23, Issue of August 15, pp. 14869–14872 (1991).
Beyer et al., *Advances in Enzymology,* pp. 23–175, John Wiley & Sons, New York (1982).
Brandley, Brian K. et al., "Carbohydrate Ligands of the LEC Cell Adhesion Molecules," *Cell,* vol. 63, pp. 861–863 (Nov. 30, 1990).
Brandley and Schnarr, *J. Leukocyte Biol.,* 40:97–111 (1986).
Brossmer et al., *Biochem. Biophys. Acta,* 96:1282–1289 (1980).
Campanero et al., *J. Cell Biol.,* 110:2157–2165 (1990).
Chernyak et al., *Carbohydr. Res.,* 128:269–282 (1984).
Christian et al., *Carbohydr. Res.,* 194:49–61, (1989).
Coutinho et al., *Immunol. Rev.,* 78:211–224 (1984).

(List continued on next page.)

*Primary Examiner*—Kathleen K. Fonda
*Attorney, Agent, or Firm*—Burns, Doane, Swecker & Mathis, LLP

[57] ABSTRACT

Disclosed are methods for reducing the degree of antigen induced inflammation in a sensitized mammals. The disclosed methods employ oligosaccharide glycosides related to blood group determinants having a type I or type II core structure wherein the administration of such oligosaccharide glycosides is after initiation of the mammal's immune response but at or prior one-half the period of time required to effect maximal antigen-induced inflammation.

4 Claims, 63 Drawing Sheets

OTHER PUBLICATIONS

Dahmen et al., *Carbohydr. Res.*, 118:292–301 (1983).
Dall'Olio, Fabio et al., "Immunosuppressive Activity of Tamm–Horsfall Glycoprotein Oligoaccharides: Effect of Removal of Outer Sugars and Conjugation with a Protein Carrier," *Academic Press*, pp. 303–315 (1991).
Ekborg et al., *Carbohydr. Res.*, 110:55–67 (1982).
Ekblom, Peter et al., "The Extracellular Matrix and Kidney Differentiation," in *Membranes in Growth and Development*, pp. 429–442 (1982).
Feizi, Ten, "Blood group–related oligosaccharides are ligands in cell–adhesion events*," *Biochemical Society Transactions*, vol. 20, pp. 274–278 (1992).
Fernandez–Santana et al. *J. Carbohydr. Chem.*, 8:531–537 (1989).
Frazier and Glaser, *Annu. Rev. Biochem.*, 48:491–523 (1979).
Fügedi et al., *Glycoconj. J.*, 4:97–108 (1987).
Galeotti et al., Eds., Membranes in Tumor Growth, Amsterdam, Elsevier, p. 77 (1984).
Glaser, in Mediator of Developmental Processes (Subtency, S. and Wessels, N.K., Eds.) New York, Academic Press, pp. 79–97 (1980).
Gross et al., *Biochemistry*, 28:7386–7392 (1989).
Hasegawa et al., "Preparation of phosphorylated acyloligosaccharides as pharmaceuticals," *CA Selects: Carbohydrates (Chemical Aspects)*, Issue 22, p. 8, 1989.
Hasegawa et al., *J. Carbohydr. Chem.*, 8:135–144 (1989).
Higa and Paulson, *J. Biol. Chem.*, 260:8838–8849 (1985).
Hodgson, John, "Carbohydrate–based Therapeutics," *Bio/Technology*, vol. 9, pp. 609–613, Jul. 1991.
Jacobson, *Developmental Neurobiology*, New York, Plenum Press, p. 5 (1978).
Kameyama et al., *Carbohydr. Res.*, 209:$C_1$–$C_4$ (1991).
Neuberger, *Biol. Cell.*, 51 (Special Issue): 113 (1984).
Kitajima et al., "Preparation of code factor–related$\beta\beta$— and $\alpha\beta$–trehalose derivates as immunostimulants," CA Selects: *Carbohydrates (Chemical Aspects)*, Issue 24, p. 25 (1990).
Kunz et al., "Preparation of tetraoligosaccharides as momomers for schizophyllan," CA Selects: *Carbohydrates (Chemical Aspects)*, Issue 16, p. 14 (1991).
Ladisch et al., *Cancer Res.*, 43:3808–3813 (1983).
Larsen et al., *Cell*, 63:467–474 (1990).
Lee et al., *Carbohydr. Res.*, 37:193 et seq. (1974).
Lowe et al., *Cell*, 63:475–485 (1990).
Nicolson et al., *Invas. Metas.*, 5:144–158 (1985).
Okamoto and Goto, *Tetrahedron*, 46, No. 17, pp. 5835–5837 (1990).
Palcic et al., *Carbohydr. Res.*, 190:1–11 (1989).
Paulsen and Lebuhn, *Carbohydr. Res.*, 125:21–45 (1984) (Abstract only).
Paulsen et al., *Carbohydr. Res.*, 104:195–219 (1982) (English Abstract Only).
Paulsen, *Angew. Chem., Int. Ed. Eng.*, 21:155–173 (1982).
Paulson, in *The Receptors*, vol. II (Comm., P.M., Ed.), New York, Academic Press, pp. 131–219 (1985).
Phillips et al., *Science*, 250:1130–1132 (1990).
Rana et al., *Carbohydr. Res.*, 91:149–157 (1981).
Reuter and Schauer, *Glycoconjugate J.*, 5:133–135 (1988).
Sabesan and Lemieux, *Can. J. Chem.*, 62:644–654 (1984).
Schmidt, *Angew. Chem. Int. Ed. Eng.*, 25:212–235 (1986).
Schwartz et al., *Immunol. Rev.*, 40:153–180 (1978).
Sharon, "Lectin–Like Bacterial Adherence to Animal Cells," in *Attachment of Microorganisms to the Gut Mucosa* (Boeheker, E.D., Ed.) Boca Raton, Florida, CRC Press, pp. 129–147 (1984).
Sleytr et al., *Arch. Microbiol.*, 146:19–24 (1986).
Smith and Ziola, *Immunology*, 58:245–250 (1986).
Springer and Laskey, *Nature*, 349:196–197 (1991).
Sugiyama et al., "Sialic acid 1,7–lactone derivatives as immunomodulators and antiviral agents," *Chemical Abstracts*, vol. 109, 1988.
Tiemeyer, Michael et al., "Carbohydrate ligands for endothelial–leukocyte adhesion molecule 1," *Proceedings of the National Academy*, vol. 88, pp. 1138–1142, Feb. 1991.
Toone et al., *Tetrahedron*, No. 17, 45:5365–5422 (1989).
Tyrrell, D. et al., "Structural requirements for the carbohydrate ligand of E–selectin," *Proc. Natl. Acad. Sci., USA*, vol. 88: 10372–10376 (Nov. 1991).
Unverzagt et al., *J. Amer. Chem. Soc.*, 112:9308–9309 (1990).
Walz et al., *Science*, 250:1132–135 et seq. (1990).
Wassarman, "Fertilization," in *Cell Interactions and Development: Molecular Mechanisms* (Yamada,K.M., Ed.) New York, John Wiley and Sons, pp. 1–27 (1983).
Zbiral et al., *Monatsh. Chem.*, 199:127–141 (1988).
Ziola and Hader, *J. Neuroimmunol.*, 7:315–330 (1985).
CAS Abstract No. 110:95715p, 1989.
CAS Abstract No. 113:132714x, 1990.
CAS Abstract No. 113:231933z, 1990.
CAS Abstract No. 112:91796j, 1990.
U.S. Patent Application Serial No. 07/538,853.
U.S. Patent Application Serial No. 07/619,319.
U.S. Patent Application Serial No. 07/632,390.
Prieelset et al., *J. Biol. Chem.*, 256:10456–104633 (1981).
Eppenberger–Castoriet et al., *Glycoconj. J.*, 6:101–114 (1989).
Lemieuxet et al., *Can. J. Chem.*, 60:63–67 (1982).
Nicolaouet et al., *J. Amer. Chem. Soc.*, 112:3693–3695 (1990).
Hindsgaulet et al., *Carbohydr. Res.*, 109:109–142 (1982).
Jainet et al., *Carbohydro. Res.*, 208:51–58 (1980).
Nilsson et al., *Carbohydr. Res.*, 183:71 et seq. (1988).
Ali et al., *Carbohydr. Res.*, 216:271–287 (1991).
Kukowskaa–Latallo et al., *Genes and Development*, 4:1288–1303 (1990).
Inazu et al., *Bull. Soc. Chim., Jap.*, 611:4467 (1988).
Bernotas et al., *Biochem. J.*, 270:539–540 (1990).
Greig et al., *J. Chem. Soc.* p. 879 (1961).
Piekarska–Bartowzewicz et al., *Carbohydr. Res.*, 203:302–307 (1990).
Petitou et al., *Carbohydr. Res.*, 147:221–236 (1986).
Trumtel et al., *Carbohydr. Res.*, 191:29–52 (1989).
Lemieux et al., *J. Amer. Chem. Soc.*, 97:4076–4083 (1975).
Bodanszky et al., *The Practice of Peptide Synthesis*, Springer–Verlag (1984).
Gross et al., *Eur. J. Biochem.*, 168:595–602 (1987).
Conradt et al., *FEBS Lett.*, 170:295–300 (1984).
Christian et al., *Carbohydr. Res.*, 162:1–11 (1987).
Haverkamp et al., *Hoppe–Seyler's Z. Physiol. Chem.*, 360:159–166 (1979) (abstact only).
Gross et al., *Glycoconj. J.*, 4:145–156 (1987).
Hagedorn et al., *XIIIth Carbohydr. Symp. Ithaca* (1986) A4.
Zbiral et al., *Carbohydr. Res.*, 194:C15–C18 (1989).
Belkhouya et al., *Tetrahedron Letters*, 3971–3980 (1991) (Abstract only).

Sialic Acids in "Cell Biology Monographs," *Schauer,* Editor, vol. 10 (1982).
Dumas et al., *Bioorg. Med. Letters,* 1:425–428 (1991).
Gokhale et al., *Can. J. Chem.,* 68:1063–1071 (1990).
Smith et al., *Infection and Immunity,* 31: 129 (1980).
Petrakova et al., *Can. J. Chemistry,* 70:233–240 (1992).
Ichikana et al., *Anal. Biochem.,* 202:215–138 (1992).
Weinstein etal., *J. Biol. Chem.,* 257:13835–13844 (1982).
Sticher et al., *Biochem. J.,* 253:577–580 (1988).
Dean et al., *Chromatogr.,* 165:301–319 (1979).
Matsumoto et al., *Anal. Biochem.,* 116:103–110 (1981).
Schmidt et al., *Liebigs Ann. Chem.,* 121–124 (1991).
Nunez et al., *Can. J. Chem.,* 59:2086–2095 (1981).
Veeneman et al., *Tetrahedron Lett.,* 32:6175–6178 (1991).
Hanessian, *Carbohydr. Res.,* 2:86–88 (1966).

Chardrasckaran, et al., *J. Biol. Chem.,* 267(33) (1992).
Kato, et al., *J. Biol. Chem.,* 264(6) (1989).
Ichikawa, et al., *J. Amer. Chem. Soc.,* 113:6300–6302.
Lasky, et al., *Science,* 258:5085 (1992).
Chemical Abstracts, vol. 112, pp. 839–840, (1990), 112:179707s, "Preparation and formulation of sialosylceramides and glycerolipids for treatement of autoimmune dieases".
Chemical Abstracts, vol. 114, pp. 859, (1991), 114: 122975Q, "Preparation of amide bond–containing sialoysyl glycerolipids as immunomodulators".
Springer *Nature* Aug. 2, 1990, 346, 425–434.
Abbas et al., "Cellular and Molecular Immunology", W.B. Saunders Company (Philadelphia, PA), pp. 246–248 and 213, 1991, Month Not Available.

FIG. 3
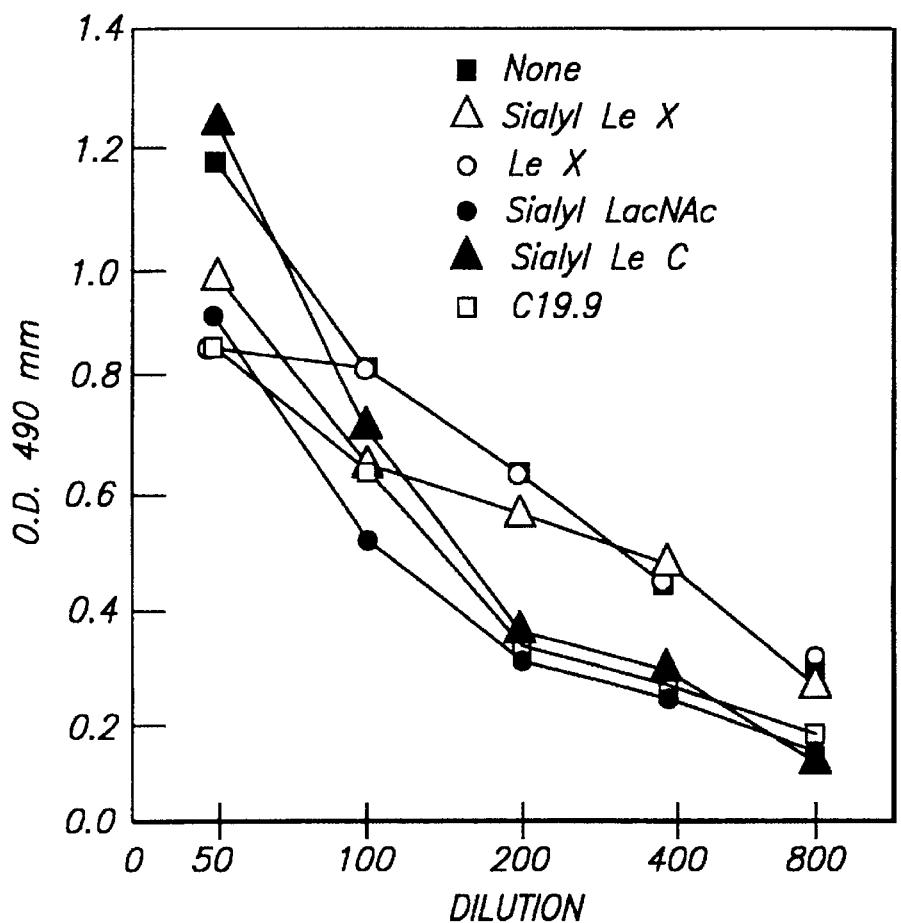
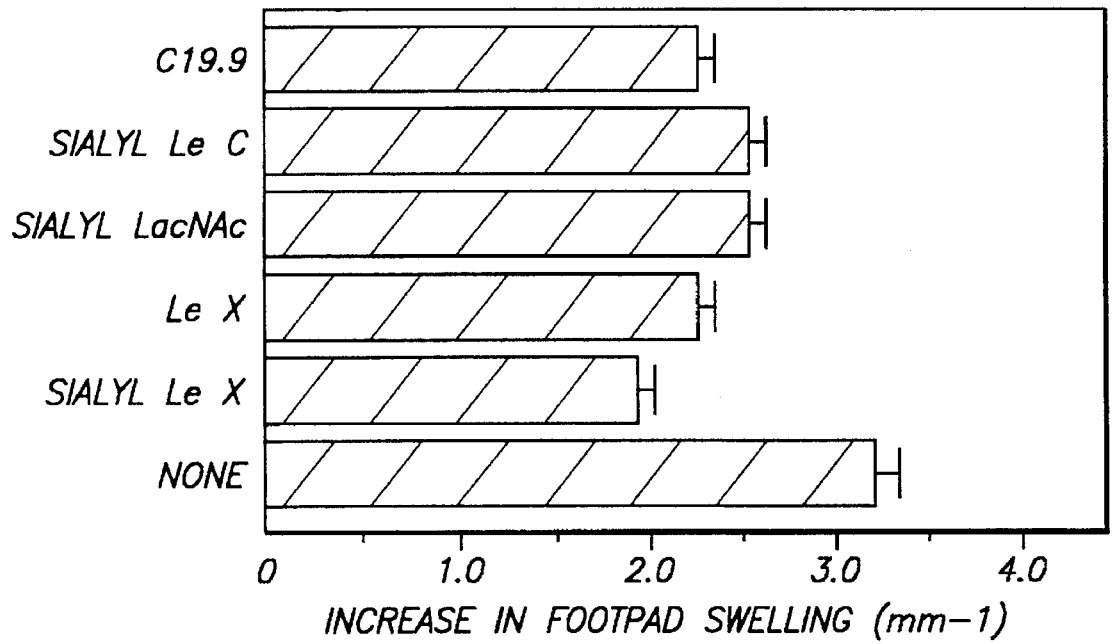
FIG. 5

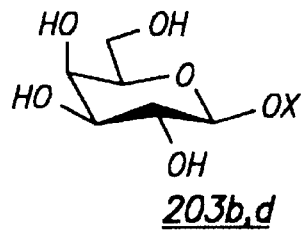
203b,d
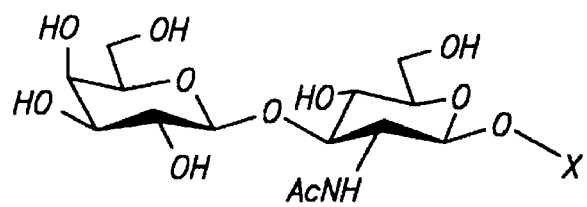
204a,b,c,d
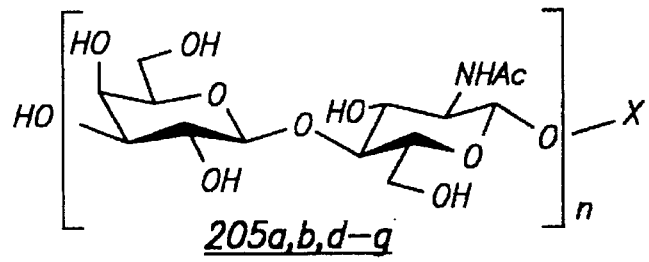
205a,b,d-g
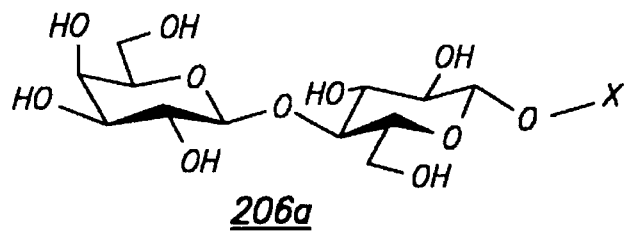
206a
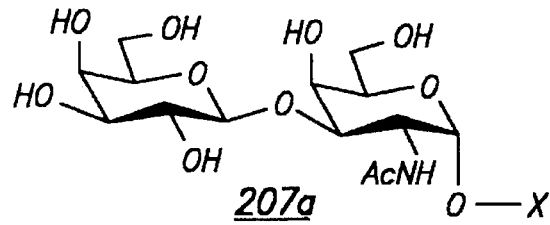
207a
$X_1 = (CH_2)_8CH_2OH$
$X_2 = (CH_2)_8CO_2CH_3$
$X_3 = (CH_2)_5OCH_2CH=CH_2$
$X_4 = CH_3$
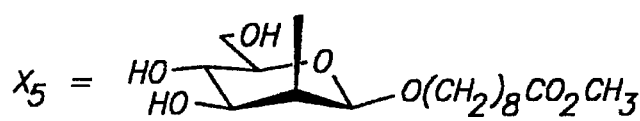
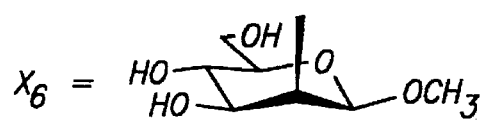
FIG. 34

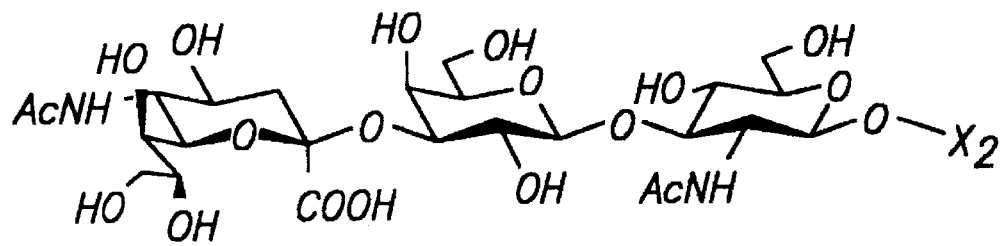
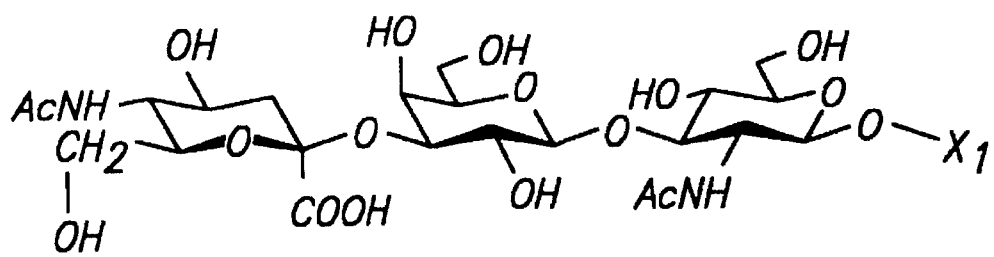
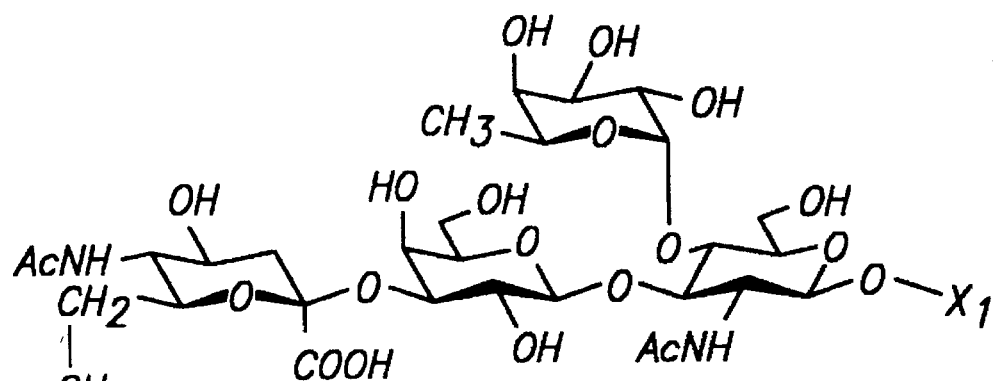
FIG. 41

TIME DEPENDENT ADMINISTRATION OF OLIGOSACCHARIDE GLYCOSIDES RELATED TO BLOOD GROUP DETERMINANTS HAVING A TYPE I OR TYPE II CORE STRUCTURE IN REDUCING INFLAMMATION IN A SENSITIZED MAMMAL ARISING FORM EXPOSURE TO AN ANTIGEN

CROSS-REFERENCE TO RELATED APPLICATIONS

This application is a continuation of application Ser. No. 08/081,214, filed Jun. 25, 1993 now abandoned, which is a continuation of U.S. Ser. No. 07/988,518 filed Dec. 10, 1992, now abandoned, which, in turn, is a continuation-in-part of U.S. Ser. No. 07/895,930 filed Jun. 9, 1992, now abandoned, which, in turn, is a continuation in part of U.S. Ser. No. 07/889,017 filed May 26, 1992, now abandoned, which, in turn, is a continuation-in-part of U.S. Ser. No. 07/714,161 filed Jun. 10, 1991, now abandoned; all of which applications are incorporated herein by reference in their entirety.

BACKGROUND OF THE INVENTION

1. Field of the Invention

This invention is directed to methods for reducing the degree of inflammation arising from a secondary immune response in a mammal due to antigen exposure (challenge) by the time dependent administration of an oligosaccharide glycoside related to blood group determinants having a type I [βGal(1→3)GlcNAc] or a type II [βGal(1→4)GlcNAc] core structure.

The methods of this invention are directed to the discovery that the reduction in antigen induced inflammation in sensitized mammals by administration of oligosaccharide glycosides related to blood group determinants having a type I or a type II core structure is critically dependent on the point in time when that oligosaccharide glycoside is administered.

2. References

The following publications and patent applications are cited in this application as superscript numbers at the relevant portion of the application:

1. Gaeta, et al., U.S. patent application Ser. No. 07/538,853, filed 15 Jun. 1990.
2. Paulson, et al., U.S. patent application Ser. No. 07/619,319, filed 28 Nov. 1990.
3. Paulson, et al., U.S. patent application Ser. No. 07/632,390, filed 21 Dec. 1990.
4. Brandley, et al., PCT International Patent Application No. PCT/US91/05416; published 20 Feb. 1992.
5. Lowe, PCT International Patent Application No. PCT/US91/07678; published 14 May 1992.
6. McEver, PCT International Patent Application No. PCT/US91/05059, published 6 Feb. 1992.
7. Furie, et al., PCT International Patent Application No. PCT/US92/01915, published 1 Oct. 1992.
8. Seed, et al., PCT International Patent Application No. PCT/US91/08605, published 11 Jun. 1992.
9. Venot, et al., U.S. Pat. No. 5,352,670.
10. Kashem, et al., U.S. Pat. No. 5,374,655.
11. Venot, et al., U.S. patent application Ser. No. 07/887,747, filed 22 May 1992.
12. Ratcliffe, et al., U.S. Pat. No. 5,079,353, issued 7 Jan. 1992.
13. Ippolito, et al., U.S. patent application Ser. No. 07/895,930, filed 9 Jun. 1992.
14. Venot, et al., U.S. patent application Ser. No. 07/887,746, filed 22 May 1992.
15. Ekborg, et al., Carbohydr. Res., 110: 55–67 (1982).
16. Dahmen, et al., Carbohydr. Res., 118: 292–301 (1983).
17. Rana, et al., Carbohydr. Res., 91: 149–157 (1981).
18. Amvam-Zollo, et al., Carbohydr. Res., 150: 199–212 (1986).
19. Paulsen, et al., Carbohydr. Res., 104: 195–219 (1982).
20. Chernyak, et al., Carbohydr. Res., 128: 269–282 (1984).
21. Fernandez-Santana, et al., J. Carbohydr. Chem., 8: 531–537 (1989).
22. Lee, et al., Carbohydr. Res., 37: 193 et seq. (1974).
23. Ratcliffe, et al., U.S. Pat. No. 5,344,870.
24. Reuter, et al., Glycoconjugate J., 5: 133–135 (1988).
25. Palcic, et al., Carbohydr. Res., 190: 1–11 (1989).
26. Prieels, et al., J. Biol. Chem., 256: 10456–104633 (1981).
27. Eppenberger-Castori, et al., Glycoconj. J., 6: 101–114 (1989)
28. Lemieux, et al., Can. J. Chem., 60: 63–67 (1982).
29. Nicolaou, et al., J. Amer. Chem. Soc., 112: 3693–3695 (1990).
30. Hindsgaul, et al., Carbohydr. Res., 109: 109–142 (1982).
31. Okamoto, et al., Tetrahedron, 46, No. 17, pp. 5835–5837 (1990).
32. Abbas, et al., Proc. Japanese-German Symp. Berlin, pp. 20–21 (1988).
33. Paulsen, Agnew. Chem. Int. Ed. Eng., 21: 155–173 (1982).
34. Schmidt, Agnew. Chem. Int. Ed. Eng., 25: 212–235 (1986).
35. Fugedi, et al., Glycoconj. J., 4: 97–108 (1987).
36. Kameyama, et al., Carbohydr. Res., 209: $C_1$–$C_4$ (1991).
37. Ratcliffe, et al., U.S. Pat. No. 5,344,870.
38. Matta, et al., Carbohydro. Res., 208: 51–58 (1980).
39. Norberg, et al., Carbohydr. Res., 183: 71 et seq. (1988)
40. Richardson, et al., Carbohydr. Res., 216: 271–287 (1991)
41. Kukowskaa-Latallo, et al., Genes and Development, 4: 1288–1303 (1990).
42. Jiang, et al., U.S. patent application Ser. No. 07/848,223, filed Mar. 9, 1992.
43. Inazu, et al., Bull. Soc. Chim., Jap., 611: 4467 (1988).
44. Bernotas, et al., Biochem. J., 270: 539–540 (1990).
45. Wollenberg, et al., U.S. Pat. No. 4,612,132, issued Sep. 21, 1986.
46. Greig, et al., J. Chem. Soc., p. 879 (1961).
47. Piekarska-Bartowzewicz, et al., Carbohydr. Res., 203: 302–307 (1990).
48. Petitou, et al., Carbohydr. Res., 147: 221–236 (1986).
49. Trumtez, et al., Carbohydr. Res., 191: 29–52 (1989).
50. Lemieux, et al., J. Amer. Chem. Soc., 97: 4076–4083 (1975).
51. Bodanszky, et al., The Practice of Peptide Synthesis, Springer-Verlag (1984).
52. Higa, et al., J. Biol. Chem., 260: 8838–8849 (1985).
53. Brossmer, et al., Biochem. Biophys. Research Commun., 96: 1282–1289 (1980).
54. Gross, et al., Eur. J. Biochem., 168: 595–602 (1987).
55. Gross, et al., Eur. J. Biochem., 177: 583–589 (1988).
56. Christian, et al., Carbohydr. Res., 194: 49–61 (1989).
57. Conradt, et al., FEBS Lett., 170: 295–300 (1984).
58. Christian, et al., Carbohydr. Res., 162: 1–11 (1987).
59. Haverkamp, et al., Hoppe-Seyler's Z. Physiol. Chem., 360: 159–166 (1979).
60. Gross, et al., Glycoconj. J., 4: 145–156 (1987).
61. Hagedorn, et al., XIIIth Carbohydr. Symp. Ithaca (1986) A4.

62. Zbiral, et al., Carbohydr. Res., 194: C15–C18 (1989).
63. Belkhouya, et al., Tetrahedron Letters, 3971–3980 (1991).
64. Sialic Acids in "Cell Biology Monographs", Schauer, Editor, Vol. 10 (1982).
65. Kukowska-Latallo, et al., Genes and Development, 4: 1288–1303 (1990).
66. Dumas, et al., Bioorg. Med. Letters, 1: 425–428 (1991).
67. Gokhale, et al., Can. J. Chem., 68: 1063–1071 (1990).
68. Smith, et al., Immunology, 58: 245 (1986).
69. Sleytr, et al., Arch. Microbiol., 146: 19 (1986).
70. Ziola, et al., J. Neuroimmunol., 7: 315–330 (1985).
71. Smith, et al., Infection and Immunity, 31: 129 (1980).
72. Petrakova, et al., Can. J. Chemistry, 70: 233–240 (1992).
73. Ichikana, et al., Anal. Biochem., 202: 215–138 (1992)
74. Weinstein, et al., J. Biol. Chem. 257: 13835–13844 (1982).
75. Sticher, et al., Biochem. J., 253: 577–580 (1988).
76. Dean, et al., Chromatogr., 165: 301–319 (1979).
77. Mazid, et al., U.S. Pat. No. 5,059,535, "Process for the Separation and Purification of Sialyl Transferases" issued Oct. 22, 1992.
78. Matsumoto, et al., Anal. Biochem., 116: 103–110 (1981).
79. Schmidt, et al., Liebigs Ann. Chem., 121–124 (1991)
80. Nunez, et al., Can. J. Chem., 59: 2086–2095 (1981)
81. Veeneman, et al., Tetrahedron Lett., 32: 6175–6178 (1991)
82. Hanessian, Carbohydr. Res., 2: 86–88 (1966).
83. Zbiral, et al., Monatsh. Chem., 119: 127–141 (1988).
84. Hasegawa, et al., J. Carbohydr. Chem., 8:135–144 (1989).
85. Kean, et al., J. Biol. Chem., 241: 5643–5650 (1960).
86. Gross, et al., Biochemistry, 28: 7386–7392 (1989).
87. Lemieux, et al., U.S. Pat. No. 4,137,401 (1976).
88. Lemieux, et al., U.S. Pat. No. 4,195,174 (1978).
89. Paulsen, et al., Carbohydr. Res., 125: 21–45 (1984).
90. Sabesan, et al., Can. J. Chem., 62: 644–652 (1984).
91. Lemieux, et al., U.S. Pat. No. 4,767,845 (1987).
92. Alais, et al., Carbohydr. Res., 207: 11–31 (1990).
93. Unverzagt, et al., J. Amer. Chem. Soc., 112: 9308–9309 (1990).
94. Toone, et al., Tetrahedron, No. 17, 45:5365–5422 (1989).

All of the above publications and patent applications are herein incorporated by reference in their entirety to the same extent as if each individual publication or patent application was specifically and individually indicated to be incorporated by reference in its entirety.

3. State of the Art

The administration to mammals of different oligosaccharide glycosides related to blood group determinants having a type I or type II core structure, such as αNeu5Ac(2→3)βGal(1–4)-[α-L-Fuc(1–3)]-βGlcNAc-OR ("Sialyl Lewis$^x$-OR"), αNeu5Ac(2→3)βGal(1–3)-[α-L-Fuc(1–4)]-βGlcNAc-OR (Sialyl Lewis$^4$-OR), αNeu5Ac(2→6)βGal-(1–4)-[α-L-Fuc(1–3)]-βGlcNAc-OR, and the like, has been disclosed by Gaeta, et al.[1], Paulson, et al.[2,3], Brandley, et al.[4], Lowe[5], McEver[6], Furie, et al.[7], among others, to reduce inflammation in the mammal arising from a variety of conditions such as injury, infection, exposure to an antigen, etc. These disclosures are based on the fact that an integral step in the inflammatory process in a mammal is the adherence of leukocytes to one or more selectins and the discovery that such oligosaccharide glycosides adhere/bind to one or more selectins involved in the inflammatory response thereby interfering with the binding of the leukocyte to those selectins.

Specifically, the presence of selectins such as ELAM-1 (Endothelium Leucocyte Adhesion Molecule-1) on the vascular endothelium and/or the presence of PADGEM (also referred to as GMP-140) on either the vascular endothelium or on activated platelets and/or the presence of L-selectin on high endothelial venuels (HEV) in the peripheral and mesenteric lymph nodes is believed to be stimulated by an inflammatory event such as exposure to an antigen, myocardial infarction, lung injury, etc. In turn, adhesion of circulating leukocytes (e.g., neutrophils, monocytes, etc.) to ELAM-1 and/or PADGEM located on the stimulated vascular endothelium and/or to PADGEM located on activated platelets are believed to be primary events of the inflammatory response. Additionally, the L-selectin is believed to be present on neutrophils and, accordingly, may play some role in the inflammatory process.

Based on in-vitro data demonstrating that certain oligosaccharide glycosides related to blood group determinants having a type I or type II core structure (e.g., Sialyl Lewis$^x$ and Sialyl Lewis$^4$) bind to the ELAM-1[1,2,3,4,5,6] selectin and possibly other selectins and that certain oligosaccharide glycosides related to blood group determinants having a type I or type II core structure (e.g., αNeu5Ac(2→6)βGal(1–4)-[α-L-Fuc(1–3)]-βGlcNAc) bind to the ELAM-1[4] and PADGEM[7] selectins, it was postulated that these oligosaccharide glycosides would reduce inflammation when administered prophylactically[1,2,3,4] or therapeutically[1,2,3,4,5,6,7] to a mammal by interfering with adhesion between ELAM-1, PADGEM, and/or other selectins and the circulating leukocytes.

In disease/inflammatory conditions, the Gaeta, et al.[1], Paulson, et al.[2,3] and Brandley, et al.[4] references recite that the therapeutic administration of the therein disclosed oligosaccharide glycosides can be conducted on a patient already suffering from the disease/inflammatory condition. According to the Gaeta, et al.[1] and Paulson, et al.[2,3] references, the therein disclosed oligosaccharide glycosides can be used to treat a variety of disease/inflammatory conditions including disease conditions arising from antigen exposure such as rheumatoid arthritis, asthma, dermatitis, psoriasis, and inflammatory bowel disease as well as inflammatory conditions arising from an injury including frost-bite injury, reperfusion injury, acute leukocyte-mediated lung injury, etc. The Gaeta, et al.[1] and Paulson, et al.[2,3] references specifically recite that for inflammation arising from reperfusion or other injury, the therein disclosed oligosaccharide glycoside should ideally be administered as soon as possible after the injury. However, no guidance is provided by these or by the Brandley, et al.[4], Lowe[5], McEver[6] or Furie, et al.[7] references as to when such oligosaccharide glycosides specifically should be therapeutically administered to a mammal sensitized to an antigen after subsequent antigen exposure.

This invention is directed to the discovery that, in order to reduce inflammation in the case of antigen challenge (exposure) in a sensitized mammal, the oligosaccharide glycoside related to blood group determinants must be administered after initiation of the mammal's secondary immune response to the antigen challenge but at or prior to one-half that period of time where the mammal experiences maximal inflammatory response.

Specifically, the data set forth in the examples below evidence that administration of the oligosaccharide glycoside related to a blood group determinant having a type I or type II core structure prior to initiation of the mammal's immune response, provides no reduction in inflammation. Additionally, administration of the oligosaccharide glycoside at a point in time after one-half that period of time where the mammal experiences maximal inflammatory response to the antigen exposure results in minimal reduction in inflammation. In fact, the data evidence that it is only when the oligosaccharide glycoside related to blood group determinants having a type I or type II core structure is administered after the sensitized mammal's secondary immune response has been initiated to antigen challenge but at or prior to about one-half that period of time where the mammal experiences maximal inflammatory response to the antigen challenge does significant reduction in inflammation occur.

These findings are particularly surprising in view of the fact that the Gaeta, et al.[1], Paulson, et al.[2,3], Brandley, et al.[4] references state that the therein disclosed oligosaccharide glycoside can be administered either prophylactically or therapeutically and further in view of the fact that none of the Gaeta, et al.[1], Paulson, et al.[2,3], Brandley, et al.[4], Lowe[5], McEver[6], Furie et al.[7] references disclose any criticality with regard to the point in time when such oligosaccharide glycosides should be therapeutically administered to a mammal in order to reduce the degree of inflammation arising from the mammal's secondary immune response to an antigen challenge.

SUMMARY OF THE INVENTION

In view of the above, in one of its method aspects, this invention is directed to a method for reducing the degree of inflammation in a mammal arising from the initiation of a mammal's secondary immune response due to antigen exposure which method comprises administering to said mammal an inflammation reducing effective amount of an oligosaccharide glycoside related to blood group determinants having a type I or type II core structure wherein said administration is after initiation of the mammal's secondary immune response to the antigen exposure but at or prior to one-half that period of time required for maximal inflammatory response to the antigen exposure.

In another of its method aspects, this invention is directed a method for reducing the degree of inflammation in a mammal arising from initiation of a mammal's secondary immune response due to antigen exposure which method comprises administering to said mammal from about 0.5 to about 50 mg/kg of an oligosaccharide glycoside selected from the group consisting of an oligosaccharide glycoside of Formula I

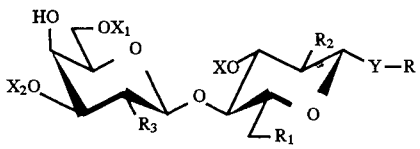

and Formula II

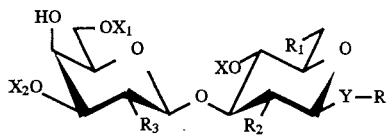

wherein said administration is after initiation of the mammal's secondary immune response to the antigen exposure but at or prior to one-half that period of time required for maximal inflammatory response to the antigen exposure, where R is selected from the group consisting of hydrogen, a saccharide-$OR_{19}$, an oligosaccharide-$OR_{19}$ of from 2 to 7 saccharide units, and an aglycon having at least one carbon atom where $R_{19}$ is hydrogen or an aglycon of at least one carbon atom;

Y is selected from the group consisting of oxygen, sulfur, and —NH—;

$R_1$ is selected from the group consisting of hydrogen, —$NH_2$, —$N_3$, —$NHSO_3H$, —$NR_5C(O)R_4$, —N=C$(R_5)_2$, —$NHCH(R_5)_2$, —$NHR_6$, —$N(R_6)_2$, —OH, —$OR_6$, —$S(O)R_6$, —$S(O)_2R_6$ and sulfate, wherein $R_4$ is selected from the group consisting of
  hydrogen,
  alkyl of from 1 to 4 carbon atoms,
  —$OR_7$ wherein $R_7$ is alkyl of from 1 to 4 carbon atoms, or alkyl of from 2 to 4 carbon atoms substituted with a hydroxyl group, and
  —$NR_8R_9$ wherein $R_8$ and $R_9$ are independently selected from the group consisting of hydrogen and alkyl of from 1 to 4 carbon atoms, each $R_5$ is selected from the group consisting of hydrogen and alkyl of from 1 to 4 carbon atoms, each $R_6$ is alkyl of from 1 to 4 carbon atoms, $R_2$ is selected from the group consisting of hydrogen, —$N_3$, —$NH_2$, —$NHSO_3H$, —$NR_{11}C(O)R_{10}$, —N=C$(R_{11})_2$, —$NHCH(R_{11})_2$, —$NHR_{12}$, —$N(R_{12})_2$, —OH and —$OR_{12}$, wherein $R_{10}$ is selected from the group consisting of
  hydrogen,
  alkyl of from 1 to 4 carbon atoms,
  —$OR_{13}$ wherein $R_{13}$ is alkyl of from 1 to 4 carbon atoms, or alkyl of from 2 to 4 carbon atoms substituted with a hydroxyl group, and
  —$NR_{14}R_{15}$ wherein $R_{14}$ and $R_{15}$ are independently selected from the group consisting of hydrogen and alkyl of from 1 to 4 carbon atoms, each $R_{11}$ is selected from the group consisting of hydrogen and alkyl of from 1 to 4 carbon atoms;

each $R_{12}$ is alkyl of from 1 to 4 carbon atoms, $R_3$ is selected from the group consisting of hydrogen, fluoro, sulfate and hydroxy;

X is selected from the group consisting of hydrogen, L-fucosyl, 4-sulfo-L-fucosyl, and 4-phospho-L-fucosyl;

$X_1$ is selected from the group consisting of hydrogen, sialyl, sulfate, phosphate, and —$CHR_{18}COOH$ where $R_{18}$ is selected from the group consisting of hydrogen, alkyl of from 1 to 7 carbon atoms and —COOH;

$X_2$ is selected from the group consisting of hydrogen, sialyl, sulfate, phosphate, and —$CHR_{18}COOH$ where $R_{18}$ is selected from the group consisting of hydrogen, alkyl of from 1 to 7 carbon atoms and —COOH; and pharmaceutically acceptable salts thereof; and with the proviso if X is hydrogen, then either at least one of $X_1$ or $X_2$ is not hydrogen or $R_3$ is sulfate, and with the further proviso that only one of $X_1$ and $X_2$ is sialyl.

In yet another of its method aspects, this invention is directed to a method for reducing the degree of inflammation in a mammal arising from initiation of a mammal's secondary immune response due to antigen exposure as well as inducing tolerance in the mammal to later exposure to the antigen which method comprises administering to the mammal from about 0.5 to about 5 mg/kg of an oligosaccharide glycoside selected from the group consisting of an oligosaccharide glycoside of Formula I

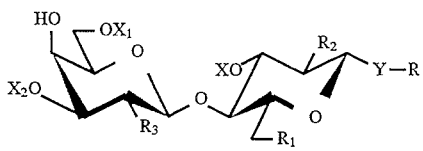

and Formula II

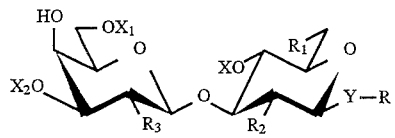

wherein said administration is after initiation of the mammal's secondary immune response to the antigen exposure but at or prior to one-half that period of time required for maximal inflammatory response to the antigen exposure, where R is selected from the group consisting of hydrogen, a saccharide-$OR_{19}$, an oligosaccharide-$OR_{19}$ of from 2 to 7 saccharide units, and an aglycon having at least one carbon atom where $R_{19}$ is hydrogen or an aglycon of at least one carbon atom;

Y is selected from the group consisting of oxygen, sulfur, and —NH—;

$R_1$ is selected from the group consisting of hydrogen, —$NH_2$, —$N_3$, —$NHSO_3H$, —$NR_5C(O)R_4$, —N=C($R_5$)$_2$, —NHCH($R_5$)$_2$, —$NHR_6$, —N($R_6$)$_2$, —OH, —$OR_6$, —S(O)$R_6$, —S(O)$_2R_6$ and sulfate, wherein $R_4$ is selected from the group consisting of
hydrogen,
alkyl of from 1 to 4 carbon atoms,
—$OR_7$ wherein $R_7$ is alkyl of from 1 to 4 carbon atoms, or alkyl of from 2 to 4 carbon atoms substituted with a hydroxyl group, and
—$NR_8R_9$ wherein $R_8$ and $R_9$ are independently selected from the group consisting of hydrogen and alkyl of from 1 to 4 carbon atoms, each $R_5$ is selected from the group consisting of hydrogen and alkyl of from 1 to 4 carbon atoms, each $R_6$ is alkyl of from 1 to 4 carbon atoms, $R_2$ is selected from the group consisting of hydrogen, —$N_3$, —$NH_2$, —$NHSO_3H$, —$NR_{11}C(O)R_{10}$, —N=C($R_{11}$)$_2$, —NHCH($R_{11}$)$_2$, —$NHR_{12}$, —N($R_{12}$)$_2$, —OH and —$OR_{12}$, wherein $R_{10}$ is selected from the group consisting of
hydrogen,
alkyl of from 1 to 4 carbon atoms,
—$OR_{13}$ wherein $R_{13}$ is alkyl of from 1 to 4 carbon atoms, or alkyl of from 2 to 4 carbon atoms substituted with a hydroxyl group, and
—$NR_{14}R_{15}$ wherein $R_{14}$ and $R_{15}$ are independently selected from the group consisting of hydrogen and alkyl of from 1 to 4 carbon atoms, each $R_{11}$ is selected from the group consisting of hydrogen and alkyl of from 1 to 4 carbon atoms;

each $R_{12}$ is alkyl of from 1 to 4 carbon atoms, $R_3$ is selected from the group consisting of hydrogen, fluoro, sulfate and hydroxy;

X is selected from the group consisting of hydrogen, L-fucosyl, 4-sulfo-L-fucosyl, and 4-phospho-L-fucosyl;

$X_1$ is selected from the group consisting of hydrogen, sialyl, sulfate, phosphate, and —$CHR_{18}COOH$ where $R_{18}$ is selected from the group consisting of hydrogen, alkyl of from 1 to 7 carbon atoms and —COOH;

$X_2$ is selected from the group consisting of hydrogen, sialyl, sulfate, phosphate, and —$CHR_{18}COOH$ where $R_{18}$ is selected from the group consisting of hydrogen, alkyl of from 1 to 7 carbon atoms and —COOH; and pharmaceutically acceptable salts thereof; and with the proviso if X is hydrogen, then either at least one of $X_1$ or $X_2$ is not hydrogen or $R_3$ is sulfate, and with the further proviso that only one of $X_1$ and $X_2$ is sialyl.

Preferably, $R_2$ is —$NH_2$, —$N_3$, —$NHC(O)R_{10}$ and $R_3$ is preferably —OH or sulfate.

Preferably, $X_2$ is sialyl or a sulfate group.

When $X_2$ is a sialyl group, X is preferably a fucosyl group.

In Formula I, when $X_2$ is a sulfate group, X is preferably hydrogen.

In one preferred embodiment, the oligosaccharide glycoside related to blood group determinants having a type I or type II core structure is selected from the group of oligosaccharide glycosides A–N set forth in Example A hereinbelow.

Preferably, the oligosaccharide glycoside related to blood group determinants having a type I or type II core structure is administered to the mammal at least 1 hour after the mammal has been exposed to the antigen, more preferably from about 1 to 10 hours after the mammal has been exposed to the antigen. In another preferred embodiment, the oligosaccharide glycoside related to blood group determinants having a type I or type II core structure is administered to the mammal from about 1 to 5 hours after the mammal has been exposed to the antigen.

BRIEF DESCRIPTION OF THE DRAWINGS

FIG. 3 illustrates secondary antibody responses (i.e., as determined by the amount of antibody measured by quantification of o-phenylenediamine O.D. at 490 nm) two weeks after primary immunization and one week after challenge with the L111 S-Layer protein antigen and the effect different oligosaccharide glycosides related to blood group determinants had on these responses when the mice were treated with these oligosaccharide glycosides 5 hours after challenge.

FIG. 4 illustrates the effect of an oligosaccharide glycoside related to blood group determinants having type I or type II core structures, i.e, Sialyl Lewis$^x$-OR where R=8-methoxycarbonyloctyl, on the inflammatory DTH response in immunized mice challenged with the L111 S-Layer protein antigen wherein the mice were treated at various times before or after challenge with 100 µg of Sialyl Lewis$^x$-OR.

FIG. 5 illustrates the long term (8 weeks) immunosuppression generated in immunized mice after an injection with 5 mg/kg of oligosaccharide glycosides related to blood group determinants having type I or type II core structures, 5 hours after challenge with 20 µg of the L111 S-Layer protein antigen on day 7.

In this figure, because the 3,4-dihydroxyl groups of the 6-benzyl and 2-N-phthaloyl blocked glucosamine 15 are not blocked, reaction with 1-bromo-2,3,4,6-tetraacetyl galactose will result in formation of both the blocked βGal(1→4) βGlcNH$_2$-OR derivative 48 and the blocked βGal(1→3) βGlcNH$_2$-OR derivative (not shown). In turn, these materials can be further derivatized at an appropriate point in the synthesis so as to provide for N-functionalized derivatives of oligosaccharide glycosides related to blood group determinants having a type I or type II structure.

Figure 23A:
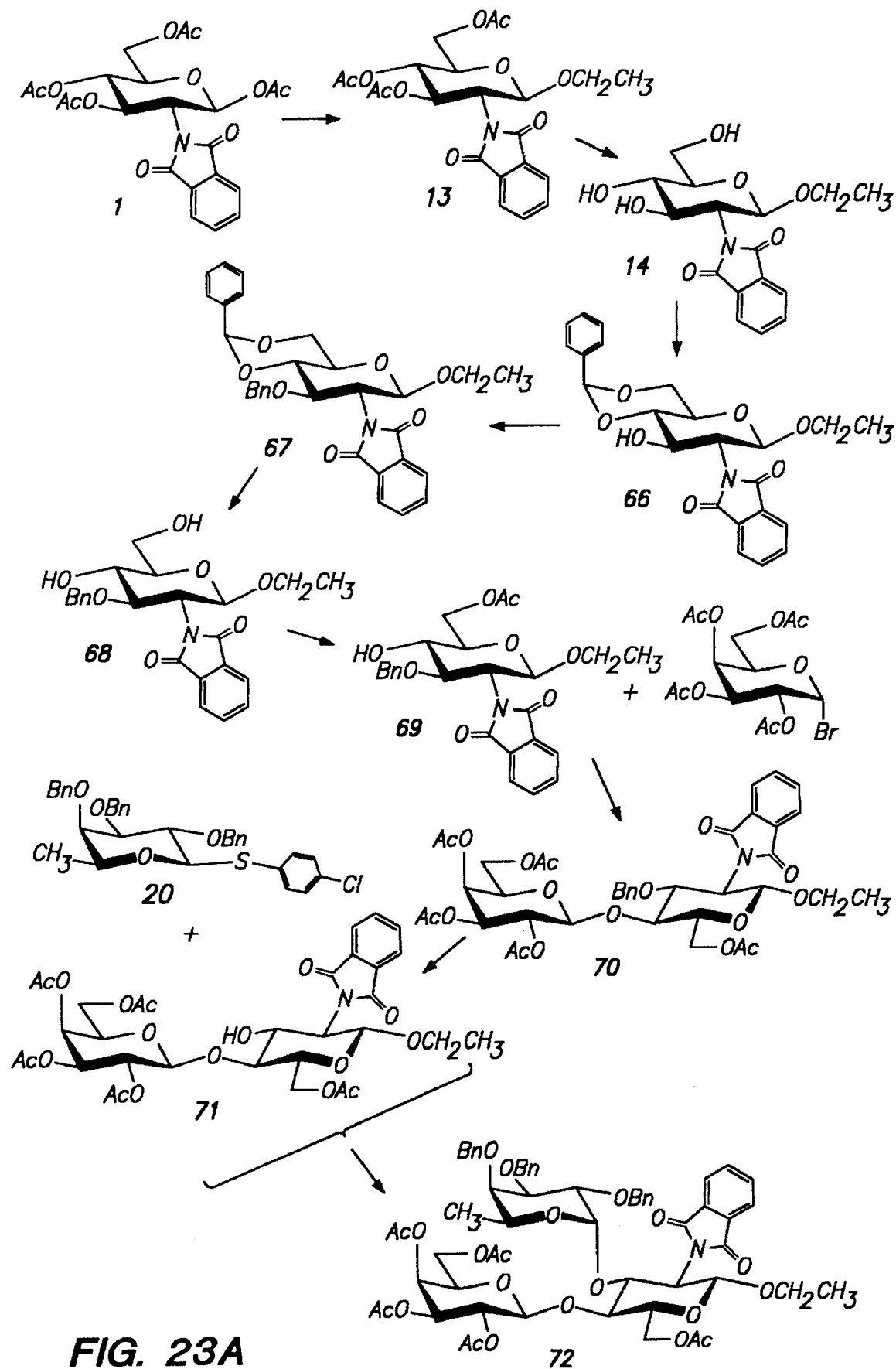
Figure 23B:
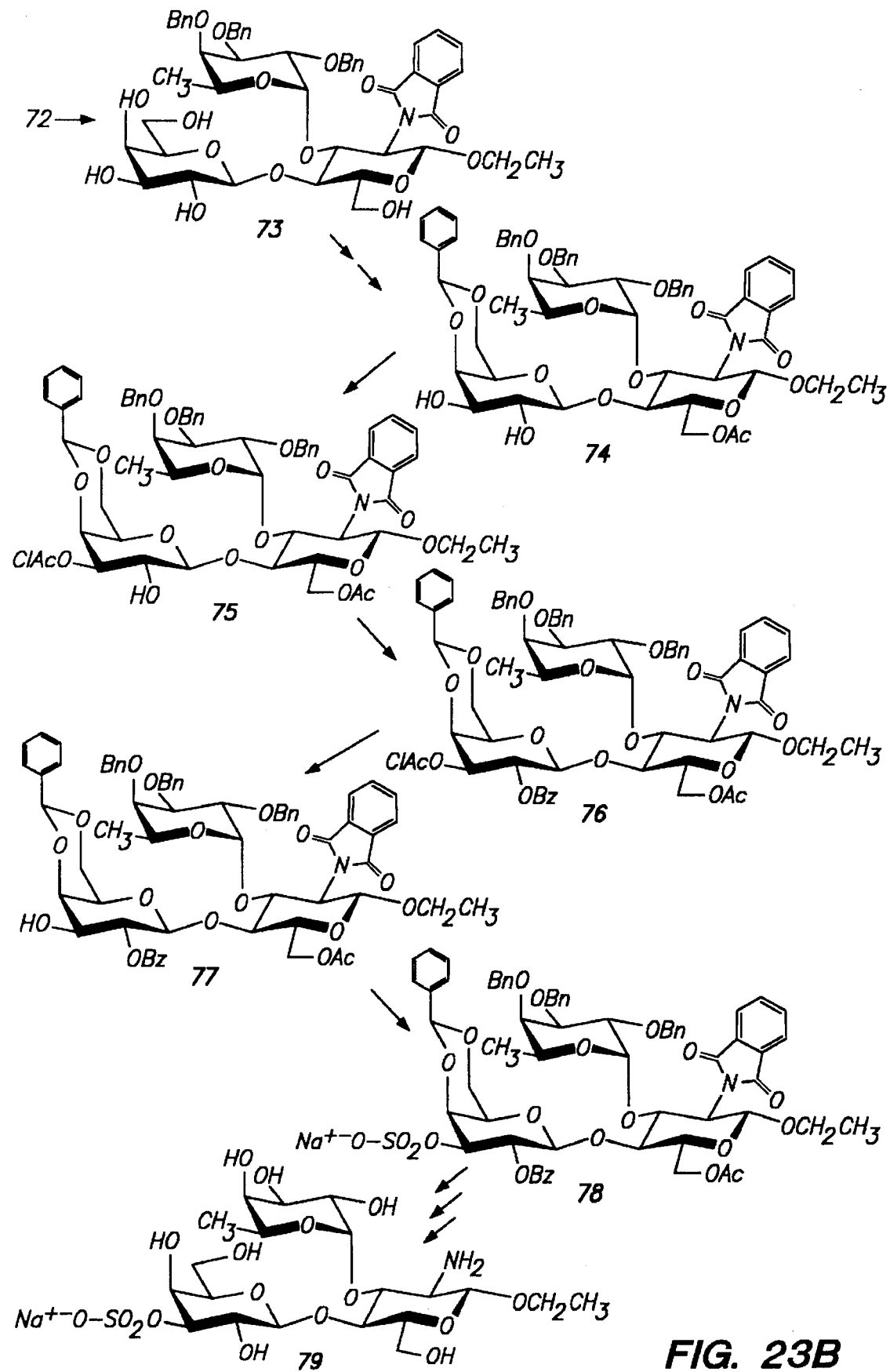

FIGS. 23A and 23B illustrate a second synthesis of modified Lewis$^x$ compounds bearing a sulfate substituent at the 3-position of the galactose and which utilize a different N-phthaloyl blocked glucosamine intermediate that allows for the selective preparation of 2-amino or N-functionalized Lewis$^x$ derivatives. In this figure, only the 4-position of the glucosamine is not blocked so that only the blocked βGal (1→4)βGlcNH$_2$-OR derivative 70 is formed.

Figure 24A:
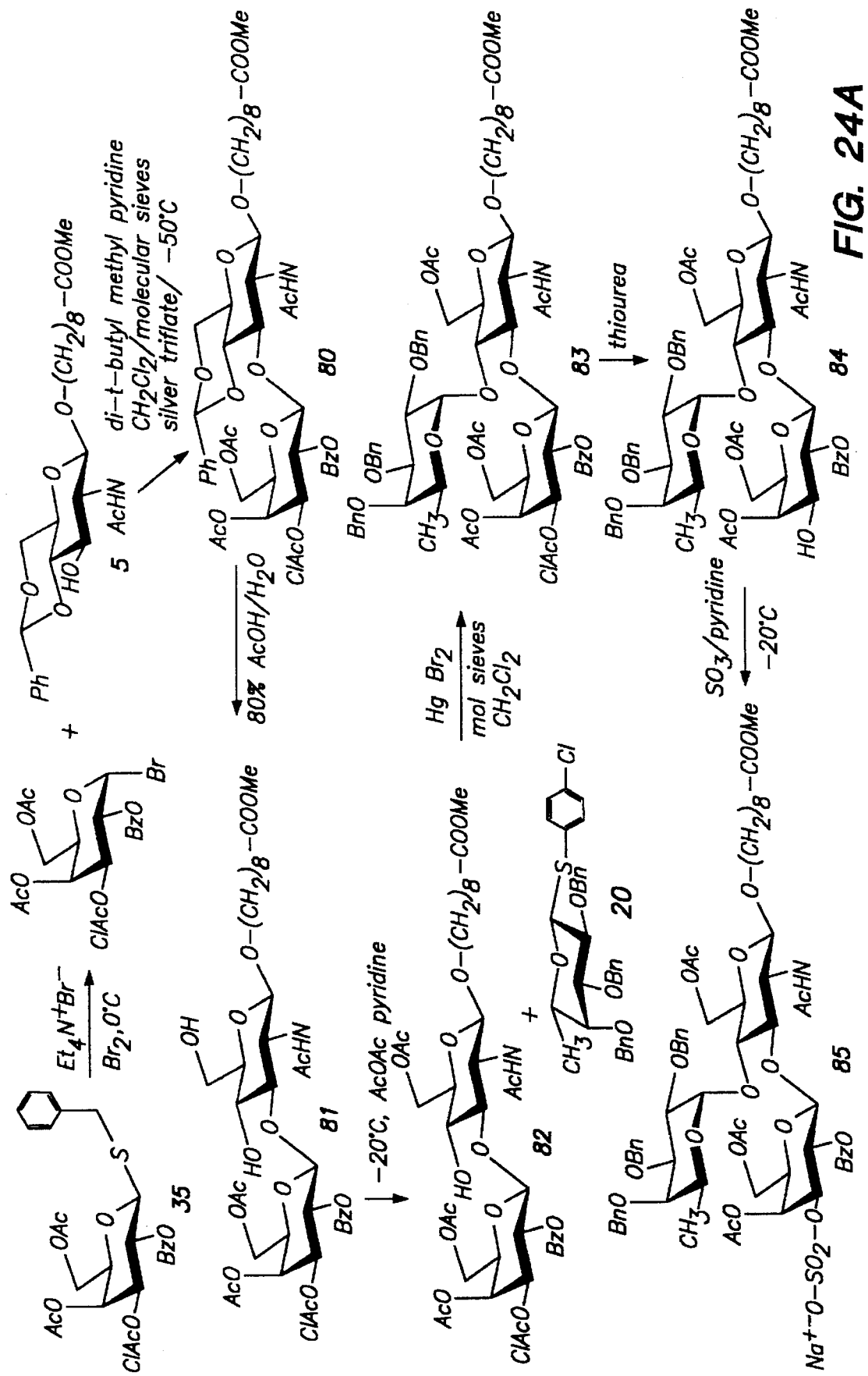
Figure 24B:
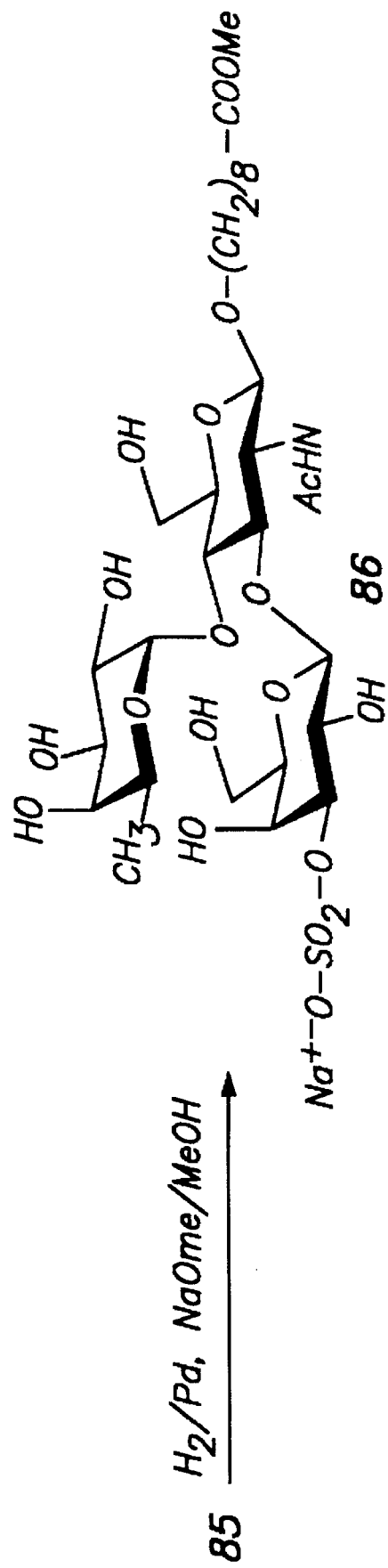

FIGS. 24A and 24B illustrate the preparation of modified Lewis$^A$ analogues having a sulfate substituent in the 3 position of the galactose unit. In this scheme, the 2,3 positions of galactose are differentially blocked so that the 3-position can be selectively deblocked and then selectively converted to the sulfate substituent.

Figure 25:
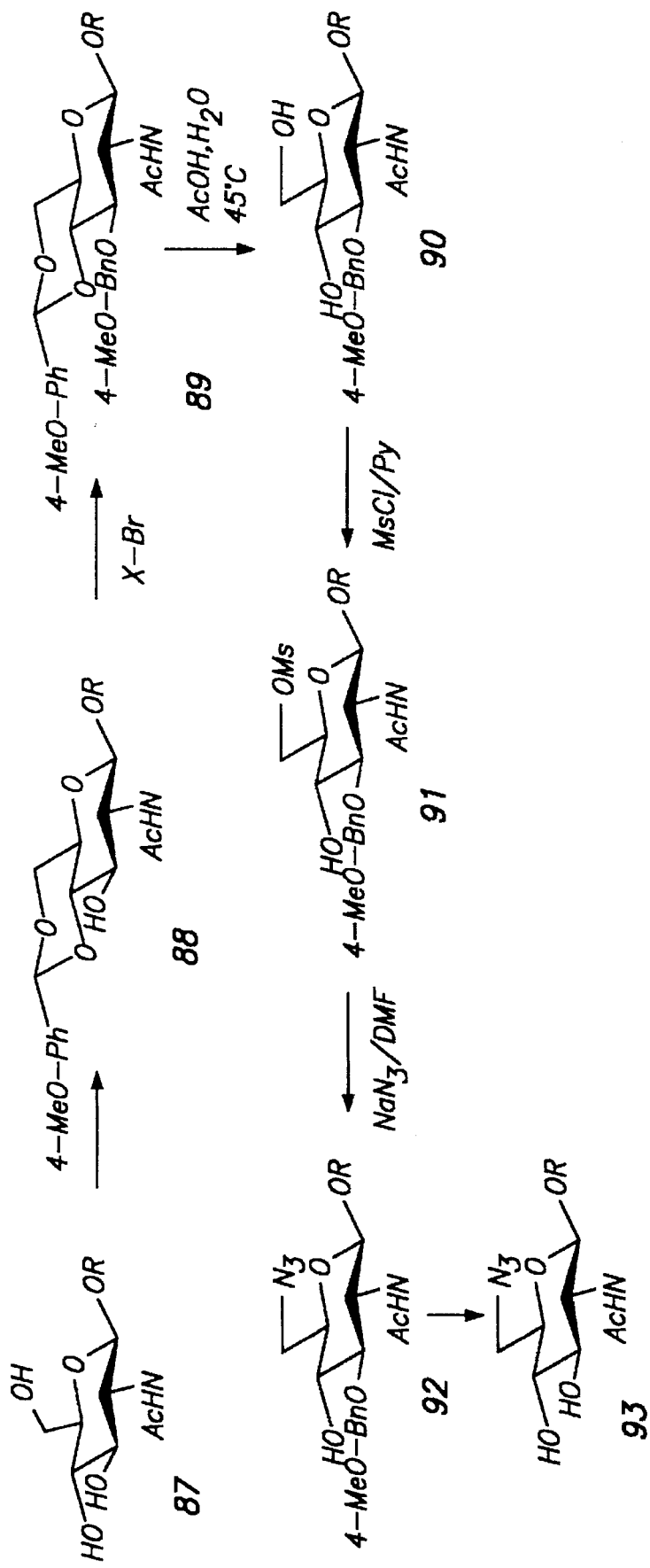

FIG. 25 illustrates the synthesis of the 6-azido derivative of GlcNAc-OR.

Figure 26:
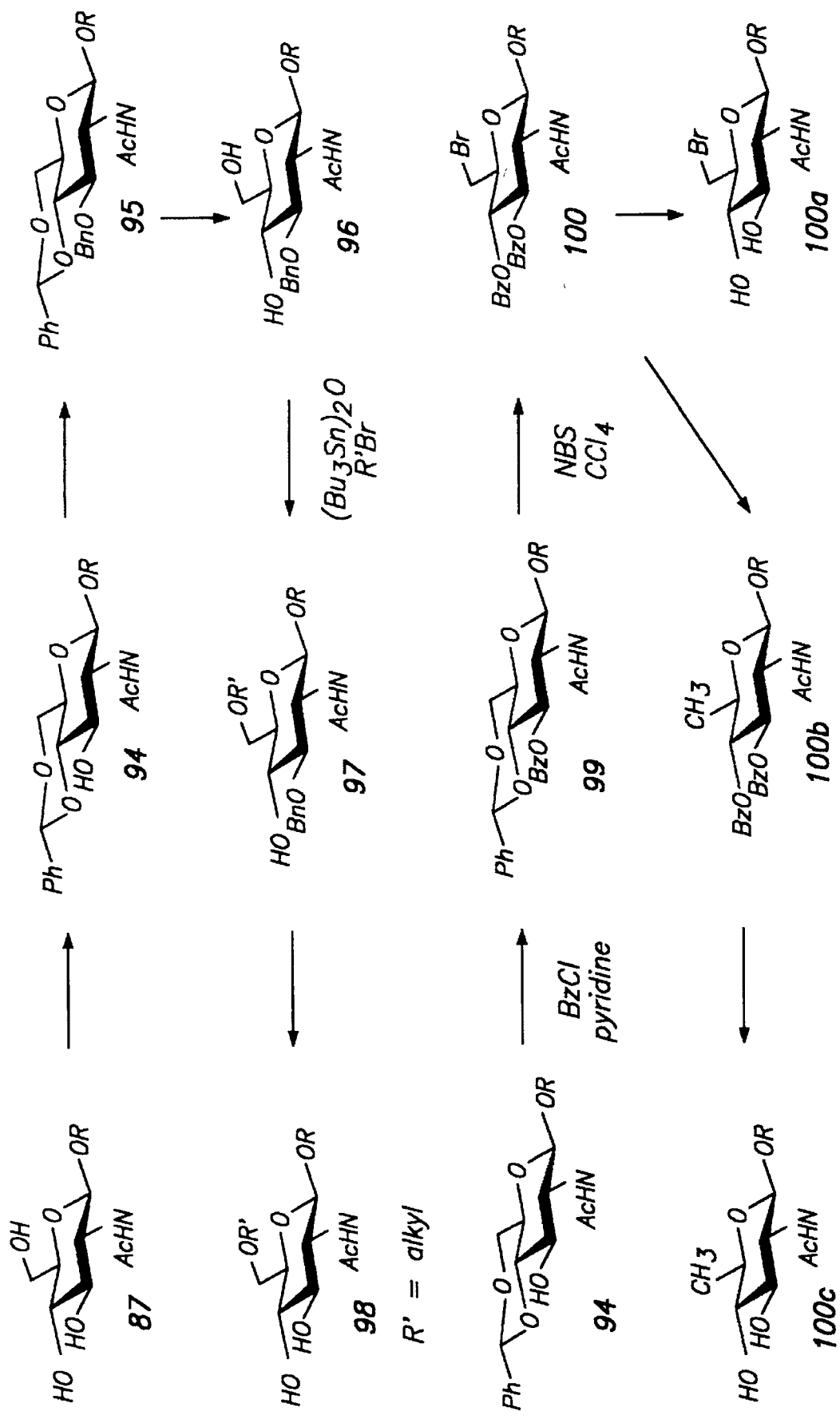

FIG. 26 illustrates the synthesis of the 6-alkoxy derivatives, 6-bromo derivatives, and the 6-deoxy derivatives of GlcNAc.

Figure 27A:
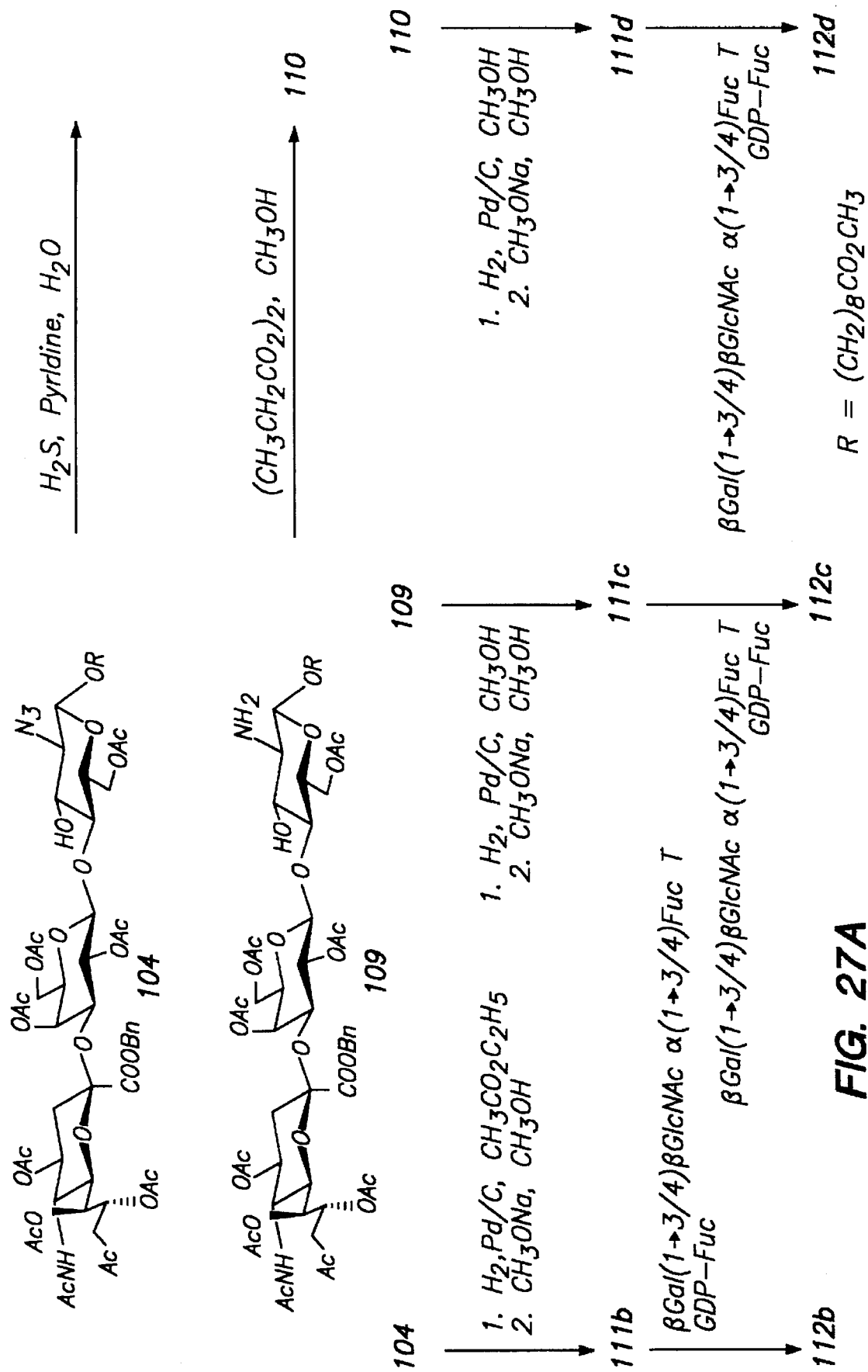
Figure 27B:
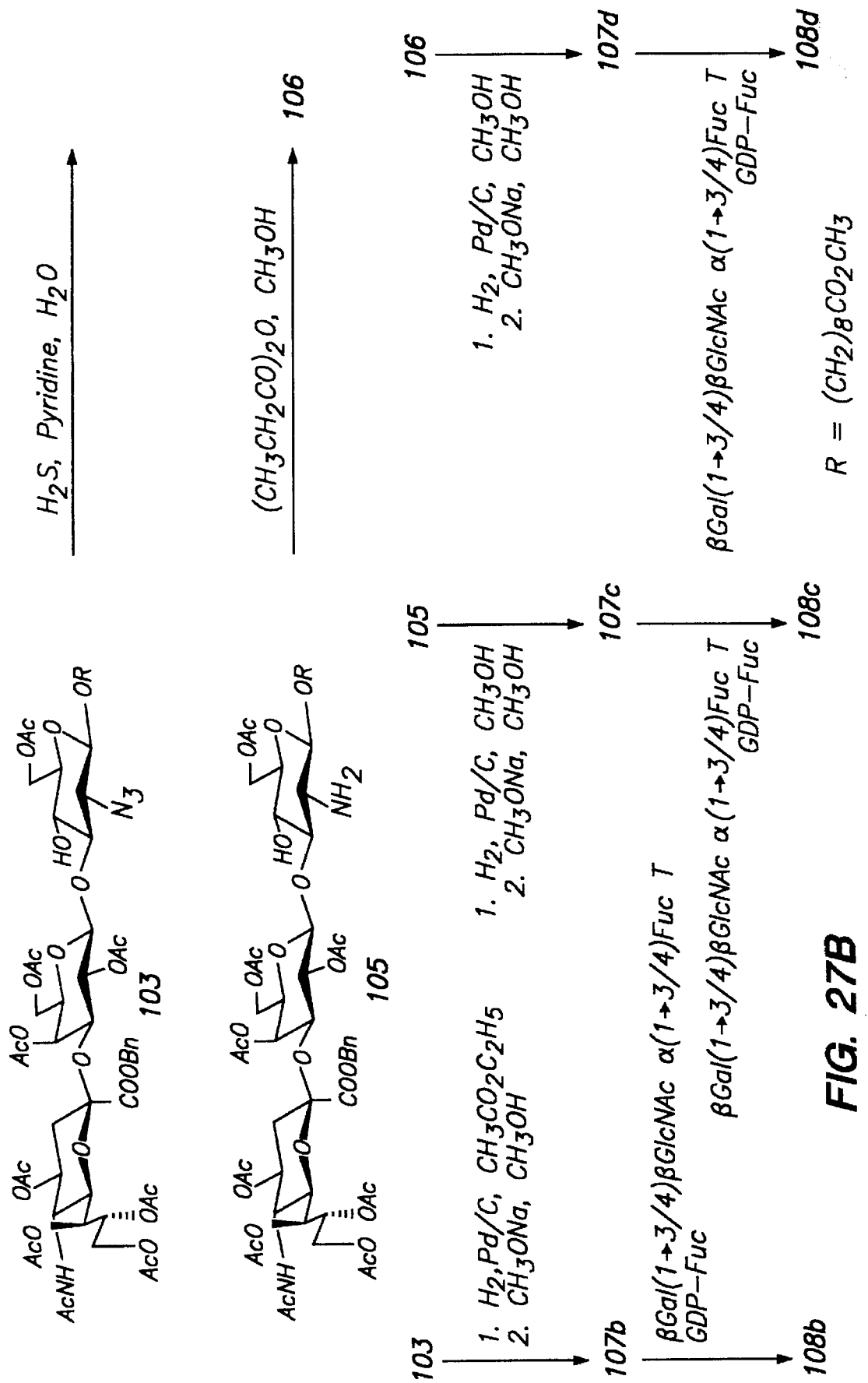

FIGS. 27A and 27B illustrate general reaction schemes for the chemo-enzymatic synthesis of the analogues of sialyl Lewis$^x$ (compound 112b–d) and Sialyl Lewis$^A$ (compounds 108a–d) wherein Ac represent acetyl, Bn represents benzyl, and R represents —(CH$_2$)$_8$CO$_2$CH$_3$.

Figure 28:
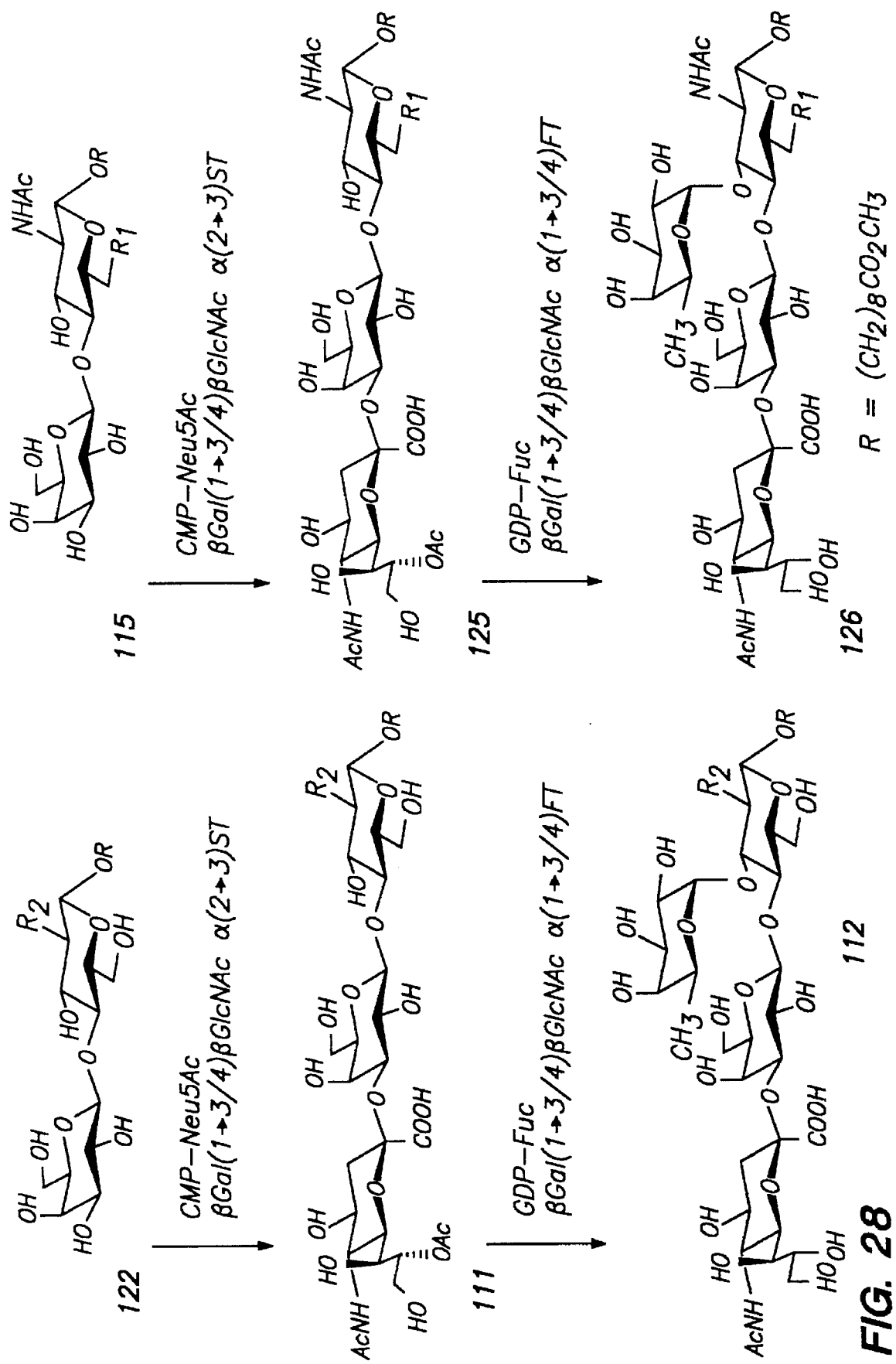

FIG. 28 illustrates an alternative chemo-enzymatic synthesis of analogues of sialyl Lewis$^x$ modified at the C-2 and/or C-6 positions of the N-acetylglucosamine unit.

Figure 29A:
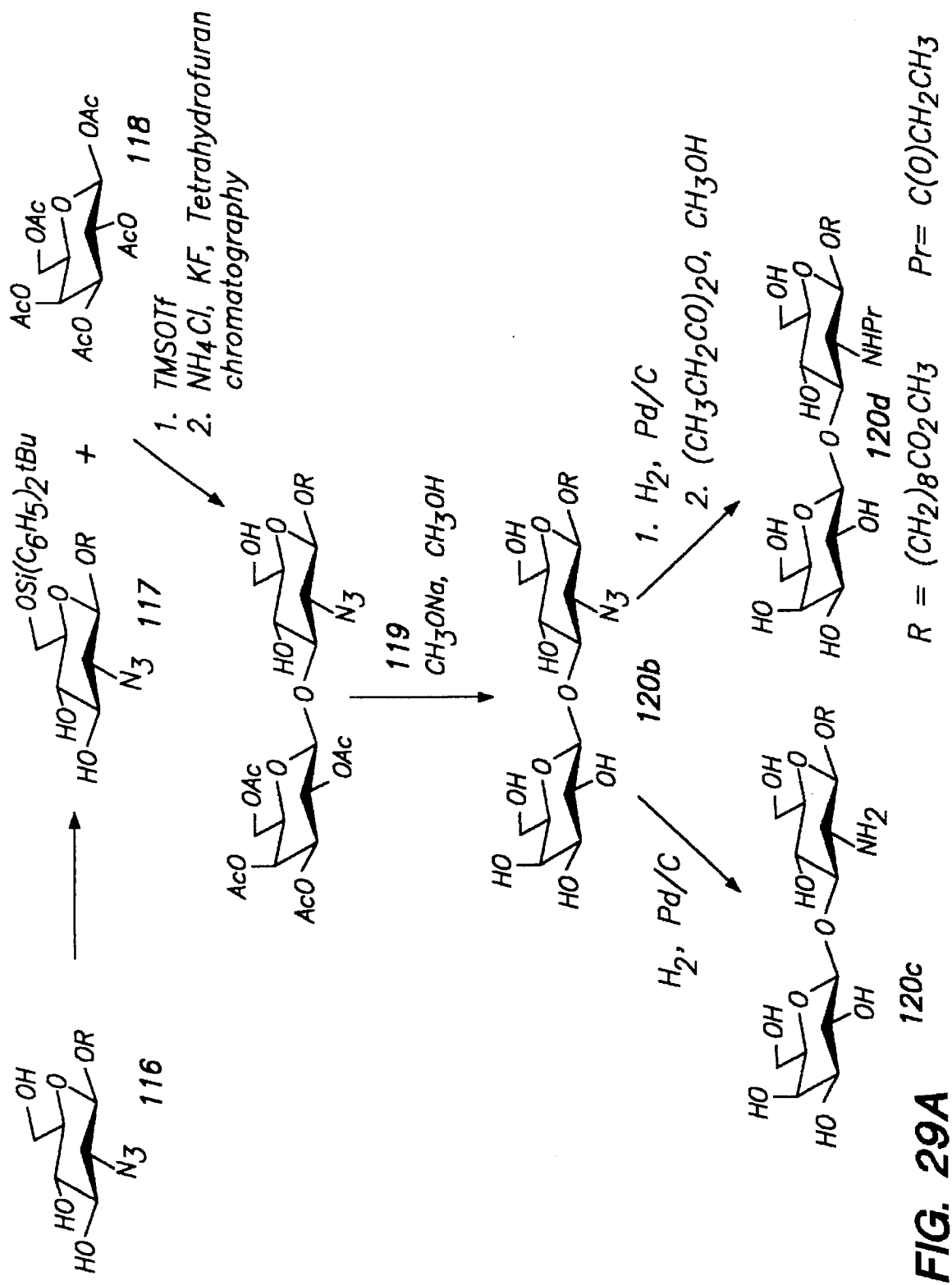

FIGS. 29A & B and 30A and B illustrate general schemes for the synthesis of type I and type II structures.

Figure 31A:
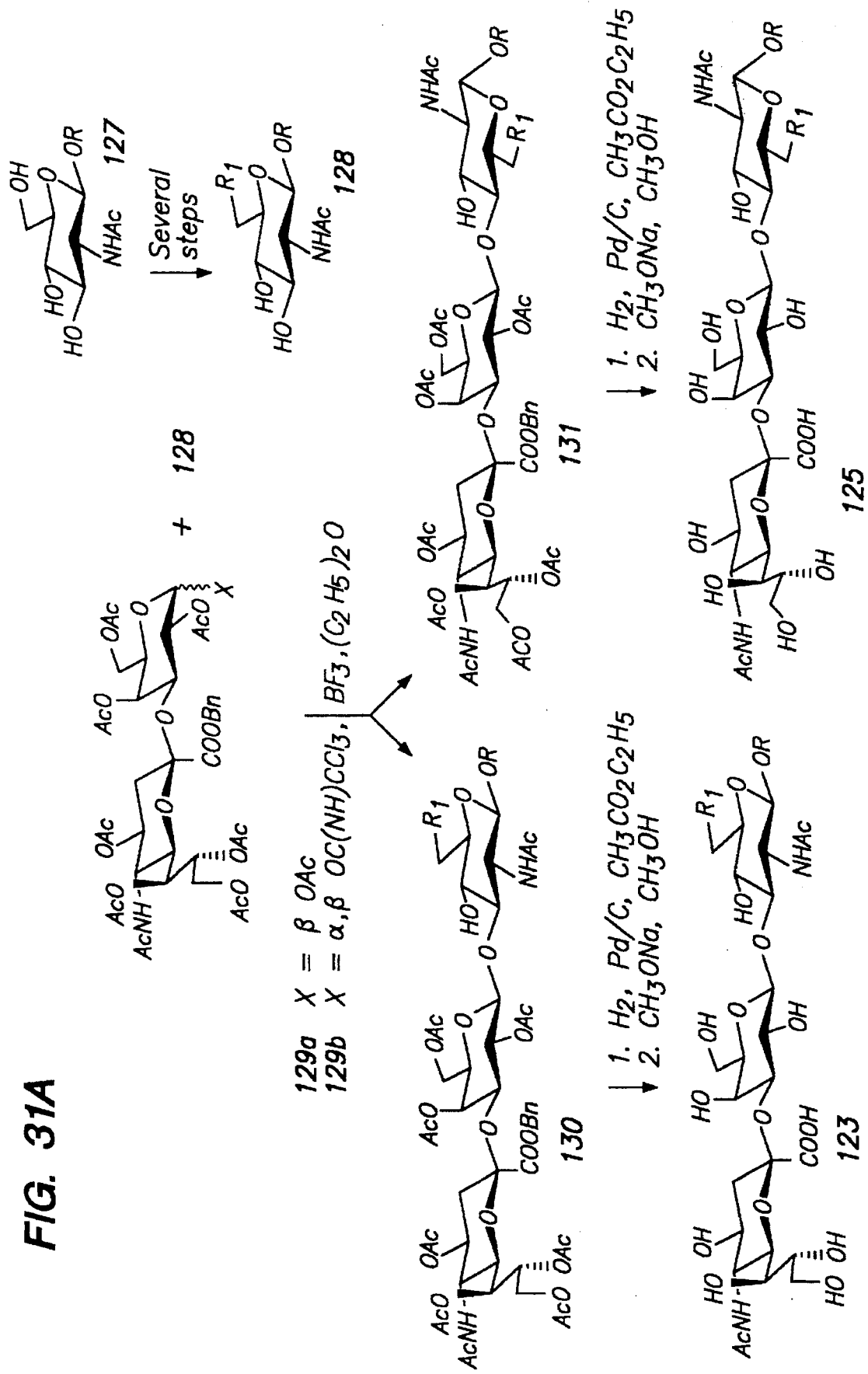
Figure 31B:
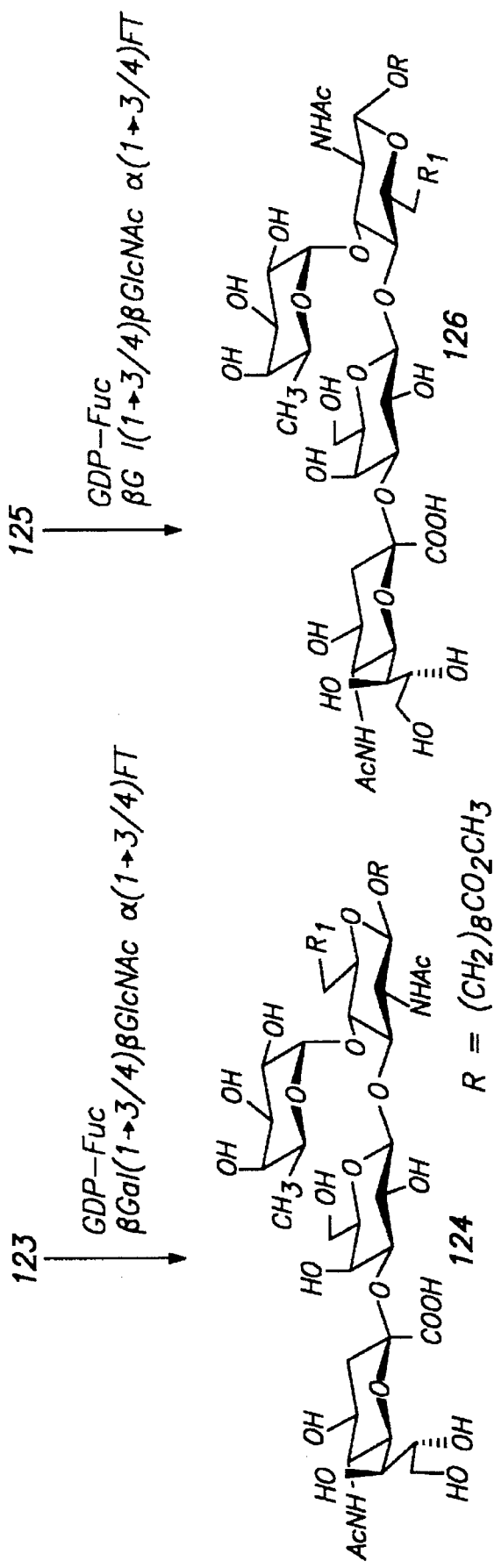

FIGS. 31A and 31B illustrate a general reaction scheme for the chemo-enzymatic synthesis of analogues of sialyl Lewis$^x$ and sialyl Lewis$^A$ modified at the C-6 position of the N-acetylglucosamine unit.

Figure 32A:
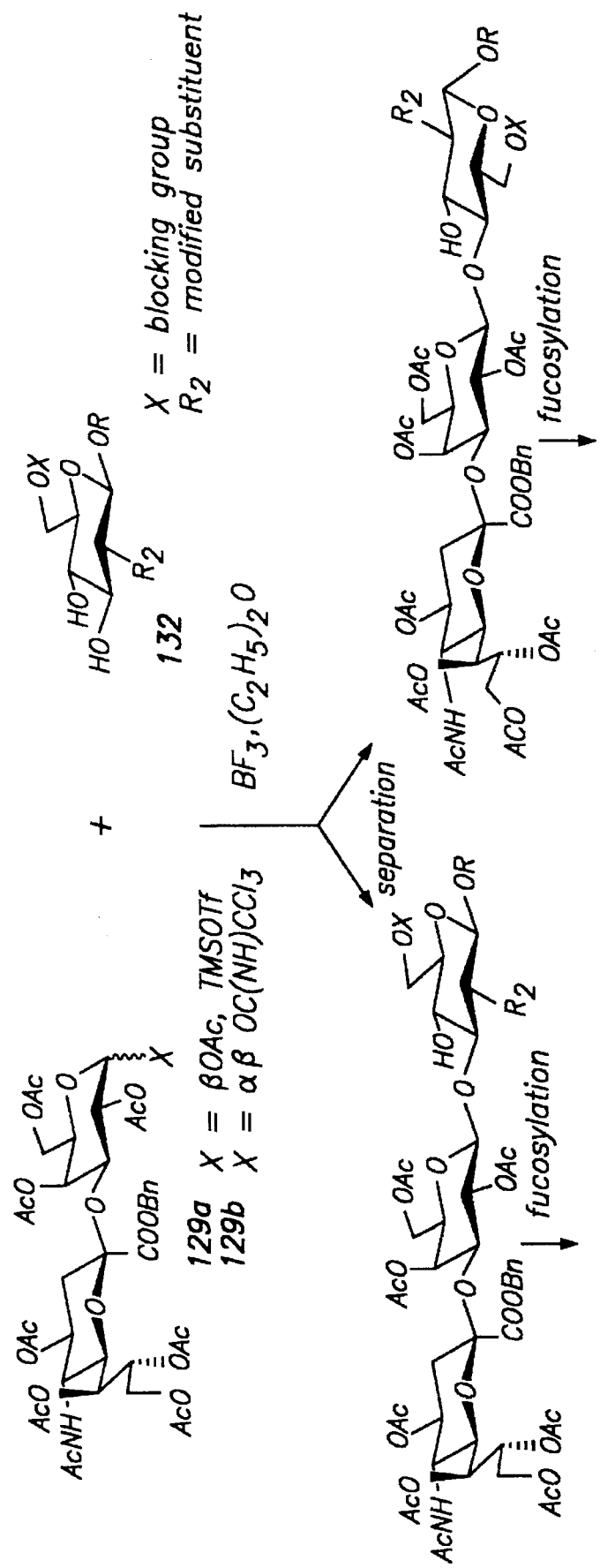
Figure 32B:
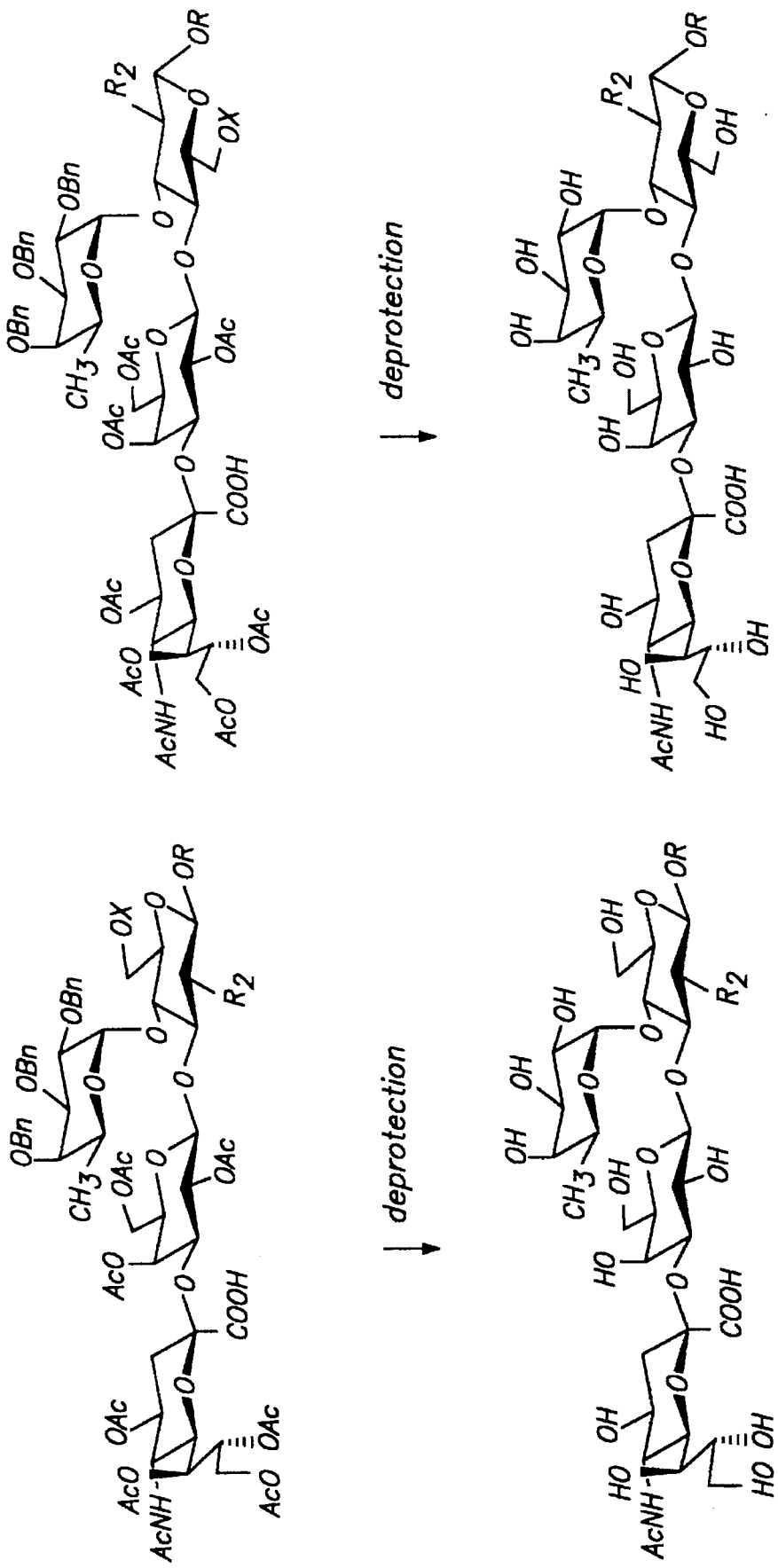

FIGS. 32A and 32B illustrate a general reaction scheme for the total chemical synthesis of analogues of sialyl Lewis$^x$ and sialyl Lewis$^A$ modified at the C-2 position of the N-acetylglucosamine unit.

Figure 33A:
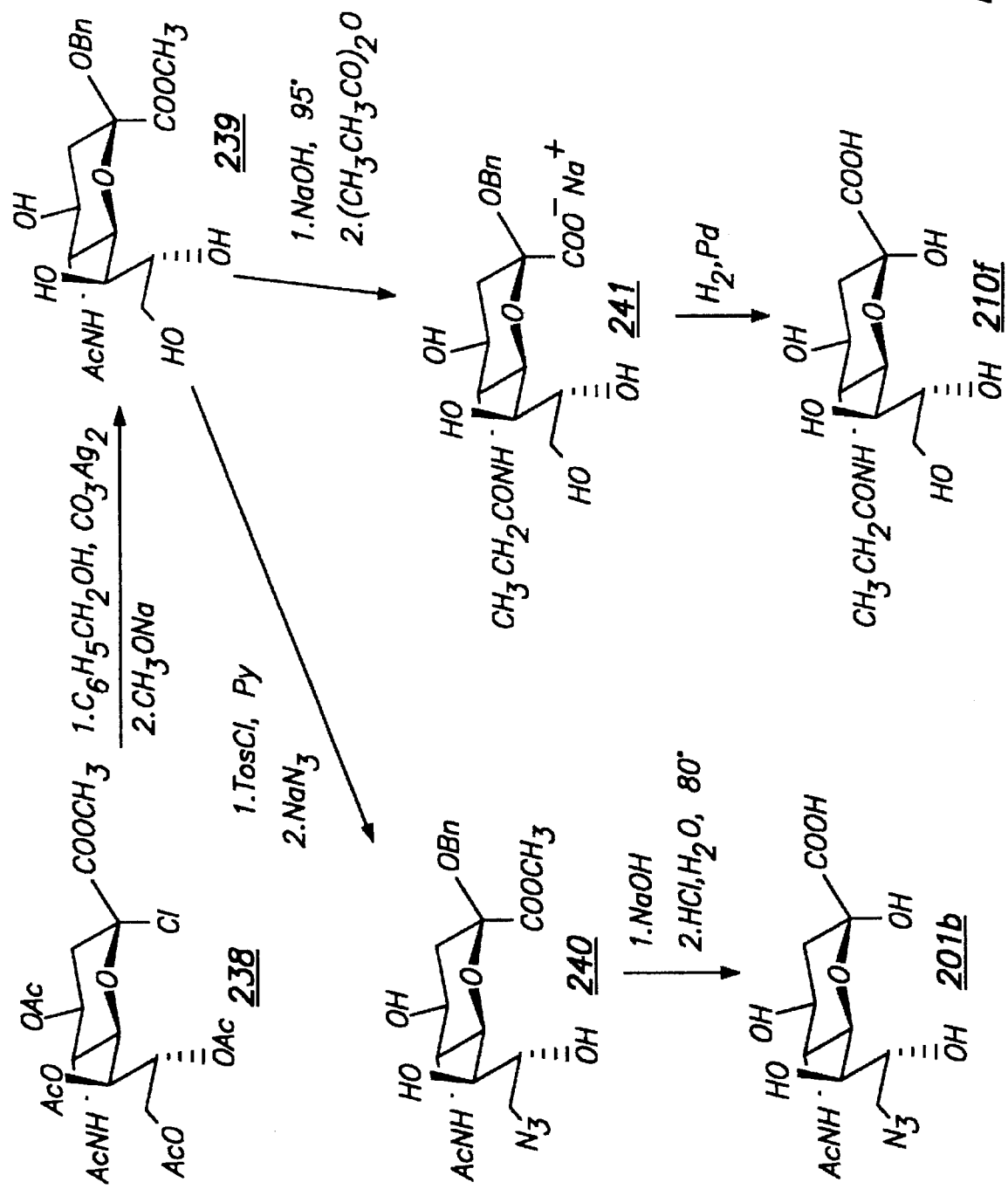
Figure 33B:
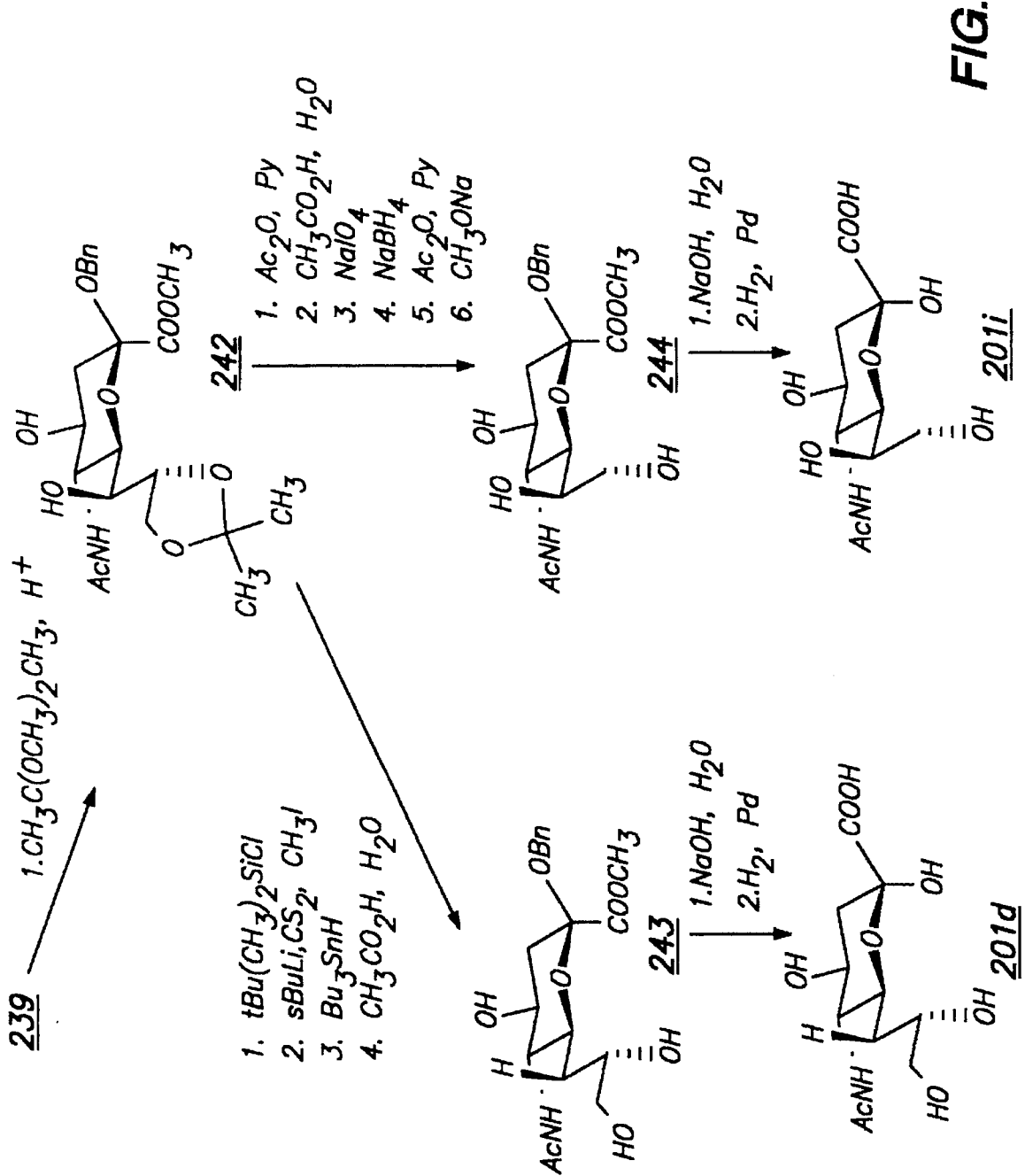

FIGS. 33A and 33B illustrate a general synthetic scheme used for the synthesis of derivatives of Neu5Ac.

FIG. 34 illustrates the structures of mono- and oligosaccharide glycosides 203b to 207a. In FIG. 34, the X substituent in compound 203b is X$_2$, the X substituent in compound 203d is X$_4$, the X substituent in compound 204a is X$_1$, the X substituent in compound 204b is X$_2$, the X substituent in compound 204c is X$_3$, the X substituent in compound 204d is X$_4$, the X substituent in compound 205a is X$_1$, the X substituent in compound 205b is X$_2$, the X substituent in compound 205d is X$_4$, the X substituent in compound 205e is X$_5$, the X substituent in compound 205f is X$_6$, the X substituent in compound 205g is X$_2$, the X substituent in compound 206a is X$_2$, and the X substituent in compound 207a is X$_2$ where X$_1$, X$_2$, X$_3$, X$_4$, X$_5$ and X$_6$ are as defined in FIG. 34.-

Figure 35:
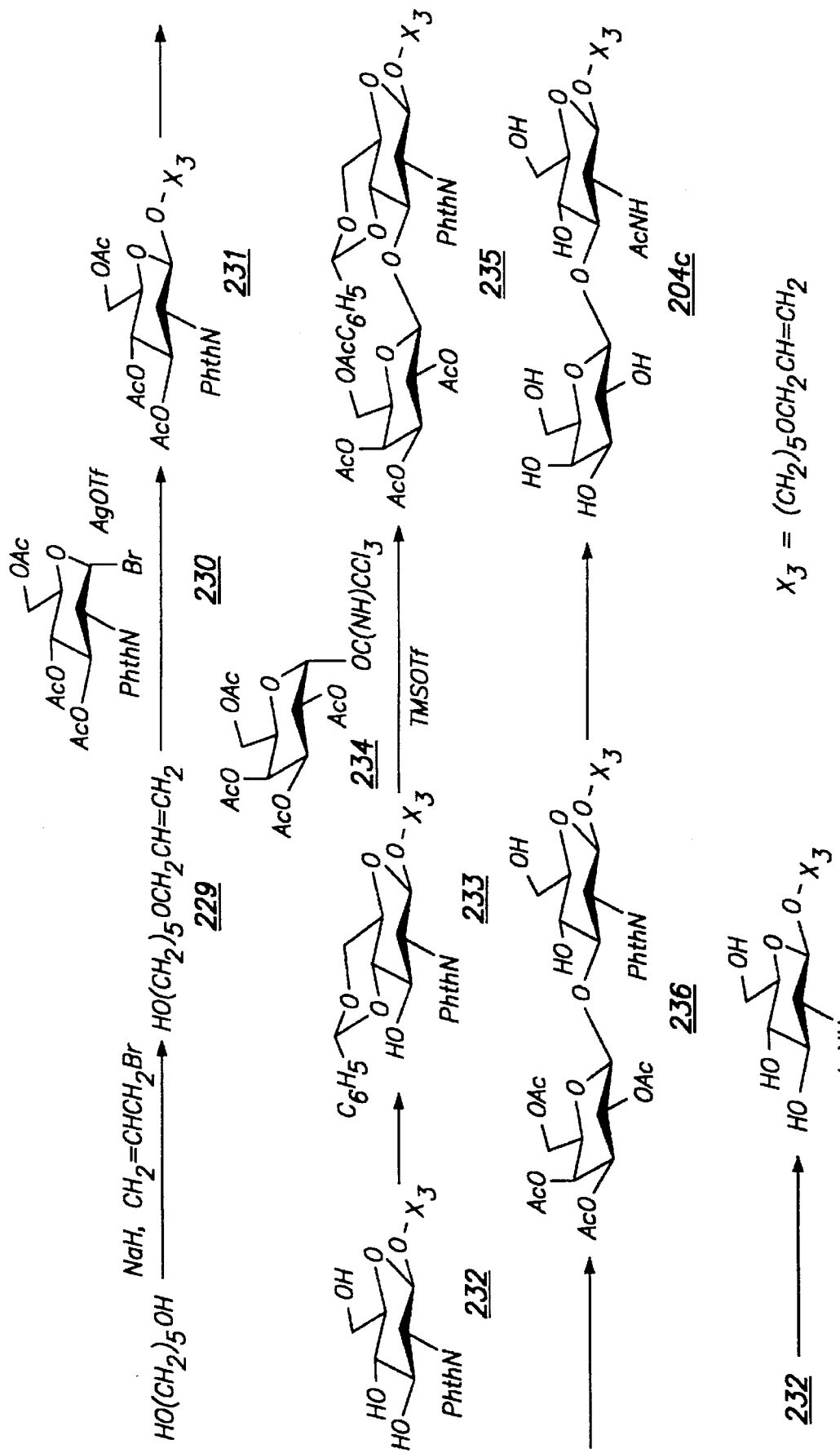

FIG. 35 illustrates a general reaction scheme for the synthesis of oligosaccharide glycoside 204c as specified in Example 38 and for the synthesis of monosaccharide glycoside 237 as specified in Example 39.

Figure 36:
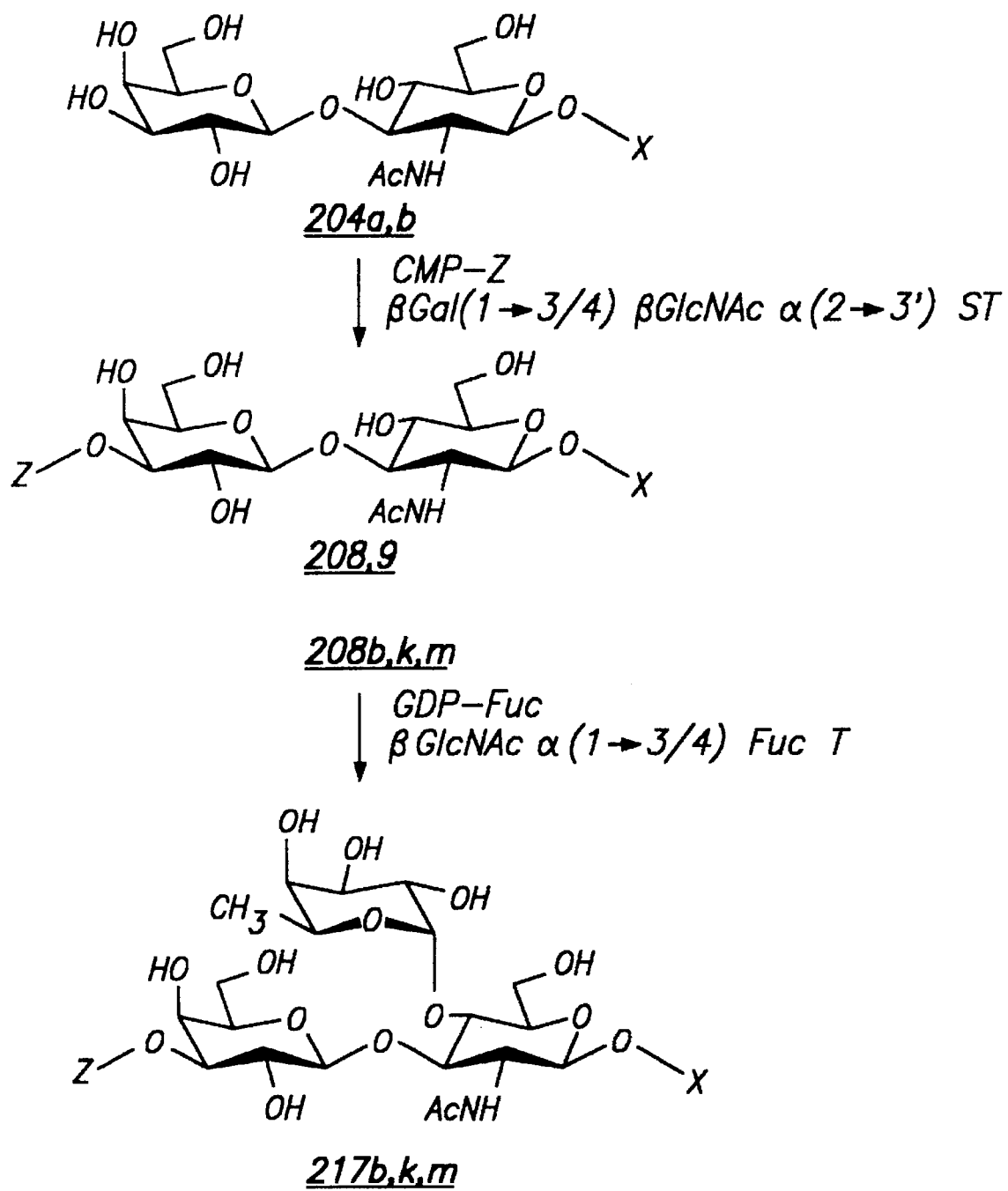

FIG. 36 illustrates the enzymatic transfer of Neu5Ac, of analogues thereof (collectively "sialic acids") by the βGal(1→3/4)βGlcNAcα(2→3')-sialyltransferase to a βGal (1→3)βGlcNAc- terminal structure. FIG. 36 also illustrates the enzymatic transfer of L-fucose onto the sialylated oligosaccharide glycosides. In FIG. 36, when the X substituent in acceptor compound 204a is X$_1$, and the sialic acid (Z) is 201a, 201b, 201c, 201d, and 201f, products 208a, 208b, 208c, 208d, and 208f are prepared respectively. When the X substituent in acceptor compound 204b is X$_2$, and the sialic acid (Z) is 201c, 201e, 201g, and 201i, products 209c, 209e, 209g, and 209i are prepared respectively. When the X substituent in acceptor compound 208b is X$_1$, and the sialic acid (Z) is 201b, product 217b is prepared. When the X substituent in acceptor compound 208k is X$_1$, and the sialic acid (Z) is 201k, product 217k is prepared. When the X substituent in acceptor compound 208m is X$_1$, and the sialic acid (Z) is 201m, product 217m is prepared. See FIGS. 42 and 41 for acceptors 208k and 208m.

Figure 37:
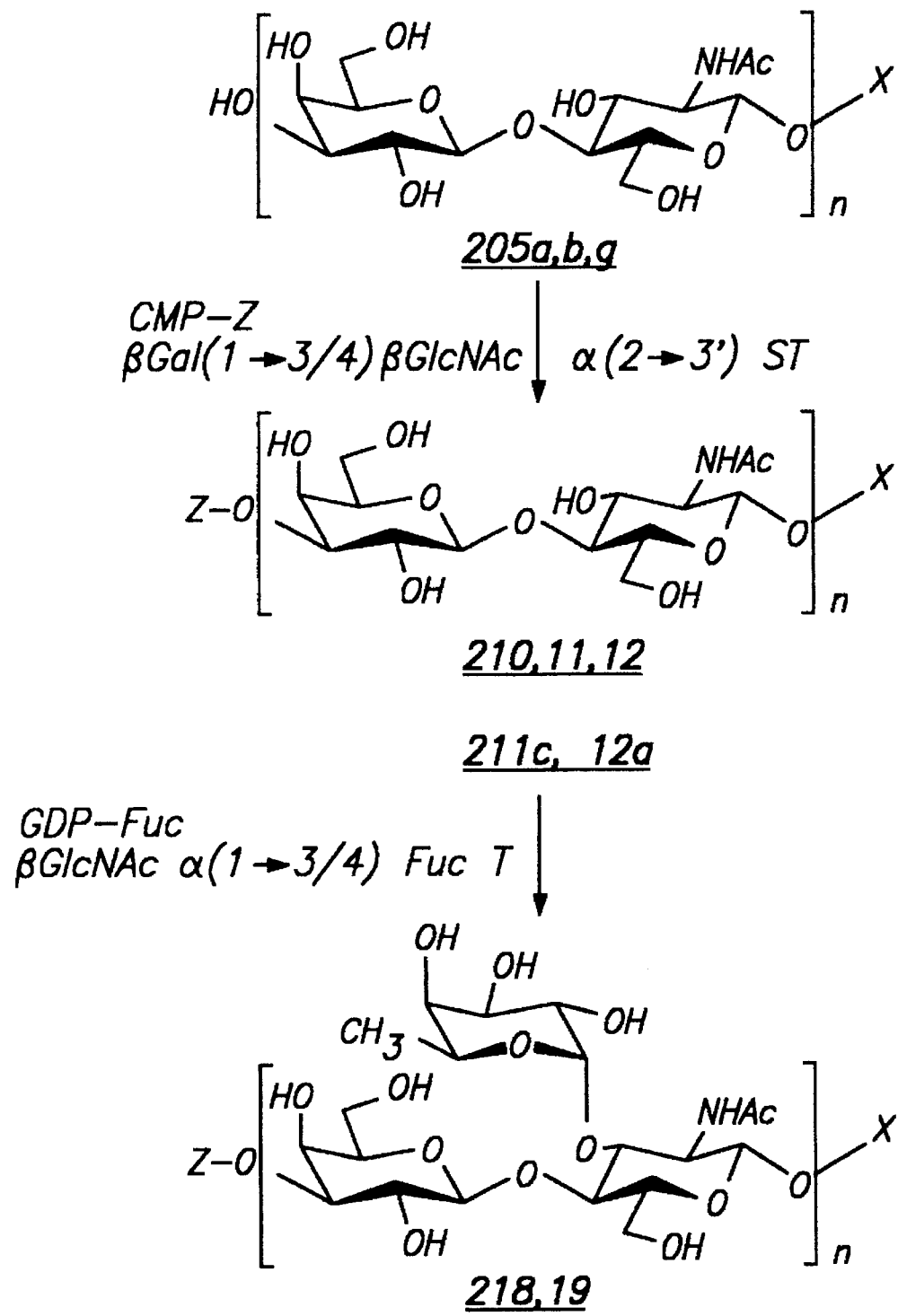

FIG. 37 illustrates the enzymatic transfer of Neu5Ac, analogues thereof (collectively "sialic acids") by the βGal (1→3/4)βGlcNAcα(2→3')sialyltransferase to a βGal(1→4) βGlcNAc- terminal structure. FIG. 37 also illustrates the enzymatic transfer of L-fucose onto the sialylated oligosaccharide glycosides. In FIG. 37, when the acceptor is compound 205a, n is 1, the X substituent is X$_1$, and the sialic acid (Z) is 201b and 201c, products 210b and 210d are prepared respectively. When the acceptor is compound 205b, n is 1, the X substituent is X$_2$, and the sialic acid (Z) is 201c, product 211c is prepared. When the acceptor is compound 205g, n is 2 and the X substituent is X$_2$, and the sialic acid (Z) is 201a, product 212a is prepared. When the acceptor is compound 211c, n is 1, the X substituent is X$_2$, and the sialic acid (Z) is 201c, product 218c is prepared. When the acceptor is compound 212a, n is 2, the X substituent is X$_2$ and the sialic acid (Z) is 201a, product 219a is prepared.

Figure 38:
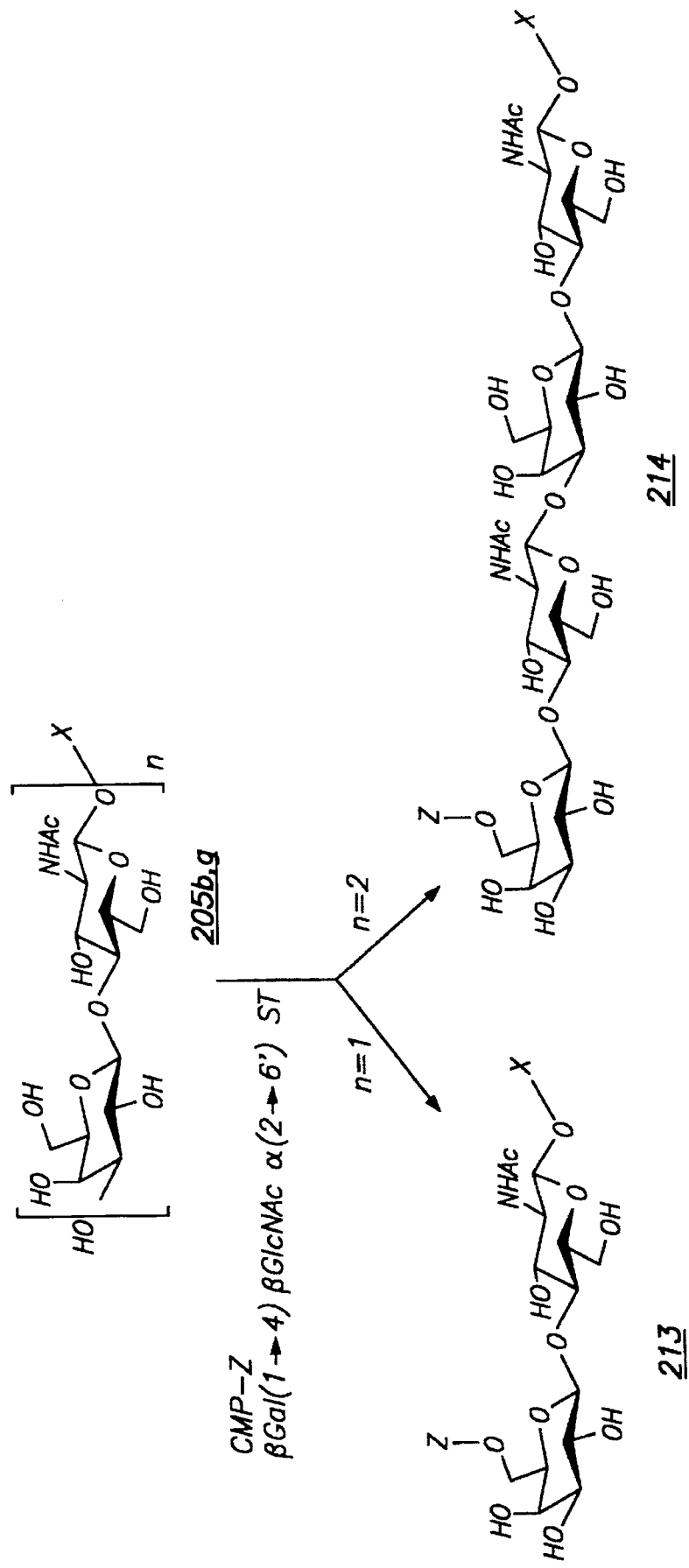

FIG. 38 illustrates the enzymatic transfer of Neu5Ac, analogues thereof by the βGal(1→4)βGlcNAcα(2→6') sialyltransferase to a βGal(1→4)βGlcNAc- terminal structure. In FIG. 38, when the acceptor is compound 205b, n is 1, the X substituent is X$_2$, and the sialic acid (Z) is 201a, 201b, 201c, 201d, 201e, 201f, 201g, and 201h, products 213a, 213b, 213c, 213d, 213e, 213f, 213g, and 213h are prepared respectively. When the acceptor is compound 205g, n is 2, the X substituent is X$_2$, and the sialic acid (Z) is 201g, product 214g is prepared.

Figure 39:
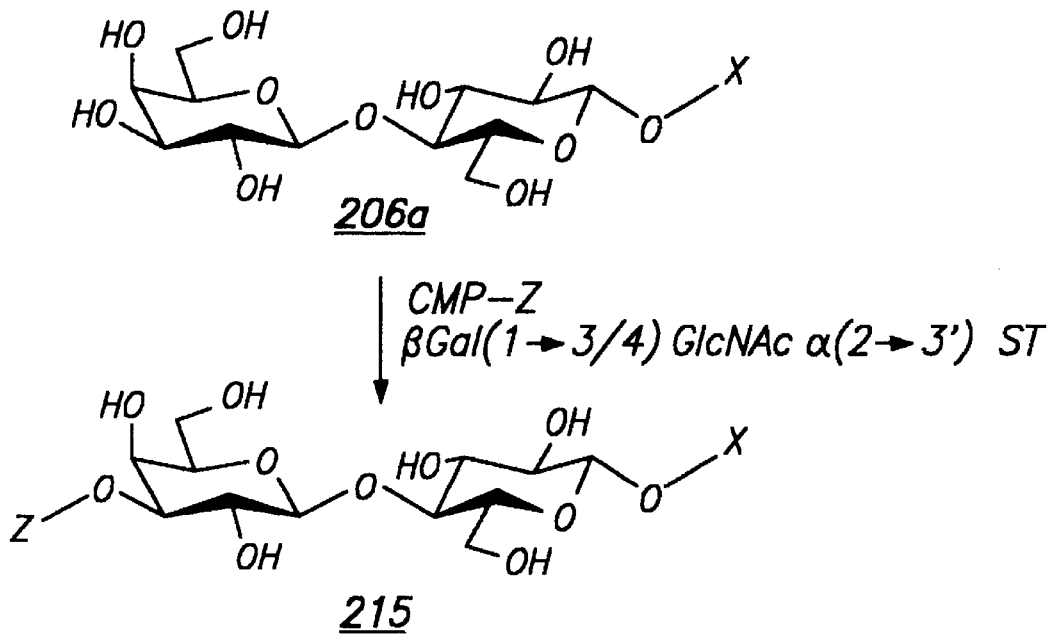

FIG. 39 illustrates the enzymatic transfer of Neu5Ac, analogues thereof by the βGal(1→3/4)βGlcNAcα(2→3')-sialyltransferase to a βGal(1→4)βGlc- (lactose) terminal structure. In FIG. 39, when the acceptor is compound 206a, the sialic acid is 201c, product 215c is prepared.

Figure 40:
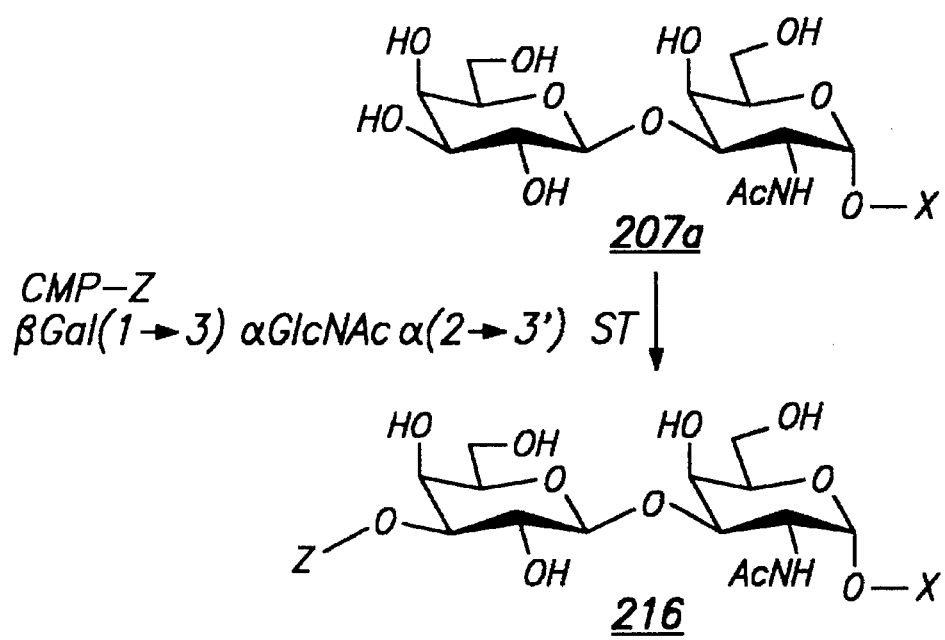

FIG. 40 illustrates the enzymatic transfer of Neu5Ac, analogues thereof by the βGal(1→3)αGalNAcα(2→3') sialyltransferase to a βGal(1→3)αGalNAc- ("T") terminal structure. In FIG. 40, when the acceptor is compound 207a, the sialic acid is 201c, product 216c is prepared.

Figure 42:
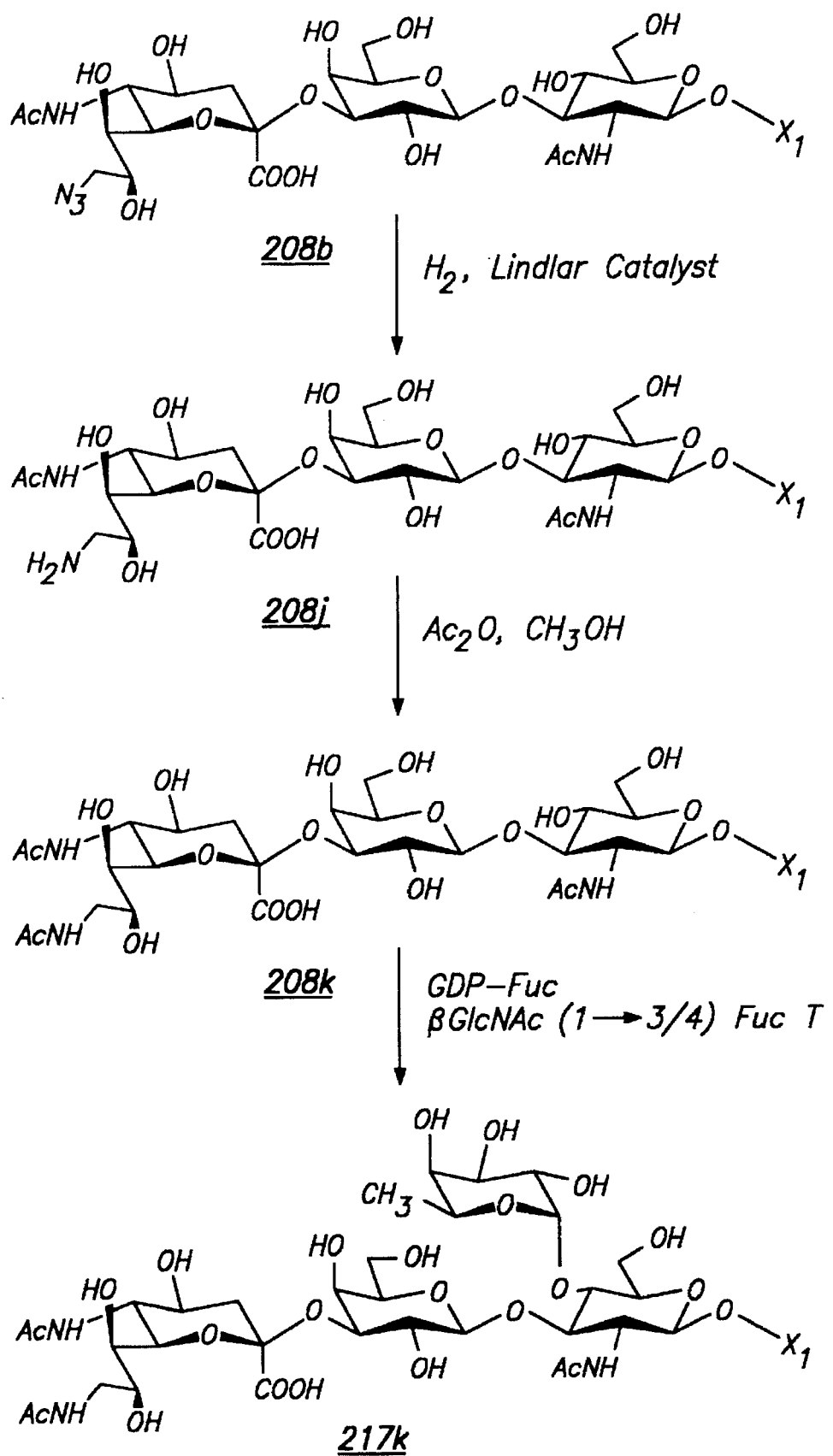

FIGS. 41 and 42 illustrate the reaction schemes involved in the synthesis of analogues of sialyl Lewis$^A$ by chemical modification of a sialylated hapten.

Figure 43:
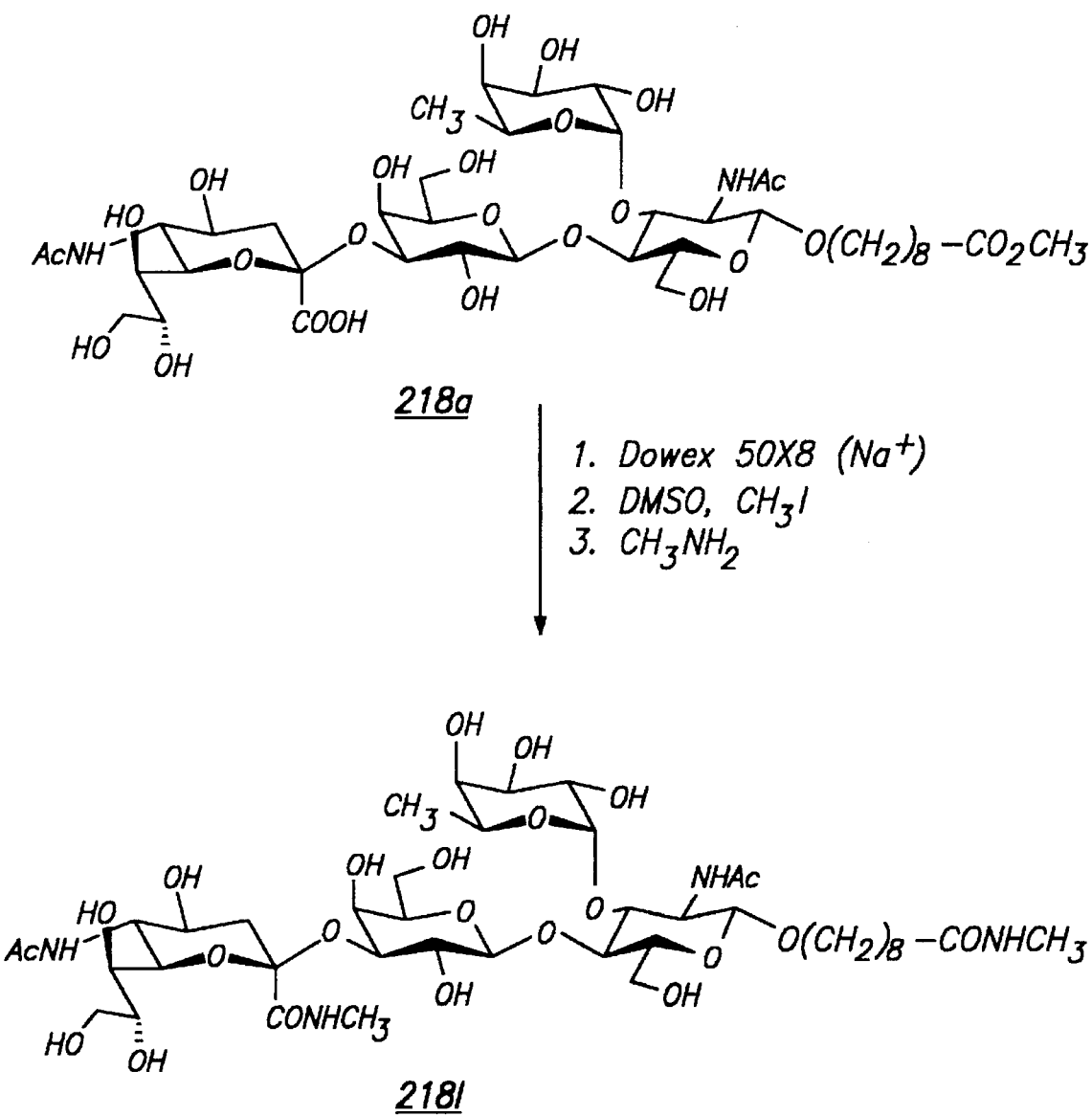

FIG. 43 illustrates the reaction schemes involved in the synthesis of analogues of sialyl Lewis$^x$ by chemical modification of a sialylated hapten.

Figure 44A:
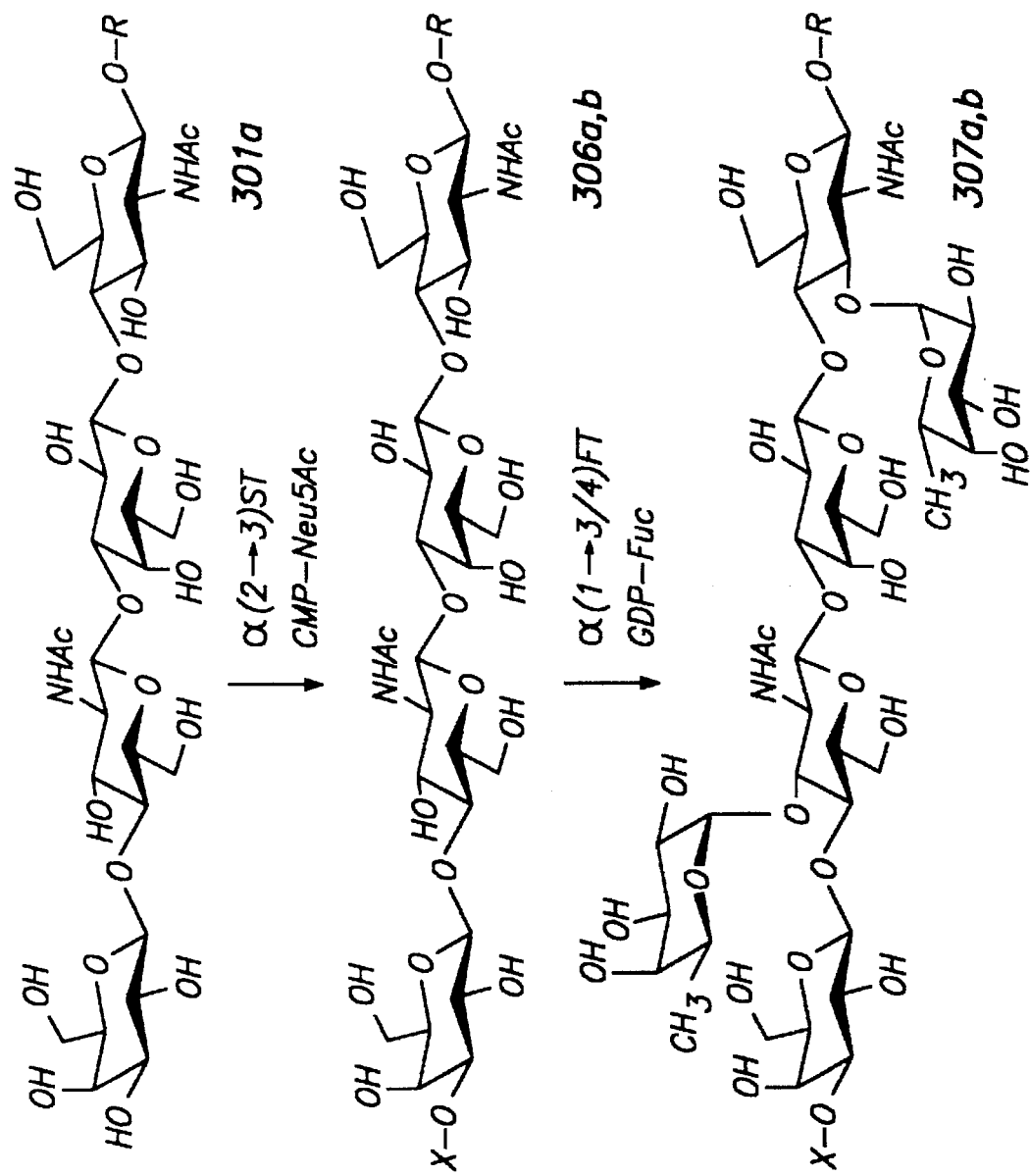
Figure 44B:
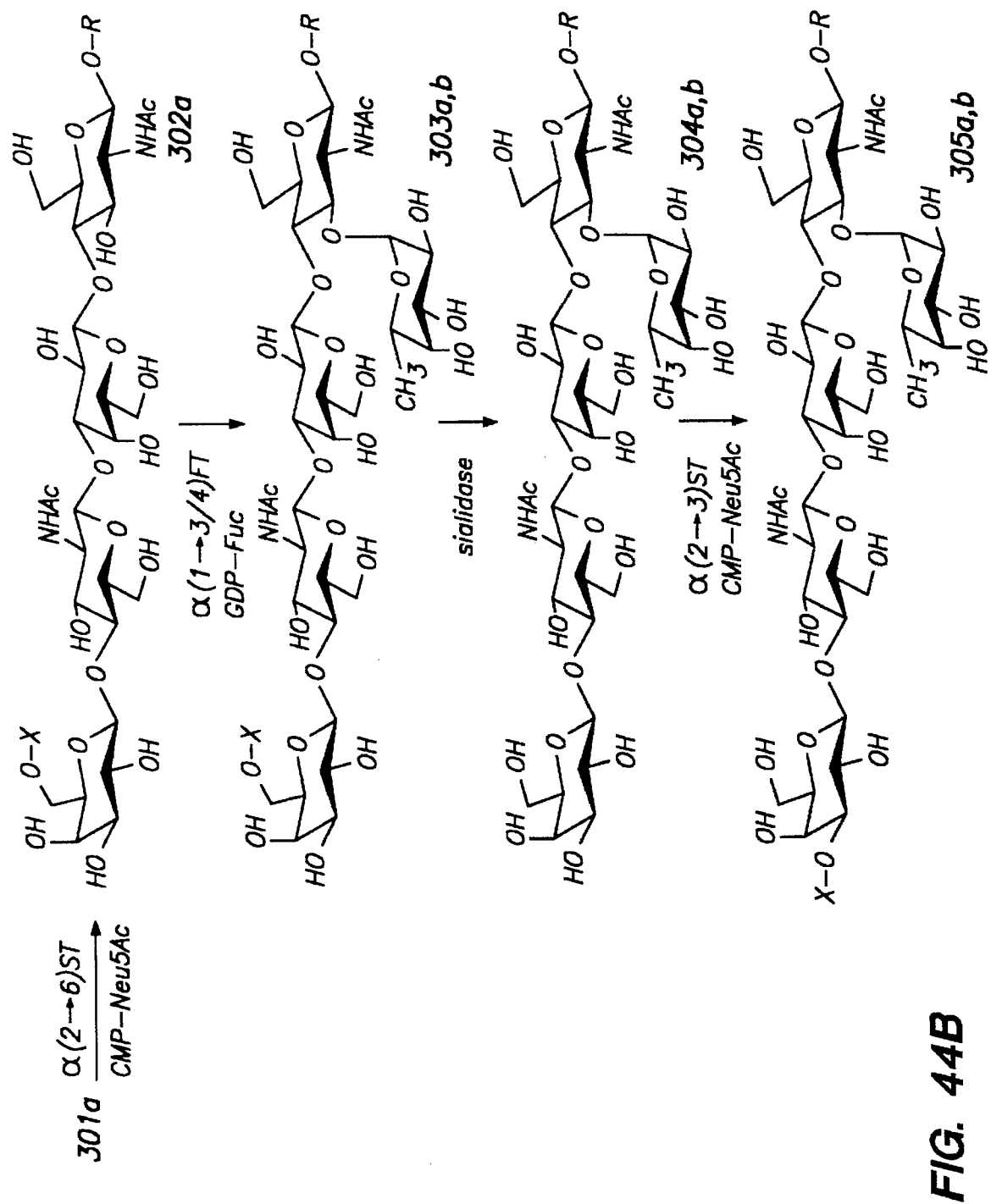

FIGS. 44A and B illustrate the synthetic pathway leading to Sialyl dimeric Lewis$^x$ and internally monofucosylated derivatives thereof. In FIGS. 44A and B, the nomenclature for compound 301a is βGal(1–4)βGlcNAc(1–3)βGal(1–4) βGlcNAc-OR, sometimes called di-N-acetyllactosaminyl tetrasaccharide. Similarly, the hexasaccharide moiety present in compounds 305a and 305b in FIGS. 44A and B is sometimes called VIM-2 epitope or CD-65[5] and 307a and 307b are called sialyl dimeric Lewis$^x$. In FIGS. 44A and B, R is (CH$_2$)$_8$CO$_2$CH$_3$ for compounds 301a, 302a, 303a, 304a, 305a, 306a and 307a; and R is (CH$_2$)$_8$CO$_2$H for compounds 303b, 304b, 305b, 306b and 307b. Also, in FIGS. 44A and 44B, X=αNeu5Ac, α(2→3)ST=rat liver α(2→3) sialyltransferase, α(2→6)ST=rat liver α(2→6) sialyltransferase, and α(1→3/4)FT=milk α(1→3/4) fucosyltransferase.

Figure 45:
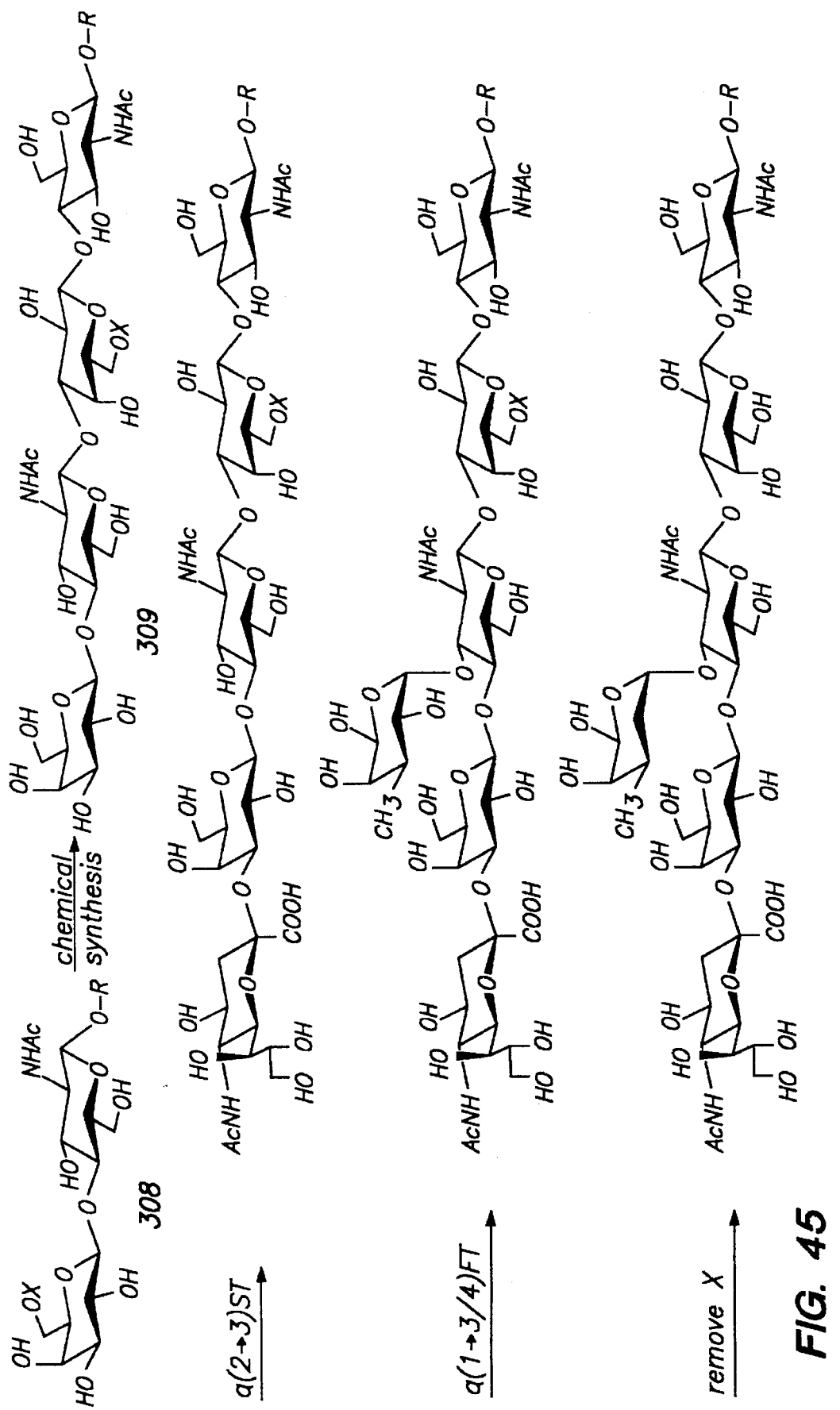

FIG. 45 illustrates the synthetic pathway leading to the externally monofucosylated derivatives of the sialyl di-N-acetyllactosaminyl hapten.

Figure 46A:
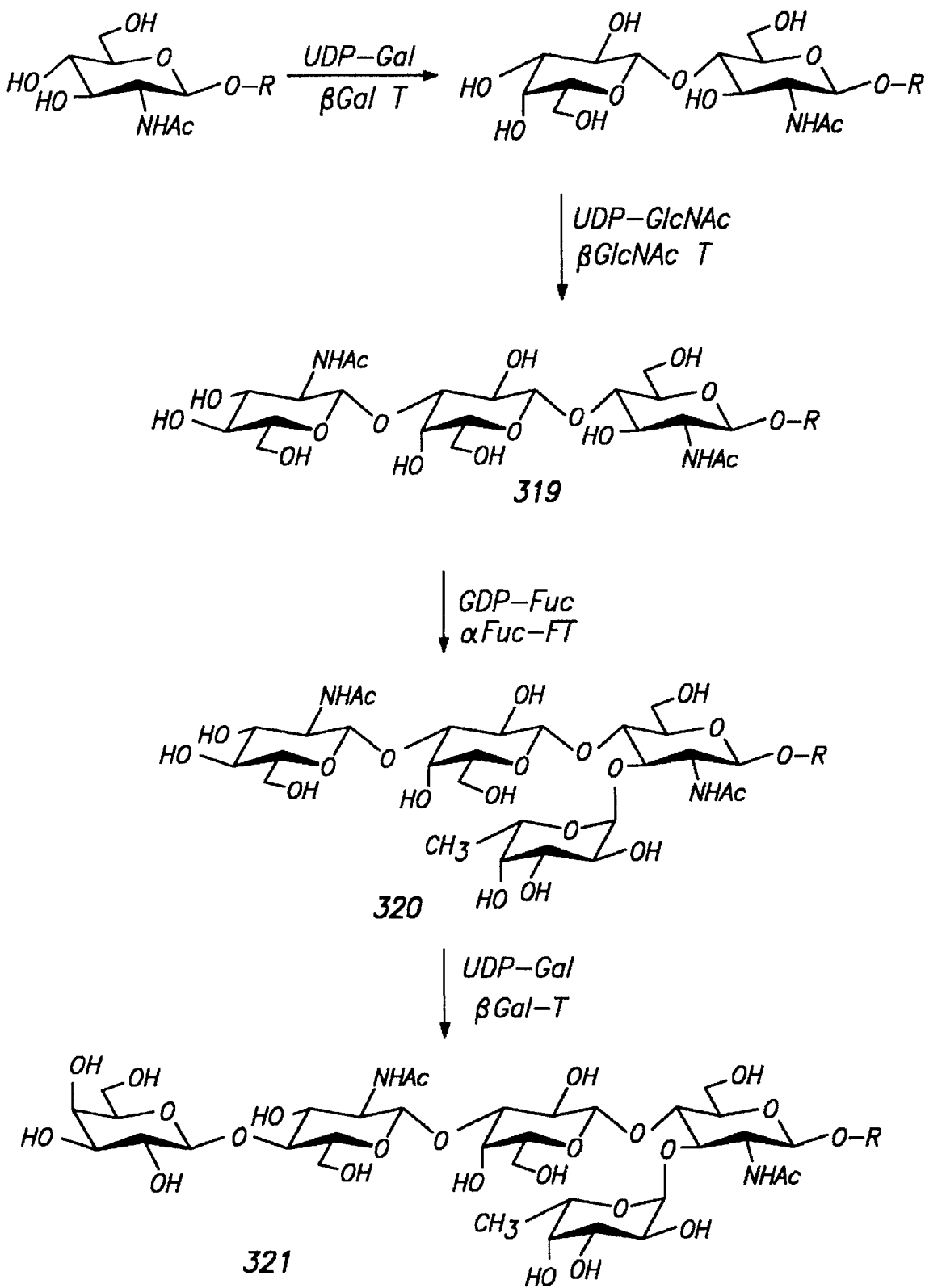

FIGS. 46A and B illustrate an enzymatic pathway leading to monofucosylated and monosialylated compounds.

Figure 47A:
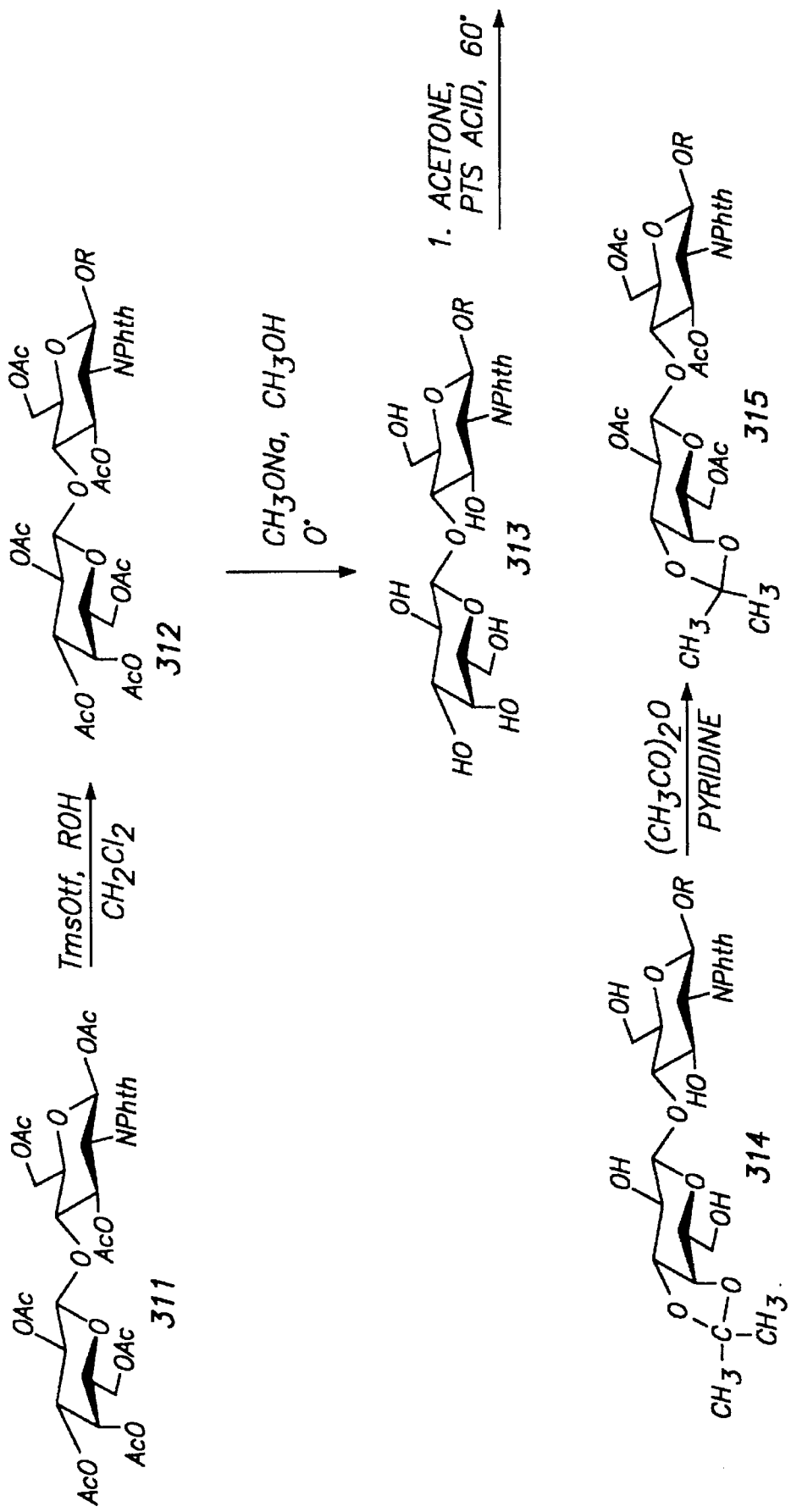
Figure 47B:
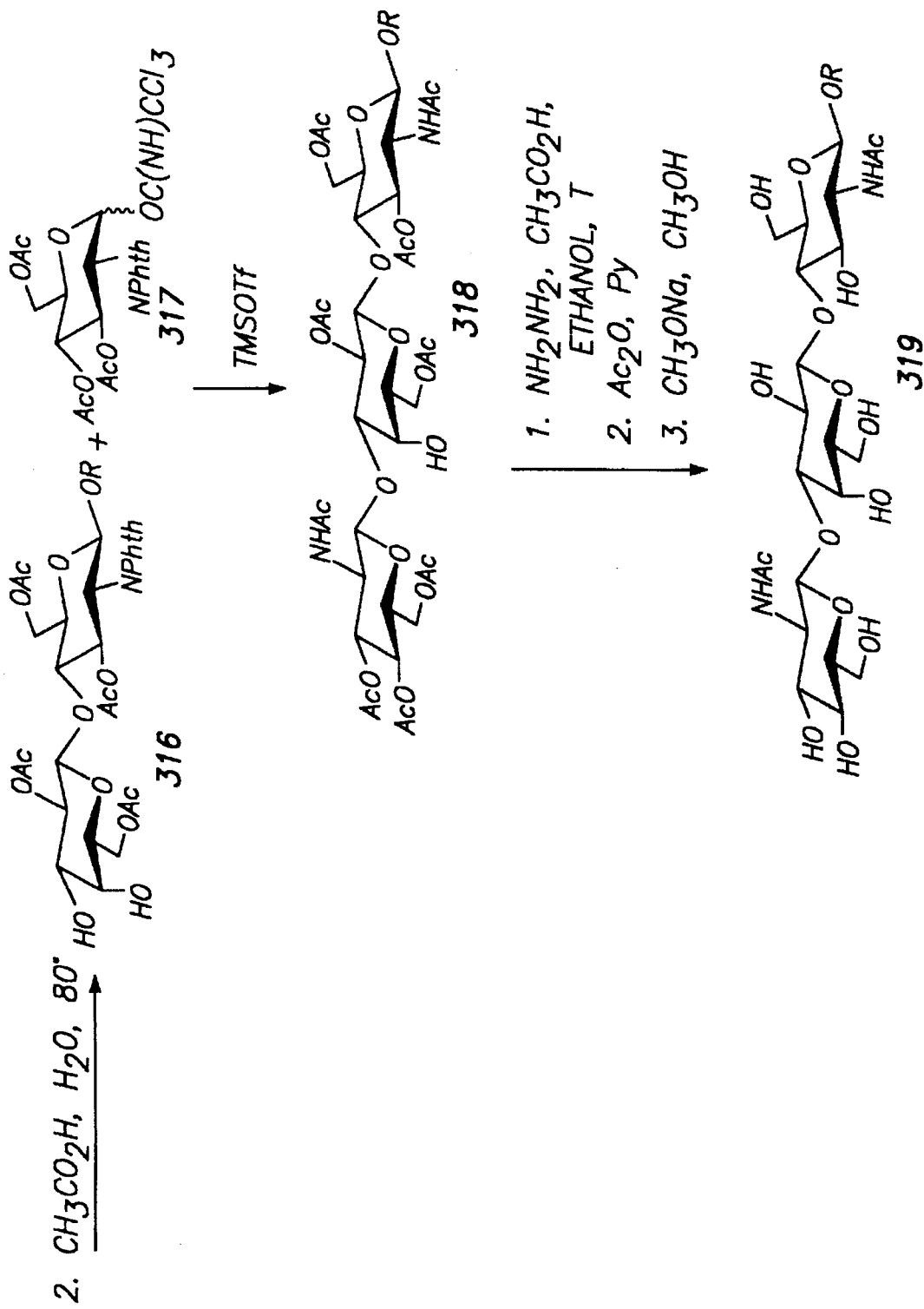

FIGS. 47A and B illustrate an alternative chemical synthesis of trisaccharide 319 which can then be used as per FIGS. 46A and B to prepare monofucosylated and monosialylated compounds.

Figure 46B:
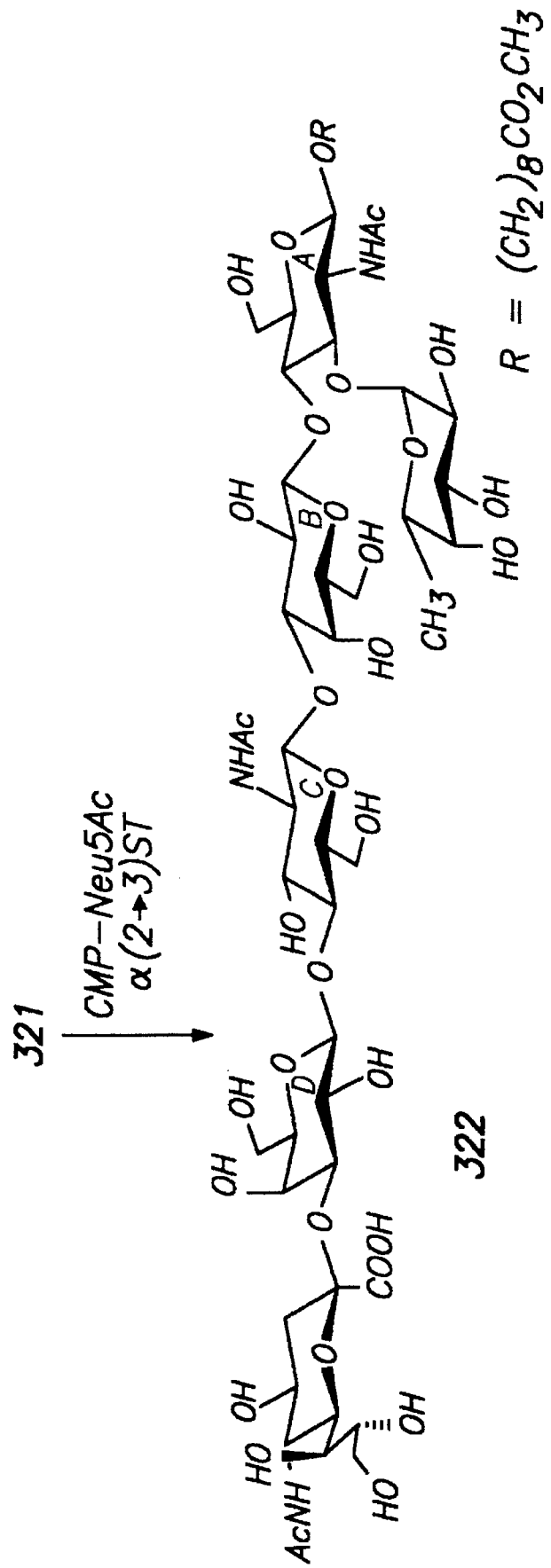
Figure 48A:
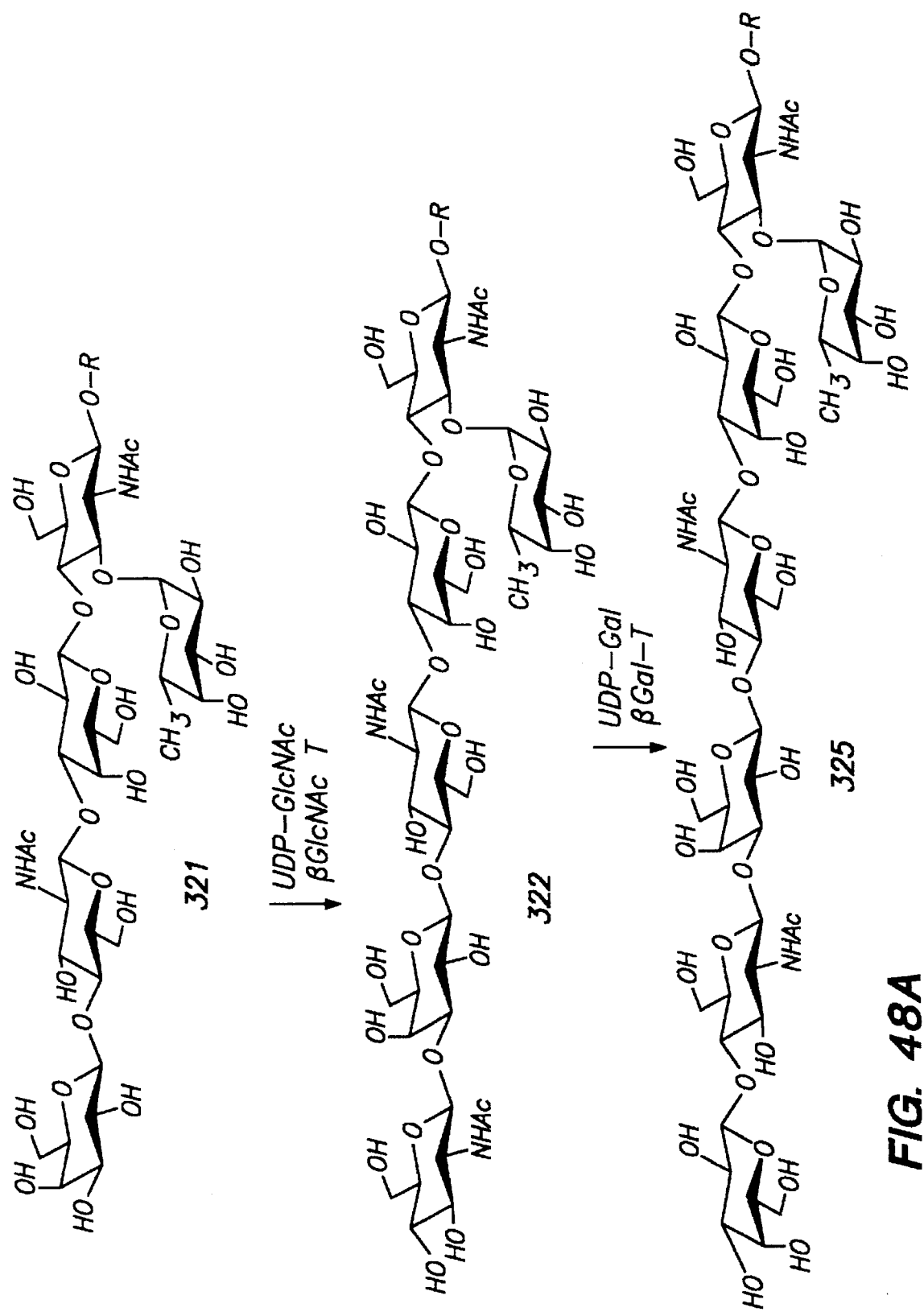
Figure 48B:
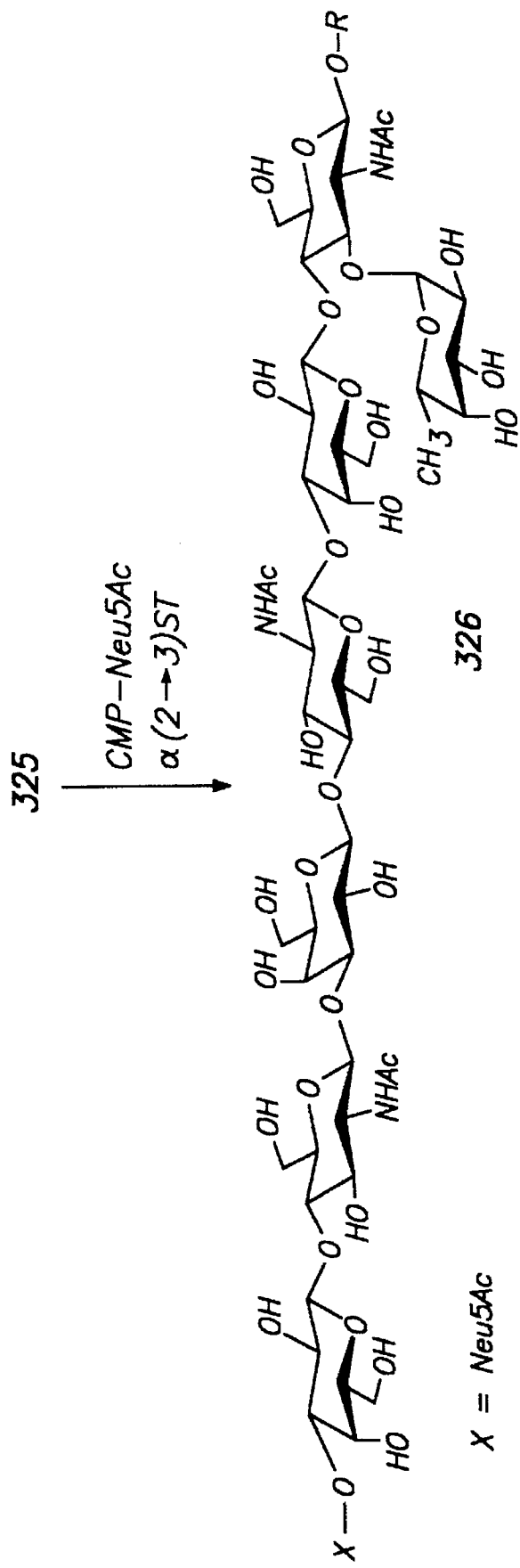

FIGS. 48A and B illustrate that the enzymatic pathway set forth in FIG. 46 can be used to extend the structure of the hexasaccharide glycosides.

DETAILED DESCRIPTION OF THE PREFERRED EMBODIMENTS

As noted above, this invention is directed to the discovery that, in order to reduce antigen induced inflammation in sensitized mammals, the oligosaccharide glycoside related to blood group determinants having a type I or a type II core structure must be administered after initiation of the mammal's secondary immune response to the antigen challenge but prior to one-half that period of time where the mammal experiences maximal inflammatory response.

However, prior to discussing this invention in further detail, the following terms will first be defined.

A. Definitions

As used herein, the following terms have the definitions given below:

The term "sensitized mammal" refers to those mammals which have been previously exposed to an antigen and, accordingly, their immune systems have become educated to that antigen. Typically, initial exposure of an antigen to a mammal primes or educates the mammal's immune response to later exposure to that antigen with minimal inflammation during such initial exposure.

The term "secondary immune response" refers to the effector phase of a mammal's immune response to an antigen to which it has been previously been sensitized. A mammal's secondary immune response is typically accompanied by inflammation at the point of antigen exposure.

The term "antigen" refers to any protein, peptide, carbohydrate, nucleic acid or other non-endogenous substance which when exposed to a mammal induces an immune response in that mammal.

Disease conditions believed to be caused by antigen exposure include, by way of example, psoriasis, asthma, dermatitis, rheumatoid arthritis, delayed type hypersensitivity, inflammatory bowel disease, multiple sclerosis, viral pneumonia, bacterial pneumonia, and the like.

The term "period for maximal inflammation" refers to the period of time typically required to achieve maximal inflammation in a sensitized mammal due to exposure to a specific antigen. This period of time depends on several factors such as the specific antigen to which the mammal has been exposed, the particular mammalian species exposed to the antigen, etc. Accordingly, the period of time required to effect maximal antigen induced inflammation in a sensitized mammal will vary for, by way of example, asthma as opposed to rheumatoid arthritis.

Moreover, while the specific time required to effect maximal inflammation will vary somewhat in a given mammalian species, the time typically required to effect maximal inflammation for different antigen exposures in human and other mammals resulting in asthma, rheumatoid arthritis, psoriasis, DTH, etc. is known in the art or are readily ascertainable by the skilled artisan. For example, in the case of a DTH response in mice, maximal inflammation is typically 24 hours after antigen exposure.

The term "blood group determinants having a type I or a type II core structure" refers to an oligosaccharide glycoside (a) having a core type I disaccharide structure of βGal(1→3)βGlcNAc or a core type II disaccharide structure of βGal(1→4)βGlcNAc or analogues thereof; (b) having from 2 to 9 saccharide units provided that if the oligosaccharide glycoside has only 2 saccharide units then the oligosaccharide glycoside has at least one substituent which carries a charge at physiological pH such as a sulfate group, a phosphate group or a carboxyl group (e.g., —CHR$_{18}$COOH) at either the 2, 3 or 6 position of the galactose unit; (c) which is terminated with a —YR group on the reducing sugar.

Oligosaccharides of the formula βGal(1→3)βGlcNAc and βGal(1→4)βGlcNAc are core structures of human type I and type II blood group determinants respectively because all type I and type II blood group determinants contain such core disaccharide structures.

Analogues of blood group determinants having the core type I or type II structures include those wherein one or both of the monosaccharide units of these disaccharide structures has been chemically modified so as to introduce and/or remove one or more functionalities. For example, such modification can result in the removal of an —OH functionality (i.e., the formation of a deoxy substituent), the introduction of: an amine functionality, a halo functionality, an azide functionality, an amide functionality, a carbamate functionality, a sulfate functionality, a phosphate functionality, a carboxyl functionality (e.g., —CHR$_{18}$COOH), and the like.

Preferred oligosaccharide glycosides related to blood group determinants having a core type I or type II structure are represented by Formula I and II:

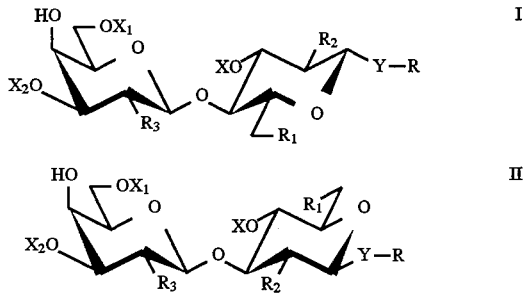

where

R is selected from the group consisting of hydrogen, a saccharide-OR$_{19}$, an oligosaccharide-OR$_{19}$ of from 2 to 7 saccharide units, and an aglycon having at least one carbon atom where R$_{19}$ is hydrogen or an aglycon of at least one carbon atom;

Y is selected from the group consisting of oxygen, sulfur, and —NH—;

R$_1$ is selected from the group consisting of hydrogen, —NH$_2$, —N$_3$, —NHSO$_3$H, —NR$_5$C(O)R$_4$, —N=C(R$_5$)$_2$, —NHCH(R$_5$)$_2$, —NHR$_6$, —N(R$_6$)$_2$, —OH, —OR$_6$, —S(O)R$_6$, —S(O)$_2$R$_6$ and sulfate, wherein R$_4$ is selected from the group consisting of
 hydrogen,
 alkyl of from 1 to 4 carbon atoms,
 —OR$_7$ wherein R$_7$ is alkyl of from 1 to 4 carbon atoms, or alkyl of from 2 to 4 carbon atoms substituted with a hydroxyl group, and —$NR_8R_9$ wherein $R_8$ and $R_9$ are independently selected from the group consisting of hydrogen and alkyl of from 1 to 4 carbon atoms, each $R_5$ is selected from the group consisting of hydrogen and alkyl of from 1 to 4 carbon atoms, each $R_6$ is alkyl of from 1 to 4 carbon atoms, $R_2$ is selected from the group consisting of hydrogen, —$N_3$, —$NH_2$, —$NHSO_3H$, —$NR_{11}C(O)R_{10}$, —N=C$(R_{11})_2$, —$NHCH(R_{11})_2$, —$NHR_{12}$, —$N(R_{12})_2$, —OH and —$OR_{12}$, wherein $R_{10}$ is selected from the group consisting of
hydrogen,
alkyl of from 1 to 4 carbon atoms,
—$OR_{13}$ wherein $R_{13}$ is alkyl of from 1 to 4 carbon atoms, or alkyl of from 2 to 4 carbon atoms substituted with a hydroxyl group, and
—$NR_{14}R_{15}$ wherein $R_{14}$ and $R_{15}$ are independently selected from the group consisting of hydrogen and alkyl of from 1 to 4 carbon atoms, each $R_{11}$ is selected from the group consisting of hydrogen and alkyl of from 1 to 4 carbon atoms;

each $R_{12}$ is alkyl of from 1 to 4 carbon atoms, $R_3$ is selected from the group consisting of hydrogen, fluoro, sulfate and hydroxy;

X is selected from the group consisting of hydrogen, L-fucosyl, 4-sulfo-L-fucosyl, and 4-phospho-L-fucosyl;

$X_1$ is selected from the group consisting of hydrogen, sialyl, sulfate, phosphate, and —$CHR_{18}COOH$ where $R_{18}$ is selected from the group consisting of hydrogen, alkyl of from 1 to 7 carbon atoms and —COOH;

$X_2$ is selected from the group consisting of hydrogen, sialyl, sulfate, phosphate, and —$CHR_{18}COOH$ where $R_{18}$ is selected from the group consisting of hydrogen, alkyl of from 1 to 7 carbon atoms and —COOH; and pharmaceutically acceptable salts thereof;

with the proviso if X is hydrogen, then either at least one of $X_1$ or $X_2$ is not hydrogen or $R_3$ is sulfate, and with the further proviso that only one of $X_1$ and $X_2$ is sialyl.

The term "aglycon of at least one carbon atom" refers to non-saccharide containing residues having at least one carbon atom. In a preferred embodiment, the aglycon moiety, R, is selected from the group consisting of -(A)-Z' wherein A represents a bond, an alkylene group of from 2 to 10 carbon atoms, and a moiety of the form —$(CH_2$—$CR_{20}G)_n$— wherein n is an integer equal to 1 to 5; $R_{20}$ is selected from the group consisting of hydrogen, methyl, or ethyl; and G is selected from the group consisting of hydrogen, halogen, oxygen, sulphur, nitrogen, phenyl and phenyl substituted with 1 to 3 substituents selected from the group consisting of amine, hydroxyl, halo, alkyl of from 1 to 4 carbon atoms and alkoxy of from 1 to 4 carbon atoms; and Z' is selected from the group consisting of hydrogen, methyl, phenyl, aminophenol, nitrophenol and, when G is not oxygen, sulphur or nitrogen and A is not a bond, then Z' is also selected from the group consisting of —OH, —SH, —$NH_2$, —$NHR_{21}$, —$N(R_{21})_2$, —C(O)OH, —$C(O)OR_{21}$, —C(O)NH—$NH_2$, —$C(O)NH_2$, —$C(O)NHR_{21}$, —$C(O)N(R_{21})_2$, and $OR_{22}$ wherein each $R_{21}$ is independently alkyl of from 1 to 4 carbon atoms and $R_{22}$ is an alkenyl group of from 3 to 10 carbon atoms.

Numerous aglycons are known in the art. For example, an aglycon comprising a para-nitrophenyl group (i.e., —YR=—$OC_6H_4pNO_2$) has been disclosed by Ekborg, et al.[15] At the appropriate time during synthesis, the nitro group can be reduced to an amino group which can be protected as N-trifluoroacetamido. The trifluoroacetamido group can later be removed thereby unmasking the amino group which can be used to further functionalize the aglycon group.

An aglycon group containing sulfur is disclosed by Dahmen, et al.[16] Specifically, this aglycon group is derived from a 2-bromoethyl group which, in a substitution reaction with thionucleophiles, has been shown to lead to aglycons possessing a variety of terminal functional groups such as —$OCH_2CH_2SCH_2SCO_2CH_3$ and —$OCH_2CH_2SC_6H_4$-$pNH_2$.

Rana, et al.[17] discloses a 6-trifluoroacetamido)hexyl aglycon (—O—$(CH_2)_6$—$NHCOCF_3$) in which the trifluoroacetamido protecting group can be removed unmasking the primary amino group which can then be used to further functionalize the aglycon.

Other exemplifications of known aglycons include the 7-methoxycarbonyl-3,6,dioxaheptyl aglycon[18] (—$OCH_2$—$CH_2)_2OCH_2CO_2CH_3$; the 2-(4-methoxycarbonylbutanecarboxamido)ethyl[19] aglycon (—$OCH_2CH_2NHC(O)(CH_2)_4CO_2CH_3$); an allyl aglycon[20] (—$OCH_2CH$=$CH_2$), which, by radical co-polymerization with an appropriate monomer, leads to co-polymers; other allyl aglycons[21] are known [e.g., —$O(CH_2CH_2O)_2CH_2CH$=$CH_2$]. Additionally, allyl aglycons can be derivatized in the presence of 2-aminoethanethiol[22] to provide for an aglycon —$OCH_2CH_2CH_2SCH_2CH_2NH_2$. Still other aglycons are illustrated hereinbelow.

Additionally, as shown by Ratcliffe et al.[37], R group can be an additional saccharide-$OR_{19}$ or an oligosaccharide-$OR_{19}$ containing an aglycon at the reducing sugar terminus.

Preferably, the aglycon moiety is a hydrophobic group and most preferably, the aglycon moiety is a hydrophobic group selected from the group consisting of —$(CH_2)_8COOCH_3$, —$(CH_2)_5OCH_2CH$=$CH_2$ and —$(CH_2)_8CH_2OH$.

Saccharide units (i.e., sugars) useful in the oligosaccharide glycosides related to blood group determinants having a type I or type II core structure include by way of example, all natural and synthetic derivatives of glucose, galactose, N-acetylglucosamine, N-acetylgalactosamine, fucose, sialic acid (as defined below), 3-deoxy-D,L-octulosonic acid and the like. In addition to being in their pyranose form, all saccharide units in the oligosaccharide glycosides related to blood group determinants are in their D form except for fucose which is in its L form.

The term "sialic acid" or "sialyl" means all naturally occurring structures of sialic acid and analogues of sialic acid which, as their CMP-derivatives, are compatible with the βGal(1→3/4)βGlcNAc α(2→3)sialyltransferase and/or the βGal(1→4)βGlcNAc α(2→6)sialyltransferase. In this regard, any sialic acid which, as its CMP-derivative, is recognized by either of these sialyltransferases so as to bind to the enzyme and is then available for transfer to an oligosaccharide glycoside having a type I or type II structure is said to be compatible with these sialyltransferases.

Naturally occurring structures of sialic acid include, by way of example, 5-acetamido-3,5-dideoxy-D-glycero-D-galacto-nonulopyranosylonic acid ("Neu5Ac"), N-glycoyl neuraminic acid (Neu5Gc) and 9-O-acetyl neuraminic acid (Neu5,9Ac$_2$). A complete list of naturally occurring sialic acids known to date are provided by Schauer[64].

Analogues of sialic acid refers to analogues of naturally occurring structures of sialic acid including those wherein the sialic acid unit has been chemically modified so as to introduce and/or remove one or more functionalities from such structures. For example, such modification can result in the removal of an —OH functionality, the introduction of an amine functionality, the introduction of a halo functionality, and the like.

Certain analogues of sialic acid are known in the art and include, by way of example, 9-azido-Neu5Ac, 9-amino-Neu5Ac, 9-deoxy-Neu5Ac, 9-fluoro-Neu5Ac, 9-bromo-Neu5Ac, 7-deoxy-Neu5Ac, 7-epi-Neu5Ac, 7,8-bis-epi-Neu5Ac, 4-O-methyl-Neu5Ac, 4-N-acetyl-Neu5Ac, 4,7-dideoxy-Neu5Ac, 4-oxo-Neu5Ac, as well as the 6-thio analogues of Neu5Ac. The nomenclature employed herein in describing analogues of sialic acid is as set forth by Reuter et al.[24]

CMP-nucleotide derivative of sialic acid refers to the cytidine-5-monophosphate derivative of a naturally occurring sialic acid or an analogue thereof. In the case where the sialic acid is Neu5Ac, the CMP derivative has the formula:

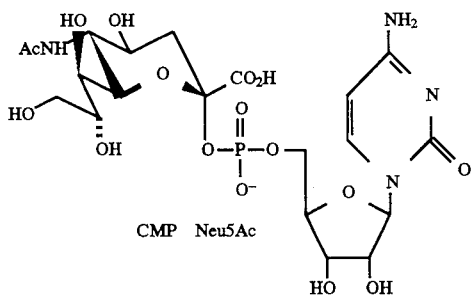

The term "fucose" or "fucosyl" refers to L-fucose and analogues thereof which, as their GDP-derivatives, are compatible with βGal(1→3/4)βGlcNAc α(1→3/4) fucosyltransferase. As noted below, this fucosyltransferase is readily isolated from human milk. Additionally, it is contemplated that these fucose or fucosyl compounds will be compatible with other fucosyltransferases of appropriate specificity such as cloned fucosyltransferases[65,66].

In regard to the above, any fucose compound which, as its GDP-derivative, is recognized by the βGal(1→3/4) βGlcNAc α(1→3/4)fucosyltransferase so as to bind to the enzyme and is then available for transfer to a compound of Formula I and Formula II above (X=H) is said to be compatible with this fucosyltransferase.

Analogues of fucose refer to naturally occurring and synthetic analogues of fucose including those where the fucose unit has been chemically modified so as to introduce and/or remove one or more functionalities from this structure. For example, such modification can result in the removal of an —OH functionality, the introduction of an amine functionality, the introduction of a halo functionality, and the like.

Certain compatible analogues of fucose are known in the art and include, by way of example, 3-deoxyfucose, arabinose, and the like.[67]

The GDP-derivative of fucose refers to guanosine 5'-(β-L-fucopyranosyl)diphosphate and any and all compatible salts thereof which has the formula:

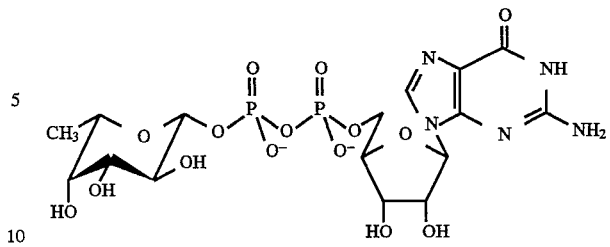

Methods for preparing GDP-fucose are known in the art. However, GDP-fucose is preferably prepared by the method described by Jiang et al.[42] in U.S. patent application Ser. No. 07/848,223 which is incorporated herein by reference in its entirety.

The term "amino acid or polypeptidyl residue" refers to product obtained by reacting an appropriate form of an amino acid or a polypeptide with an oligosaccharide glycoside related to blood group determinants having a type I or type II core structure and which has an amine functionality (—NH$_2$) at the 2 or 6 positions of the GlcNAc unit under conditions where the amine reacts with a carboxyl group or activated carboxyl group on the amino acid or polypeptide to form an amide bond. The particular amino acid or polypeptide employed is not critical. However, in a preferred embodiment, the polypeptide contains from about 2 to about 5 amino acids and preferably from about 2 to 3 amino acids.

The term "pharmaceutically acceptable salts" includes the pharmaceutically acceptable addition salts of oligosaccharide glycosides related to blood group determinants having a type I or type II core structure capable of forming salts and are derived from a variety of organic and inorganic counter salts well known in the art and include, by way of example only, sodium, potassium, calcium, magnesium, ammonium, tetralkylammonium, and the like.

The term "removable blocking group" or "blocking group" refers to any group which when bound to one or more hydroxyl groups of the galactose, N-acetylglucosamine, the sialic acid (including the hydroxyl group of the carboxylic acid moiety), the fucose, etc., units of oligosaccharide glycosides related to blood group determinants having a type I or type II core structure prevents reactions from occurring at these hydroxyl groups and which protecting group can be removed by conventional chemical or enzymatic steps to reestablish the hydroxyl group. The particular removable blocking group employed is not critical and preferred removable hydroxyl blocking groups include conventional substituents such as benzyl, acetyl, chloroacetyl, benzylidene, t-butyldiphenylsilyl and any other group that can be introduced either enzymatically or chemically onto a hydroxyl functionality and later selectively removed either by enzymatic or chemical methods in mild conditions compatible with the nature of the product. One such additional contemplated blocking group is a α-galactose which can be removed enzymatically with an α-galactosidase.

The term "sulfate" such as used to define the substituents —X, —X$_1$, and —X$_2$ refers to substituents which, with the oxygen of a hydroxyl group of the galactose unit and/or fucose group, form a sulfate group (i.e., —O—S(O)$_2$—OH). Thus, when X, X$_1$ or X$_2$ is a sulfate, the resulting —OX, —OX$_1$ and/or —OX$_2$ group is —O—S(O)$_2$—OH, which readily forms pharmaceutically acceptable salts thereof (e.g., —O—S(O)$_2$—O$^-$Na$^+$). Contrarily, the term "sulfate" as it is used for R$_3$ refers to the —O—S(O)$_2$—OH group, which also readily forms pharmaceutically acceptable salts thereof (e.g., —O—S(O)$_2$—O$^-$Na$^+$).

The term "phosphate" such as used to define the substituents —X, —X$_1$, and —X$_2$ refers to substituents which, with the oxygen of a hydroxyl group of the galactose unit and/or fucose group, form a phosphate group (i.e., —O—P(O)—(OH)$_2$). Thus, when X, X$_1$ or X$_2$ is a phosphate, the resulting —OX, —OX$_1$ and/or —OX$_2$ group is —O—P(O)—(OH)$_2$, which readily forms pharmaceutically acceptable salts thereof (e.g., —O—P(O)—(O$^-$Na$^+$)$_2$).

B. Methodology

As shown below in the examples, oligosaccharide glycosides related to blood group determinants having a type I or type II core structure are effective in reducing the degree of antigen induced inflammation in a sensitized mammal provided that such oligosaccharide glycosides are administered after initiation of the mammal's secondary immune response and at or prior to one-half the period required for maximal inflammation induced by the antigen exposure. The data in Examples A–L substantiate the criticality of when these oligosaccharide glycosides are administered and demonstrate that if the oligosaccharide glycoside related to blood group determinants having a type I or type II core structure are administered before initiation of the mammal's secondary immune response, no reduction in inflammation is achieved. Likewise, these examples also demonstrate that if the oligosaccharide glycoside related to blood group determinants having a type I or type II core structure are administered after one-half the period of time required for the mammal to effect maximal inflammation, then minimal reduction in inflammation is achieved.

Additionally, Examples A–L demonstrate that oligosaccharide glycosides related to blood group determinants having a type I or type II core structure can induce tolerance to still later exposure to the antigen when administered during the critical period after exposure of the immune system to the antigen.

In view of the above, the oligosaccharide glycosides related to blood group determinants having a type I or type II core structure are preferably administered to the patient at least about 0.5 hours after exposure to an antigen; more preferably, from at least about 1 to 10 hours after exposure to the antigen and still more preferably from at least about 1 to 5 hours after antigen exposure.

Oligosaccharide glycosides related to blood group determinants are effective in reducing antigen induced inflammation in a sensitized mammal when administered at a dosage range of from about 0.5 mg to about 50 mg/kg of body weight, and preferably from about 0.5 to about 5 mg/kg of body weight. The specific dose employed is regulated by the particular antigen induced inflammation being treated as well as by the judgment of the attending clinician depending upon factors such as the severity of the inflammation, the age and general condition of the patient, and the like. The pharmaceutical compositions described herein can be administered in a single dose or in multiple doses or in a continuous infusion over the critical time frame up to one-half the period required for maximal inflammation.

Oligosaccharide glycosides related to blood group determinants having a type I or type II core structure are preferably administered parenterally, intranasally, intrapulmonarily, transdermally and intravenously, although other forms of administration are contemplated.

In addition to providing suppression of antigen induced inflammation in a sensitized mammal, administration of oligosaccharide glycosides related to blood group determinants having a type I or a type II core structure also imparts tolerance to still later challenges from the same antigen. In this regard, rechallenge by the same antigen weeks after administration of such oligosaccharide glycosides results in a significantly reduced immune response.

The methods of this invention are preferably achieved by use of a pharmaceutical composition suitable for use in the parenteral administration of an effective amount of an oligosaccharide glycoside related to blood group determinants having a type I or type II core structure. These compositions comprise a pharmaceutically inert carrier such as water, buffered saline, etc. and an effective amount of an oligosaccharide glycoside related to blood group determinants having a type I or a type II core structure (or mixtures thereof) so as to provide the above-noted dosage of the oligosaccharide glycoside when administered to a patient. It is contemplated that suitable pharmaceutical compositions can additionally contain optional components such as a preservative, etc.

It is further contemplated that other suitable pharmaceutical compositions can include oral compositions, transdermal compositions or bandages etc., which are well known in the art.

It is still further contemplated that the oligosaccharide glycoside related to a blood group determinant having a type I or a type II core structure can be incorporated as a part of a liposome or a micelle which can then be formulated into a pharmaceutical composition.

C. Preparation of Oligosaccharide Glycosides

The oligosaccharide glycosides related to blood group determinants having a core type I or type II structure are readily prepared by complete chemical syntheses, by chemical/enzymatic syntheses wherein glycosyltransferases are employed to effect the sequential addition of one or more of sugar units onto a GlcNAc-OR saccharide structure, a Lewis$^C$-OR disaccharide structure, a LacNAc-OR disaccharide structure, or onto derivatives of such structures and chemical syntheses are employed to effect modifications on one or more of the saccharide structures, or by complete enzymatic synthesis starting with the GlcNAc-OR saccharide glycoside.

Specifically, enzymatic means to prepare oligosaccharide glycosides related to blood group determinant having a type I or type II core structure can be used at different steps. For example, L-fucose can be enzymatically transferred onto Lewis$^C$, lactose, N-acetyllactosamine (LacNAc), sialylated Lewis$^C$, sialylated lactose, sialylated N-acetyllactosamine, suitable derivatives thereof, and the like, by an appropriate fucosyltransferase such as the βGal(1→3/4)βGlcNAc α(→3/4)fucosyltransferase which is readily obtained from human milk[25,26,27].

The LacNAc-OR disaccharide can be made enzymatically from an N-acetyl glucosamine glycoside (βGlcNAc-OR) and the known bovine milk β-galactose(1→4)transferase. The Lewis$^C$ glycoside (i.e., βGal(1→3)βGlcNAc-OR) can be made chemically.

Additionally, it is contemplated that sulfotransferases may be used to effect sulfation at the 3-position of galactose on either the type I or type II structures. As is apparent and if desired, sulfotransferation can be followed by transfer of fucose using an appropriate fucosyltransferase as described above.

Alternatively, chemical and enzymatic means can be coupled wherein, for example, the sulfated, phosphorylated, or —CHR$_{18}$COOH substituted LacNAc-OR structure or sulfated, phosphorylated, or —CHR$_{18}$COOH substituted βGal(1→3)βGlcNAc-OR structure is made chemically and the fucosyl group, if desired, can be transferred enzymatically.

Chemical synthesis is a convenient method for preparing either the complete oligosaccharide glycoside; for chemically modifying a saccharide unit which can then be chemically or enzymatically coupled to an oligosaccharide glycoside; or for chemically preparing an oligosaccharide glycoside to which can be enzymatically coupled one or more saccharide units.

Several chemical syntheses of blocked intermediates exist[28,29,30]. These intermediates are suitable for the preparation of oligosaccharide glycosides related to blood group determinants having a type I or a type II core structure using methods known in the art.

Chemical modifications include introduction of the sulphate or phosphate group or a —OCHR$_{18}$COOH at the 3 and/or 6 position of the terminal galactose, introduction of modification at the 2- and 6- positions of N-acetylglucosamine, introduction of functionality at the 2-position of the galactose and the like as well as modifications of sialic acid and/or fucose. Methods for the preparation of such oligosaccharide glycosides related to blood group determinants is set forth in Venot et al.,[9]; Kashem, et al.,[10]; Venot, et al.,[11]; Ratcliffe, et al.,[12] Ippolito, et al.[13], and Venot, et al.[14], each of which is incorporated herein by reference in their entirety.

Examples 1 to 53 hereinbelow and FIGS. 17 to 48 attached hereto elaborate on a variety of synthetic schemes which result in the preparation of oligosaccharide glycosides related to blood group determinants having a type I or type II core structure. Well known modifications of these procedures will lead to other such oligosaccharide glycosides.

In the description below as well as in the examples and figures, reference is made to the —OR group at the reducing sugar. However, it is understood that this group could also be —NHR or —SR the preparation of which is well known in the art.

C1. CHEMICAL AND CHEMICAL/ENZYMATIC SYNTHESIS OF SACCHARIDE MONOMERS

Chemical methods for the synthesis of oligosaccharide glycosides related to blood group determinants containing a type I or type II core structure are known in the art. These materials are generally assembled using suitably protected individual monosaccharides including glucosamine, fucose and galactose, and suitably protected individual disaccharides such as lactose-OR, N-acetyllactosamine-OR or βGal(1→3)βGlcNAc-OR intermediates.

The specific methods employed are generally adapted and optimized for each individual structure to be synthesized. In general, the chemical synthesis of all or part of the oligosaccharide glycosides related to blood group determinants having a type I or a type II core structure first involves formation of a glycosidic linkage on the anomeric carbon atom of the reducing sugar. Specifically, an appropriately protected form of a naturally occurring or of a chemically modified saccharide structure (the glycosyl donor) is selectively modified at the anomeric center of the reducing unit so as to introduce a leaving group comprising halides, trichloroacetimidate, acetyl, thioglycoside, etc. The donor is then reacted under catalytic conditions well known in the art with an aglycon or an appropriate form of a carbohydrate acceptor which possess one free hydroxyl group at the position where the glycosidic linkage is to be established. A large variety of aglycon moieties are known in the art and can be attached with the proper configuration to the anomeric center of the reducing unit. Appropriate use of compatible blocking groups, well known in the art of carbohydrate synthesis, will allow selective modification of the synthesized structures or the further attachment of additional sugar units or sugar blocks to the acceptor structures.

After formation of the glycosidic linkage, the saccharide glycoside can be used to effect coupling of additional saccharide unit(s) or chemically modified at selected positions or, after conventional deprotection, used in an enzymatic synthesis. In general, chemical coupling of a naturally occurring or chemically modified saccharide unit to the saccharide glycoside is accomplished by employing established chemistry well documented in the literature. See, for example, Okamoto et al.[31], Abbas et al.[32], Paulsen[33], Schmidt[34], Fugedi et al.[35], Kameyama et al.[36] and Ratcliffe, et al.[37]

Similarly, the use of enzymatic methods for the preparation of oligosaccharide glycosides is also documented[25,94].

Figure 17A:
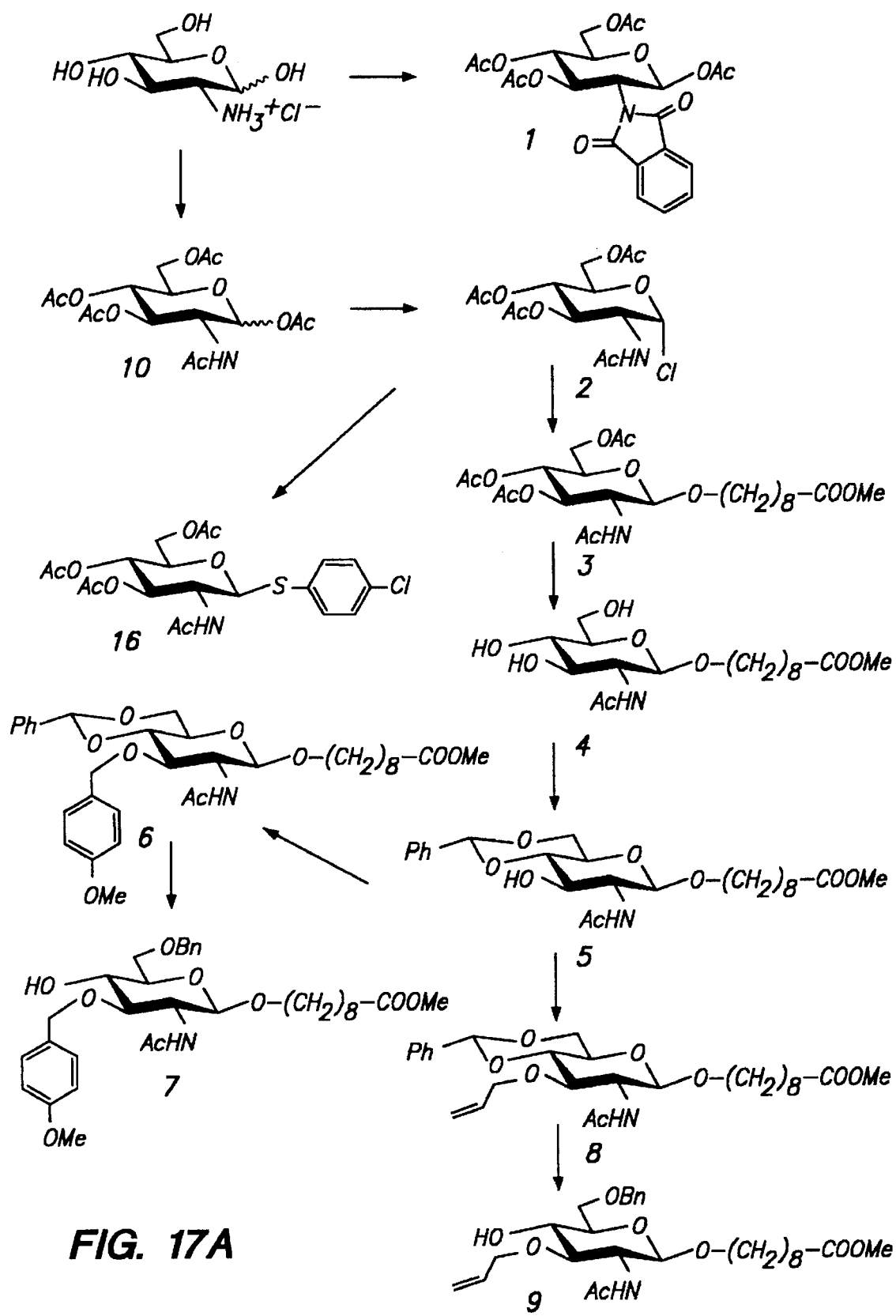
FIGS. 17A and 17B illustrate reaction schemes for the synthesis of partially blocked N-acetylglucosamine derivatives which are then used to prepare oligosaccharide glycosides related to blood group determinants having a type I or type II core structure.
Figure 17B:
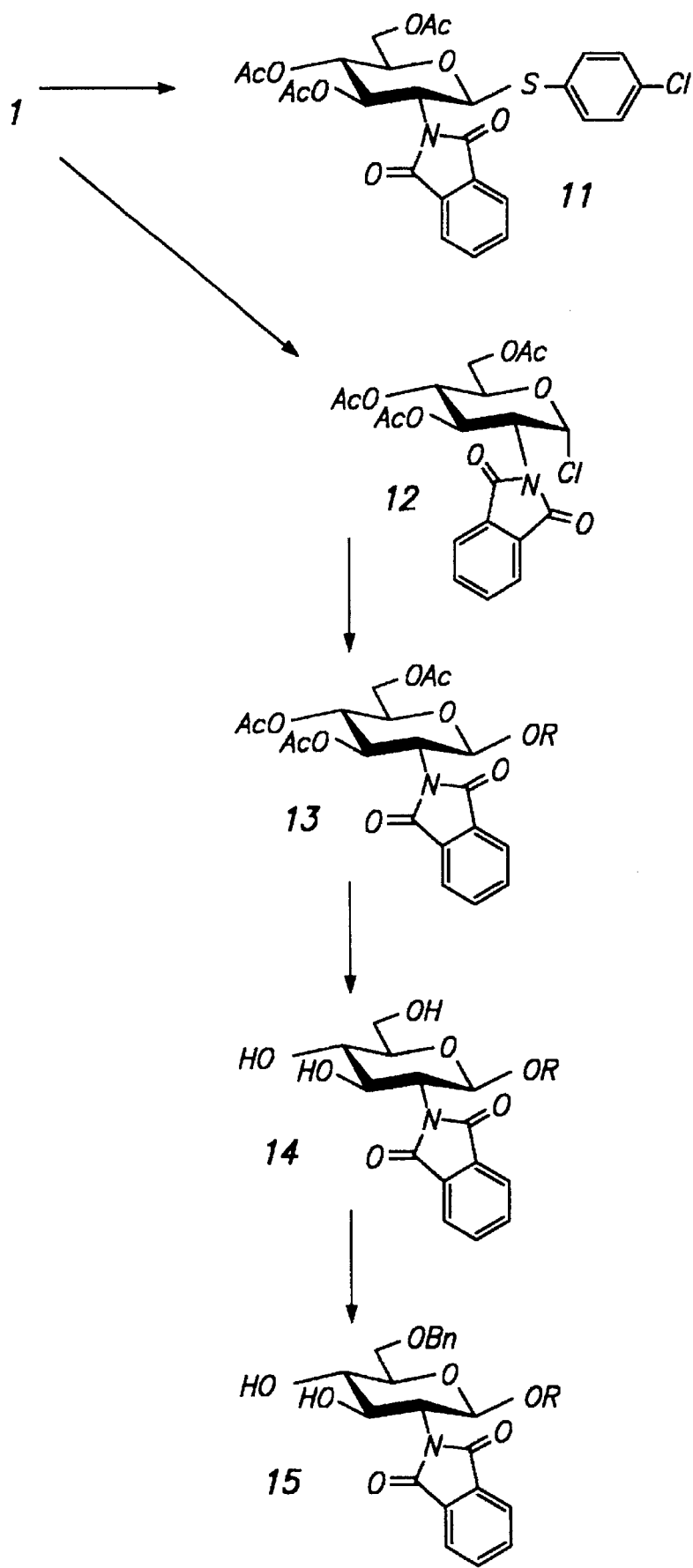

C1(i)—Preparation of Oligosaccharide Glycosides related to Blood Group Determinants having a type I or a type II core structure with sulfate, phosphate or carboxyl substitution on the galactose unit FIGS. 17A and 17B illustrate the synthesis of numerous blocked derivatives of glucosamine and N-acetylglucosamine which are useful in the preparation of blocked LacNH$_2$—OR, LacNAc-OR, βGal(1→3)βGlcNAc-OR, βGal(1→3)βGlcNH$_2$—OR, etc. structures which, in turn, can be used to prepare oligosaccharide glycosides related to blood group determinants having a type I or type II core structure particularly those containing sulfate, phosphate or carboxyl substitution on the galactose unit.

Specifically, in FIG. 17A, glucosamine hydrochloride is slurried in dichloroethane containing an equivalent of anhydrous sodium acetate to which acetic anhydride is added dropwise and, after addition is completed, the solution is refluxed for a period of from about 12–16 hours to provide for the peracylated compound 10 (about 3:1 ratio of α/β).

Alternatively, the glucosamine hydrochloride is first taken up in methanol and then treated with 1 equivalent of metallic sodium to neutralize the HCl. Phthalic anhydride is then added quickly to the reaction mixture followed shortly thereafter by triethylamine to provide for the phthalimido derivative. This compound is then isolated and acetylated with acetic anhydride/pyridine using conventional techniques to provide for peracylated compound 1 having a phthalimide blocking group protecting the amine.

Afterwards, the aglycon is formed by conventional techniques. For example, compound 10 is converted to 1-α-chloro compound 2 by well known chemistry which involves bubbling saturating amounts of hydrogen chloride directly into a dichloroethane solution of compound 10. In this regard, the solution used to prepare compound 10 can be used in this reaction after that solution has been quenched into water to remove acetic anhydride and sodium acetate, dried and recovered. The reaction generally proceeds over a period of about 4–6 days and hydrogen chloride is bubbled into the solution periodically (e.g., about once every 1–2 days). After reaction completion, the solution is quenched in aqueous sodium bicarbonate at about 0°–5° C. and the product is recovered after drying the organic layer and stripping the solution to provide for compound 2 (one spot on t.l.c.)

Compound 2 is then converted to the 1-β-(CH$_2$)$_8$COOCH$_3$ aglycon by well known chemistry which involves reaction of compound 2 with HO(CH$_2$)$_8$COOCH$_3$ in anhydrous dichloromethane containing molecular sieves in the presence of an equivalent amount of mercuric cyanide. The reaction is generally conducted at room temperature for a period of about 12 to 24 hours. Upon reaction completion (as evidenced by t.l.c.), the reaction solution is filter through silica and the resulting solution is quenched by adding the reaction solution to cold water. The organic layer is recovered and the washed twice with an aqueous potassium iodide (5 weight/vol percent) solution and then with a saturated aqueous sodium bicarbonate solution. The resulting organic solution is then dried and the solvent removed by stripping to provide for compound 3.

The 3, 4, and 6 hydroxyl groups of compound 3 are then deprotected by reaction with sodium methoxide in methanol to provide for N-acetylglucosamine-OR, compound 4. This compound can reacted with $C_6H_5CH(OCH_3)_2$ in, for example, an acidic medium in an appropriate solvent at around 40°–50° C. for about 4–6 hours to provide for the 4,6-O-diprotected benzylidene compound 5. In turn, compound 5 can be reacted with p-methoxybenzyl trichloroacetimidate in an appropriate solvent (e.g., DMF, dichloromethane) in the presence of a catalytic amount of an acid (e.g., p-toluenesulfonic acid—pTSA) to provide for the p-methoxybenzyl protected 3-hydroxy compound 6. Treatment of compound 6 with sodium cyanoborohydride in tetrahydrofuran followed by the dropwise addition of HCl saturated ether at about 0° C. leads to compound 7.

Alternatively, compound 5 can be blocked at the 3-hydroxyl group by reaction with, for example, allyl bromide and base (e.g., barium hydroxide/barium oxide) to provide for compound 8. Treatment of compound 8 with sodium cyanoborohydride in tetrahydrofuran followed by the dropwise addition of HCl saturated ether at about 0° C. leads to compound 9.

Because compounds 7 and 9 contain only a free hydroxyl group at the 4-position of the blocked GlcNAc-OR saccharide, subsequent reaction with an appropriately blocked galactose will result in formation of a blocked type II LacNAc-OR structure [βGal(1→4)βGlcNAc-OR].

Because compound 5 contains a free hydroxyl group only at the 3-position of the blocked GlcNAc-OR saccharide, subsequent reaction with an appropriately blocked galactose will result in formation of a blocked type I structure [βGal(1→3)βGlcNAc-OR].

Alternatively, compound 1 can be converted to compound 11 by reaction of compound 1 with an equivalent of p-chlorothiophenol in dichloromethane at room temperature in the presence of 2 equivalents of boron trifluoride etherate ($BF_3$.etherate) to provide for compound 11.

In yet another embodiment, compound 1 is converted to compound 12 (or the bromo analogue) by following similar procedures set forth above for compound 2.

Compound 12 is converted to compound 13 by reaction with an alcohol (e.g., ethanol—R=$CH_2CH_3$) in a manner similar to that of compound 3 with the exception that the alcohol replaces $HO(CH_2)_8COOCH_3$. Compound 13 is then converted to compound 14 with sodium methoxide/methanol and is then converted to compound 15 by reaction with bis[tributyltin] oxide in refluxing toluene containing tetraethylammonium bromide followed by reaction with benzyl bromide.

Because compound 15 contains free hydroxyl groups at the 3- and 4-positions of the blocked GlcNAc-OR saccharide, subsequent reaction with an appropriately blocked galactose will result in formation of both a type I structure [βGal(1→3)βGlcNAc-OR] and a type II structure [βGal(1-4)βGlcNAc-OR] which are readily separated by conventional techniques including chromatography.

Compound 16 is prepared by treating p-chlorothiophenol with 0.95 equivalents of potassium hydroxide in ethanol followed by heating the solution to about 40°–50° C. and then adding about 0.5 equivalents of compound 2 to the reaction solution. The reaction is maintained at 40°–50° C. for about 1–2 hours and the product 16 precipitates upon cooling the solution and is recovered by filtration.

Figure 18:
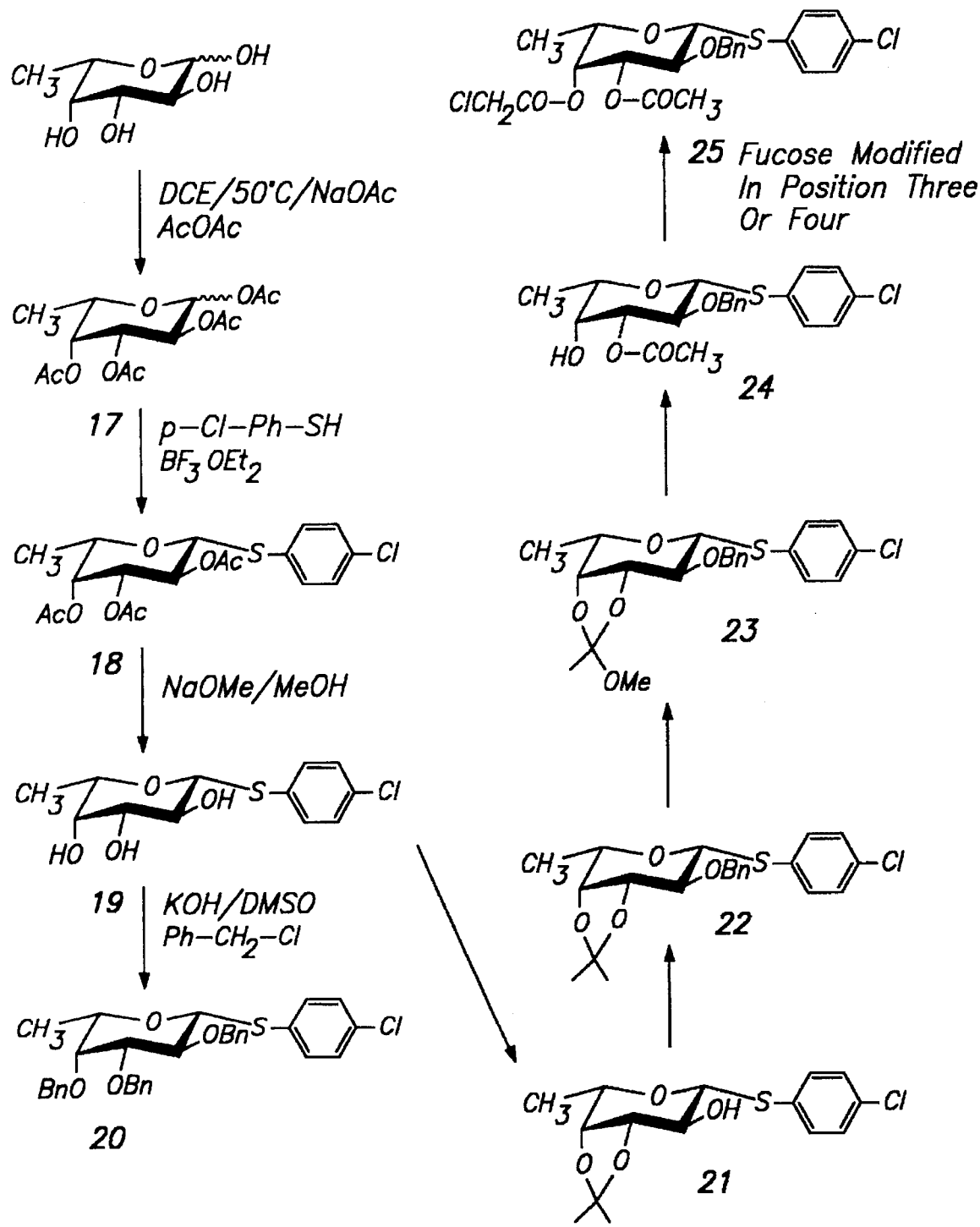
FIG. 18 illustrates reaction schemes for the synthesis of blocked fucose derivatives which are then used to prepare oligosaccharide glycosides related to blood group determinants having a type I or type II core structure.

In FIG. 18, the synthesis of compounds 17–20 are set forth in the examples hereinbelow. The process to produce the highly crystalline fucose intermediate 20 from L-fucose as shown in FIG. 18 is novel. This procedure optimizes the production of β-fucopyranose tetraacetate 17 by adding acetic anhydride (AcOAc) dropwise to a slurry of fucose and about equimolar amounts (e.g., about 1.1 equivalents) of sodium acetate (NaOAc) maintained at about 50°–55° C. in dichloroethane (DCE) and stirred at this temperature for a sufficient period of time to result in formation of compound 17 (e.g., for about 2–3 days). The reaction mixture is treated with water, quenched into ice water, extracted with additional dichloromethane and dried and partially concentrated to provide the peracylated compound 17 (about 4:1 β/α ratio of 1-acetate).

Compound 17 is then reacted with an approximately equivalent amount of p-chlorothiophenol (p-Cl-Ph-SH) and approximately 1 to 3 (preferably 2) equivalents of boron trifluoride etherate ($BF_3.OEt_2$) in a suitable solvent (e.g., dichloromethane) to provide for the p-chlorophenyl 2,3,4-tri-O-acetyl-β-thiofucopyranoside, compound 18. The reaction conditions employed are not critical and temperatures of from about 0° to about 25° C. (preferably at room temperature) and reaction times of about 3 to about 16 hours can be used.

Compound 18 is quickly deacetylated under Zemplen conditions (NaOMe, MeOH) to yield p-chlorophenyl β-thiofucopyranoside 19 as a crystalline product in 55–65% overall yield from fucose after recrystallization from an appropriate solvent (e.g., isobutanol). Again, the reaction conditions employed are not critical and temperatures of from about 15° to about 30° C. and reaction times of about 1 to about 10 hours can be used.

Compound 19 is, in turn, readily benzylated with benzyl chloride or benzyl bromide to yield p-chlorophenyl 2,3,4-tri-O-benzyl-β-thiofucopyranoside, compound 20, in 45–50% overall yield from fucose. As before, the reaction conditions employed are not critical and temperatures of from about 15° to about 30° C. and reaction times of about 24 to about 48 hours can be used. In general, at least 3 equivalents of benzyl chloride or bromide are employed and the reaction is generally conducted in the presence of at least about 4–5 equivalents of a suitable base (e.g., potassium hydroxide—KOH) in a suitable inert solvent (e.g., dimethoxysulfoxide—DMSO).

In a preferred embodiment, about 3 equivalent of base are added to the reaction system prior to addition of about 3 equivalents benzyl chloride or benzyl bromide. After about 18 hours, an additional 1.5 equivalents of base and an additional equivalent of benzyl chloride are added.

The simple reagents, easy processing and highly crystalline products eliminate the chromatography that frequently has been required using heretofore described methodology.

The synthesis of compounds 21–24 are conducted by following known techniques, for example those described by Matta et al.[38] In the procedure of Matta et al., compound 23 can be converted to either a 3-acetyl (compound 24) or the 4-acetyl blocking group (not shown). In turn, both of these compounds are then blocked at the remaining hydroxyl group with a chloroacetyl blocking group by acetylation with chloroacetylchloride in pyridine/dichloromethane at about 0° C. This results in compounds which have differentially protected 3,4-hydroxy groups. The chloroacetyl blocking group in either compound can be selectively removed at the appropriate point in the synthesis by treatment with thiourea in pyridine/ethanol (6:1) and then reacted to form the sulfate or phosphate in the manner described below.

Figure 19A:
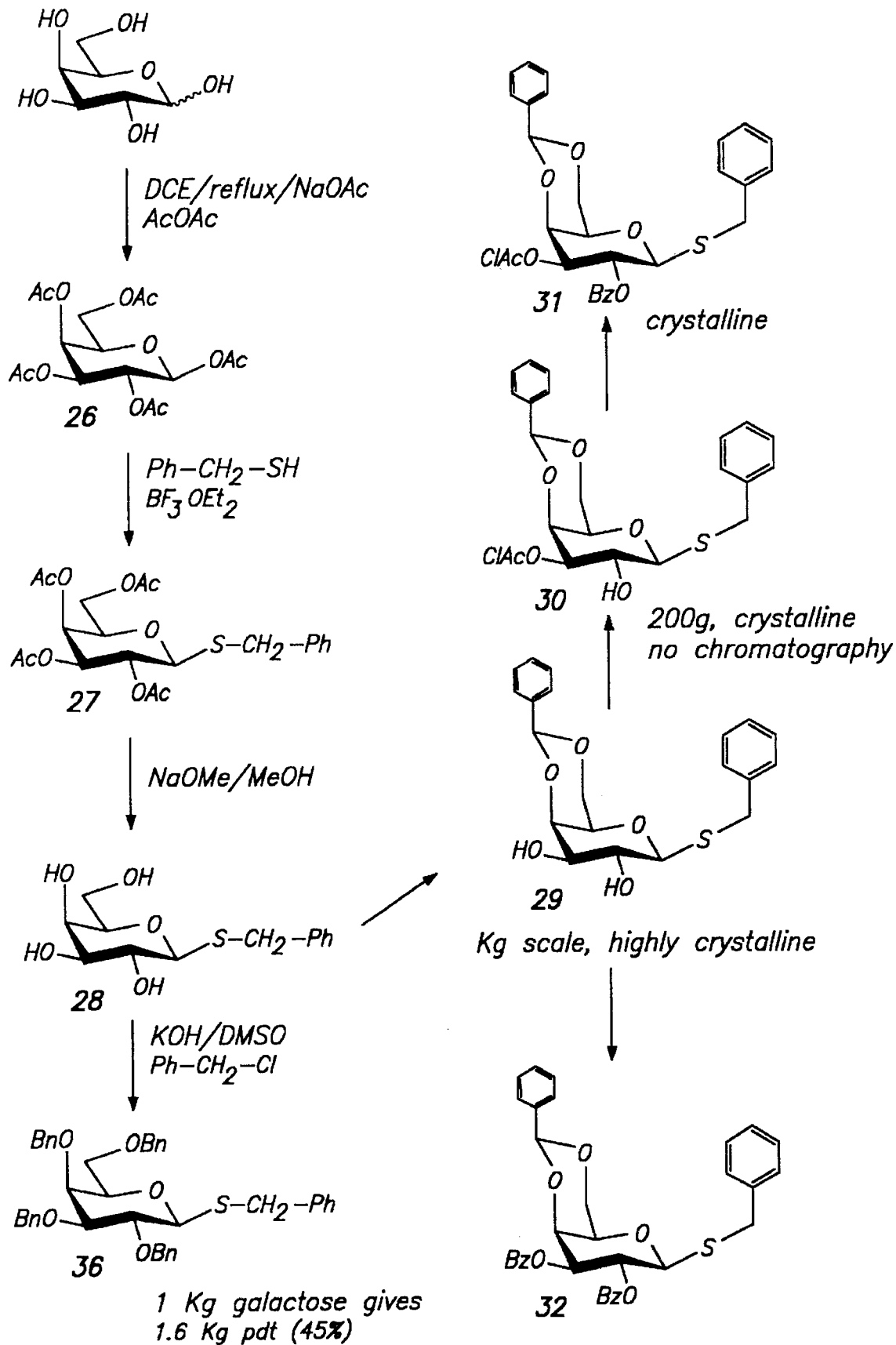
FIGS. 19A and 19B illustrate reaction schemes for the synthesis of partially blocked galactose derivatives which are then used to prepare oligosaccharide glycosides related to blood group determinants having a type I or type II core structure.
Figure 19B:
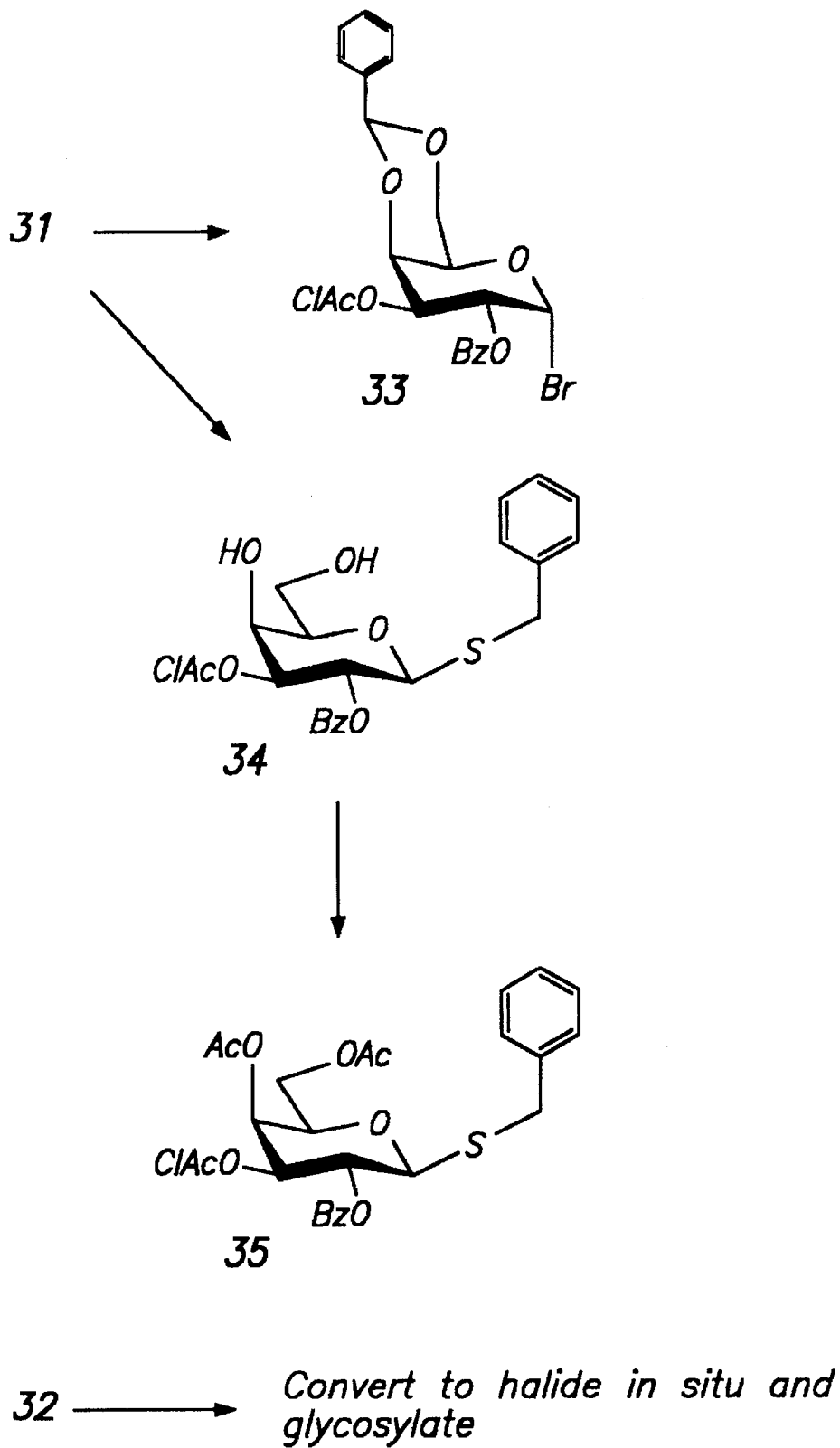

The synthesis of compounds 26–31 are depicted in FIGS. 19A and 19B and are set forth in the examples hereinbelow. In this figure, the synthesis of compounds 26, 27, 28, and 36 parallels that of compounds 17, 18, 19, and 20 as set forth above and illustrated in FIG. 18. In this regard, benzyl 4,6-O-benzylidene-2-O-benzoyl-3-O-chloroacetyl-β-D-thiogalactopyranoside (compound 31) has been produced without the necessity of chromatography. D-Galactose pentaacetate 26 is produced by slurring D-galactose and about an equimolar amount (e.g., about 1.1 equivalents) of sodium acetate (NaOAc) in dichloroethane (DCE), heating to reflux and adding at least 5 equivalents of acetic anhydride (AcOAc) dropwise to the refluxing solution (about 80°–85° C.) and then maintaining the reaction system at this temperature for a sufficient period of time (about 16–32 hours) to result in formation of compound 26. This procedure optimizes the yield of β-D-galactose pentaacetate 26 and controls the exotherm of heretofore known procedures.

After workup of the solution in a similar manner to that described above for compound 17, the product is treated with approximately equimolar amounts of benzyl mercaptan (Ph-CH2—SH) and from about 1–3 (preferably two) equivalent of boron trifluoride etherate ($BF_3.OEt_2$) in dichloromethane. The reaction conditions are not critical and the reaction is preferably conducted at from about 0° C. to about 30° C. for a period about 6 to 16 hours to yield after crystallization from hot methanol or hot isopropanol 55–65% of benzyl 2,3,4,6-tetra-O-acetyl β-D-thiogalactopyranoside, compound 27.

Deacetylation under Zemplen conditions (sodium methoxide/methanol) leads to compound 28. Deacetylation reaction conditions are not critical and the reaction is generally conducted at room temperature for a period of from about 2 to about 15 hours. After the deacetylation reaction is complete (as judged by t.l.c.), the solution is neutralized with an acid ion exchange resin, filtered and evaporated to dryness to provide for compound 28. The residue is crystallized from hot acetone and the product is taken up in dimethylformamide or acetonitrile and treated with from 1 to 2 equivalents (preferably 1.4 equivalents) of benzaldehyde dimethyl acetal and about 0.25 to 3 weight percent of p-toluenesulphonic acid (based on compound 28). The reaction conditions are not critical and preferably the reaction is conducted at room temperature and is generally complete in about 12 to 24 hours. After neutralization, the benzyl 4,6-O-benzylidene β-D-thiogalactopyranoside, 29, is isolated and crystallized from hot isopropanol.

Benzyl 4,6-O-benzylidene-3-O-chloroacetyl-β-D-thiogalactopyranoside 30 is prepared by chloroacetylation using from about 1 to 3 (preferably 2) equivalents of chloroacetylchloride which is added to a dimethylformamide (DMF) solution containing benzyl 4,6-O-benzylidene β-D-thiogalactopyranoside 29. The chloroacetylchloride is added dropwise while maintaining the DMF solution at from about −40° to about −15° C. (preferably at −25° C.). Under these conditions, it is unexpectedly been found that the use of DMF permits selective chloroacetylation of compound 29 without the need for additional base. The reaction is generally complete in about 10–24 hours.

Benzyl 4,6-O-benzylidene-3-O-chloroacetyl-β-D-thiogalactopyranoside (compound 30) is benzoylated with at least 1 equivalent (and preferably about 2 equivalents) of benzoyl chloride in a suitable solvent containing a base (e.g., pyridine/methylene chloride) with from about 0.1 to about 1 weight percent of dimethylaminopyridine [DMAP] as a catalyst. The reaction conditions are not critical and preferably the reaction is conducted at from about 0° C. to about 30° C. and for about 1 to about 4 hours (preferably room temperature for 2 hours) to give crystalline benzyl 4,6-O-benzylidene 2-O-benzoyl-3-O-chloroacetyl-β-D-thiogalactopyranoside, compound 31, in approximately 10–20% overall yield from galactose.

The advantage of this approach is that after subsequent assembly, the blocked intermediates will be simply deblocked and modified by sulfation or phosphorylation. The material is crystalline and the process obviates the need for chromatography.

The sulfates and phosphates of the galactose moiety of oligosaccharide glycosides related to blood group determinants having a type I or a type II core structure can also be made using compound 32 in the synthesis of these compounds. This compound is made by direct benzoylation of both the 2,3-hydroxyl groups of compound 29. However, after deblocking, both the 2 and 3 hydroxyl groups of galactose are then available for sulfation and phosphorylation and the selectivity is not as efficient. Selectivity can be improved by, for example, conducting the sulfation reaction at a low temperature (e.g., −50° C.).

Compound 29 can be converted to the 2,3-dibenzoyl protected compound 32 in a manner similar to that described above for the preparation of compound 31. In this case, 3–5 equivalents of benzoyl chloride are generally employed.

Compounds 31 and 32 are converted to compounds 33 and 32a (shown in FIG. 21A) via known methodology (Norberg, et al.[39]) using bromine tetraethylammonium bromide.

Alternatively, compound 31 can be converted to compound 34 by contacting compound 31 with 80% acetic acid/water at approximately 50° C. for about 1–2 hours. Compound 34 is then converted to compound 35 by treatment with acetic anhydride/pyridine in dichloromethane.

In another embodiment, compound 32 is treated with sodium cyanoborohydride and ceric chloride to provide for the benzyl-2,3-O-dibenzoyl-4-O-benzyl-β-D-thiogalactopyranoside (not shown). In turn, this compound is chloroacetylated at the 6-hydroxyl group. After formation of the type I or type II backbone, the chloroacetyl group can be selectively removed (as described above) and then either phosphorylated or sulfated so as to provide for the 6-phosphate or 6-sulfate derivative.

SYNTHESIS OF TYPE II STRUCTURES

Figure 20A:
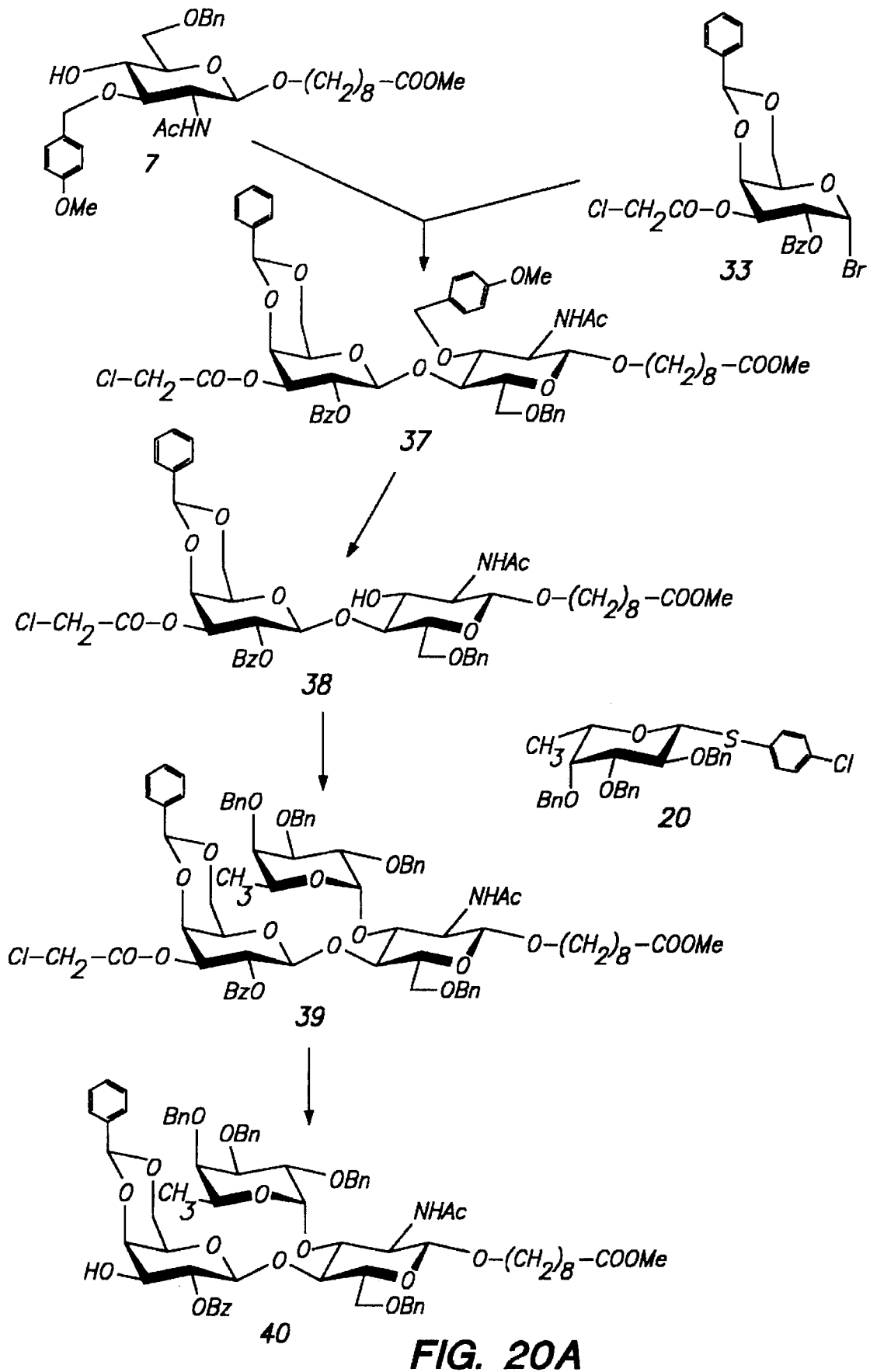
FIGS. 20A and 20B illustrate the synthesis of modified Lewis$^x$ compounds having a sulfate substituent in the 3 position of the galactose unit. In this scheme, the 2,3 positions of galactose are differentially blocked so that the 3-position can be selectively deblocked and then selectively converted to the sulfate substituent.
Figure 20B:
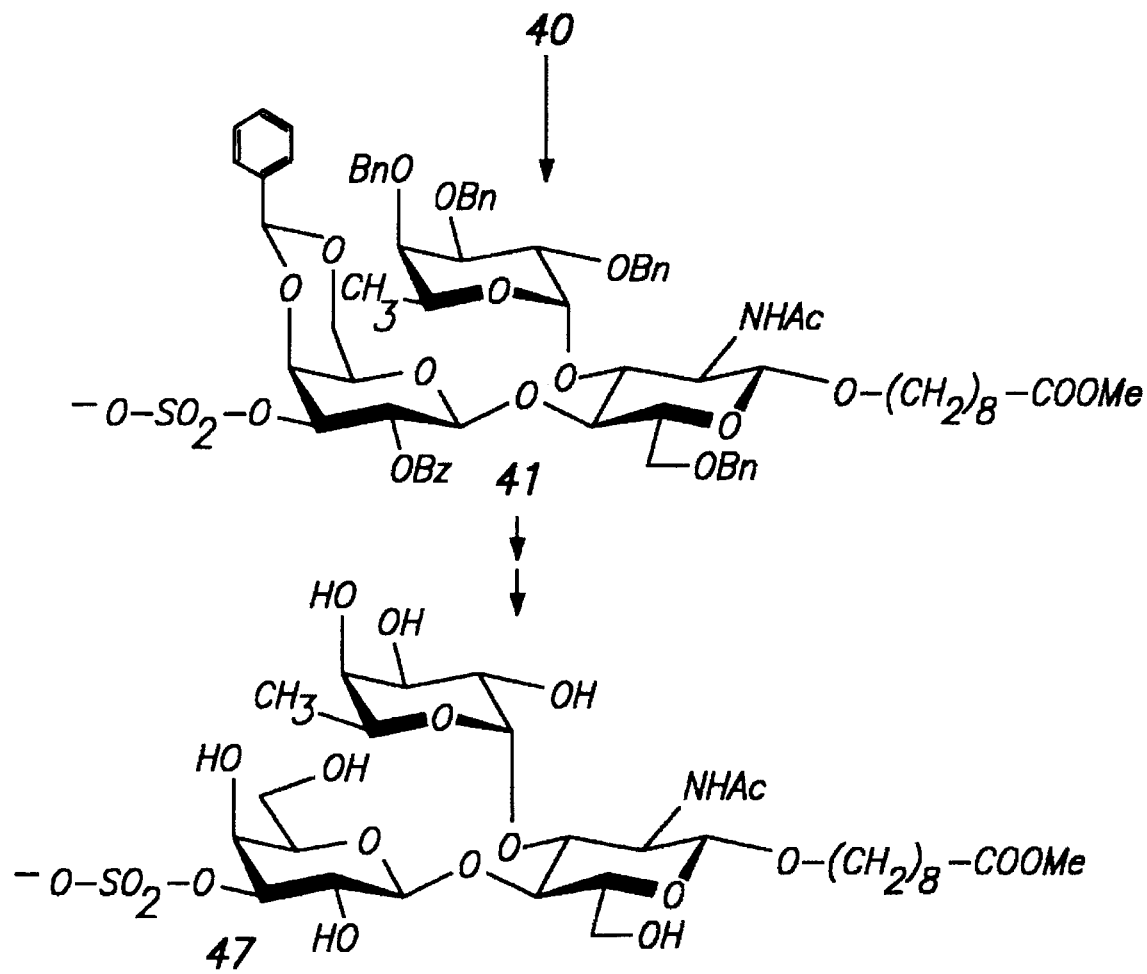

FIGS. 20A and 20B illustrate one method for synthesizing blocked type II backbones which can be used to prepare oligosaccharide glycosides related to blood group determinants having type II core structures which can optionally be converted to blocked Lewis$^x$ type structures.

Specifically, in FIGS. 20A and 20B, the 2,3 hydroxyl groups of the galactose are differentially blocked so that at the appropriate point in the synthetic scheme, the chloroacetyl protecting group at the 3-position of galactose is selectively removed and then converted to the sulfate, phosphate or —$OCHR_{18}COOH$ group. Also, as noted above, the chloroacetyl protecting group can be selectively placed at the 6-position of the galactose and then selectively removed so as to allow for the formation of the sulfate, phosphate or —$OCHR_{18}COOH$ group at the 6-position of galactose.

Specifically, in FIG. 20, compound 7 and compound 33 are combined to form compound 37. This is accomplished by dissolving compound 7 and approximately 1.5 equivalents of compound 33 in dichloromethane containing molecular sieves to which is added about 1 equivalent (based on compound 7) of 2,6-di-t-butyl-4-methylpyridine. The reaction is stirred for 30 minutes at room temperature and then cooled to −50° C. An anhydrous toluene solution containing approximately a slight excess (e.g., about 1.2 equivalents) of silver trifluoromethane sulfonate is then added to the solution and the reaction is allowed to warm to −15° C. over 2 hours and maintained at that temperature for an additional 5 hours.

At this time, the molecular sieves are removed by filtration by passing through celite and the recovered solution is quenched by addition to a saturated sodium bicarbonate solution. The organic extract is then washed with water, with aqueous 0.5N HCl, and then with water. The organic solution is then dried and concentrated in vacuo to provide a crude product of compound 37. This is then purified by conventional techniques such as column chromatography using silica gel and hexane-ethyl acetate (1:1) as the eluant.

When desired, a Lewis$^x$ structure can be prepared from compound 37. Specifically, to a dichloromethane solution containing compound 37 can be added an excess of dichlorodicyanoquinone (DDQ) which selectively removes the p-methoxybenzyl protecting group to provide compound 38. This compound is fucosylated with an excess of compound 20 (about 1.3–1.5 equivalents) in dichloromethane containing mercuric bromide or cupric bromide and about 1–1.5 volume percent DMF to give blocked Lewis$^x$ compound 39. After work-up and chromatography compound 39 is treated with thiourea to remove the chloroacetyl group and the compound is sulfated with sulphur trioxide/pyridine complex in DMF at 0° C. for 2 hours to provide compound 41. The blocking groups on compound 41 are then removed by conventional techniques to provide for the Lewis$^x$ analogue having a sulfate group at the 3-position of the galactose unit. However, in this embodiment, it has been found that removal of the benzoyl group (Bz) in compound 41 is accompanied by some deacylation of the —NHAc group on the GlcNAc unit and possibly some other side reactions. Accordingly, chromatography is necessary to obtain pure compound 41. In any event, it is that fucosylation in the above reactions, fucosylation is not necessary.

Alternatively, compound 25 (or the 3-chloroacetyl analogue of compound 25 described above—not shown) can be used in place of compound 20 in the above synthesis. Removal of the chloroacetyl blocking groups on the 3-hydroxyl of the galactose and the 4-hydroxyl of the fucose provides an facile route to the preparation of a disulfated or diphosphorylated Lewis$^x$ derivatives.

In another embodiment, compound 40 can then be alkylated by first adding an appropriated base (e.g., silver oxide, barium hydroxide, sodium hydride) and then adding benzyl bromoacetate (BrCH$_2$COOBn) or other similar acetates (e.g., BrCHR$_{18}$COOBn—where R$_{18}$, is alkyl of from 1 to 7 carbon atoms or —COOBn) to the reaction medium in an appropriate solvent such as DMF. After reaction completion, the benzyl ester(s) is (are) readily removed by conventional hydrogenation techniques which additionally removes the other benzyl protecting groups and the benzylidene protecting group. Treatment with sodium methoxide/methanol provides for a —OCH$_2$COOH (or —OCHR$_{18}$COOH where R$_{18}$ is alkyl of from 1 to 7 carbon atoms or —COOH) substituted to the 3-position of galactose. Similar type chemistry can be performed at the 6-hydroxyl group of the galactose or at the 4-hydroxyl group of the fucose by use of appropriate blocking groups.

In another embodiment, compound 40 can be treated by known methods[30] to provide for the 3-phosphate compound. Specifically, compound 40 can be treated with diphenylphosphorochloridate and 4-dimethylaminopyridine (1:1) in pyridine at 0° C. The solution is allowed to warm to room temperature over 0.5 hours and stirred for 15 hours. The resulting compound is then hydrogenated under conventional conditions (first with H$_2$ in EtOH with Pd on carbon for 15 hours and then with H$_2$ in EtOH with PtO$_2$ for 3 hours) to provide for the phosphate derivative at the 3-position of galactose. Further deprotection leads to the modified Lewis$^x$ compound having a phosphate substituent at the 3-position of galactose) which is purified and converted to its disodium salt by contacting a solution of this compound with a sodium form of Dowex 50 x 8.

As is apparent, the procedures set forth above can also be used to introduce a phosphate or a —OCHR$_{18}$COOH group at the 6-position of galactose or a phosphate group on the fucose.

Figure 21A:
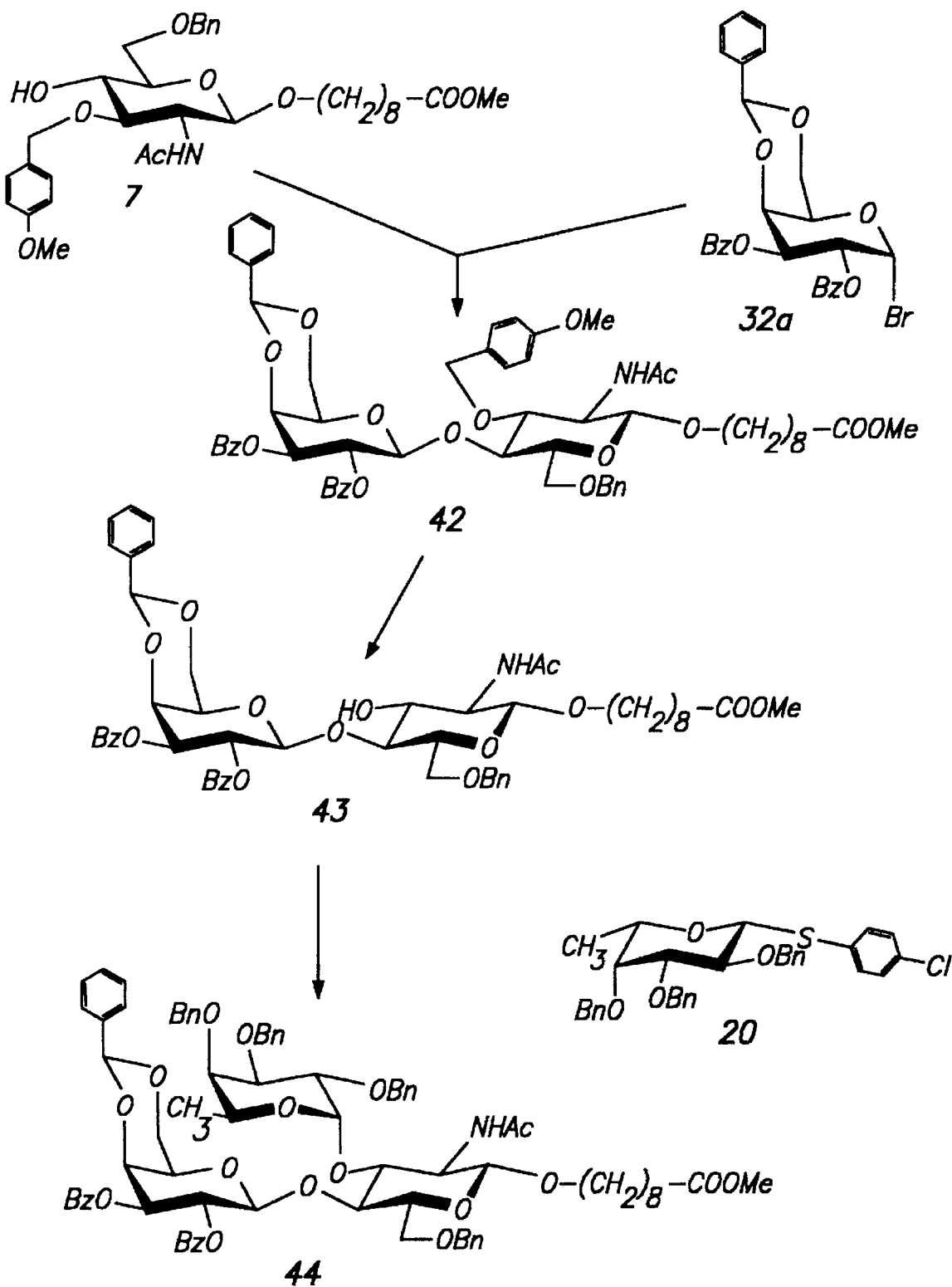
FIGS. 21A and 21B illustrate the synthesis of modified Lewis$^x$ compounds having a sulfate substituent in the 3 position of the galactose unit. In this scheme, the 2,3 positions of galactose are not differentially blocked. Accordingly, deprotection of the 3-position of the galactose unit also results in deprotection of the 2-position and subsequent reaction to form the sulfate at the 3-position does not proceed with 100% yield but rather some of the product has a sulfate substituent at the 2-position of the galactose which is then separated by chromatography.
Figure 21B:
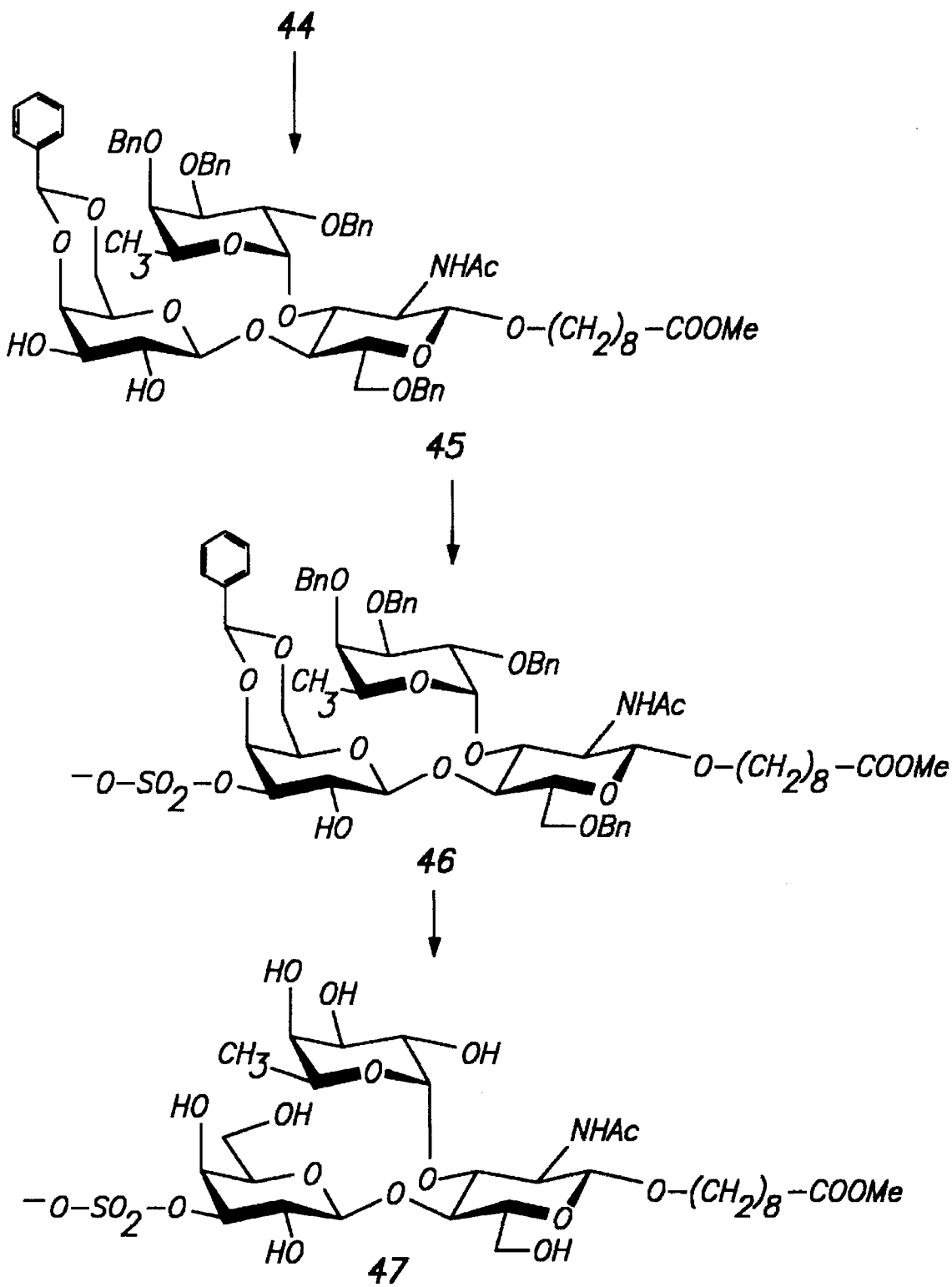

FIGS. 21A and 21B illustrate another method for synthesizing blocked type II backbones and the optional conversion of these blocked backbones to blocked Lewis$^x$ structures. In this figure, the 2,3 hydroxyl groups of the galactose are not differentially blocked and, accordingly, while the resulting compound 45 (and the type I analogue) is useful for preparing the 3-sulfate (as part of a mixture with the 2-sulfate and 2,3-disulfate which can be purified by chromatography) it is not as versatile as the synthetic scheme set forth in FIGS. 20A and 20B.

In any event, in FIG. 21A, compound 7 and approximately 1.6–1.7 equivalents of compound 32a are dissolved in dichloromethane containing molecular sieves to which is added about 1 equivalent (based on compound 7) of 2,6-di-t-butyl-4-methylpyridine. The reaction is stirred for 30 minutes at room temperature and then cooled to −50° C. An anhydrous toluene solution containing approximately a slight excess (e.g., about 1.2 equivalents) of silver trifluoromethane sulfonate is then added to the solution and the reaction was allowed to warm to −15° C. over 2 hours and maintained at that temperature for an additional 5 hours.

After reaction completion, the reaction system was worked up to provide a crude product of compound 42. This is then purified by conventional techniques such as column chromatography using silica gel and toluene-ethyl acetate (1:1) as the eluant.

When desired, a Lewis$^x$ structure can be prepared from compound 42. Specifically, to a dichloromethane solution containing compound 42 is added an excess of dichlorodicyanoquinone (DDQ) which selectively removes the p-methoxybenzyl protecting group to provide compound 43. This compound is fucosylated with an excess of compound 20 (about 1–3 equivalents and preferably about 1.3–1.5 equivalents) in dichloromethane containing mercuric bromide or cupric bromide and about 12 volume percent DMF to give blocked Lewis$^x$ compound 44. After work-up and chromatography compound 44 is treated with sodium methoxide/methanol to remove the benzoyl blocking groups at the 2,3-positions of the galactose so as to provide for compound 45. This compound is then sulfated with sulphur trioxide/pyridine complex in DMF at from −50° to 0° C. for 2 hours to provide compound 46. Compound 46 is produced as a mixture of the 3-sulfate, the 2-sulfate, and the 2,3-disulfate which is separated by chromatography (e.g., column chromatography on silica). Conventional deprotection of the removable protecting groups provides for the sulfate derivative at the 3-position of galactose for Lewis$^x$, compound 47, which can be passed onto an anion exchange resin (sodium form) to generate the sodium salt.

In order to improve the selectivity for the generation of the 3-sulfate in this step, lower temperatures, e.g., −50° to –30° C., can be employed. Alternatively, compound 45 can be chloroacetylated under typical conditions to provide for a mixture of the 2- and 3-chloroacetyl protecting groups. This mixture can be separated by chromatography and the resulting purified components can be used to prepare 2- or 3-sulfated products selectively.

Additionally, lactose can be used in the methods of this invention in place of LacNAc by merely placing a suitable blocking group at the 2-hydroxy of the glucose moiety of the lactose structure[40]. Differential blocking of the lactose provides for a composition having a selectively removable blocking group at the 3 and/or 6 position of the galactose. This compound is then selectively deblocked at the 3 and/or 6 position and then derivatized to the 3 and/or 6 sulfate, phosphate or —OCHR$_{18}$COOH. Afterwards, the remaining blocking groups are removed and the fucosyl unit added enzymatically (see below).

SYNTHESIS OF TYPE I STRUCTURES

While FIGS. 20 and 21 illustrate the synthesis of oligosaccharide glycosides related to blood group determinants having a type II core structure, oligosaccharide glycosides related to blood group determinants having a type I core structure are readily prepared in a similar manner, as illustrated in FIGS. 24A and 24B, using appropriately blocked GlcNAc-OR structures. The βGal(1→3)βGlcNAc-OR type I structures, and derivatives thereof, can be prepared, for example, from compounds 5 and 35. Specifically, compound 35 is first converted to the 1-α-bromo derivative via known methodology (Norberg et al.[39]) using bromine (Br$_2$) and tetraethylammonium bromide (Et$_4$N$^+$Br$^-$) at about 0° C. About 1.5 equivalents of this compound and compound 5 are dissolved in dichloromethane (Cl$_2$CH$_2$) containing molecular sieves to which is added about 1 equivalent (based on compound 5) of 2,6-di-t-butyl-4-methylpyridine. The reaction is stirred for 30 minutes at room temperature and then cooled to –50° C. An anhydrous toluene solution containing approximately a slight excess (e.g., about 1.2 equivalents) of silver trifluoromethane sulfonate (silver triflate) is then added to the solution and the reaction is allowed to warm to –15° C. over 2 hours and maintained at that temperature for an additional 5 hours. Afterwards, the solution is allowed to come to room temperature and stirred overnight.

At this time, pyridine and dichloromethane are added and the molecular sieves are removed by filtration by passing through celite and the recovered solution is quenched by addition to a saturated sodium bicarbonate solution. The organic extract is then washed with water, with aqueous 0.5N HCl, and then with water. The organic solution is then dried and concentrated in vacuo to provide a crude product which is then purified by conventional techniques such as column chromatography using silica gel and hexane-ethyl acetate (1:1) as the eluant to provide for compound 80. The benzylidene protecting group of compound 80 is then selectively removed by treatment with 80% acetic acid (AcOH) in water (H$_2$O) to provide for compound 81. Compound 81 is selectively acetylated at the 6-hydroxy group of the GlcNAc unit by treatment with acetic anhydride (AcOAc) in pyridine at about –20° C. to provide for compound 82 (i.e., 8-methoxycarbonyloctyl-2-acetamido-3(2-O-benzoyl-3-chloroacetyl-4,6-di-O-acetyl-β-D-galactopyranosyl)-6-O-acetyl-2-deoxy-β-D-glucopyranoside). This compound is then fucosylated with, for example, compound 20 in the manner similar to compound 38 as described above to provide for compound 83 and then deblocked and sulfated in the manner described above for compounds 40, 41, and 47 to provide for compounds 84, 85, and 86.

Alternatively, compound 32 is converted to the 1-α-bromo derivative via known methodology (Norberg et al.[39]) as described above and the resulting compound is then treated with sodium cyanoborohydride and ceric chloride to provide for the benzyl-2,3-O-dibenzoyl-4-O-benzyl-β-D-thiogalactopyranoside (not shown). In turn, this compound is chloroacetylated at the 6-hydroxyl group and then reacted with compound 5 in the manner described above to provide for the 8-methoxy-carbonyloctyl-2-acetamido-3(4-O-benzoyl-6-chloroacetyl- 2,3-di-O-benzoyl-β-D-galactopyranosyl)-6-O-acetyl-2-deoxy-β-D-glucopyranoside. This compound is then treated in the manner described above for compound 82 so as to provide for a type I derivative having a sulfate, phosphate or a —O(CHR$_{18}$COOH) substituent at the 6-position of the galactose.

In yet another embodiment, both type I and type II structures can be made simultaneously by combining compound 15 and compound 33 under appropriate conditions well known in the art. For example, compound 15 and approximately 1.5 equivalents of compound 33 are added to dichloromethane containing molecular sieves to which is added about 1 equivalent (based on compound 15) of 2,6-di-t-butyl-4-methylpyridine. The reaction is stirred for 30 minutes at room temperature and then cooled to –50° C. An anhydrous toluene solution containing approximately a slight excess (e.g., about 1.2 equivalents) of silver trifluoromethane sulfonate is then added to the solution and the reaction is allowed to warm to –15° C. over 2 hours and maintained at that temperature for an additional 5 hours. Afterwards, the solution is allowed to come to room temperature and stirred overnight.

At this time, pyridine and dichloromethane are added and the molecular sieves are removed by filtration by passing through celite and the recovered solution is quenched by addition to a saturated sodium bicarbonate solution. The organic extract is then washed with water, with aqueous 0.5N HCl, and then with water. The organic solution is then dried and concentrated in vacuo to provide a crude product which contains both the type I and type II structures which are separated and purified by conventional techniques such as column chromatography using silica gel and hexane-ethyl acetate (1:1) as the eluant.

The ratio of type I structure to type II structure resulting from this reaction can be improved by using the 2-NAc derivative of GlcNH$_2$ compound 15. This compound can be readily prepared by reacting compound 15 with hydrazine, acetylating the resulting product with acetic anhydride/ pyridine and then deacetylating the 3,4-hydroxyl groups by treatment with sodium methoxide/methanol.

3D. ENZYMATIC REACTIONS

In addition to the chemical syntheses of oligosaccharide glycosides related to blood group determinants having a type I or a type II core structure as described above, the appropriately blocked type I [βGal(1→3)βGlcNAc-OR] and type II [βGal(1→4)βGlcNAc-OR] structures and derivatives thereof can be selectively deblocked to provide for a hydroxyl group at the 3-position of galactose and then sulfated, phosphorylated, or converted to —OCHR$_{18}$COOH (each of which are described above). The resulting compound is then totally deblocked and can be fucosylated by using, for example, βGal(1→3/4)βGlcNAc α(1→3/4) fucosyltransferase[41]. It being understood that the when such a fucosyltransferase is employed, the galactose unit of this disaccharide must contain a 6-hydroxyl substituent.

The enzymatic transfer of fucose onto the 4-position of GlcNAc to form Lewis$^A$ structures and to the 3-position of GlcNAc to form Lewis$^x$ structures requires the prior synthesis of its nucleotide (GDP) derivatives. Synthesis of GDP-fucose is preferably accomplished in the manner recited by Jiang et al.[42] and which is exemplified in the examples hereunder.

GDP-fucose (GDP-Fuc) is then combined with βGal(1→4)βGlcNAc-OR or βGal(1→3)βGlcNAc-OR (including derivatives thereof) in the presence of a suitable fucosyltransferase (e.g., βGal(1→3/4)βGlcNAc e(1→3/4) fucosyltransferase) under conditions wherein fucose is transferred to the 3 position of GlcNAc of the derivatized βGal(1→4)βGlcNAc-OR or the 4-position of the derivatized βGal(1-3)βGlcNAc-OR compound to form a Lewis$^x$ or Lewis$^A$ structures respectively.

Suitable fucosylation conditions, known in the art, include the addition of the fucosyltransferase to a mixture of the derivatized βGal(1→4)βGlcNAc-OR (or alternatively the derivatized βGal(1→3)βGlcNAc-OR compound) and the GDP-fucose in a appropriate buffer such as 50 mM sodium cacodylate in appropriate conditions of pH and temperature such as at a pH of 6.5 and a temperature between 30° and 45° C., preferably 35° to 40° C. while incubating for about 12 hours to 4 days. The resulting fucosylated product can be isolated and purified using conventional methodology comprising HPLC, ion exchange-, gel-, reverse-phase- or adsorption chromatography.

It is also contemplated that the deblocked type I and II structures can be sulfated by use of an appropriate sulfotransferase.

Alternatively, type II structures containing a sulfate, phosphate or carboxyl substituent at the 2 and/or 3-positions of the galactose unit can be sialylated to form the 6-sialyl derivative on the galactose unit by use of known βGal(1→4) βGlcNAc α(2→6)sialyltransferase. However, as noted above, such sialylated structures cannot then be used to form fucosyl derivatives at the 3-position of the GlcNAc unit by use of the βGal(1→3/4)βGlcNAc α(1→3/4) fucosyltransferase.

2E. MODIFICATION ON THE 2 AND/OR 6 POSITIONS OF GlcNAc

FIGS. 22A and 22B and FIGS. 23A and 23B illustrate two different syntheses for the retention of the 2-amino substituent on the glucosamine unit of oligosaccharide glycosides related to blood group determinants having a type I or a type II core structure (e.g., derivatives of Gal(1→3)βGlcNAc-OR or βGal(1→4)βGlcNAc-OR where the NAc group of GlcNAc has been converted to an amine). As shown below, the retention of the amino group on the glucosamine unit allows for the facile preparation of different 2-substituted derivatives. Also, as is apparent, the methodology found in FIGS. 22 and 23 also permit the selective formation of the 3-sulfate, 3-phosphate, 3-CHR$_{18}$COOH, 6-sulfate, 6-phosphate, and 6-CHR$_{18}$COOH while retaining an NHAc group on the GlcNAc unit.

Figure 22A:
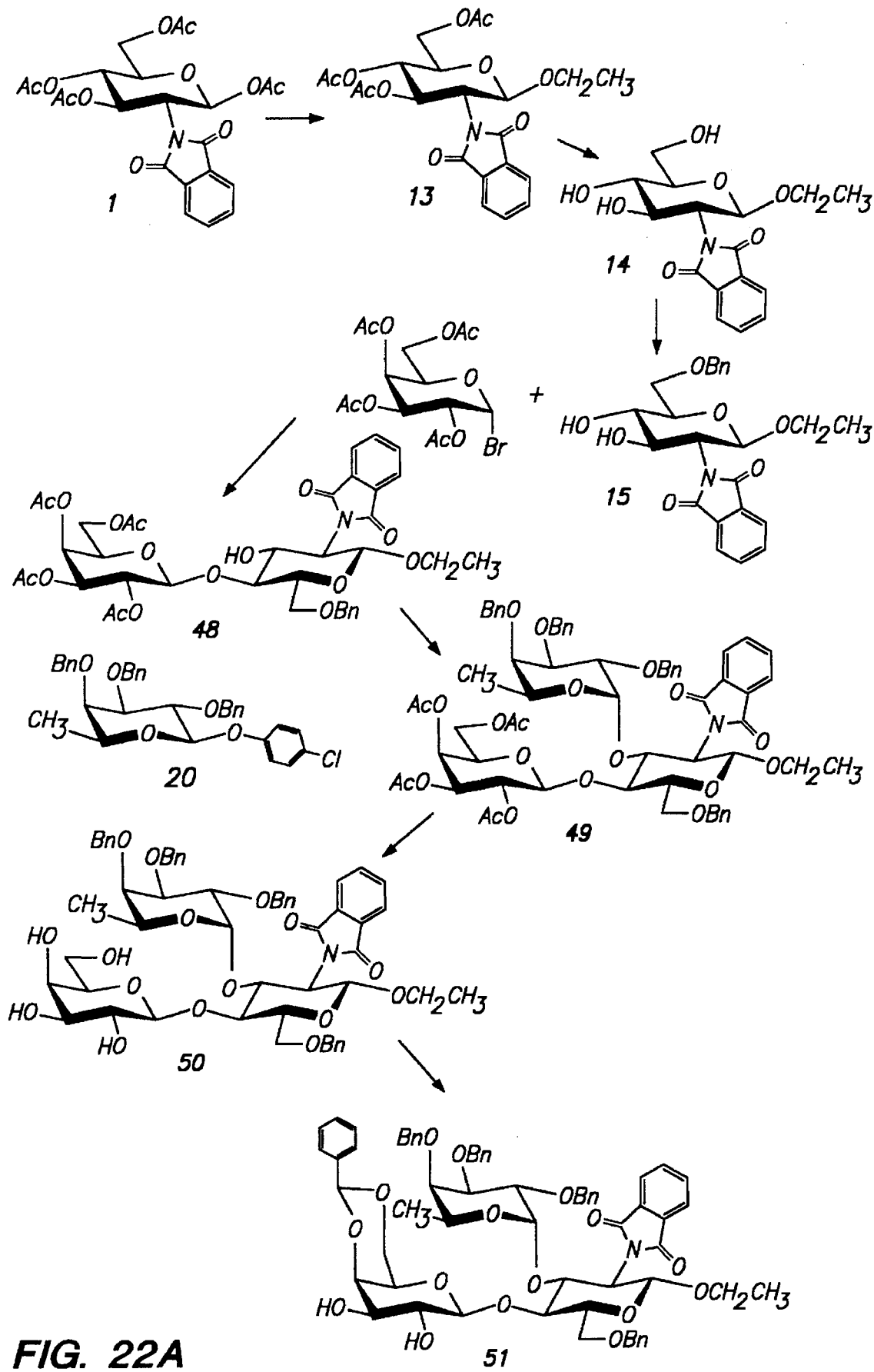
FIGS. 22A and 22B illustrate the synthesis of modified Lewis$^x$ derivatives bearing a sulfate substituent at the 3-position of the galactose and which utilize a 6-benzyl and 2-N-phthaloyl blocked glucosamine which can be later deblocked to provide for a glucosamine derivative.
Figure 22B:
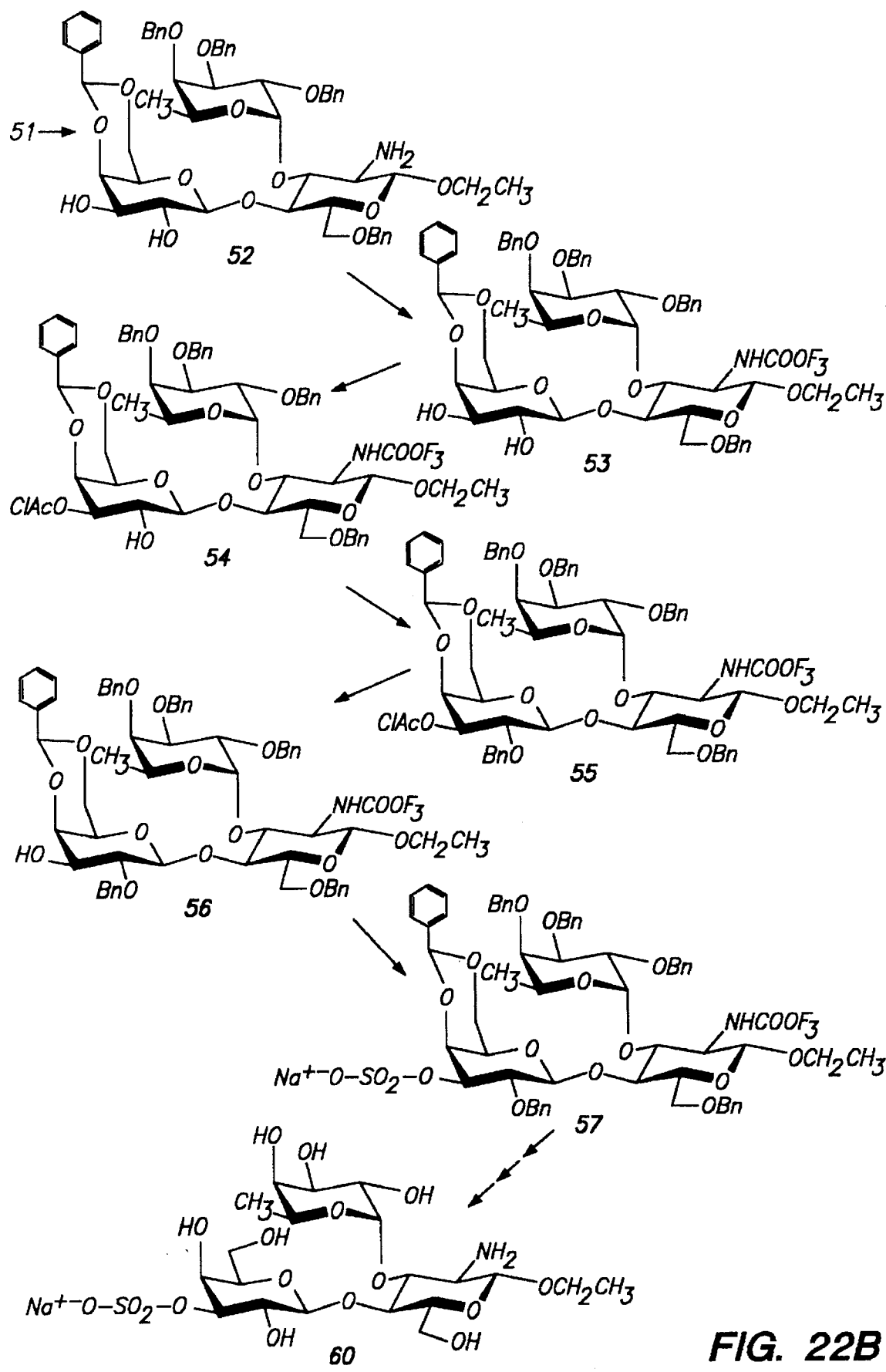

In FIGS. 22A and 22B, compounds 1, 13, 14, and 15 are prepared in the manner described above and illustrated in FIGS. 17A and 17B. Likewise, 1-α-bromo-2,3,4,6-tetracetylgalactose is prepared by first forming the peracetylated derivative of galactose, compound 26. Compound 26 is then converted to the 1-α-bromo derivative via known methodology (HBr/Acetic acid—at about 0° C. to 20° C.) so as to provide for 1-α-bromo-2,3,4,6-tetracetylated galactose.

The 1-α-bromo-2,3,4,6-tetracetylated galactose (about 1.2 to about 1.5 equivalents) is added dropwise to a solution of compound 15 in dichloromethane at about –50° C. in the presence of excess calcium sulfate, about 4 equivalents of silver carbonate and about 0.5 equivalents of silver triflate. The reaction is then allowed to warm to –30° C. and maintained there for about 1–3 days. The reaction is then quenched by the addition of methanol, warmed to room temperature, and filtered through celite. The filtrate is washed with aqueous sodium bicarbonate and aqueous ethylene diamine tetraacetic acid (EDTA). The recovered solution is dried and then stripped in vacuo to provide a crude product containing both the type I structure (not shown) and the type II structure (compound 48). The residue is chromatographed on a silica gel column eluted with toluene:acetone:methanol (20:3:1) to give compound 48 as well as the type I analogue (not shown).

For convenience sake, further reactions are shown on compound 48, it being understood however, that the same reactions could be conducted on the type I analogue.

If these type II (or type I) structures are to be fucosylated so as to provide for Lewis$^x$ structures (or Lewis$^A$ structures), then this can be accomplished as follows. Compound 20 is reacted with one equivalent of bromine in dichloromethane at –20° C. for about 1 hour to provide for the 1-α-bromo derivative of compound 20. The solution is then quenched with a cold aqueous sodium bicarbonate solution. The organic solution is dried and concentrated to approximately half the original volume in vacuo at room temperature. About 2 equivalents of this compound are then add to a dichloromethane solution of compound 48 that further contains about 2 equivalents of mercuric bromide (HgBr$_2$), molecular sieves and tetraethylammonium bromide. The reaction is stirred at room temperature for approximately 48 hours and the solution is filtered through celite and the filtrate washed with water, a 5% EDTA solution, saturated aqueous sodium bicarbonate, and then water. The organic layer is then dried and the solvent removed in vacuo to provide for compound 49 which is purified by chromatography on silica gel.

Compound 49 is converted to compound 50 by conventional Zemplen conditions and compound 50 is then converted to compound 51 by conventional methodology (e.g., benzaldehyde dimethylacetal, DMF, pTSA). In turn, compound 51 is treated with hydrazine acetate in methanol at room temperature for about 1–5 hours to provide for compound 52 which is converted to compound 53 by contacting with trifluoroacetic anhydride in methanol. Alternatively, compound 52 serves as a convenient point in the synthesis to convert this amine to an amide, a carbamate, a urea, a —NHSO$_3$H group, etc. in the manner described below.

Compound 53 can then be sulfated in the same manner as described above for compound 45. Alternatively, compound 53 can be differentially blocked at the 2,3 hydroxyl groups of the galactose by converting the 3-hydroxyl group of compound 53 to a chloroacetyl group which is achieved in the manner described above for compound 29 so as to provide for compound 54. Compound 54 is then treated under conditions described above for blocking the remaining free hydroxyl group with a benzyl group so as to provide for compound 55. In turn, compound 55 is selectively deblocked with thiourea to provide for compound 56 in the same manner described above for compound 39 (to provide compound 40). Compound 56 is then selectively sulfated in the manner described above to provide for compound 57. Alternatively, compound 56 can be converted to the 3-phosphate group on the galactose by reaction with diphenylphosphorochloridate and 4-dimethylaminopyridine (1:1) in pyridine at 0° C. The solution is allowed to warm to room temperature over 0.5 hours and stirred for 15 hours. The resulting compound is then hydrogenated under conventional conditions (first with $H_2$ in EtOH with Pd on carbon for 15 hours and then with $H_2$ in EtOH with $PtO_2$ for 3 hours) to provide for the phosphate derivative at the 3-position of galactose. Further deprotection leads to the modified Lewis$^x$ compound having a phosphate substituent at the 3-position of galactose) which is purified and converted to its disodium salt by contacting a solution of this compound with a sodium form of Dowex 50 x 8. Compound 56 can also be converted to the —$CHR_{18}COOH$ in the manner described above.

Lastly, compound 57 is deblocked by conventional techniques to provide for compound 60 which is a Lewis$^x$ analogue having a 2-amino glucose saccharide unit instead of a GlcNAc saccharide and further having a sulfate or other substituent at the 3-position of the galactose saccharide unit.

In the above case, use of the benzyl blocking group on the 2-position provides for a more effective synthesis since this group as well as the other benzyl protecting groups are readily removed under hydrogenation conditions.

FIGS. 23A and 23B parallels somewhat the chemistry depicted in FIGS. 22A and 22B but, because the 3-hydroxyl group of the $GlcNH_2$ derivative is blocked (compound 69), this synthesis results only in type II structures. In particular, in FIGS. 23A and 23B, compound 13 is prepared by the methods described above. This compound is then deacetylated by conventional techniques (sodium methoxide/ methanol) to provide for compound 14 which is then benzylidenated under conventional techniques to provide compound 66. Compound 66 is then treated with benzyl chloride and sodium hydride in dimethylformamide at about −20° C. to 20° C. to provide for compound 67. The benzylidene group of compound 67 is then removed with 80% aqueous acetic acid at about 80° C. for about 1–4 hours to provide for compound 68. This compound is then selectively acetylated at the 6-position by use of approximately equimolar amounts of acetyl chloride/pyridine in dichloromethane at about −10° C. to provide for compound 69. Approximately 1.2–1.5 equivalents of the 1-α-bromo-2,3,4,6-tetraacetylated galactose (described above) are added dropwise to a solution of compound 69 in dichloromethane maintained at about −30° C. in the presence of about 1.3 equivalents of 2,6,-di-t-butyl-4-methylpyridine and about 1.3 equivalents of silver triflate. The reaction is then maintained at −30° C. for 1 hour and then allowed to warm to 5° C. and maintained there for about 2 hours. The reaction is then quenched by the addition of methanol, warmed to room temperature, and filtered through celite. The filtrate is washed with aqueous sodium bicarbonate. The recovered solution is dried and then stripped in vacuo to provide a crude product containing compound 70 which is purified by chromatography on a silica gel column eluted with ethyl acetate:hexanes (1:2) to give compound 70.

Figure 6:
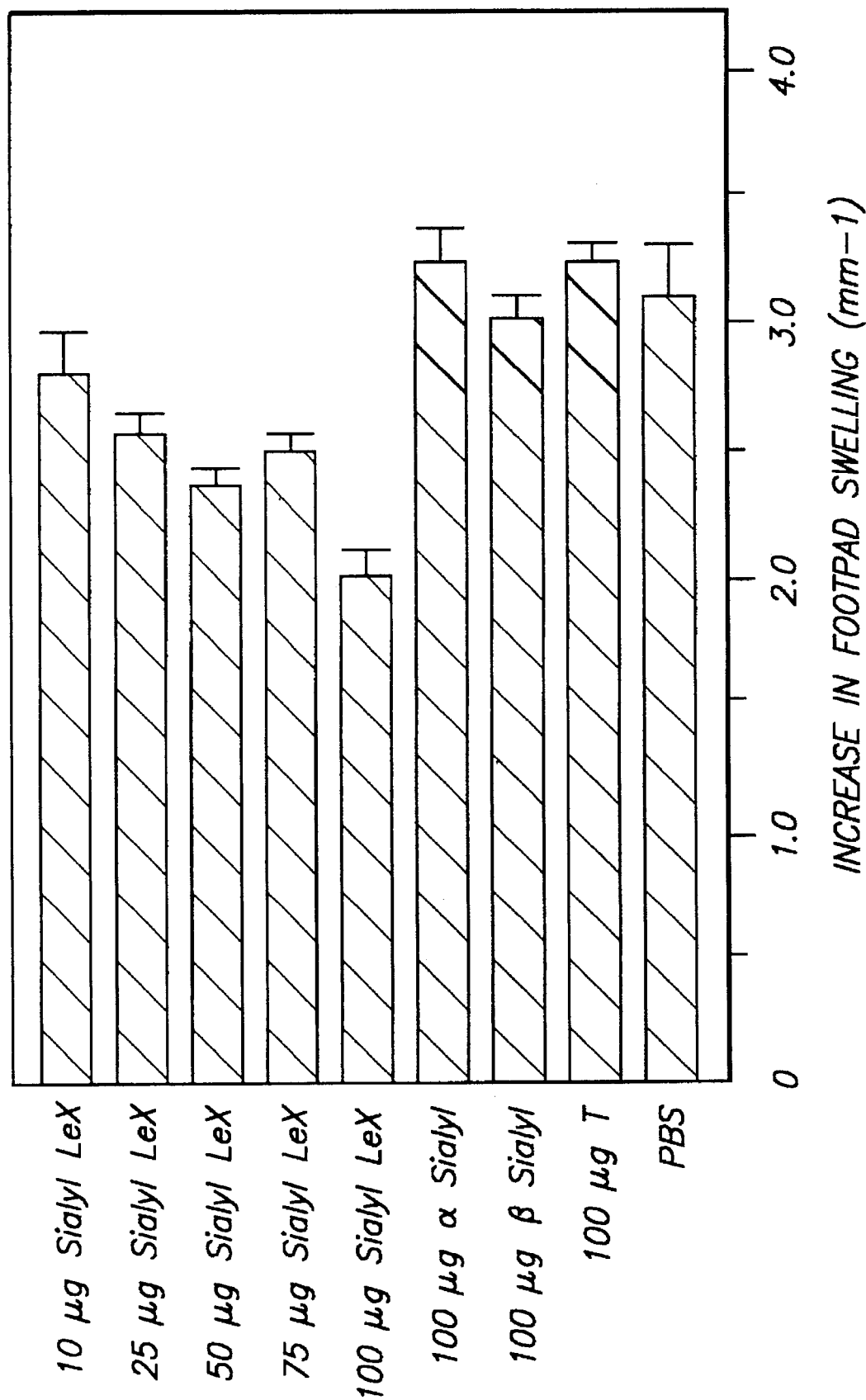
FIG. 6 illustrates the long term (6 weeks) immunosuppression generated in immunized mice after an injection with varying amounts of mono- and oligosaccharide glycosides including an oligosaccharide glycoside related to blood group determinants having type I or type II core structure 5 hours after challenge with 20 µg of the L111 S-Layer protein antigen on day 7.

The benzyl protecting group is then removed by hydrogenolysis ($H_2$/Pd on C) to provide for compound 71. Compound 71, in turn, is fucosylated in the same manner as described above for compound 48 (to provide for compound 49 as illustrated in FIG. 6) so as to provide for compound 72. Compound 72 is deacetylated by conventional techniques described above to provide for compound 73. Compound 73 is then converted to compound 74 by conventional methodology (e.g., benzaldehyde dimethylacetal, DMF, pTSA), followed by selective acetylation at the 6-position of the partially protected $GlcNH_2$ derivative by an approximately equivalent amount of acetyl chloride/pyridine in dichloromethane maintained at about −50° to about −20° C.). Compound 74 is then converted to compound 79 in the same manner (described above) as compound 53 was treated to provide for compound 60.

Alternatively, the free hydroxyl groups of compound 74 can be acetylated with acetyl chloride/pyridine in the manner described above and the benzylidene group selectively opened by sodium cyanoborohydride and ceric or aluminum chloride to give the 2,3-diacetyl-4-benzyl-6-hydroxy derivative on the galactose moiety (not shown). This compound is then functionalized at the 6-position of the galactose so as to contain a sulfate, phosphate or —$CHR_{18}COOH$ group at this position.

In addition to the above, the 2,6 positions of the GlcNAc unit can be modified prior to coupling so as to provide for type I and type II structures modified at these positions which can optionally be further modified in the manner described above to prepare the sulfated, phosphorylated or —$CHR_{18}COOH$ substituted structures. As shown by Venot et al., U.S. patent application Ser. No. 07/887,747, filed May 22, 1992 as Attorney Docket No. 000475-011 and entitled "MODIFIED SIALYL LEWIS$^A$ COMPOUNDS" and by Venot et al., U.S. patent application Ser. No. 07/887,746, filed May 22, 1992 as Attorney Docket No. 000475-029 and entitled "MODIFIED SIALYL LEWIS$^x$ COMPOUNDS", modification at the 2 and/or 6-positions of the GlcNAc moiety of type I structures [βGal(1→3)βGlcNAc-OR] and on type II structures [βGal(1→3)βGlcNAc-OR—LacNAc-OR] still permit the use of the βGal(1→3/4)βGlcNAc α(1→3/4)fucosyltransferase on the deblocked compound. The disclosures of both of these applications are incorporated herein by reference in their entirety.

i. Modification at the 2-position of GlcNAc

Modification at the 2-position of GlcNAc can be accomplished by a variety of ways. For example, the known[37] 2-azido-2-deoxy-glucose-OR compound (prepared, for example, by azidonitration of 4,5,6-triacetylglucal) can be protected at the 6 position with a removable protecting group (i.e., Si($C_6H_5$)$_2$tBu) by conventional techniques[37] and then combined with an appropriate blocked galactose compound in the manner described above to provide a mixture of blocked βGal(1→3)GlcN$_3$-OR and βGal(1→4)GlcN$_3$-OR derivatives which are readily separated by conventional techniques.

At the appropriate time during synthesis of oligosaccharide glycosides related to blood group determinants having type I or type II core structures, the azido group is reduced to an amino group which can be protected as N-trifluoroacetamido. In turn, the trifluoroacetamido group is removed at the appropriate point in the synthesis thereby unmasking the amino group.

The amino group can also be derivatized by conventional methods to provide for —$NR_{11}C(O)R_{10}$, —$NHSO_3H$, —$N=C(R_{11})_2$, —$NHCH(R_{11})_2$, —$NHR_{12}$, and —$N(R_{12})_2$ groups. For example, the —$NH_2$ group can be reacted, using conventional techniques:

with a carboxylic acid, anhydride or chloride to provide for amides. Alternatively, the desired acid can be activated, as reported by Inazu et al[43] and then reacted with the amino group. The carboxylic acid, anhydride, chloride, or activated acid is selected so as to provide for an $R_{10}$ group (i.e., as part of the —$NR_{11}C(O)R_{10}$ substituent) which is hydrogen or alkyl of from 1 to 4 carbon atoms, with an aldehyde or ketone (of from 1 to 4 carbon atoms) at controlled pH to form an imine [—$N=C(R_{11})_2$]

which upon reduction (e.g., with sodium cyanoborohydride) provides for an alkylamine substituent [i.e., —NHCH($R_{11}$)$_2$] as reported by Bernotas et al.[44], with a cyclic carbonate such as ethylene carbonate or propylene carbonate which ring opens upon reaction with the amine to form a carbamate group having an HO-alkylene-OC(O)NH— substituent where alkylene is from 2 to 4 carbon atoms as reported by Wollenberg et al.[45], U.S. Pat. No. 4,612,132, with a chloroformate [i.e., ClC(O)OR$_{13}$] in the manner disclosed by Greig et al.[46]. In this case, the chloroformate has an R$_{13}$ group which is alkyl of from 1 to 4 carbon atoms, with O═C(O—C$_6$H$_4$-pNO$_2$)$_2$ which leads to an activated intermediate which is then reacted with an amine (HNR$_{14}$R$_{15}$) to provide for ureas [—NHC(O)NR$_{14}$R$_{15}$] as described by Piekarska-Bartoszewicz et al.[47], with trimethylamine, sulfur trioxide (SO$_3$) so as to form the —NHSO$_3$H group as described by Petitou[48], and with derivatized formic acid or other materials to form a formamide (—NH—CHO)[49] which can be further functionalized to the isocyano (—N═C═O) and reduced to the deoxy derivative by tributyltin hydride (Bu$_3$SnH)[49].

Alternatively, the 2-deoxy (R$_2$═H) and 2-alkoxy glucose derivatives [i.e., derivatives of GlcNAc where the NAc has been replaced by —H (deoxy) or by an —OR$_{12}$ (alkoxy)] are prepared using a synthetic scheme similar to that recited by Trumtez et al.[49] Specifically, the known 3,4,6-triacylated 1,2-ortho ester of glucose is deacylated under conventional conditions to give the 1,2-ortho ester of glucose. This compound is then converted to the 3,4,6-tribenzyl 1,2-ortho ester of glucose using conventional techniques. The 1,2-ortho ester of the resulting compound is then opened by conventional techniques to provide a protected glycosyl donor such as the 1-α-bromo-2-acetyl-3,4,6-tribenzyl derivative of glucose. This 1-α-bromo derivative is then converted to the glycoside (—OR) by conventional techniques and the 2-acetyl group is then removed. The 2-position is now ready for formation of the 2-deoxy by conventional methods such as first treating with carbon disulfide and methyl iodide in the presence of one equivalent of a base to form the —C(S)SCH$_3$ derivative, followed by reaction with tributyltin hydride or for the preparation of the 2-alkoxy. The remaining protecting groups are removed so as to provide for 2-deoxyglucose glycoside or a 2-alkoxyglucose glycoside which can then be derivatized in the manner described above and illustrated in FIG. 1 without the need to form the aglycon.

ii. Modification at the 6-Position of GlcNAc

As shown in FIG. 26, the 6-deoxy derivative of GlcNAc-OR is synthesized from a known benzylidene ring blocked saccharide (8-methoxycarbonyloctyl-2-acetamido-4,6-O-benzylidene-2-deoxy-β-D-glucopyranoside)[50] which is protected at the 3-hydroxy position with a removable benzoyl blocking group (Bz) by reaction with benzoic anhydride or benzoyl chloride in pyridine. Further conversion of this compound by reaction with N-bromosuccinimide and barium carbonate in carbon tetrachloride (CCl$_4$) at 65° C. leads to the 3,4-dibenzoyl-6-bromo-GlcNAc-OR compound. This compound is, in turn, converted to the 3,4-dibenzyl-6-deoxy-GlcNAc-OR by reaction with (C$_4$H$_9$)$_3$SnH in the presence of AIBN (azo bis-isobutyronitrile) at 110° C. followed by treatment with methanol/sodium methoxide. This compound can then be deprotected by conventional techniques to provide for the 6-deoxyGlcNAc-OR glycoside which can then be derivatized in the manner described above and illustrated in FIGS. 17A and 17B without the need to form the aglycon as shown in FIGS. 17A and 17B.

The 6-azido derivatives of GlcNAc-OR can be prepared in the manner described in FIG. 25. Specifically, GlcNAc-OR, compound 87, is converted to the p-methoxybenzylidene blocked compound 88 by reaction with (CH$_3$O)$_2$CH—C$_6$H$_4$-p-OCH$_3$. This compound is then protected at the 3-hydroxyl position by reaction with 4-CH$_3$O—C$_6$H$_4$—CH$_2$Br to provide for compound 89 where X is 4-CH$_3$O—C$_6$H$_4$—CH$_2$—. Compound 89 is partially deprotected at the 4 and 6 positions by reaction with acetic acid (AcOH) in water at about 45° C. to provide for compound 90. The 6-mesylate, compound 91, is prepared by reacting compound 90 with mesyl chloride in pyridine (MsCl/py). The 6-azido derivative, compound 92, is then formed by reaction with sodium azide in dimethylformamide (DMF) and removal of the 3-blocking group with dichlorodicyanoquinone (DDQ) yields compound 93.

The 6-mesyl compound 91 can also be derivatized to any of a number of 6-substituents including alkoxy substituents, and the like by well known chemistry.

The 6-azido compound 92 can be derivatized to the 6-amino at an appropriate point in the synthesis of the oligosaccharide glycosides related to blood group determinants having a type I or type II core structure in the manner described above. The 6-amino derivative can then be further functionalized by conventional methods to provide for —NR$_5$C(O)R$_4$, —NHSO$_3$H, —N═C(R$_5$)$_2$, —NHCH(R$_5$)$_2$, —NHR$_6$ and —N(R$_6$)$_2$. For example, the —NH$_2$ group can be reacted, using conventional techniques:

a carboxylic acid, anhydride or chloride to provide for amides. Alternatively, the desired acid can be activated, as reported by Inazu et al[43] and then reacted with the amino group. The carboxylic acid, anhydride, chloride, or activated acid is selected so as to provide for an R$_4$ group (i.e., as part of the —NR$_5$C(O)R$_4$ substituent) which is hydrogen or alkyl of from 1 to 4 carbon atoms, with an aldehyde or ketone (of from 1 to 4 carbon atoms) at controlled pH to form an imine [—N═C(R$_5$)$_2$] which upon reduction (e.g., with sodium cyanoborohydride) provides for an alkylamine substituent [i.e., —NHCH(R$_5$)$_2$] as reported by Bernotas et al.[44], with a cyclic carbonate such as ethylene carbonate or propylene carbonate which ring opens upon reaction with the amine to form a carbamate group having an HO-alkylene-OC(O)NH— substituent where alkylene is from 2 to 4 carbon atoms as reported by Wollenberg et al.[45], U.S. Pat. No. 4,612,132, with a chloroformate [i.e., ClC(O)OR$_7$] in the manner disclosed by Greig et al.[46]. In this case, the chloroformate has an R$_7$ group which is alkyl of from 1 to 4 carbon atoms, with O═C(O—C$_6$H$_4$-pNO$_2$)$_2$ which leads to an activated intermediate which is then reacted with an amine (HNR$_8$R$_9$) to provide for ureas [—NHC(O)NR$_8$R$_9$] as described by Piekarska-Bartoszewicz et al.[47], with trimethylamine, sulfur trioxide (SO$_3$) at pH 9.5 so as to form the —NHSO$_3$H group as described by Petitou[48,] and with derivatized formic acid or other materials to form a formamide (—NH—CHO)[49] which can be further functionalized to the isocyano (—N═C═O) and reduced to the deoxy derivative by tributyltin hydride (Bu$_3$SnH)[49].

The 6-alkoxy derivatives of GlcNAc can be prepared in the manner described in FIG. 26. Specifically, GlcNAc-OR, compound 87, is reacted with $C_6H_5CH(OCH_3)_2$ in an acidic medium in acetonitrile to provide for the 4,6-diprotected benzylidene compound 94. In turn, compound 94 can be reacted with benzyl (Bn) bromide and sodium hydride in the presence of dimethylformamide at around 0° C. to provide for a benzyl protecting group at the 3-position, i.e., compound 95. Deprotection at the 4,6 positions by contacting compound 95 with acetic acid and water at about 80°–90° C. provides for compound 96. Reaction of compound 96 with dibutyltin oxide [$(Bu)_2SnO$] and $R_6Br$ provides for the 6-alkoxy compound 97. Conventional deprotection of the benzyl group with hydrogen in palladium/carbon yields compound 98.

In another embodiment, compound 94 can be reacted with [$C_6H_5C(O)]_2O$ in pyridine to provide for a benzoyl protecting group (Bz) at the 3-position, i.e., compound 99. Reaction of compound 99 with N-bromosuccinimide in carbon tetrachloride yields the 6-bromo compound 100. Compound 100 can be reacted with tributyltin hydride [$(Bu)_3SnH$] in toluene to provide for the 6-deoxy compound 100b which after conventional deprotection of the benzoyl groups with sodium methoxide in methanol gives the 6-deoxy compound 100c.

The 6-$SR_6$ compounds are prepared from the 6-mesyl derivative, compound 91, by reaction with potassium thioacetate, $CH_3C(O)S^-K^+$, to give the thioacetate derivative at the 6-position. This derivative is then treated with mild base to produce the 6-SH derivative. The 6-SH can be reacted with an alkyl halide (e.g., $CH_3Br$) to provide the —$SR_6$ derivatives which, in turn, can be partially or fully oxidized to the 6-sulfone or the 6-sulfoxide derivatives, —$S(O)R_6$ and —$S(O)_2R_6$ where $R_6$ is alkyl of from 1 to 4 carbon atoms.

C1(ii) Alternative Methods For Preparing Oligosaccharide Glycosides Related to Blood Group Determinants Having a Type I or Type II Core Structure Alternative methods for preparing oligosaccharide glycosides related to blood group determinants having type I or type II core structures can be employed using known chemistry. Additionally, certain of the type I or type II core structures can be enzymatically converted to Lewis$^A$ and Lewis$^X$ structures, to sialylated type I or type II structures, and to sialyl Lewis$^A$ and sialyl Lewis$^X$ structures.

The following discussion is directed to the preparation of sialyl Lewis$^A$ and sialyl Lewis$^X$ structures modified at the 2 and/or 6 positions of the N-acetylglucosamine (GlcNAc) unit and/or at the 2 position of the galactose unit of these structures. It being understood, however, that one skilled in the art could readily prepare modified Lewis$^A$ and Lewis$^X$ structures or sialylated type I or type II structures merely by omitting the sialylation step in the case of Lewis$^A$ and Lewis$^X$ and merely by omitting the fucosylation step in the case of sialylated type I or type II structures.

Derivatives of sialyl Lewis$^X$, modified at the 2 and/or 6 positions of the N-acetylglucosamine unit and/or at the 2-position of the galactose unit are prepared by first synthesizing the βGal(1→4)βGlcNAc-OR backbone or the βGal(1→3)βGlcNAc-OR backbone derivatized at the 2 and/or 6 positions of the N-acetylglucosamine unit and/or at the 2 position of the galactose unit. These backbones are then sequentially sialylated and fucosylated using the βGal(1→3/4)βGlcNAc α(2→3)sialyltransferase and the βGal(1→3/4) βGlcNAc α(1→3/4)fucosyltransferase or other suitable sialyl- or fucosyltransferases. In this regard, it has been previously disclosed that this sialyltransferase requires the presence of a hydroxyl group at the 3, 4, and 6 positions of galactose, and a hydroxyl group at the 4-position of the GlcNAc unit in type I structures or at the 3-position of the GlcNAc unit in type II structures[11,14]. Likewise, it has been previously disclosed that this fucosyltransferase requires the presence of hydroxyl groups at the 6-position of the galactose unit and at the 4-position of the GlcNAc unit for type I structures and at the 3-position of the GlcNAc unit for type II structures[11,14]. However, both the βGal(1→3/4)βGlcNAc α(2→3)sialyltransferase and the βGal(1→3/4)βGlcNAc α(1→3/4)fucosyltransferase tolerate substitution at the 2,6 positions of the GlcNAc unit and some substitution at the 2 position of the galactose unit in type I and type II structures[11,14].

The use of such sialyltransferases and fucosyltransferase provides for the facile synthesis of analogues of sialyl Lewis$^X$ and sialyl Lewis$^A$ including those having modification on either the sialyl and/or fucosyl groups. For example, use of such sialyltransferases permits the transfer of Neu5Ac or compatible analogues of Neu5Ac to the backbone structure[9]; whereas the use of such fucosyltransferases permits the transfer of fucose and compatible analogues thereof to these backbone structures.

General schemes for these alternative methods for preparing sialyl Lewis$^X$ derivatives and, in some cases, sialyl Lewis$^A$ derivatives are set forth in FIGS. 27A–33. It being understood that where only sialyl Lewis$^X$ is disclosed, similar methods can be used to prepare sialyl Lewis$^A$ derivatives as evidenced by the Examples.

Specifically, trisaccharide 104 set forth in FIG. 27 is a known compound and is disclosed by Ratcliffe, et al[12,37]. This compound is then derivatized by conventional steps well known in the art to provide for a trisaccharides 111b, 111c, and 111d described in the Examples.

Specifically, hydrogenation ($H_2$) of the benzyl ester (—COOBn) of trisaccharide 104 at atmospheric pressure in ethyl acetate ($CH_3CO_2C_2H_5$) in the presence of 5% palladium on carbon (Pd/C), followed by de-O-acetylation with sodium methoxide in methanol ($CH_3ONa$, $CH_3OH$) provided trisaccharide 111b. The use of ethyl acetate as solvent is recommended in the first step in order to leave the 2-azido group untouched. Only a very small amount of impurity is formed in this step which can be separated by conventional separation techniques (e.g., chromatography).

Alternatively, reduction of the 2-azido group of tetrasaccharide 104 by hydrogen sulfide ($H_2S$) in a mixture of pyridine, water and triethylamine provided the 2-amino trisaccharide 109. Reduction of the benzyl ester (—COOBn) followed by de-O-acetylation (as described above) lead to trisaccharide 111c.

Trisaccharide 111d is prepared by first conducting N-propionylation of trisaccharide 109 using propionic anhydride [$(CH_3CH_2CO)_2O$] in methanol ($CH_3OH$) to provide for trisaccharide 110. Trisaccharide 110 was accompanied by a small amount of the corresponding 4-O-propionylated material which can be separated by conventional separation techniques (e.g., chromatography). Removal of the acetyl and benzyl protecting groups, as indicated above, provided the trisaccharide 111d.

Trisaccharide 111c can also be derivatized by conventional methods to provide for —$NR_{11}C(O)R_{10}$, —$NHSO_3H$, —$N=C(R_{11})_2$, —$NHCH(R_{12})_2$, —$NHR_{12}$, —$N(R_{12})_2$, and an amino acid or polypeptidyl residue derivatives by conventional methods. For example, the —$NH_2$ group can be reacted, using conventional techniques:

with a carboxylic acid, anhydride or chloride to provide for amides. Alternatively, the desired acid can be activated, as reported by Inazu et al[43] and then reacted with the amino group. The carboxylic acid, anhydride, chloride, or activated acid is selected so as to provide for an $R_{10}$ group (i.e., as part of the —$NR_{11}C(O)R_{10}$ substituent) which is hydrogen or alkyl of from 1 to 4 carbon atoms.

- with an aldehyde or ketone (of from 1 to 4 carbon atoms) at controlled pH to form an imine [—N=C($R_{11}$)$_2$] which upon reduction (e.g., with sodium cyanoborohydride) provides for an alkylamine substituent [i.e., —NHCH($R_{11}$)$_2$] as reported by Bernotas et al.[44].

- with a cyclic carbonate such as ethylene carbonate or propylene carbonate which ring opens upon reaction with the amine to form a carbamate group having an HO-alkylene-OC(O)NH— substituent where alkylene is from 2 to 4 carbon atoms as reported by Wollenberg et al.[45], U.S. Pat. No. 4,612,132,

- with a chloroformate [i.e., ClC(O)O$R_{13}$] in the manner disclosed by Greig et al.[46]. In this case, the chloroformate has an $R_{13}$ group which is alkyl of from 1 to 4 carbon atoms.

- with O=C(O—$C_6H_4$-p$NO_2$)$_2$ which leads to an activated intermediate which is then reacted with an amine (HN$R_{14}R_{15}$) to provide for ureas [—NHC(O)N$R_{14}R_{15}$] as described by Piekarska-Bartoszewicz et al.[47],

- with trimethylamine, sulfur trioxide ($SO_3$) so as to form the —NHSO$_3$H group as described by Petitou[48], and with derivatized formic acid or other materials to form a formamide (—NH—CHO)[49] which can be further functionalized to the isocyano (—N=C=O) and reduced to the deoxy derivative by tributyltin hydride ($Bu_3SnH$)[49].

- with an appropriate form of an amino acid or polypeptide moiety activated at the acid group as reported by Bodanszky et al.[51];

Trisaccharides 111b, 111c, and 111d and derivatives derived therefrom can then be fucosylated by contacting the appropriate trisaccharide with βGal(1→3/4)βGlcNAc e(1→3/4)fucosyltransferase in the presence of GDP-fucose (GDP-Fuc) so as to provide tetrasaccharides 112b, 112c, and 112d which are analogues of sialyl Lewis$^x$.

FIG. 28 illustrates a general scheme for preparing the sialyl Lewis$^x$ analogues from an appropriately derivatized βGal(1–4)βGlcNAc-OR structure by the sequential enzymatic sialylation and fucosylation of this structure. FIG. 28 only illustrates modification at the 2 or 6 position of the N-acetylglucosamine (GlcNAc) structure. However, it is understood that the modifications can be combined to provide for modification at both the 2 and 6 position of the N-acetylglucosamine. It is further understood that while FIG. 28 illustrates only a 2-hydroxyl group at the 2 position of the galactose, this position may also be substituted with hydrogen or fluoro. Such substituted galactose compounds are known in the art. Substitution of these galactose compounds in the reactions depicted in the figures lead to these modified galactose units in the sialyl Lewis$^x$ analogues.

Enzymatic Sialylation

In FIG. 28, sialylation is accomplished by use of the βGal(1→3/4)βGlcNAc α(2→3)sialyltransferase [i.e., βGal (1→3/4)βGlcNAc α(2→3)ST]. The enzymatic transfer of sialic acid onto the 3-position of galactose to form α-sialyl (2→3)βGal- requires the prior synthesis (i.e., activation) of its nucleotide (CMP) derivatives. Activation of sialic acid is usually done by using the enzyme CMP-sialic acid synthase which is readily available and the literature provides examples of the activation of various analogues of sialic acid such as 9-substituted Neu5Ac[52,53,54,55–57], 7-epi-Neu5Ac[58], 7,8-bis-epi-Neu5Ac[58], 4-O-methyl-Neu5Ac[59], 4-deoxy-Neu5Ac[60], 4-acetamido-Neu5Ac[62], 7-deoxy-Neu5Ac[56], 4,7-dideoxy-Neu5Ac[56], the 6-thio derivatives of Neu5Ac[61] and Neu5OH (KDN).

The resulting CMP-sialic acid analogue, illustrated in FIG. 28 as the CMP derivative of Neu5Ac (i.e., CMP-Neu5Ac), is then combined with the derivatized βGal(1→4) βGlcNAc-OR compound in the presence of the βGal(1→3/4)βGlcNAc α(2→3)sialyltransferase under conditions wherein sialic acid is transferred to the 3 position of the galactose to form a αNeu5Ac(2-3)βGal- linkage. Suitable conditions, known in the art, include the addition of the sialyltransferase to a mixture of the derivatized βGal(1→4) βGlcNAc-OR compound and of the CMP-sialic acid in a appropriate buffer such as 0.1M sodium cacodylate in appropriate conditions of pH and temperature such as at a pH of 6.5 to 7.5 and a temperature between 25° and 45° C., preferably 35°–40° C., while incubating for 12 hours to 4 days. The resulting sialylated product can be isolated and purified using conventional methodology comprising HPLC, ion exchange-, gel-, reverse-phase-or adsorption chromatography.

Enzymatic fucosylation

In FIG. 28, fucosylation is accomplished by use of βGal(1→3/4)βGlcNAc α(1→3/4)fucosyltransferase [i.e., βGal(1-3/4)βGlcNAc α(1→3/4)FT]. The enzymatic transfer of fucose onto the 3-position of GlcNAc to form αFuc(1→3) βGlcNAc requires the prior synthesis of its nucleotide (GDP) derivatives. Synthesis of GDP-fucose is preferably accomplished in the manner recited by Jiang et al.[42] and which is exemplified in the examples hereunder.

GDP-fucose (GDP-Fuc) is then combined with the sialylated βGal(1→4)βGlcNAc-OR compound in the presence of the βGal(1→3/4)βGlcNAc α(1→3/4)fucosyltransferase under conditions wherein fucose is transferred to the 4 position of the GlcNAc unit of the sialylated βGal(1→4) βGlcNAc-OR compound so as to form a αNeu5Ac(2→3) βGal(1→4)[αFuc(1→3)]βGlcNAc-OR compound (when the sialic acid is αNeu5Ac) derivatized in the βGal(1→4) βGlcNAc backbone. Suitable conditions, known in the art, include the addition of the fucosyltransferase to a mixture of the derivatized αNeu5Ac(2→3)βGal(1→4)βGlcNAc-OR compound (when the sialic acid is αNeu5Ac) and of the GDP-fucose in a appropriate buffer such as 50 mM sodium cacodylate in appropriate conditions of pH and temperature such as at a pH of 6.5 and a temperature between 30° and 45° C., preferably 35°–40° C., while incubating for 12 hours to 4 days. The resulting sialylated and fucosylated product can be isolated and purified using conventional methodology comprising HPLC, ion exchange-, gel-, reverse-phase- or adsorption chromatography.

In the case of trisaccharides 111b–d, preparative fucosylation of these trisaccharides was performed according to Palcic et al.[25] The products were purified as indicated therein. The structures of trisaccharides 111b–d were confirmed by $^1$H-n.m.r. at 300 MHz and those of the resulting sialyl Lewis$^x$ compounds 112b–d by $^1$H-n.m.r. at 500 MHz FIGS. 29A and B illustrate the chemical synthesis of specific disaccharide derivatives of βGal(1→3)βGlcNAC-OR and βGal(1→4)βGlcNAc-OR structures starting with saccharide monomers. In this regard, the chemical coupling of the galactose and GlcNAc-OR units results in the formation of both βGal(1→3)βGlcNAc-OR (type I backbone) and βGal(1→4)βGlcNAc-OR (type II backbone) which can be separated by conventional purification techniques (i.e., chromatography).

Figure 29B:
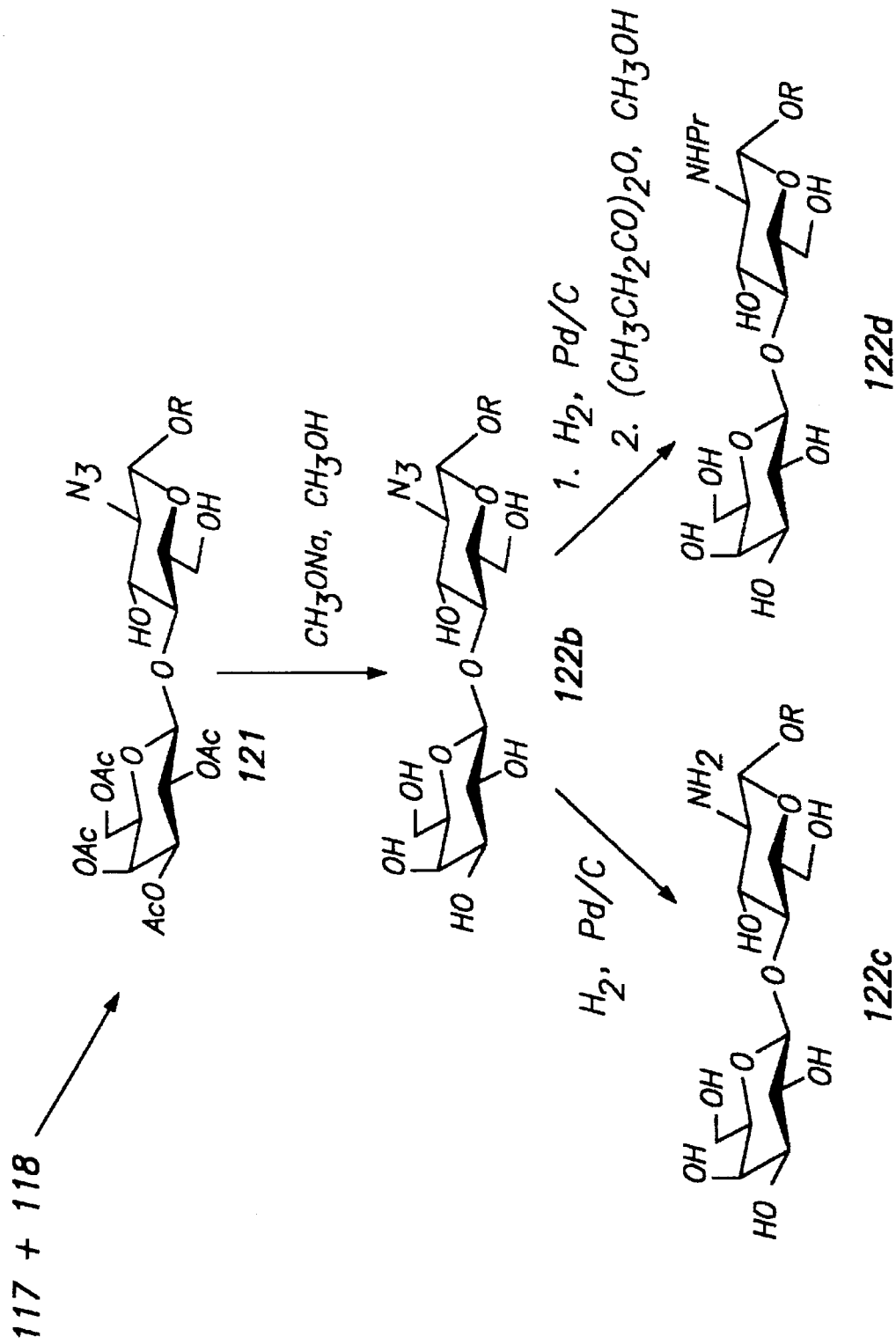

Specifically, in FIGS. 29A and 29B, the known[12,37] 2-azido compound 116 is protected at the 6 position with a removable protecting group (i.e., Si(C$_6$H$_5$)$_2$tBu) by conventional techniques[12,37]. This derivative 117 is then combined with a fully acylated derivative of galactose 118 in the presence trimethylsilyltrifluoromethanesulfonate (TMSOTf) and afterwards ammonium chloride (NH$_4$Cl), potassium fluoride (KF) in tetrahydrofuran are added. The reaction yields a mixture of type I and type II derivatives (i.e., βGal(1→3)βGlcNAc-OR and βGal(1→4)βGlcNAc-OR derivatives), compounds 119 and 121, which are separated by conventional methods such as chromatography.

Either derivative 119 or 121 is then deprotected with a mixture of sodium methoxide in methanol (CH$_3$ONa/CH$_3$OH) to provide for derivative 120b or 122b respectively which can be converted to either the amine derivative 120c or 122c respectively or the propionate (Pt) derivative 120d or 122d respectively following similar procedures set forth above for trisaccharides 111c and 111d.

Alternatively, derivative 119 or 121 can be tosylated by conventional techniques to provide for a tosyl group at the 6-position of the GlcNAc derivative. The tosyl derivative can then be used to form a 6-halo substituent by a substitution reaction using the appropriate nucleophilic reagent or a 6-alkoxy substituent by alkylation with an alkyl halide in the presence of bis-tributyltin hydride, and the like.

Additionally, while not shown in FIG. 29, the 2-deoxy (R$_2$=H) and 2-alkoxy glucose derivatives are prepared using a synthetic scheme similar to that recited by Trumtez, et al.[49] Specifically, the known 3,4,6-triacylated 1,2-ortho ester of glucose is deacylated under conventional conditions to give the 1,2-ortho ester of glucose. This compound is then converted to the 3,4,6-tribenzyl 1,2-ortho ester of glucose using conventional techniques. The 1,2-ortho ester of the resulting compound is then opened by conventional techniques to provide a protected glycosyl donor such as the 1-α-bromo-2-acetyl-3,4,6-tribenzyl derivative of glucose. This 1 α-bromo derivative is then converted to the glycoside (—OR) by conventional techniques and the 2-acetyl group is then removed. The 2-position is now ready for formation of the 2-deoxy by conventional methods (e.g., first treating with carbon disulfide and methyl iodide in the presence of one equivalent of a base to form the —C(S)SCH$_3$ derivative, followed by reaction with tributyltin hydride) or for the preparation of the 2-alkoxy.

Figure 30A:
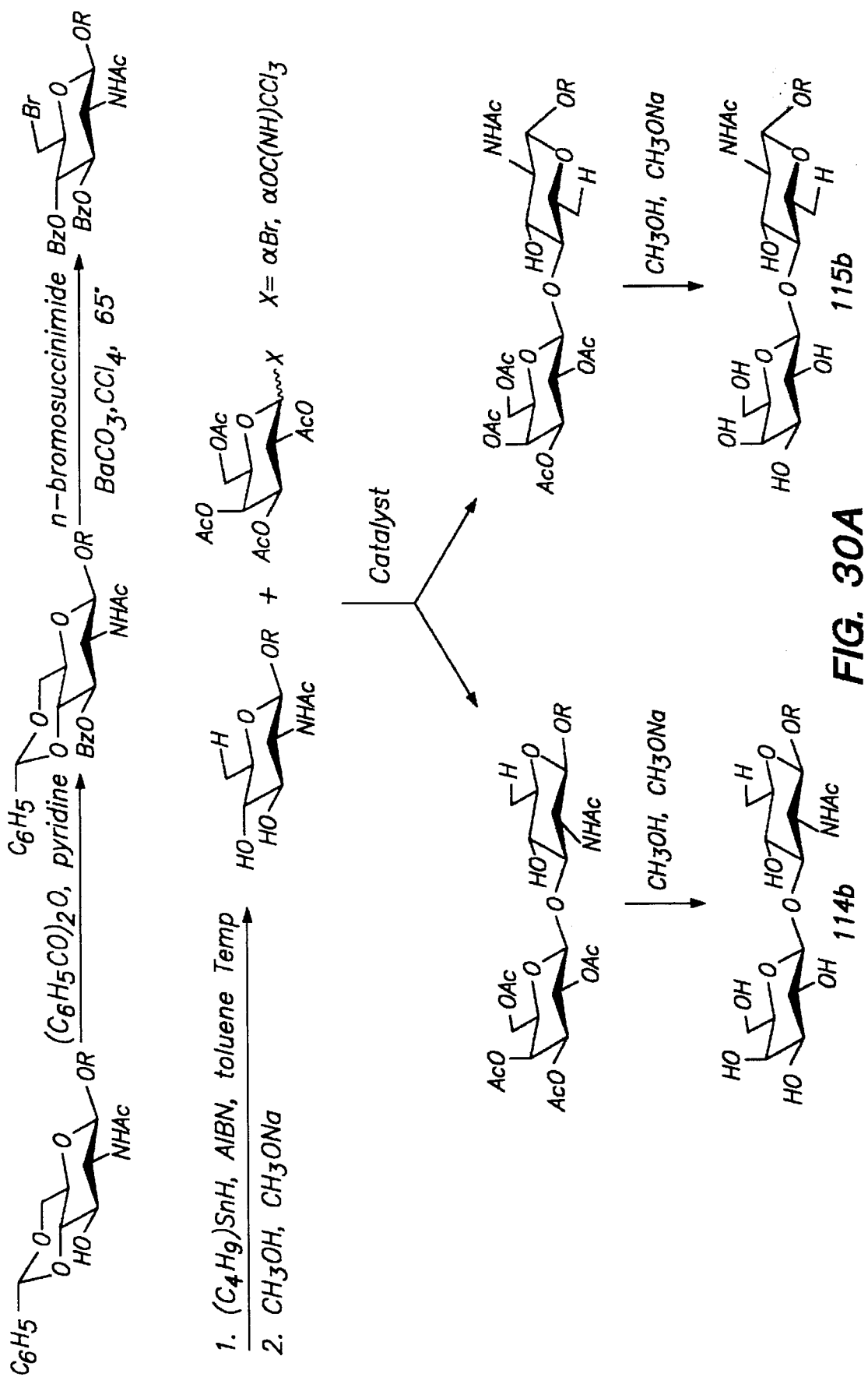
Figure 30B:
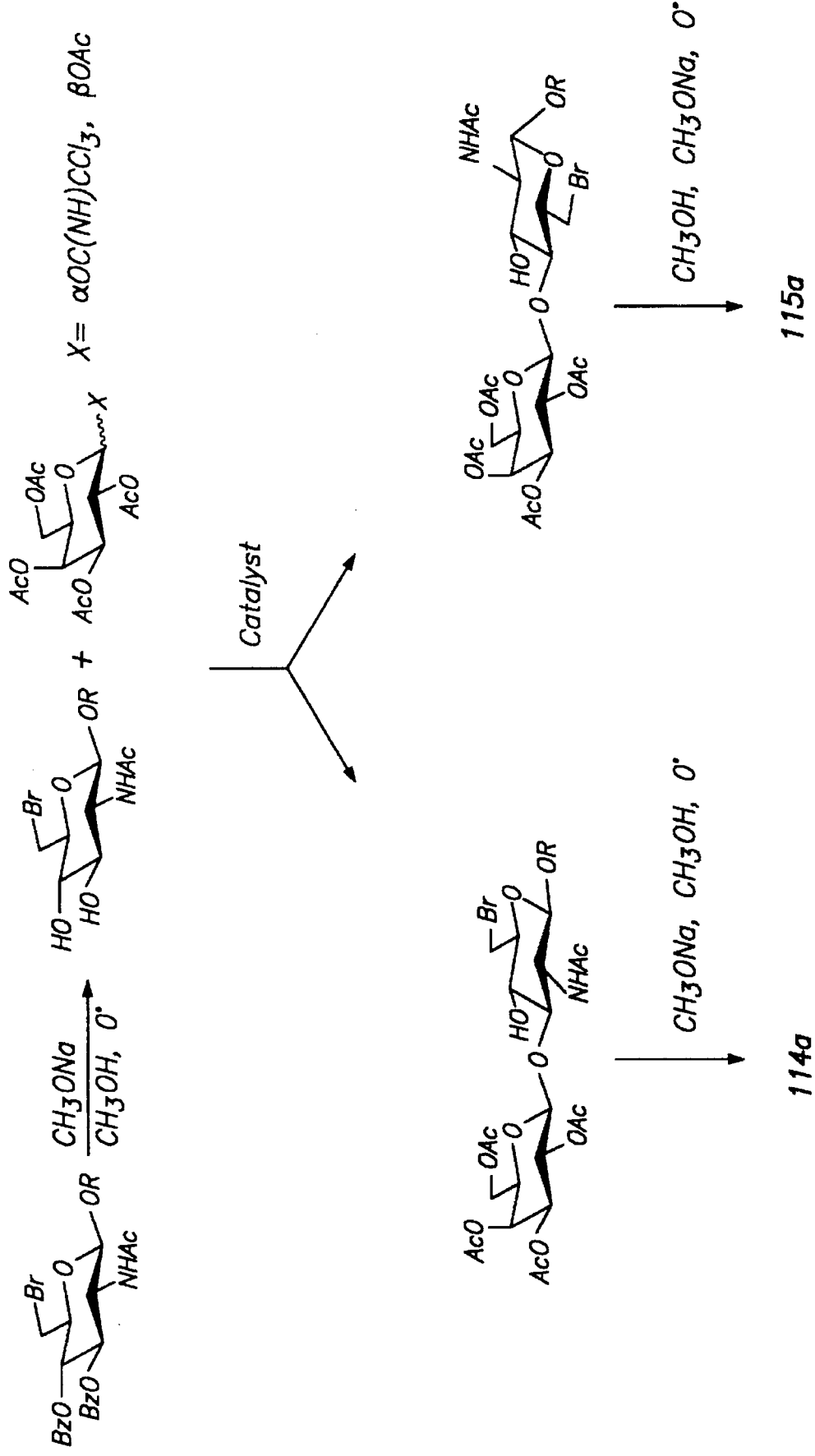

FIGS. 30A and 30B illustrate the synthesis of the 6-deoxy derivatives on the GlcNAc unit of βGal(1→3)βGlcNAc-OR and βGal(1→4)GlcNAc-OR, compounds 114b and 115b, and the 6-bromo derivative on the GlcNAc unit of βGal (1→4)GlcNAc-OR, compound 115a. The 6-deoxy compounds 114b and 115b are synthesized from a known benzylidene ring blocked saccharide (8-methoxycarbonyloctyl 2-acetamido-4,6-O-benzylidene-2-deoxy-β-D-glucopyranoside) which is protected at the 3-hydroxy position with a removable benzoyl blocking group (Bz) by reaction with benzoic anhydride in pyridine. Further conversion of this compound by reaction with N-bromosuccinimide and barium carbonate in carbon tetrachloride (CCl$_4$) at 65° C. leads to the 3,4-dibenzoyl-6-bromo-GlcNAc compound. This compound is, in turn, converted to the 3,4-dibenzoyl-6-deoxy-GlcNAc by reaction with (C$_4$H$_9$)$_3$SnH in the presence of AIBN (azo bis-isobutyronitrile) at 110° C. followed by treatment with methanol/sodium methoxide. The resulting 6-deoxy-GlcNAc glycoside is reacted with a known 2,3,4,6-tetraacylated derivative of galactose having an appropriate leaving group at the 1 position to permit formation of a β linkage. Suitable leaving groups include α-bromo and α-trichloroacetamidate [α-C(=NH)CCl$_3$]. The reaction is conducted in the presence of a catalyst which facilitates β linkage formation. Suitable catalysts include silver trifluoromethane sulfonate in the presence of tetra-N-methyl urea when the precursor is a galactosyl bromide; and boron trifluoride etherate when the donor is galactosyl trichloroacetamidate. The reaction leads to a mixture βGal(1→3) βGlcNAc-OR and βGal(1→4)GlcNAc-OR protected compounds which can be isolated and separated by conventional techniques (e.g., chromatography). Removal of the removal protecting groups then leads to compound 114b or 115b.

As also shown in FIG. 30B, the 6-bromo-GlcNAc glycoside precursors can be reacted with a known 2,3,4,6-tetraacylated derivative of galactose having an appropriate leaving group at the 1 position to permit formation of a β linkage so as to provide for a route to the 6-bromo compounds. Suitable leaving groups include αC(=NH)CCl$_3$ and the reaction is conducted in the same manner as that employed to prepare compound 115a (i.e., βGal(1→4) βGlcNAc-OR having a bromo group at the 6-position of the GlcNAc unit).

FIGS. 31A & B and 32A & B illustrate the chemical synthesis of α-sialyl(2→3)βGal(1→4)βGlcNAc-OR and α-sialyl(2→3)βGal(1→3)βGlcNAc-OR derivatives modified at the 6-position (FIGS. 31A & B) or the 2-position (FIG. 32) of the GlcNAc derivative by using one of the procedures described in Ratcliffe et al.[12,37]

Specifically, as illustrated in FIGS. 31A & B, the appropriate 6-substituted derivatives of GlcNAc-OR are prepared as above from either known[50] glycoside 127 or from the known benzylidene ring blocked saccharide protected form depicted in FIGS. 30A and 30B (which is derived from glycoside 127) as described in detail above. The 6-derivatized blocked material (as depicted in FIG. 5) is then deblocked using conventional methods to provide for compound 128 which is a 6-derivative of GlcNAc.

Compound 128 is then combined with disaccharide 129b in a manner known in the art[12,37] to provide for trisaccharides 130 and 131 having conventional removable blocking groups on the Neu5Ac and the galactose units. Specifically, compound 129b is synthesized from the disaccharide 129a by known methods and is then reacted with compound 128 in the presence of an appropriate catalyst such as [BF$_3$.O (C$_2$H$_5$)$_2$] to give a mixture of the corresponding trisaccharides 130 and 131, respectively. The ratio of compounds 130:131 will depend upon the nature of the substituent R$_1$ and on the reaction conditions. In any event, trisaccharides 130 and 131 are typically separated and purified by conventional techniques including chromatography. Removal of the blocking groups on trisaccharides 130 and 131 is also conventional (i.e., addition of hydrogen in the presence of palladium on carbon followed by treatment with sodium methoxide in the presence of methanol) and leads to the trisaccharide αNeu5Ac(2→3)βGal(1→3)βGlcNAc-OR 123 and αNeu5Ac(2→3)βGal(1→4)βGlcNAc-OR 125. Fucosylation of trisaccharides 123 and 125 is preferably conducted with GDP-fucose (GDP-Fuc) in the presence of βGal(1→3/4)βGlcNAc α(1→3/4)fucosyltransferase [βGal(1→3/4) βGlcNAc α(1→3/4)FT] to lead to sialyl Lewis$^a$ analogues 124 or to sialyl Lewis$^x$ analogues 126 modified at the 6-position of the GlcNAc unit.

When the R$_1$ substituent is azido (—N$_3$—the synthesis of which is described below), this substituent can be further functionalized to other appropriate R$_1$ substituents as described above either at the monosaccharide level (as shown in FIGS. 31A and B) or at the trisaccharide 130 or 134 level. For example, if the $R_1$ group of trisaccharide 130 or 134 is an azido group, then this group can be functionalized in trisaccahride 130 or 131 to provide for the amino, amido, imino, etc. substituents described above.

In any event, functionalization is generally at a point in the synthesis where the to-be formed functional group does not interfere with any of the further intended reactions. For example, if an R functional group in monosaccharide 128 would interfere with the coupling reaction between disaccharide 129b and monosaccharide 128 then this functional group can be introduced into trisaccharide 130 or 131.

In FIGS. 32A and 32B, the appropriate 2-substituted 6-protected derivatives of GlcNAc-OR, compound 132, are prepared, for example, from the known blocked saccharide 117 depicted in FIG. 29.

Compound 132 is then combined with disaccharide 129a or 129b using methods known in the art such as those described by Ratcliffe et al.[12,37] to provide for trisaccharides having conventional removable blocking groups on the Neu5Ac, on the Gal, and on the 6-position of the GlcNAc units. Specifically, compound 129b is synthesized from the disaccharide 129a and is then reacted with compound 132 in the presence of an appropriate catalyst such as [$BF_3 \cdot O(C_2H_5)_2$] to give a mixture of the corresponding type I or type II linked trisaccharides, respectively. The ratio of the type I to type II compounds will depend upon the nature of the substituent $R_2$ and on the reaction conditions. In any event, these trisaccharides are typically separated and purified by conventional techniques including chromatography. Fucosylation of either of these protected type I or type II trisaccharides is then accomplished by reaction of the trisaccharide with an appropriate fucosyl donor such as tetra-O-benzyl-fucopyranosyl bromide as recited by Ratcliffe et al.[12,37] Removal of the blocking groups on the resulting tetrasaccharide is also conventional and leads to sialyl Lewis$^x$ and sialyl Lewis$^A$ analogues modified at the 2-position of the GlcNAc unit.

Alternatively and in a preferred embodiment, fucosylation is accomplished by contacting the deprotected trisaccharide with GDP-fucose (GDP-Fuc) in the presence of βGal(1→3/4)βGlcNAc α(1→3/4)-fucosyltransferase [βGal(1→3/4)βGlcNAc α(1→3/4)FT] to lead to sialyl Lewis$^A$ or sialyl Lewis$^x$ analogues modified at the 2-position of the GlcNAc unit.

As noted above, when the $R_2$ substituent is azido (—$N_3$), this substituent can be further functionalized to other appropriate $R_2$ substituents as described above either at the monosaccharide level or at the protected trisaccharide level. For example, if the $R_2$ group of the protected trisaccharide is an azido group, then this group can be functionalized in this trisaccahride to provide for the amino, amido, imino, etc. substituents described above. Functionalization is generally at point in the synthesis where the to-be formed functional group does not interfere with any of the further intended reactions. For example, if an $R_2$ functional group in monosaccharide 132 would interfere with the coupling reaction between disaccharide 129b and monosaccharide 132 then this functional group can be introduced into the protected trisaccharide.

Other derivatives at the 6-position of the GlcNAc can be prepare by art recognized methods and then these compounds can be coupled to the galactose to form βGal(1→3) βGlcNAc-OR derivatives and βGal(1→4)βGlcNAc-OR derivatives which can be separated by conventional techniques (e.g., chromatography). The βGal(1→3)βGlcNAc-OR and βGal(1→4)βGlcNAc-OR derivatives, in turn, can be sialylated and fucosylated as described above, to provide the sialyl Lewis$^A$ and sialyl Lewis$^x$ derivatives modified at the 6-position.

In regard to the above, compound 128 having a chloro, bromo or iodo substituent at the 6 position can be prepared by direct halogenation of the unmodified GlcNAc-OR using the methods reported by Belkhouya et al.[63]

The 6-azido derivatives of GlcNAc-OR can be prepared in the manner described earlier in FIG. 25. As also described earlier, the 6-azido compound can be derivatized to the 6-amino at an appropriate point in the synthesis of the oligosaccharide glycoside related to blood group determinants having a type I or type II core structure in the manner described above for trisaccharide 103. Additionally, as still further described earlier, the 6-amino derivative can then be further functionalized by conventional methods to provide for —$NHSO_3H$, —$NR_5C(O)R_4$, —$N=C(R_5)_2$, —$NHCH(R_5)_2$, —$NHR_6$, and —$N(R_6)_2$ or an amino acid or polypeptidyl residue derivatives by conventional methods.

The 6-alkoxy, 6-bromo, and 6-deoxy derivatives of GlcNAc can be prepared in the manner described in FIG. 26.

The 6-fluoro compound is prepared from known chemistry[72] by reacting compound 49 with mesyl chloride in pyridine to form the 6-mesylate which upon reaction with tetraethylammonium fluoride provides for the 6-fluoro derivative. Deprotection of the 3 benzyl group by hydrogen and palladium on carbon gives the 6-deoxy 6-fluoro derivative of compound 40.

The above reaction schemes depict a number of 2- or 6-substituted derivatives of GlcNAc. However, it is apparent that these modifications can be combined to provide for substituents at both the 2- and 6-positions. When disubstitution is desired, the modifications are conducted at an appropriate point in the synthesis so as to be compatible with each other. That is to say that modification at the 2-position must be made with respect to the modification at the 6-position. This is within the ordinary skill of the art.

Additionally, as noted above, the desired modifications to the 2 and/or 6 derivatized materials (especially of the 2-azido) are done at appropriate point in the synthetic route so as not to introduce a functionality that is incompatible with subsequent reactions. However, in the case of the 6-substituted derivatives of GlcNAc, the βGal(1→4) linkage can be formed by using UOP-galactose and the commercial GlcNAc (1→4)galactosyl transferase, which is known to accept modification at the 6 position[73].

The following examples are offered to illustrate this invention and are not to be construed in any way as limiting the scope of this invention. Unless otherwise stated, all temperatures are in degrees Celsius. Also, in these examples, unless otherwise defined below, the abbreviations employed have their generally accepted meaning:

| | |
|---|---|
| Å | = Angstroms |
| AB | = AB pattern |
| ATP | = adenosine tri-phosphate |
| ax | = axial |
| bs | = broad singlet |
| BSA | = bovine serum albumin |
| bt | = broad triplet |
| CDP | = cytidine di-phosphate |
| $^{13}$C-n.m.r | = $C^{13}$ nuclear magnetic resonance |
| d | = doublet |
| dd | = doublet of doublets |
| ddd | = doublet of doublets of doublets |
| DDQ | = dichlorodicyanoquinone |
| DTH | = delayed-type hypersensitivity |
| eq | = equatorial |
| g | = gram |
| $^1$H-n.m.r. | = proton nuclear magnetic resonance |
| i.r. | = infra red |

| | |
|---|---|
| kg | = kilogram |
| L | = liter |
| m | = multiplet |
| mL | = milliliter |
| q | = quartet |
| s | = singlet |
| t | = triplet |
| t.l.c. | = thin layer chromatography |
| U | = Units |
| μm | = microns |
| AG 1 × 8 (formate form) | = ion exchange resin AG 1 × 8 (formate form) available from Bio-Rad Laboratories, Richmond, CA |
| Dowex 50 W × 8 (H⁺ form) | = ion exchange resin Dowex 50 × 8 (H⁺ form) available from Dow Chemical, Midland, MI |
| IR-120 resin (H⁺ form) | = amberlite resin available from Rohm & Haas, Philadelphia, PA |
| IR-C50 resin (H⁺ form) | = ion exchange resin IR-C50 (H⁺ form) available from Rohm & Haas, Philadelphia, PA |

Commercially available components are listed by manufacturer and where appropriate, the order number. Some of the recited manufacturers are as follows:
Amersham=Amersham Canada Limited, Ontario, Canada
BioRad=Bio-Rad Laboratories, Richmond, Calif.
Iatron=Iatron Laboratories, Tokyo, Japan
Merck=E. Merck AG, Darmstadt, Germany
Millipore=Millipore Corp., Bedford, Mass.
Pel-Freeze Biologicals=Pel-Freez, Rogers, Ark.
Pharmacia=Pharmacia Biosystems, Inc., Piscataway, N.J.
Serva=Serva Feinbiochemica, Heidelberg, Germany
Sigma=Sigma Chemical Company, St. Louis, Mo.
Waters=Waters Associates, Inc., Milford, Mass.

EXAMPLES

In the following examples, Examples A–L illustrate the suppression of antigen-induced inflammation in a mammal by administration of an oligosaccharide glycoside related to blood group determinants having a type I or type II core structure and the induced tolerance to later challenges with the same antigen and Examples 1–53 illustrate the synthesis of oligosaccharide glycosides related to blood group determinants having a type I or type II core structure as well as components thereof.

Example A—Inhibition of DTH Inflammatory Response

DTH inflammatory responses were measured using the mouse footpad swelling assay as described by Smith and Ziola[68]. Briefly, groups of Balb/c mice (about 19–20 grams each) were immunized with 10 μg of the L111 S-Layer protein, a bacterial surface protein[69] from *Clostridium thermohydrosulfuricum* L111-69 which has been shown to induce a strong inflammatory DTH response or with 100 μg of the OVA antigen containing 20 μg of the adjuvant (DDA—dimethyldioctadecylammonium bromide) which also induces a strong inflammatory DTH response. Seven days later, each group of mice was footpad-challenged with either 10 μg of L-111 S-Layer protein or with 20 μg of the OVA antigen (without adjuvant). The resulting inflammatory footpad swelling was measured with a Mitutoyo Engineering micrometer 24 hours after challenge.

To assess the effect of oligosaccharide glycosides related to blood group determinants having type I and type II core structures on the inflammatory DTH response, groups of mice received 100 μg of the following oligosaccharide glycosides related to blood group determinants having a type I or type II core structure:

1. αNeu5Ac(2→3)βGal(1→3)-[α-L-Fuc(1→4)]-βGlcNAc-OR (Sialyl Lewis^A or C19.9)
2. αNeu5Ac(2→3)βGal(1→3)βGlcNAc-OR (Sialyl Lewis^C or Sialyl Le C)
3. αNeu5Ac(2→3)βGal(1–4)βGlcNAc-OR (Sialyl LacNAc)
4. βGal(1→4)-[α-L-Fuc(1→3)]-βGlcNAc-OR (Lewis^X-OR or C19.9)
5. αNeu5Ac(2→3)βGal(1→4)-[α-L-Fuc(1→3)]-βGlcNAc-OR (Sialyl Lewis^X or Sialyl Le X)

R=—(CH₂)₈CO₂CH₃

Figure 1:
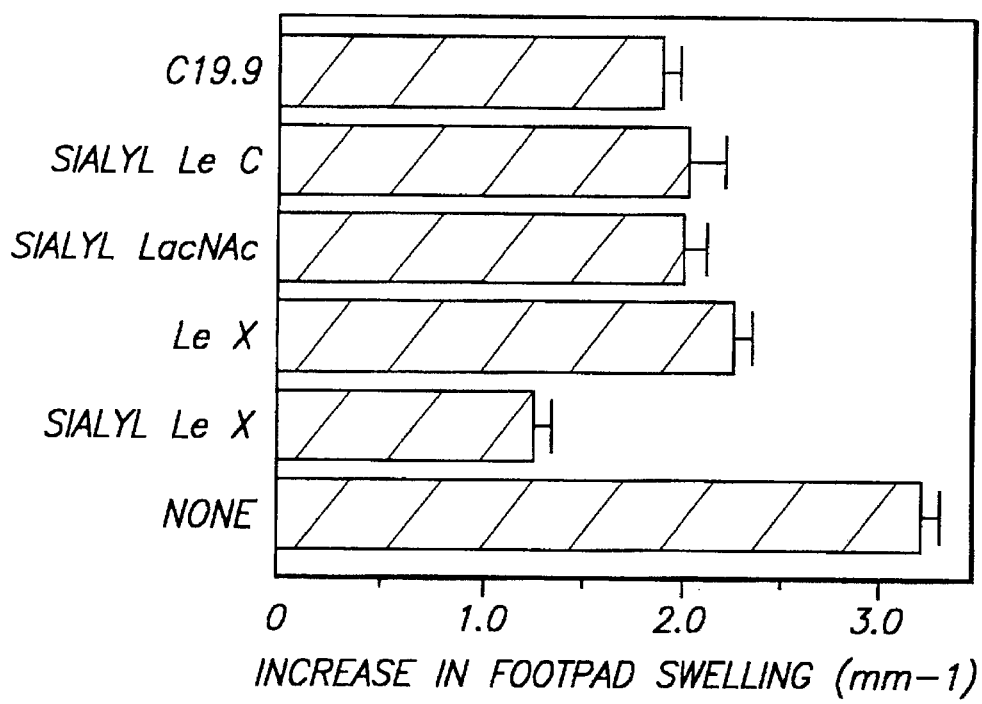
FIG. 1 illustrates the increase in footpad swelling of immunized mice arising from a DTH inflammatory response measured 24 hours after challenge with 10 μg of the L111 S-Layer protein antigen wherein some of the mice have been treated at 5 hours after the challenge with 100 μg of different oligosaccharide glycosides related to blood group determinants having type I or type II core structures.
Figure 2:
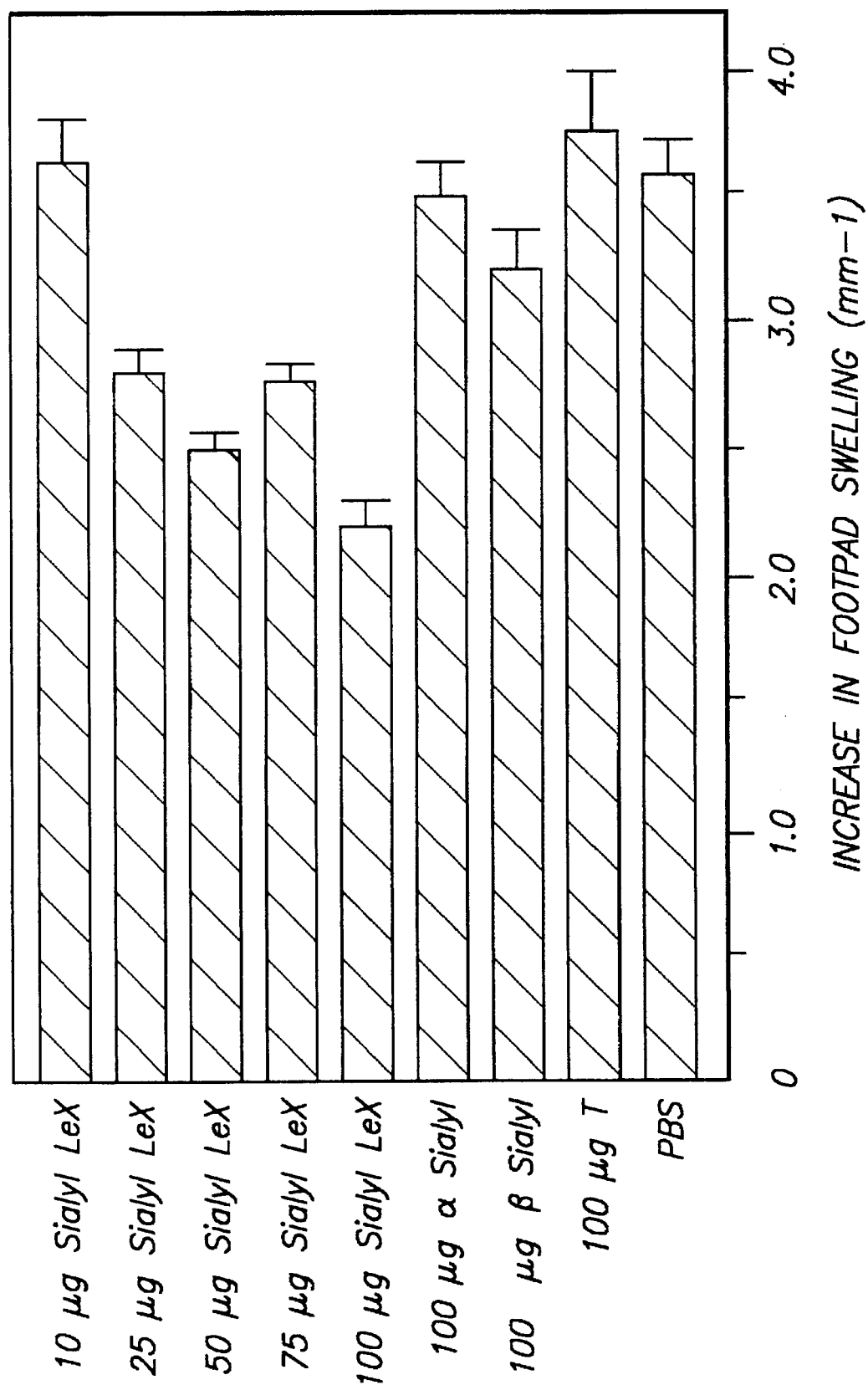
FIG. 2 illustrates the increase in footpad swelling of immunized mice arising from a DTH inflammatory response measured 24 hours after challenge with 20 μg of the L111 S-Layer protein antigen wherein some of the mice have been treated at 5 hours after challenge with various doses of different mono- and oligosaccharide glycosides including oligosaccharide glycosides related to blood group determinants having type I or type II core structures.

These compounds were injected as a solution into the tail vein, 5 hours after challenge. Control groups were left untreated or received 100 μL of phosphate-buffered saline (PBS). The results of this experiment are shown in FIG. 1. Mice injected with sialyl Lewis^X-OR had the most reduction in the footpad swelling compared to control mice. Mice injected with sialyl Lewis^A-OR, sialyl Lewis^C-OR, Lewis^X-OR, and sialyl LacNAc-OR (structures related to Sialyl-Lewis^X) also exhibited reductions in swelling compared to the footpad swelling of control mice. As shown in FIG. 2, mice injected with α-sialyl-OR, β-sialyl-OR or "T" disaccharide [βGal(1→3)αGalNAc-OR], which is neither a type I or type II structure, had essentially the extent of footpad swelling observed in control mice.

An additional oligosaccharide glycoside was tested for its ability to reduce antigen induced inflammation (DTH response) in sensitized mammals in the manner set forth above using 20 μg of the OVA antigen as the antigen challenge. The results of these experiments are set forth below:

| Antigen | Compound | Time[a] of Administration | % Reduction[b] in Inflam. |
|---|---|---|---|
| OVA | A | 5 hrs | ~76 |

[a] hours after challenge with antigen
[b] % reduction determined as per Example H below.
Compd A = αNeu5Ac(2→3)βGal(1–4)βGlcNAc(1–3)βGal(1→4)[α-L-Fuc(1–3)]βGlcNAc-OR (CD-65)

In a side-by-side analysis, 100 μg of several oligosaccharide glycosides related to blood group determinants having a type I or a type II core structure were tested for their ability to reduce antigen induced inflammation (DTH response) in sensitized mammals in the manner set forth above using 20 μg of the OVA antigen as the antigen. Administration of these oligosaccharides glycosides was conducted 5 hours after antigen challenge. The results of these experiments are set forth below:

| Compound | % Reduction[b] in Inflammation |
|---|---|
| C | ~55 |
| D | ~60 |
| E | ~24 |
| F | ~31 |
| G | ~17 |
| H | ~45 |
| I | ~53 |
| J | ~14 |

-continued

| Compound | % Reduction[b] in Inflammation |
|---|---|
| Compound C = | Sialyl Lewis[X]-OR (αNeu5Ac(2→3)βGal(1→4)-[α-L-Fuc(1→3)]-βGlcNAc-OR) |
| Compound D = | $SO_3$-Lewis[X]-OR (sulfate substituent on the 3-position of the galactose of Lewis[X]-OR) |
| Compound E = | $SO_3$-LacNAc-OR (sulfate substituent on the 3-position of the galactose of LacNAc-OR) |
| Compound F = | Sialyl Lewis[A]-OR (αNeu5Ac(2→3)βGal(1→3)-[α-L-Fuc(1→4)]-βGlcNAc-OR) |
| Compound G = | $SO_3$-Lewis[A]-OR (sulfate substituent on the 3-position of the galactose of Lewis[A]-OR) |
| Compound H = | Sialyl Lewis[C]-OR (αNeu5Ac(2→3)βGal(1→3)-βGlcNAc-OR) |
| Compound I = | $SO_3$-Lewis[C]-OR (sulfate substituent on the 3-position of the galactose of Lewis[C]-OR) |
| Compound J = | Sialyl LacNAc-OR (αNeu5Ac(2→3)βGal(1→4)-βGlcNAc-OR) (~70% pure — contains about 30% of 3 sulfate and 2,3-disulfate) |

R = —$(CH_2)_8CO_2CH_3$
[b]% reduction as per Example H below.

In another side-by-side analysis, 100 μg of several oligosaccharide glycosides related to blood group determinants having a type I or a type II core structure were tested for their ability to reduce antigen induced inflammation (DTH response) in sensitized mammals in the manner set forth above using 10 μg of the OVA antigen as the antigen. Administration of these oligosaccharides glycosides was conducted 5 hours after antigen challenge. The results of these experiments are set forth below:

| Compound | % Reduction[b] in Inflammation |
|---|---|
| A | ~47 |
| C | ~49 |
| D | ~44 |
| F | ~45 |
| K | ~44 |
| L | ~25 |
| M | ~27 |
| N | ~36 |

| | |
|---|---|
| Compd A = | CD-65 |
| Compd C = | Sialyl Lewis[X]-OR (αNeu5Ac(2→3)βGal(1→4)-[α-L-Fuc(1→3)]-βGlcNAc-OR) |
| Compd D = | $SO_3$-Lewis[X]-OR (sulfate substituent on the 3-position of the galactose of Lewis[X]-OR) |
| Compd F = | Sialyl Lewis[A]-OR (αNeu5Ac(2→3)βGal(1→3)-[α-L-Fuc(1→4)]-βGlcNAc-OR) |
| Compd K = | 2-$N_3$-Sialyl Lewis[X]-OR (αNeu5Ac(2→3)βGal(1→4)-[α-L-Fuc(1→3)]-βGlcN$_3$-OR) |
| Compd L = | 2-$N_3$-Sialyl Lewis[A]-OR (αNeu5Ac(2→3)βGal(1→3)-[α-L-Fuc(1→4)]-βGlcN$_3$-OR) |
| Compd M = | 2-$NH_2$-Sialyl Lewis[X]-OR (αNeu5Ac(2→3)βGal(1→4)-[α-L-Fuc(1→3)]-βGlcN$H_2$-OR) |
| Compd N = | 2-$NH_2$-Sialyl Lewis[A]-OR (αNeu5Ac(2→3)βGal(1→3)-[α-L-Fuc(1→4)]-βGlcN$H_2$-OR) |

R = —$(CH_2)_8CO_2CH_3$
[b]% reduction as per Example H below

The above results demonstrate that oligosaccharide glycosides related to blood group determinants having a type I or a type II core structure are effective in reducing antigen induced inflammation in a sensitized mammal.

Example B—Dose-Dependency of the Suppression of the DTH Inflammatory Response

Six groups of mice were subjected to primary immunization and challenge with L111-S-Layer protein as described under Example A, above. Five hours after challenge, groups were injected intravenously with 100 μL solutions containing 10, 25, 50, 75, or 100 μg of sialyl Lewis[X]-OR [R=—$(CH_2)_8CO_2CH_3$] or with PBS. The DTH responses for each dose group were measured 24 hours after challenge and are shown in FIG. 2. While the groups receiving PBS or 10 μg of sialyl Lewis[X] showed essentially the same extent of footpad swelling as PBS-treated controls, the groups receiving 25, 75 or 100 μg of sialyl Lewis[X] displayed reduced footpad swelling (78, 69, 75, and 56% of the PBS controls, respectively).

Example C—Lack of Suppression of the Antibody Response to the L111-S-Layer Protein Secondary antibody responses to the L111-S-Layer protein were measured two weeks after primary immunization (one week after challenge) in the sera from groups of mice immunized, challenged, and treated intravenously with sialyl Lewis[X]-OR, sialyl Lewis[A]-OR, sialyl Lewis[C]-OR, Lewis[X]-OR, and sialyl LacNAc-OR (oligosaccharide glycosides related to blood group determinants having a type I or type II backbone structure).

Antibody titers were determined using a solid phase enzyme immunoassay (EIA) as described by Ziola et al[70]. Briefly, 2 μg of L111-S-Layer protein was added per well of a Maxisorb EIA plate (Flow Laboratories, Inc., McLean, Va.). Following incubation at room temperature overnight, unabsorbed antigen was removed by inverting the wells. Each well then received 200 μl of various dilutions of mouse serum prepared in phosphate-buffered saline containing 2% (w/v) bovine serum albumin and 2% (v/v) Tween 20. After 1 hour at room temperature, the solutions were removed by inverting the wells, and the wells washed four times with distilled, de-ionized water at room temperature. Horseradish peroxidase-conjugated, goat anti-mouse immunoglobulin antibodies were then added to each well (200 μl of a 1:2000 dilution prepared in the phosphate-buffered saline/albumin/Tween 20 solution). After 1 hour at room temperature, the wells were again inverted and washed, and each well received 200 μl of enzyme substrate solution (3 mg per ml o-phenylene-diamine and 0.02% (v/v) hydrogen peroxide, freshly dissolved in 0.1M sodium citrate/phosphate buffer, pH 5.5). After the enzyme reaction had proceeded for 30 minutes in the dark at room temperature, 50 μl of 2N hydrochloric acid was added to each well and the $OD_{490}$ values were measured.

FIG. 3 graphically illustrates the titers determined with six dilution series of sera from the L111-immunized and challenged mice which were treated with sialyl Lewis[X]-OR, sialyl Lewis[A]-OR, Lewis[X]-OR, sialyl Lewis[C]-OR, and sialyl LacNAc-OR and examined for footpad swelling as described in Example A above. The dilution curves shown in FIG. 3 indicate that the development of antibodies against the L111 S-Layer protein has not been inhibited or otherwise affected by the treatments with such compounds.

Example D—Time of Administration of Compound III Relative to Challenge with Antigen A. The purpose of this part of Example D was to determine whether oligosaccharide glycosides related to blood group determinants having a type I or type II core structure could be administered to a sensitized mammal prophylactically or therapeutically in order to reduce antigen induced inflammation.

Specifically, groups of Balb/c mice, immunized and challenged with L111 S-Layer protein as described in Example A, were injected with a solution of 100 μg of sialyl Lewis[X]-OR [R=—$(CH_2)_8CO_2CH_3$] in PBS (100 μL) at different time points relative to the time of antigen challenge. One group received sialyl Lewis$^x$-OR one hour prior to the antigen challenge; another, immediately after challenge, the third group one hour after challenge, and the fourth group 5 hours after challenge. A control group was included which received PBS (100 μL) immediately after challenge.

Figure 4:
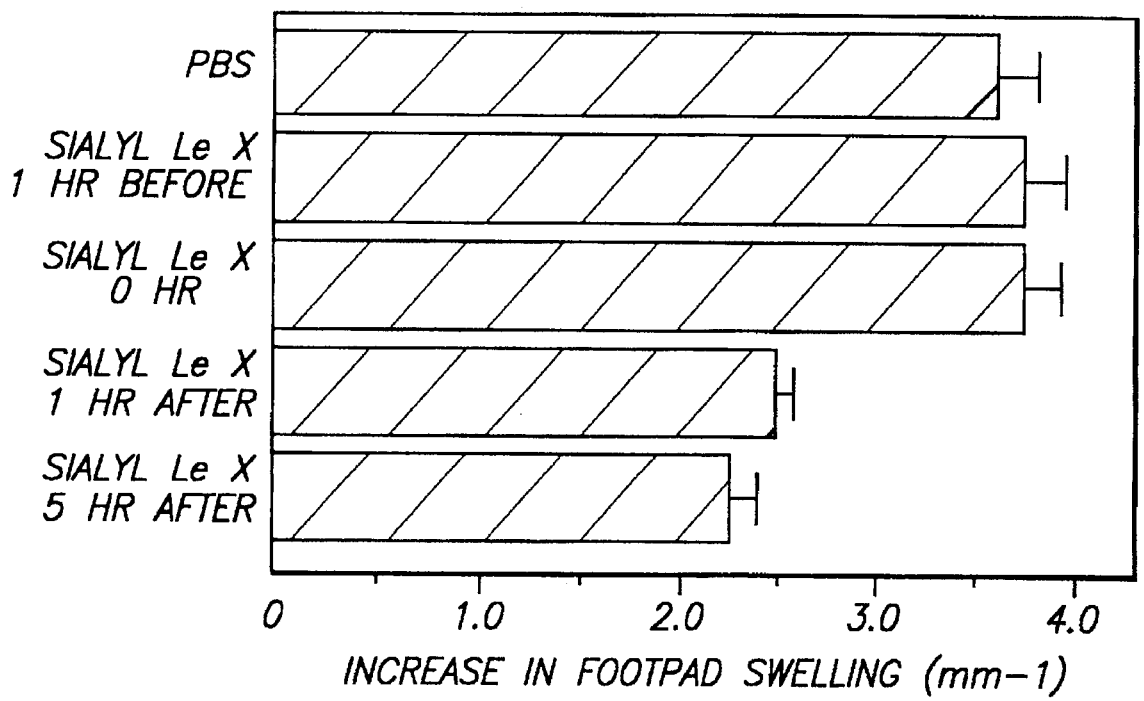

The results of this experiment are shown in FIG. 4. The DTH responses were not suppressed in those mice which had received sialyl Lewis$^x$-OR one hour before or immediately after the antigen challenge. Those groups which had received sialyl Lewis$^x$-OR one or five hours after challenge showed only 68 or 59% of the footpad swelling seen in the PBS treated controls. Accordingly, this data demonstrates that in order to reduce antigen induced inflammation in a sensitized mammal, it is necessary to administer the oligosaccharide glycoside related to blood group determinants having type I or type II core structures after initiation of the immune response.

B. The purpose of this part of Example D was to determine at what point in time oligosaccharide glycosides related to blood group determinants having a type I or type II core structure could be therapeutically administered to a sensitized mammal in order to reduce antigen induced inflammation. In this regard, the antigen induced inflammation used in this experiment was a DTH response in mice which is art recognized to provide for maximal inflammation at 24 hours after antigen exposure.

Specifically, groups of Balb/c mice, immunized and challenged with OVA antigen in a manner similar to that described in Example A, were injected with a solution of 200 μg per mouse of sialyl Lewis$^x$-OR [R=—(CH$_2$)$_8$CO$_2$CH$_3$] in PBS (100 μL) at different time points relative to the time of antigen challenge. One group of mice received sialyl Lewis$^x$-OR five hours after antigen challenge; another, at 10 hours after challenge; a third group at 12 hours after challenge; a fourth group at 15 hours after challenge; a fifth group at 18 hours after antigen challenge; and a sixth group at 24 hours after antigen challenge, and a control group was included which received PBS (100 μL) immediately after challenge.

Figure 15A:
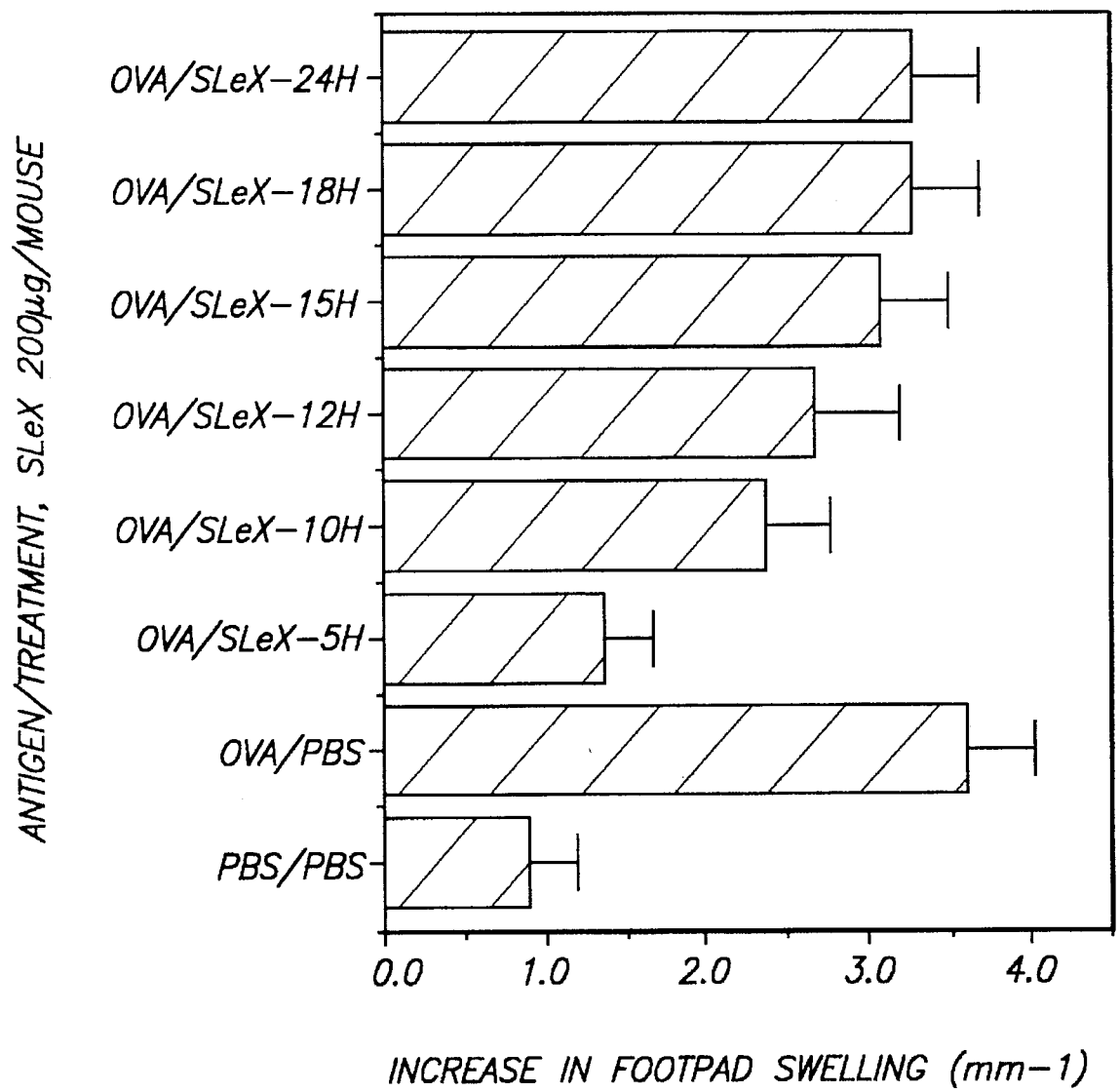
FIG. 15A illustrates the increase in footpad swelling of immunized mice arising from a DTH inflammatory response measured 24 hours after challenge with 20 µg of the OVA antigen and compared to a control group of mice wherein different groups of the mice were treated at 5 hours, 10 hours, 12 hours, 15 hours, 18 hours, and 24 hours after the challenge with 200 µg of an oligosaccharide glycoside related to blood group determinants having a type II core structure [sialyl Lewis$^x$-OR, R=—(CH$_2$)$_8$CO$_2$CH$_3$].
Figure 15B:
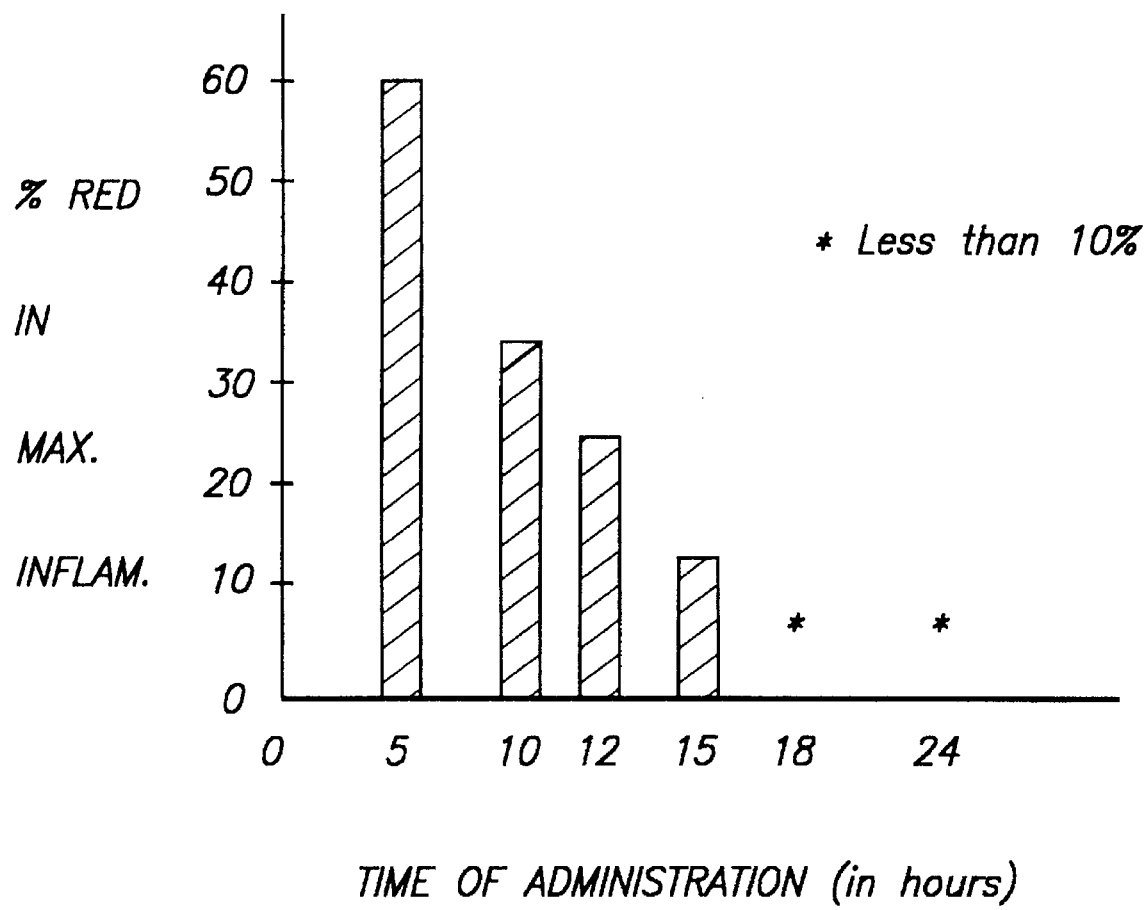
FIG. 15B illustrates percent reduction in maximal inflammation in the sensitized mice of FIG. 15A by administration of sialyl Lewis$^x$-OR where maximal inflammation is taken as the inflammation occurring at 24 hours after OVA challenge with administration of only PBS immediately after challenge.
Figure 16:
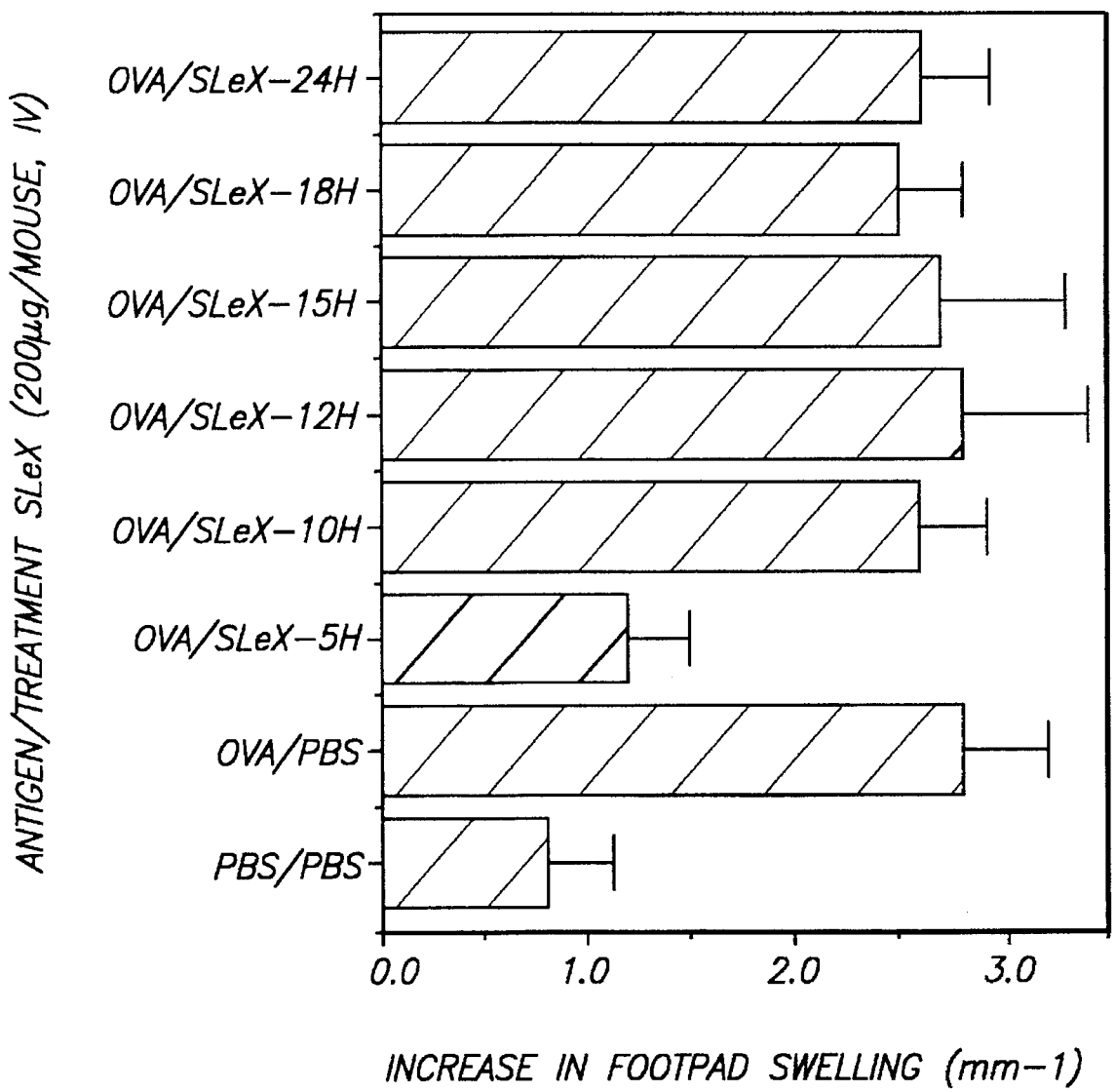
FIG. 16 illustrates the residual inflammation (as measured by an increase in footpad swelling) in the sensitized mice of FIG. 15A at 48 hours after antigen challenge.

The results of this experiment are shown in FIGS. 15A, 15B, and 16. Specifically, FIG. 15A illustrates the increase in footpad swelling arising from the DTH response to the OVA antigen challenge. The results illustrated in this figure are graphically represented in FIG. 15B to show the reduction in inflammation arising at the point in time sialyl Lewis$^x$-OR is administered to the mice as compared to the increase in inflammation for mice challenged with the OVA antigen and treated with PBS. Specifically, FIG. 16B illustrates that significant reduction (>20% reduction in inflammation) occurs only when the oligosaccharide glycoside is administered to the mice at or prior to 12 hours after antigen challenge. The reduction at 15 hours of about 12% is not considered meaningful because of the high dose (200 μg) of sialyl Lewis$^x$-OR used and the proportionally small reduction in inflammation. The reduction at 18 and 24 hours was less than 10%.

Since the maximal DTH inflammation occurs in mice about 24 hours after antigen challenge, the results of this part of Example D demonstrate that the oligosaccharide glycoside related to blood group determinants having a type I or type II core structure must be administered to the mammal at or prior to one-half that period of time required for maximal inflammatory response to antigen challenge.

FIG. 16 illustrates that the degree of residual inflammation in the challenged mice at 48 hours. In this regard, it is noted that the inflammation arising from a DTH responses is generally completed in 72 hours after antigen challenge.

Taken together, Examples A–D above establish that in order to effectively reduce antigen induced inflammation in a sensitized mammal, treatment with an effective amount of an oligosaccharide glycoside related to blood group determinants having a type I or type II core structure must be after initiation of the mammal's secondary immune response to the antigen and at or prior to one-half that period required to effect maximal inflammation to the antigen challenge.

Example E—Persistence of Suppression of the DTH Inflammatory Response at 6, 8, or 10 Weeks After Challenge i. The identical groups of mice treated with sialyl Lewis$^x$-OR, sialyl Lewis$^A$-OR, Lewis$^x$-OR, sialyl Lewis$^C$-OR, and sialyl LacNAc-OR in Example A were re-challenged with L111 S-Layer protein 8 weeks after primary immunization. Untreated controls responded with the usual degree of footpad swelling whereas all other groups showed reduced footpad swelling. Specifically, the degree of swelling in the treated mice relative to the degree of swelling in the control mices were as follows: sialyl Lewis$^x$-OR, 59%; Lewis$^x$-OR, 69%; sialyl LacNAc-OR, 78%; sialyl Lewis$^C$-OR, 78%; and sialyl Lewis$^A$-OR, 69%. (See FIG. 5).

The anti-inflammatory effect of sialyl Lewis$^x$-OR, sialyl Lewis$^A$-OR, Lewis$^x$-OR, sialyl Lewis$^C$-OR, and sialyl LacNAc-OR, given 5 hours after the first challenge (one week after primary immunization), had somewhat weakened eight weeks after primary immunization; however, the effect of Lewis$^x$-OR (the only derivative not containing a sialyl group) was equally as strong at the time of re-challenge as at the time of first challenge.

In addition to providing suppression of antigen induced inflammation in a sensitized mouse, the above data demonstrate that treatment with an oligosaccharide glycoside related to blood group determinants having a type I or type II core structure as per this invention also imparts tolerance to still later challenges from the same antigen.

ii. The identical groups of mice treated in Example B with sialyl Lewis$^x$-OR, (10 μg, 25 μg, 50 μg, 75 μg, 100 μg) or with the α or β-sialyl-OR (R=8-methoxycarbonyloctanol (100 μg), or with 100 μg of the T-disaccharide-OR (R=8-methoxycarbonyloctyl) were rechallenged six weeks after primary immunization. Footpad swelling similar to that of PBS-treated controls was observed with those mice that had been treated with α-sialyl-OR, β-sialyl-OR or the T-disaccharide-OR 5 hours after the first challenge. Mice originally treated with 10–100 μg of sialyl Lewis$^x$-OR showed footpad swelling that ranged from 90 to 65% of that displayed by the control mice (FIG. 6).

iii. The identical group of mice which had been treated in Example C with 100 μg of sialyl Lewis$^x$-OR at 1 hour before first challenge, or 5 hours after first challenge, were re-challenged with antigen 10 weeks after primary immunization. Within experimental error, footpad swelling of those mice treated before or shortly after challenge was the same as that of PBS-treated mice, whereas those mice originally treated 1 hour or 5 hours after challenge showed only about 66% of the values observed for PBS-treated controls (FIG. 7).

Figure 7:
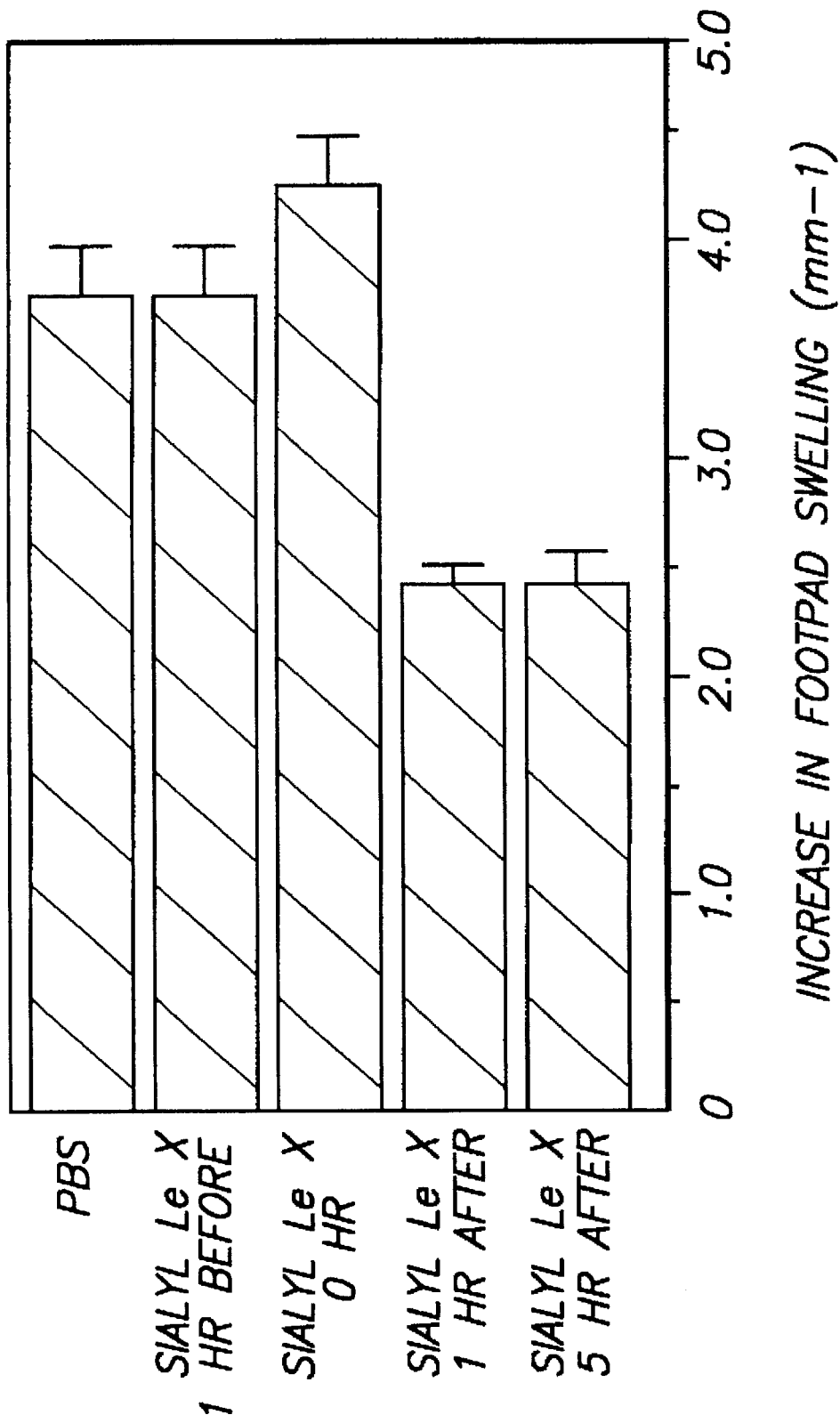
FIG. 7 illustrates the long term (10 weeks) immunosuppression generated in immunized mice after an injection with 5 mg/kg of the 8-methoxycarbonyloctyl glycoside of Sialyl Lewis$^x$ at various times before, at and after challenge with 20 µg of the L111 S-Layer protein antigen on day 7.

The results of this example are set forth in FIGS. 5–7 which demonstrate that oligosaccharide glycosides related to blood group determinants having a type I or type II core structure impart tolerance to challenges with the same antigen for at least 10 weeks after treatment.

Additional oligosaccharide glycosides were tested for their ability to induce tolerance to antigen induced inflammation (DTH response) in sensitized mammals in the manner set forth above. The results of these experiments are set forth below:

| Antigen | Compound | Time[3] of Adm. | Rechall. at # weeks | % Reduction[b] in inflam. |
|---|---|---|---|---|
| L111 | A | 5 hrs | 11 | 40% |
| SC | B | 5 hrs | 6 | 58% |

SC = 20 μg of SuperCarrier
L111 = 10 μg of L-111 S-Layer protein
Compd A = αNeu5Ac(2→3) βGal(1–4) βGlcNAc(1→3) βGal (1→4) [α-L-Fuc(1–3)] βGlcNAc-OR (CD-65)
Compd B = $SO_3$-Lewis$^x$-OR (sulfate substituent on the 3-position of the galactose of Lewis$^x$-OR)

[a]supra.
[b]supra.

Example F—Effect Cyclophosphamide Treatment Has on the Suppression Induced by 8-Methoxycarbonyloctyl Glycoside of Compound III It has been demonstrated in the literature that suppressor cells can be removed by treatment of mice with cyclophosphamide (CP). An experiment was carried out to determine if CP could modulate the suppression of cell-mediated inflammatory responses induced by the 8-methoxycarbonyloctyl glycoside of sialyl Lewis$^x$.

Specifically, this example employs immunized mice which have been previously suppressed and tolerized to DTH inflammatory responses by treatment with the sialyl Lewis$^x$-OR (R=8-methoxycarbonyloctyl) in a manner similar to that described above. Fourteen days after immunization, the mice were injected with 200 mg/kg of CP and then 17 days after immunization, the mice were challenged with 20 μg of L111 S-Layer protein antigen. 24 hours after the challenge, the extent of the DTH response was ascertained by measuring (mm$^{-1}$) the increase in footpad swelling.

Figure 8:
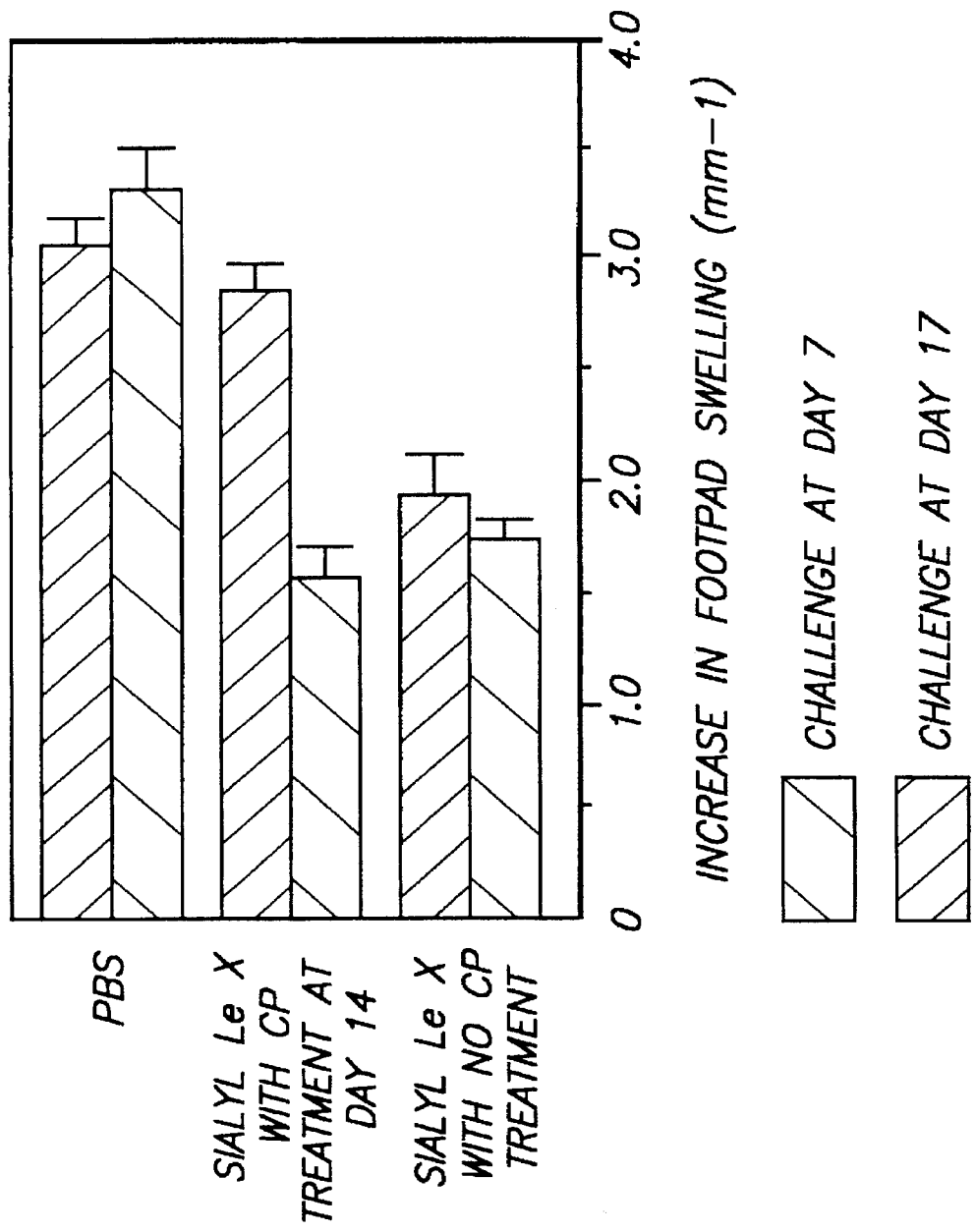
FIG. 8 illustrates the cyclophosphamide induced restoration of a DTH inflammatory response in immunized mice previously suppressed by treatment with the 8-methoxycarbonyloctyl glycoside of Sialyl Lewis$^x$.

The results of this experiment are set forth in FIG. 8 which illustrates that injection with CP prior to challenge with the L111 S-Layer protein antigen restores the DTH inflammatory response in mice that have previously undergone immunosuppressive treatment with sialyl Lewis$^x$-OR. These results suggest that tolerance induced by this oligosaccharide glycoside is mediated by CP sensitive suppressor T-cells.

Figure 9:
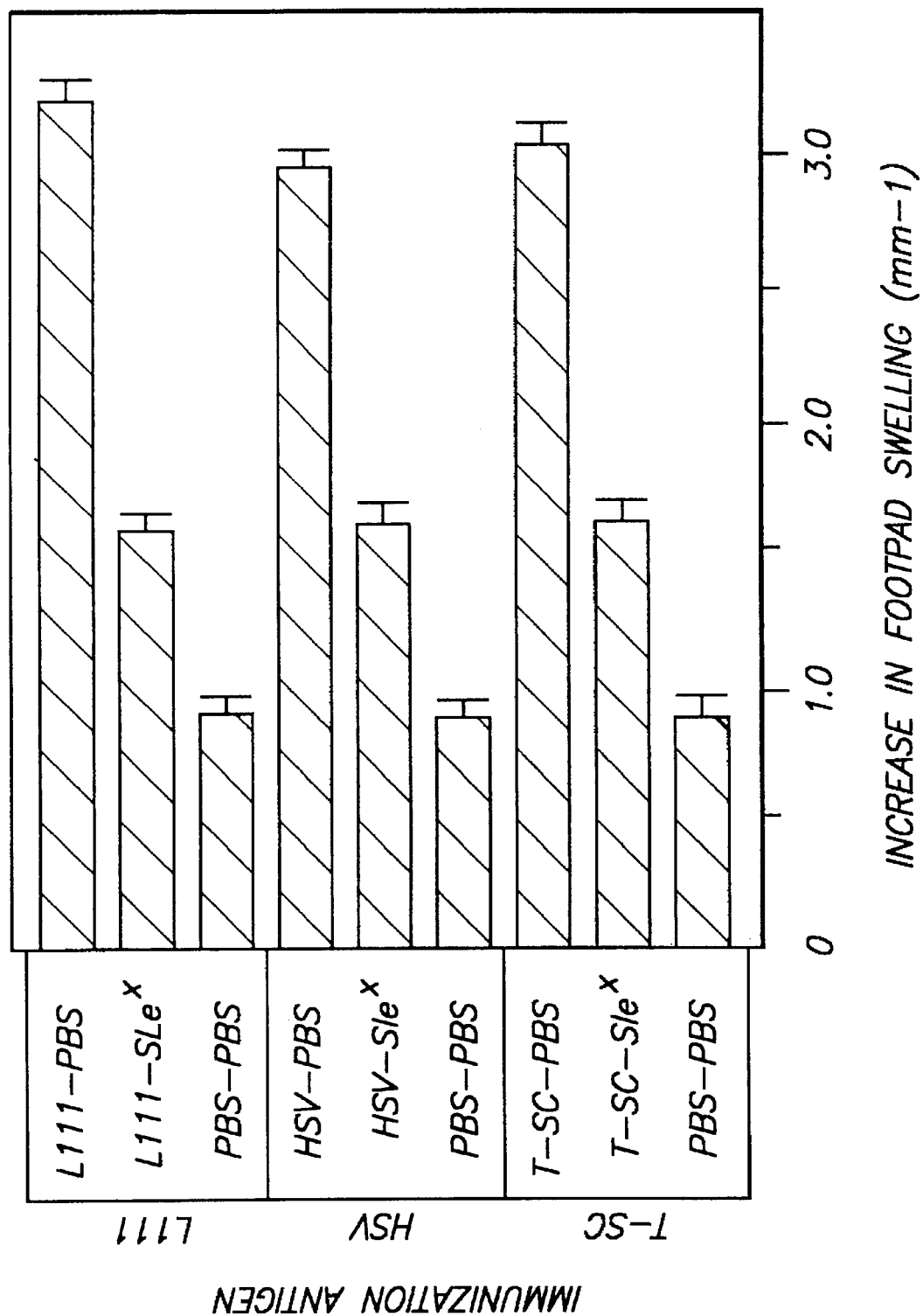
FIG. 9 illustrates that the nature of the antigen used to induce the inflammatory response does not affect the ability of the 8-methoxycarbonyloctyl glycoside of Sialyl Lewis$^x$ to regulate the DTH response.

Example G—Effect the Antigen Driving the DTH Inflammatory Response has on the Suppressive Effect Induced by the 8-Methoxycarbonyloctyl Glycoside of Sialyl Lewis$^x$ This example assesses the effect that the antigen driving the DTH inflammatory response has on the suppressive effect induced by sialyl Lewis$^x$-OR [R=—(CH$_2$)$_8$CO$_2$CH$_3$]. Mice were immunized as outlined in Example A with S-Layer L111, herpes simplex virus 1 (HSV 1)and cationized bovine serum albumin (Super Carrier™, Pierce, Rockford, Ill.). As shown in FIG. 9, the nature of the antigen used to induce the inflammatory response does not appear to affect the ability of sialyl Lewis$^x$-OR to regulate this response.

Example H—Effect of Timing of Administration of Sialyl LewisX Relative to Immunization or Challenge with Antigen Four groups of Balb/c female mice were subjected to primary immunization and challenge with HSV antigen as described in Example A with the following modifications:

1) The first group was immunized with 20 μg/mouse inactivated Herpes Simplex Virus Type I (HSV) and then challenged seven days later with 20 μg HSV.
2) The second group was immunized with 20 μg/mouse HSV and then challenged seven days later with 20 μg/mouse HSV and then 100 μg/mouse of sialyl LewisX-OR [R=—(CH$_2$)$_8$CO$_2$CH$_3$] which was injected intravenously five hours after challenge.
3) The third group was immunized with 20 μg/mouse HSV and 100 μg/mouse of sialyl LewisX-OR in 100 μl PBS injected intramuscularly at the same site. Seven days later, the mice were footpad challenged with 20 μg/mouse of HSV alone.
4) The fourth group of mice was immunized with 100 μl PBS and then seven days later challenged with 20 μg/mouse HSV. This provides a measure of the background level of footpad swelling resulting from the physical injury caused to the footpad during the antigen challenge.

The extent of the DTH inflammatory response was measured 24 hours after challenge by measuring footpad swelling with a Mitutoyo Engineering micrometer.

Figure 10:
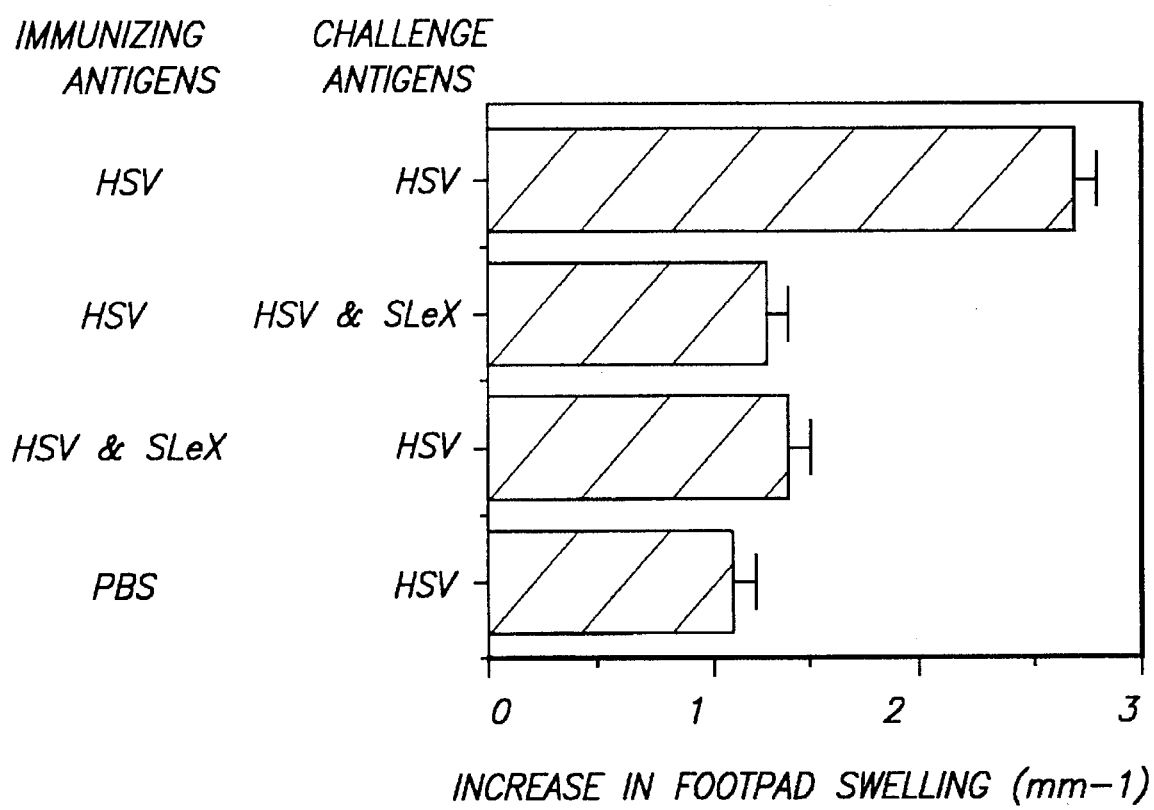
FIG. 10 illustrates the increase in foot-pad swelling of immunized mice arising from a DTH inflammatory response measured 24 hours after challenge with HSV antigen, where some of the mice were treated with Sialyl Lewis$^x$ at the time of immunization and some of the mice were treated with Sialyl Lewis$^x$ 5 hours after the challenge.

FIG. 10 shows the degree of footpad swelling observed. Percentage reduction for this and Example L was calculated by the following equation:

$$100 - 100 \times \left[ \frac{\text{Swelling of Treated Mice} - bkg \text{ swelling}}{\text{Swelling of Untreated Mice} - bkg \text{ swelling}} \right]$$

"Treated mice" are those mice which receive compound in addition to the antigen. "Untreated Mice" are those mice which do not receive compound. Background (bkg) swelling is that level of swelling observed in mice immunized with PBS alone without antigen or compound and challenged with antigen.

Mice injected with sialyl Lewis$^x$-OR at the same time as and site of immunization with HSV showed a 50% reduction in footpad swelling compared to that of mice immunized with HSV and challenged with HSV. Mice injected with sialyl Lewis$^x$-OR 5 hours after the footpad challenge with HSV showed an approximately 86.7% reduction in footpad swelling compared to that of mice immunized with HSV and challenged with HSV.

The results of this example support previous examples which show that oligosaccharide glycosides related to blood group determinants having a type I or type II core structure can suppress an immune response to an antigen if given to mice 5 hours after challenge by the antigen. This example also shows that oligosaccharide glycosides related to blood group determinants having a type I or type II core structure given to mice at the time of immunization can inhibit sensitization of the immune system to the antigen. Without being limited to any theory, it is contemplated that such compounds interfere with the ability of T helper cells to recognize antigen-presenting cells and inhibits the immune system from becoming educated about the antigen.

Example I—Effect of Sialyl LeX on the Antibody Response to HSV

Four groups of mice were treated as described in Example H. Secondary antibody responses to the HSV antigen were measured 2 weeks after primary immunization (1 week after challenge) in the sera from groups of mice described in Example H.

Antibody titres were determined as described in Example C except HSV antigen was used in place of L111 S-Layer protein.

Figure 11:
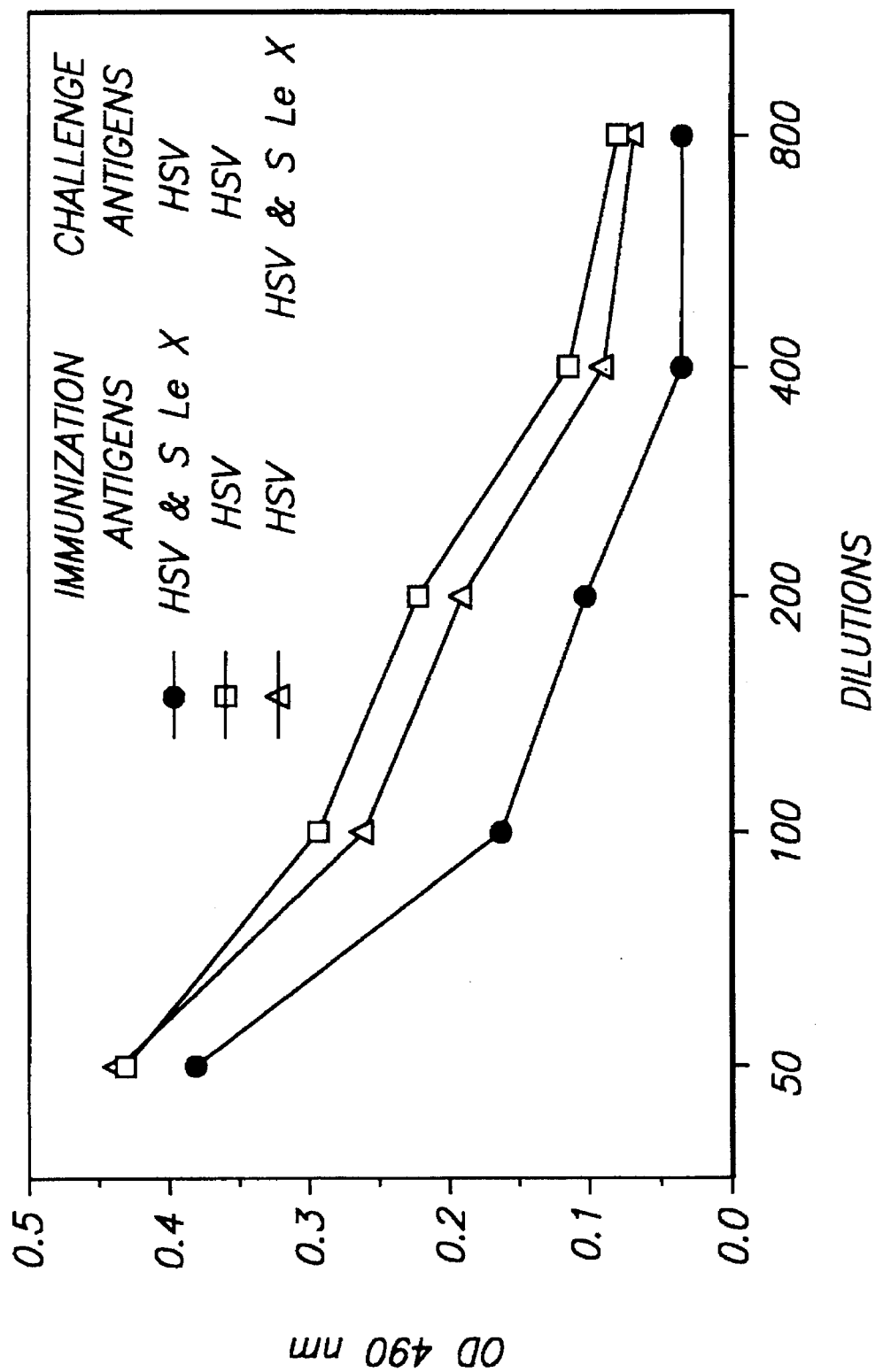
FIG. 11 illustrates the secondary antibody responses (i.e., as determined by the amount of antibody measured by quantification of o-phenylenediamine O.D. at 490 nm) two weeks after primary immunization and one week after challenge with the HSV antigen and the effect the time of administration of Sialyl Lewis$^x$ had on the these responses.

FIG. 11 graphically illustrates the titres determined with six dilution series of sera from the groups of immunized mice as described in Example H. The results of the first two groups correlated with the results obtained in Example C for the L111 S-Layer protein antigen. Treatment of mice with sialyl Lewis$^x$-OR five hours after challenge did not affect the antibody response. However, mice treated with sialyl Lewis$^x$-OR at the time of immunization showed significant reduction in the antibody response to the HSV antigen. Without being limited to any theory, it is contemplated that the above results are explained by the fact that oligosaccharide glycosides related to blood group determinants containing a type I or type II core structure (e.g., sialyl Lewis$^x$-OR) interfere with the T helper cells that are involved in the antibody response and inhibits the immune system from becoming educated about the antigen.

Example J—Effect Cyclophosphamide Treatment Has on the Induction of SleX Immunosuppression As discussed in Example F above, suppressor cells can be removed by treatment of mice with cyclophosphamide (CP). Specifically, this example employs immunized mice which have been previously suppressed and tolerized to DTH inflammatory responses by treatment with L111 S-Layer protein antigen. One group of Balb/c mice were immunized with 20 µg/mouse of the L111 S-Layer protein. Seven days later, this group of mice was footpad-challenged with 20 µg of L111 S-Layer protein. The second group of mice were immunized with 20 µg of the L111 protein and 100 µg of sialyl Lewis$^x$-OR [R=—(CH$_2$)$_8$CO$_2$CH$_3$] at the same site and seven days later were footpad challenged with 20 µg of L111. The third group of mice were injected with 200 mg/kg of CP interperitoneally two days before immunization. This group was then immunized and challenged as described for group two. The fourth group of mice were immunized with 20 µg/mouse of L111 and 100 µg/mouse of the T-disaccharide-OR at the same site and footpad challenged as described for group one. Group five was immunized 100 µl of PBS and then footpad challenged as described for group one.

Figure 12:
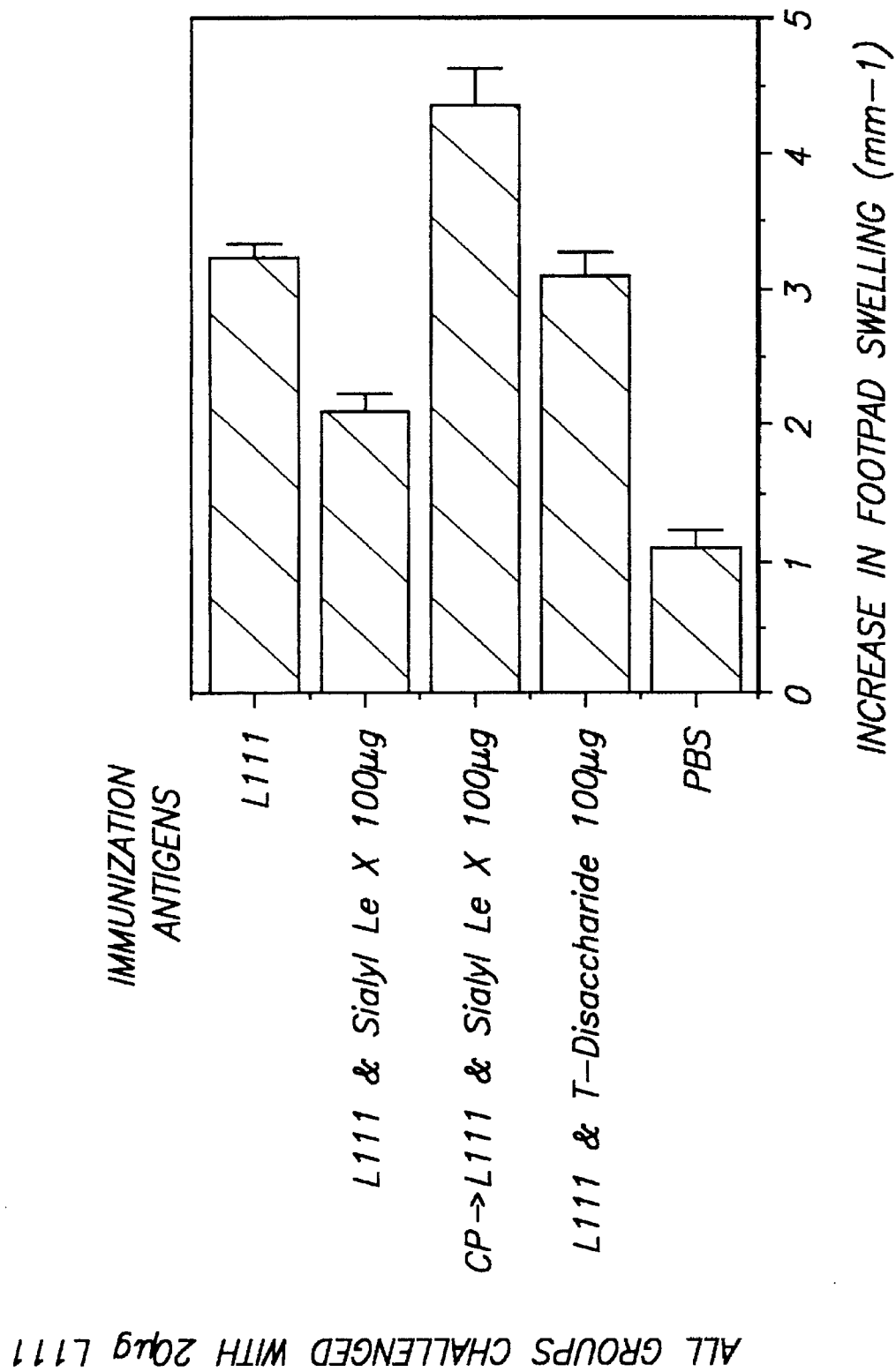
FIG. 12 illustrates the cyclophosphamide (CP) induced restoration of a DTH inflammatory response in immunized mice previously suppressed by treatment with the 8-methoxycarbonyloctyl glycoside of Sialyl Lewis$^x$.

The results are presented in FIG. 12. These results confirm the results discussed in Example H that treatment of mice with an oligosaccharide glycoside related to blood group determinants having a type I or type II core structure (e.g. sialyl Lewis$^x$-OR) at the time of immunization can suppress the immune response to an antigen. Furthermore, this example shows that the suppression of the immune response by treatment with such compounds at the time of immunization can be eliminated by cyclophosphamide treatment before immunization suggesting the involvement of cyclophosphamide sensitive suppressor T-cells.

Example K—Effect of Sites of Administration of Compound after Footpad Challenge on Inhibition of DTH Inflammatory Response Induced by OVA Groups of Balb/c female mice, age 8–12 weeks, weight about 20–25 g, were immunized with 100 µg of OVA (Albumin, Chicken Egg, Sigma, St. Louis, Mo.) and 20 µg of DDA (Dimethydioctacylammonium Bromide, Eastman Kodak, Rochester, N.Y.) in 100 µl of PBS (Phosphate Buffered Saline) intramuscularly into the hind leg muscle of the mouse.

Seven days after immunization, each group of mice was footpad-challenged with 20 µg of OVA in 20 µl of PBS. The resulting inflammatory footpad swelling was measured with a Mitutoya Engineering micrometer 24 hours after challenge.

To assess the effect of methods of administration of an oligosaccharide glycoside related to blood group determinants having a type I or a type II core structure on the suppression of the inflammatory DTH response, sialyl Lewis$^x$-OR [R=—(CH$_2$)$_8$CO$_2$CH$_3$] was administered by different routes. Certain groups of mice received, five hours after footpad-challenge, either 100 µg/mouse of sialyl Lewis$^x$-OR in 200 µl of PBS intravenously or 100 µg/mouse of sialyl Lewis$^x$-OR in 20 µl of PBS intranasally at which procedure the mice were under light anesthesia.

Figure 13:
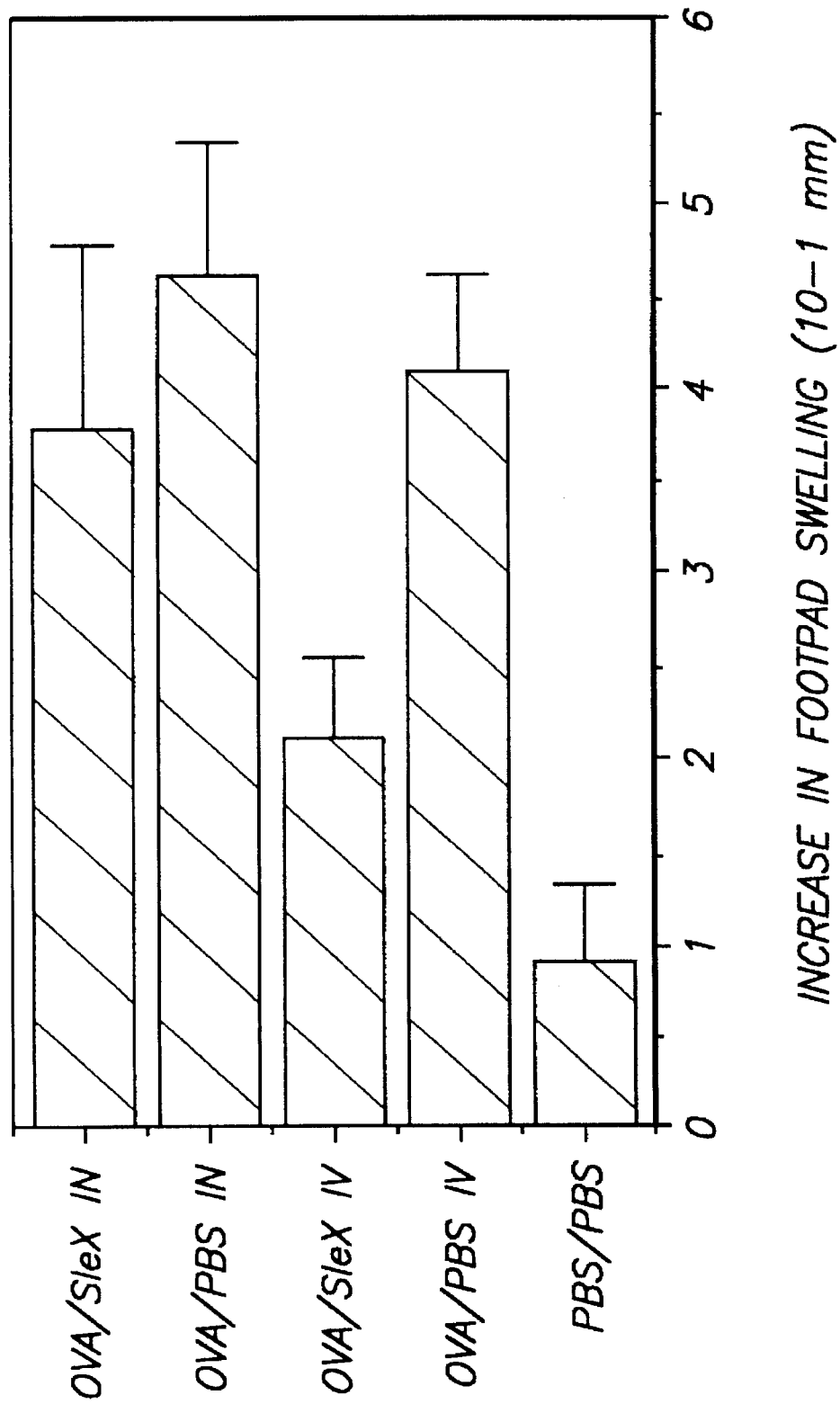
FIG. 13 illustrates the effect of the 8-methoxycarbonyloctyl glycoside of Sialyl Lewis$^x$ on the inflammatory DTH response in immunized mice challenged with the OVA antigen wherein the mice were treated with 8-methoxycarbonyloctyl glycoside of Sialyl Lewis$^x$ five hours after challenge by either intravenous (IV) or intranasal (IN) administration.

The method of administering compound intranasally is described in Smith et al.[71] which is incorporated by reference. Briefly, mice are anesthetized with Metofane (Pitman-Moore Ltd., Mississauga, Ontario, Canada) and a 50 µl drop of compound is placed on the nares of the mouse and is inhaled. Control groups were left untreated or received 200 µl PBS intravenously or 50 µl of PBS intranasally. The results of this experiment are shown in FIG. 13. These results show that administration of an oligosaccharide glycoside related to blood group determinants having a core type I or type II structure nasally five hours after challenge results in suppression of the immune response.

Example L—Time Dependency of Administration After Footpad Challenge of the Suppression of the OVA Induced DTH Inflammatory Response A group of Balb/c female mice, age 8–12 weeks, weight about 20–25 g, were immunized with 100 µg of OVA (Albumin Chicken Egg, Sigma) and 20 µg of DDA in 100 µl of PBS, intramuscularly into the hind leg muscle of the mouse. Seven days after immunization, the mice were footpad challenged with 20 µg of OVA in 20 µl of PBS. At 5, 7 or 10 hours after footpad challenge, the mice were either given intravenously 100 µg/mouse of sialyl Lewis$^x$—OR [R=—(CH$_2$)$_8$CO$_2$CH$_3$] in 200 µl of PBS or 200 µl PBS only or given intranasally 100 µg/mouse of sialyl Lewis$^x$—OR in 50 µl of PBS or 50 µl PBS only at which procedure the mice were under light anesthesia. The footpad swelling was measured 24 hours later with a Mitutoyo Engineering micrometer.

Figure 14:
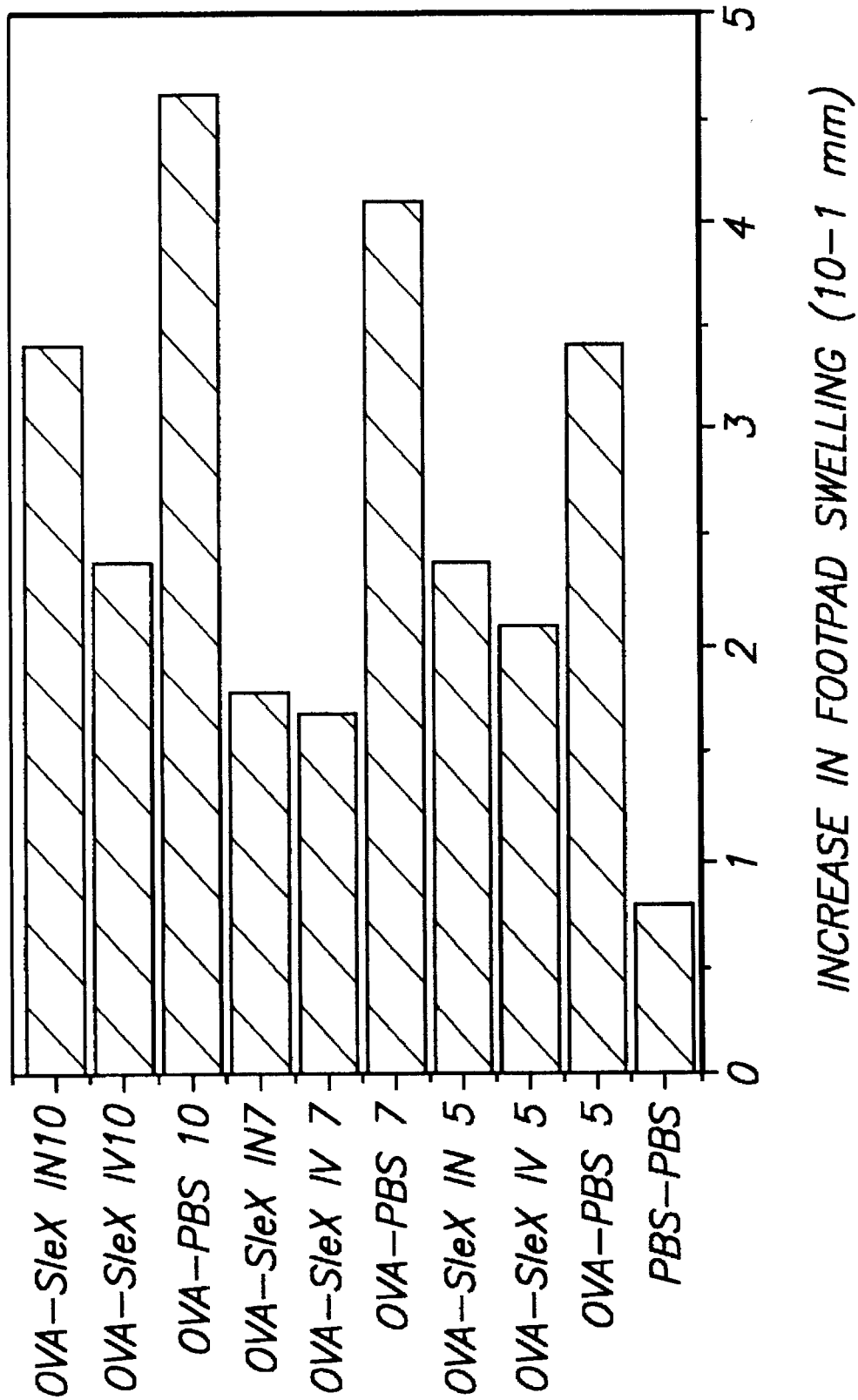
FIG. 14 illustrates the effect of the 8-methoxycarbonyloctyl glycoside of Sialyl Lewis$^x$ on the inflammatory DTH response in immunized mice challenged with the OVA antigen wherein the mice were treated with various doses of the 8-methoxycarbonyloctyl glycoside of Sialyl Lewis$^x$ five hours after challenge by either intravenous (IV) or intranasal (IN) administration.

FIG. 14 shows the results of this experiment. Specifically, administration of sialyl Lewis$^x$—OR given at 7 hours (both intranasally and intravenously) after the OVA challenge showed 70–74% reduction in footpad swelling relative to positive control mice as calculated using the formula set forth in Example H. Sialyl Lewis$^x$—OR given intravenously or intranasally at 5 hours after footpad challenge showed 63% and 54% reduction in swelling respectively. Sialyl Lewis$^x$—OR given intervenously or intranasally at 10 hours after footpad challenge showed 58% and 32% reduction in swelling respectively.

The data in Examples A–L above establish the effectiveness of oligosaccharide glycosides related to blood group determinants having a type I or a type II core structure in treating immune responses to an antigen and in inducing tolerance to still later challenges by that antigen in a sensitized mammal (mice). In view of the fact that the immune system of mice is a good model for the human immune system, such oligosaccharide glycosides will also be effective in treating human immune responses.

By following the procedures set forth in the above examples, other oligosaccharide glycosides related to blood group determinants having a type I or type II core structure could be used to suppress a cell-mediated immune response to an antigen by mere substitution for the oligosaccharide glycosides described in these examples.

SYNTHESIS

Examples 1–53 below illustrate the synthesis of numerous oligosaccharide glycosides related to blood group determinants having a type I or a type II core structure.

Examples 1–24 illustrate the synthesis of monosaccharides, disaccharides, and trisaccharides used in preparing oligosaccharide glycosides related to blood group determinants having a type I or a type II core structure as depicted in FIGS. 17 to 26.

EXAMPLE 1—Synthesis of Benzyl-2-O-benzoyl-4,6-O-benzylidene-3-O-chloroacetyl-β-D-thiogalactopyranoside (compound 31)

Dry a 20 L stirred reactor equipped with reflux condenser, heating mantle and 1 L addition funnel. Charge to this reactor 10 L of dichloroethane. Begin to stir the reactor then charge 1 kg D-galactose and 500 g anhydrous sodium acetate to the dichloroethane. Heat this slurry to reflux. Add dropwise 4 L of acetic anhydride to the reaction mixture using the 1 L addition funnel on the reactor. Reflux is to be maintained during the 2–4 hour addition period. Continue to stir and heat the mixture at reflux overnight.

When the reaction is complete as determined by t.l.c., turn off the heat to the reactor and add 250 mL of water in slow dropwise fashion using the addition funnel. This reaction is quite vigorous but is controlled by slowing the addition of the water. Stir the reaction for 1–2 hours. Charge 30 L of cold water to a 50 L stirred reactor and begin stirring. Drain the contents of the 20 L reactor into a 20 L polyethylene pail and pour into the stirring ice water in the 50 L reactor. Stir this mixture for twenty minutes. Drain the lower organic layer into a 20 L polyethylene pail. Extract the aqueous layer in the 50 L reactor with an additional 5 L of dichloromethane. Combine the dichloromethane extract with the first organic layer. Drain the aqueous layer to polyethylene pails and discard as aqueous waste.

Return the combined organic layers to the 50 L reactor and extract twice with 5 L portions of ice water for 10 minutes. Drain the organic layer to a clean 20 L polyethylene pail. Drain the aqueous to waste, return the organic layer to the 50 L reactor, stir and add 1 kg of anhydrous sodium sulfate. Stir for 1–2 hours and then drain the solution into a clean 20 L polyethylene pail and filter the solution using a 4 L vacuum filtration set [or large Buchner attached to a collector].

Concentrate the filtrate to 8 L then transfer into a clean 20 L reactor equipped with stirrer, 1 L addition funnel and cooling bath. Additional solvent can be added if the level of the solution is below the thermowell. Cool the organic solution to 0° C. using a cooling bath. Charge to this cool solution 724 g of benzyl mercaptan. Add a total of 1.1 L of colorless boron trifluoride etherate in slow dropwise fashion over 2 hours using the 1 L addition funnel. Stir the reaction 3–4 hours after the addition is complete maintaining the temperature at 0° C. The reaction is checked for completion by t.l.c. on silica gel. [The reaction can be left to sit overnight].

The reaction mixture is drained into a clean 20 L polyethylene pail. A 50 L reactor is charged with 15 L of saturated sodium carbonate solution. The 20 L polyethylene pail is slowly transferred into the slowly stirring carbonate solution at such a rate that the gas evolution is not overly vigorous. Stir the solution for 20 minutes then increase the rate of stirring. When gas evolution ceases bubble air through the entire solution for 24–36 hours. Drain the organic layer into a clean 20 L polyethylene pail and store in a hood. Extract the sodium carbonate solution with 3–5 L of dichloromethane and drain this solution into the same 20 L polyethylene pail.

Once the smell has been reduced the organic solution can be filtered using a 4 L vacuum filtration set and the filtrate evaporated under reduced pressure on the 20 L rotovap. 7 L of methanol is introduced into the rotovap flask and the residue heated with the rotavap bath till the residue dissolves in the warm methanol. The flask is rotated and allowed to cool. Cool ice water is added to the rotavap bath and the flask slowly rotated for several hours. The flask is removed from the rotovap and the white crystalline product filtered using a 4 L vacuum filtration set.

The benzyl 2,3,4,6-tetra-O-acetyl-β-D-thiogalactopyranoside (~1.3 kg) is charged into a clean dry 20 L reactor with stirring motor and 7 L of dry methanol is added to dissolve the material. The solution is treated with 3 g of freshly surfaced sodium and stirred for two hours. The reaction is checked by t.l.c. on silica gel using a retained sample of the benzyl 2,3,4,6-tetra-O-acetyl-β-D-thiogalactopyranoside with 80:20 ethyl acetate: methanol (v/v) as the eluant. The absence of starting material indicates the reaction is complete.

50 g of fresh methanol washed H$^+$ ion exchange resin is added, the reaction stirred for 15 minutes. The pH is checked using pH paper to ensure a neutral solution. The resin is filtered off under reduced pressure and the methanol is removed under reduced pressure using the 20 L rotovap. To the residue, 5 L of acetone is added to the 20 L flask and the solution warmed to reflux. The residue dissolves and is allowed to cool to room temperature at which time ice is added to the bath, the solution rotated with cooling overnight. 800–900 g of benzyl β-D-thiogalactopyranoside crystallizes and is filtered and dried under vacuum.

To 8 L of dry acetonitrile is added 800 g of benzyl β-D-galactopyranose, 600 g of benzaldehyde dimethyl acetal and 2–5 g of p-toluenesulphonic acid. The solution is stirred at room temperature overnight. The reaction progress is checked by t.l.c. When complete, the reaction is brought to pH 7 by the addition of triethylamine. The volume of acetonitrile is reduced to a minimum, 7 L of isopropanol is added and the mixture is heated to near reflux. Most of the product goes into the hot isopropanol after warming for several hours. The mixture is cooled and ice added to the bath and cooling continued overnight to give a precipitate. After filtering and drying the precipitate, 760 g of benzyl-4,6-O-benzylidene-β-D-thiogalactopyranoside is obtained.

180 g of benzyl-4,6-O-benzylidene-β-D-thiogalactopyranoside was dissolved in dry DMF and placed in a jacketed reactor. The reactor was cooled using a recirculating cooling bath maintained at a temperature of −25° C. and treated dropwise with 108 g of chloroacetyl chloride over 3 hours while stirring the reaction mixture. Stirring was continued 24 hours at this temperature then the reaction was quenched into several volumes of cold bicarbonate solution. The product was extracted into methylene chloride, water washed several times, dried over sodium sulphate and evaporated to dryness. The product was crystallized from isopropanol. Yield: 125 g of benzyl 4,6-O-benzylidene-3-O-chloroacetyl-β-D-thiogalactopyranoside.

5 g Benzyl 4,6-O-benzylidene-3-O-chloroacetyl-β-D-thiogalactopyranoside was benzoylated at room temperature in methylene chloride/pyridine using 3 equivalents of benzoyl chloride and a catalytic amount of dimethylaminopyridine. The solution is quenched into cold sodium bicarbonate solution, the organic layer is washed with saturated copper sulphate solution to remove the pyridine the organic layer dried and evaporated. The residue is taken up in hot isopropanol and benzyl 4,6-O-benzylidene-2-O-benzoyl-3-O-chloroacetyl-β-D-thiogalactopyranoside crystallizes from solution. $^1$H-n.m.r. (CDCl$_3$): δ=7.96, 7.4 (2 m, 15 H, aromatic, 5.79 (t, 1 H, H-2), 5.5 (s, 1 H, CH), 5.2 (q, 1 H, H-4, J$_{2,3}$ 9.9 Hz, J$_{3,4}$ 3.3 Hz), 4.5 (m, 2 H), 4.4 (d, 1 H), 3.99 (m, 5 H), 3.55 (s, 1 H).

EXAMPLE 2—Synthesis of 4,6-O-benzylidene-2,3-di-O-benzoyl-β-D-galactopyranosyl bromide (compound 32a)

Benzyl-4,6-O-benzylidene-β-D-thiogalactopyranoside (10 g) was dissolved in 100 mL dichloromethane and 6.35 g of pyridine was added. To the solution was added 9 g of benzoyl chloride in dropwise fashion and after 1 hour, 50 mg of dimethylaminopyridine was added to the solution and the mixture was stirred for an additional 2 to 4 hours. The progress of the reaction was checked by t.l.c. on silica gel. Benzyl-4,6-O-benzylidene-2,3-di-O-benzoyl-β-D-thiogalactopyranoside (compound 32) was isolated by quenching the reaction mixture into saturated sodium bicarbonate solution and washing the organic extract with water, 5% copper sulfate solution, water, drying and evaporating the solvent. The residue was crystallized from isopropanol to give 10.7 g of compound 32.

Compound 32, benzyl-4,6-O-benzylidene-2,3-di-O-benzoyl-β-D-thiogalactopyranoside (9.89 g), was dissolved in 100 mL of dichloromethane, cooled to 0° C., and treated with a solution of bromine (2.85 g) in 10 mL of dichloromethane. After 15 minutes, 1.8 grams of tetraethylammonium bromide was added to the mixture and the mixture stirred for 2–3 hours at room temperature (followed by t.l.c. on silica gel). A small quantity of cyclohexane was added to quench excess bromine and the reaction mixture was quenched into cold saturate sodium bicarbonate solution, washed with water, dried and volume of the solution reduced to 30 mL. This dichloromethane solution of compound 32a was used directly in the synthesis of compound 42 without further isolation and/or purification.

EXAMPLE 3—Synthesis of p-Chlorophenyl 2,3,4-tri-O-benzyl-β-L-thiofucopyranoside (compound 20)

Dry a 2 L three neck round bottomed flask, reflux condenser and 500 mL addition funnel. Then cool under a flow of nitrogen. Charge to the flask 1000 g of L-fucose, 500 g of anhydrous sodium acetate and 800 mL of dry dichloroethane. Heat the mixture with stirring to 50° C. Charge to the addition funnel 400 mL of acetic anhydride. Add the acetic anhydride to the stirring, warm (50°–55° C.) slurry in dropwise fashion at a rate that does not cool the reaction appreciably. Upon completion of the addition stir the mixture for 72 hours at this temperature, removing aliquots from the reaction mixture every 24 hours to check the progress of the reaction by t.l.c.

When the reaction appears to be complete add 200 mL of water to the warm stirring mixture dropwise over 30 min. and stir for 1 hour at this temperature. This converts the remaining acetic anhydride to acetic acid. The reaction mixture is quenched into 3–4 volumes of water. The organic layer is removed and the aqueous layer is extracted with 4 L dichloromethane. The combined organic layers are backwashed three times with 2 L portions of water. The organic layers are dried over sodium sulphate and concentrated under reduced pressure to approximately 5 L.

To the organic layer is added 925 g of p-chlorothiophenol. The organic layer is cooled with cold water. To the mixture of p-chlorothiophenol and fucose acetates is added 1.72 kg of boron trifluoride etherate in dropwise fashion. The mixture is then stirred for 6 hours (overnight is acceptable) allowing the reaction mixture to come to ambient temperature. A small aliquot is removed from the reaction mixture and quenched into sodium bicarbonate solution. Once $CO_2$ evolution has ceased, the reaction is checked for completion by t.l.c. If complete, the whole reaction mixture is quenched into 1 L of saturated sodium bicarbonate and the organic layer separated after $CO_2$ evolution has finished. The organic layer is separated and air bubbled through this layer for 1 hour.

The separated organic layer is then dried over sodium sulphate and evaporated to dryness. The residue is taken up in 1 L of dry methanol in a 2 L round bottom flask and treated with 1 g of freshly surfaced sodium. The reaction is kept under nitrogen for several hours then checked by t.l.c. for removal of the acetate groups. The reaction is neutralized with $H^+$ ion exchange resin and filtered and evaporated under reduced pressure. The residue is taken up in a minimum of hot isobutanol and the p-chlorophenyl-β-L-thiofucopyranoside crystallizes from solution after cooling overnight at 0° C. Yield: 1060 g.

p-Chlorophenyl-β-L-thiofucopyranoside is dissolved in 7 L of dry dimethylsulphoxide. To the solution is added 600 g of powdered KOH and the reaction mixture stirred for 30 minutes. Benzyl chloride (1.275 L) is added dropwise to the stirring solution and the mixture stirred overnight at room temperature. T.l.c. indicates incomplete reaction so an additional 300 g of powdered KOH is added to the reaction mixture followed 30 minutes later by 425 mL of benzyl chloride. The solution is stirred at room temperature until t.l.c. indicates the reaction is complete. If the reaction is not complete after 24 hours, powdered KOH is added followed by 200 mL of benzyl chloride. The reaction is quenched into several volumes of water, extracted with methylene chloride, backwashed twice with water, dried and evaporated. The residue is taken up in hot hexanes. p-Chlorophenyl-2,3,4-tri-O-benzyl-β-L-thiofucopyranoside crystallizes and is filtered and dried under vacuum. Yield: 1.3 kg. $^1$H-n.m.r. (CDCl$_3$): δ=7.57 (m, 19 H, aromatic), 4.99 (d, 1 H), 4.65 (m, 5 H), 4.55 (d, 1 H, $J_{1,2}$ 9.5 Hz), 3.98 (t, 1 H), 3.55 (m, 3 H), 1.26 (d, 3 H, $J_{5,6}$ 6.2 Hz, H-6).

EXAMPLE 4—Synthesis of 8-methoxycarbonyloctyl 2-acetamido-4,6-di-O-benzylidene-2-deoxy-β-D-glucopyranoside (Compound 5)

A 20 L glass reactor was charged with 8 L of dichloroethane, 1 L of acetic anhydride and 1 kg of anhydrous sodium acetate. To the stirring mixture was added 1 kg of glucosamine hydrochloride and the mixture was brought to reflux. A further 3.5 L of acetic anhydride was added dropwise to the refluxing solution over 3–4 hours and the solution maintained at reflux for 36 hours. During the last hour of reflux 200 mL of water was added dropwise to the solution. The reaction was then cooled and added to 35 L of ice water in a 50 L stirred reactor. The organic layer was removed and then water washed a second time with an additional 20 L of water. The organic layer was dried over sodium sulphate, filtered, and saturated with anhydrous gaseous HCl for 2 hours. The reaction was allowed to sit for 6 days being saturated with HCl for 1 hour every second day. 2-acetamido-2-deoxy-3,4,6-tri-O-acetyl-β-D-glucopyranosyl chloride was isolated by quenching into ice cold sodium bicarbonate solution. The organic layer was dried over sodium sulphate and evaporated to a brown solid.

Four hundred grams of 2-acetamido-2-deoxy-3,4,6-tri-O-acetyl-β-D-glucopyranosyl chloride was dissolved in 2 L of anhydrous dichloromethane containing 200 g of activated molecular sieves. 266 g of 8-methoxycarbonyloctanol was charged to the reaction mixture along with 317 g of mercuric cyanide. The solution was stirred rapidly at room temperature for 24 hours. After checking for reaction completion by t.l.c. the reaction mixture was filtered through a buchner funnel of silica and the organic layer washed twice with water, twice with a 5% solution of potassium iodide and twice with a saturated solution of sodium bicarbonate. The solution was dried over sodium sulphate and evaporated to dryness. The residue was taken up in anhydrous methanol and treated with 1 g of freshly cut sodium then stirred at room temperature overnight. The solution of 8-methoxycarbonyloctyl 2-acetamido-2-deoxy-β-D-glucopyranoside was neutralized with acid ion exchange resin and filtered and evaporated to yield 218 g of product after crystallization from isopropanol/diisopropyl ether.

Two hundred grams of 8-methoxycarbonyloctyl 2-acetamido-2-deoxy-β-D-glucopyranoside was dissolved in 1.2 L of anhydrous dimethylformamide and treated with 169 mL of dimethoxytoluene (benzylaldehyde dimethyl acetal) and 1–2 g of p-toluenesulphonic acid. The reaction was stirred and heated to 40° C. for 5 hours, then checked for completion by t.l.c. When the reaction appears complete the mixture was neutralized with triethylamine and quenched into several volumes of ice water, extracted into dichloromethane and backwashed several times with water. The organic layer was dried over sodium sulphate, evaporated to dryness and taken up in hot isopropanol. After cooling 8-methoxycarbonyloctyl-2-acetamido-4,6-O-benzylidene-2-deoxy-β-D-glucopyranoside precipitates. It is filtered and dried to yield 106 g of product. $^1$H-n.m.r. (CDCl$_3$): δ=7.41 (m,5 H, aromatic), 6.11 (d, 1 H, NH), 5.5 (s, 1 H, CH), 4.63 (d, 1 H, H-1, $J_{1,2}$ 7.4 Hz), 2.29 (t, 2 H), 1.99 (s, 3 H, Ac), 1.58 (m, 4 H), 1.29 (bs, 8 H).

EXAMPLE 5—Synthesis of 8-Methoxycarbonyloctyl 2-acetamido-3-O-p-methoxybenzyl-4,6-O-benzylidene-β-D-glucopyranoside (compound 6).

To a stirred solution of compound 5 (17.5 g, ~3 mmol) in dry dichloromethane (100 mL) and catalytic amount of p-toluenesulfonic acid (0.25 to 3 weight percent based on compound 5) was added dropwise a solution of p-methoxybenzyl trichloroacetimide (10 g in 25 mL CH$_2$Cl$_2$). The reaction mixture was stirred at room temperature overnight. Triethylamine was added to quench the reaction, the organic layer was washed with sodium bicarbonate solution and the organic layer dried and evaporated to dryness. Crystallization in hot ethanol gave 20 g of the desired product. $^1$H-n.m.r. (CDCl$_3$): δ 7.56–6.90 (m, 9 H, aromatic), 5.60 (d, 1 H, NH), 5.30 (s, 1 H, PhCH), 4.94 (d, 1 H, $J_{1,2}$ 8.0 Hz, H-1), 3.80 (s, 3 H, CH$_3$), 3.60 (s, 3 H, CH$_3$Ph), 2.30 (t, 2 H, CH$_2$CO), 1.90 (s, 3 H, AcNH), 1.80–1.10 (m, 12 H, (CH$_2$)$_6$).

EXAMPLE 6—Synthesis of 8-Methoxycarbonyloctyl-2-acetamido-2-deoxy-3-O-p-methoxybenzyl-6-O-benzyl-2-β-D-glucopyranoside (compound 7)

To a stirred solution of compound 6 (15.0 g, ~3 mmol) in 200 mL of dry THF were added, 11.0 g of sodium cyanoborohydride, 10 g of molecular sieves 4 Å and 5 mg of methyl orange. The solution was cooled to –10° C. and then ethereal hydrochloric acid was added dropwise until the solution remained acidic. On completion of the reaction, it was diluted with dichloromethane (200 mL), filtered through celite and washed successively with aqueous sodium bicarbonate (2×100 mL) and water (2×100 mL) and then the solvent dried and evaporated to give a syrup. Purification of the mixture on column chromatography using silica gel as adsorbent and eluting with hexane:ethyl acetate:ethanol (20:10:1) gave 7 in 70% yield. $^1$H-n.m.r. (CDCl$_3$): δ 7.40–6.90(m, 9 H, aromatic), 5.70(d, 1 H, NH), 4.64(d, 1 H, $J_{1,2}$ 8.0 Hz, H-1), 3.86(s, 3 H, CH$_3$O), 3.68(s, 3 H, CH$_3$OPh), 2.30(t, 2 H, CH$_2$CO), 1.90(s, 3 H, NHAc), 1.80–1.10(m, 12 H, (CH$_2$)$_6$).

EXAMPLE 7—Synthesis of 8-Methoxycarbonyloctyl 2-acetamido-2-deoxy-3-O-p-methoxybenzyl-4-O-(4,6-O-benzylidene-2,3-O-dibenzoyl-β-D-galactopyranosyl)-6-O-benzyl-2-deoxy-β-D-glucopyranoside (compound 42)

A solution of compound 7 (10.61 g, 19.7 mmol) and compound 32a (1.6–1.7 equivalents based on compound 7) and 2,6-di-t-butyl-4-methyl pyridine (3.11 g, 15.2 mmol) in 250 L of dichloromethane and 40 g of molecular sieves (4 Å) was stirred at room temperature for 30 minutes, and then cooled to –50° C. under nitrogen. A dry solution of silver triflate (4.47 g, 17.3 mmol) in toluene (40 mL) was added to the stirred mixture. The mixture was warmed to –15° C. during two hours and kept at –15° C. for an additional 5 hours. At the end of which the mixture was warmed to room temperature and stirred overnight. 3 mL of pyridine and 250 mL of dichloromethane were added to the mixture and was filtered over celite, filtrate was washed with saturated aqueous sodium hydrogen carbonate (200 mL) and then with water (200 mL), aqueous hydrogen chloride (0.5N, 200 mL) and water (200 mL), concentrated in vacuo. 6.0 g of compound 42 was crystallized as white crystals from ethyl acetate-diethyl ether-hexane. The mother liquor was concentrated, purified over chromatography (300 g silica gel, toluene:ethyl acetate, (1:1) to give 4.5 g pure compound 42. Total yield was 10.5 g (68%) Rf 0.48 (methanol:dichloromethane, 4:96). $^1$H-n.m.r. (CDCl$_3$): δ 5.80(t, 1 H, $J_{2',3'}$ 11.0 Hz, H-2'), 5.52(s, 1 H, CHPh), 5.25(dd, 1 H, $J_{3,4}$ 4.0 Hz, H-3'), 4.88(d, 1 H, $J_{1',2'}$ 11.0 Hz, H-1'), 4.70(d, 1 H, $J_{1,2}$ 9.0 Hz, H-1), 3.78(s, 2 H, CH$_3$O), 3.64(s, 3 H, CH$_3$OPh).

EXAMPLE 8—Synthesis of 8-Methoxycarbonyloctyl 2-acetamido-4-O-(4,6-O-benzylidene-2'3'-di-O-benzoyl-β-D-galactopyranosyl)-6-O-benzyl-2-deoxy-β-D-glucopyranoside (compound 43)

DDQ (126 mg, 0.5 mmol) was added to a stirred solution of compound 42 (350 mg, 185 μmol) in dichloromethane (10 mL) saturated with water. After 2 hours at room temperature, the reaction was complete, and organic layer was successively washed with aqueous sodium bicarbonate and water, dried and concentrated. Column chromatography gave the desired compound 43 in 85% yield. $^1$H-n.m.r. (CDCl$_3$): δ 5.65(dd, 1 H, $J_{2',3'}$ 10.8 Hz, H-2'), 5.61(d, 1 H, $J_{3',4'}$ 4.0 Hz, H-3'), 4.68(d, 1 H, $J_{1',2'}$ 11.0 Hz, H-1'), 4.62(d, 1 H, $J_{1,2}$ 10 Hz, H-1), 3.60(s, 3 H, COOCH$_3$).

EXAMPLE 9—Synthesis of 8-methoxycarbonyloctyl 2-acetamido-3-O-(2,3,4-tri-O-benzyl-α-L-fucopyranosyl)-4-O-(4,6-O-benzylidene-2,3-di-O-benzoyl-β-D-galactopyranosyl)-6-O-benzyl-2-deoxy-β-D-glucopyranoside(compound 44)

To a mixture of copper (cupric) bromide (40 g, 17.7 mmol) and 5 g of molecular sieves 4 Å in 10 mL of dry dichloromethane were added 1.2 mL of dry DMF and tetraethylammonium bromide (1.85 g, 8.8 mmol). The mixture was stirred at room temperature for 1 hour and then a solution of compound 43 (5.0 g, 5.75 mmol) and the thiofucoside 20 (7.5 g, 11.8 mmol) in 30 mL dry dichloromethane was added dropwise at 0° C. for 30 minutes. The mixture was stirred at room temperature for 48 hours, at the end of which time 5 mL of methanol was added and stirred for 30 minutes. Further, 3 mL of pyridine, 100 mL of ethyl acetate and 100 mL of toluene were added to the reaction mixture. The mixture was filtered over celite pad and the solvent evaporated to give a brown syrup. Purification over column chromatography with silica gel and eluted with toluene:ethyl acetate (2:1) gave the compound 44 in 86% yield. $^1$H-n.m.r. (CDCl$_3$): δ580(dd, 1 H, $J_{2',3'}$ 11.0 Hz, H-2'), 5.60(s, 1 H, CHPh), 5.50(d, 1 H, NH), 5.10(dd, 1 H, $J_{3',4'}$ 4.0 Hz, H-3'), 3.60(s, 3 H, OCH$_3$), 1.20(d, 3 H, CH$_3$, fucose).

EXAMPLE 10—Synthesis of 8-methoxycarbonyloctyl 2-acetamido-3-O-(2,3,4,-tri-O-benzyl-α-L-fucopyranosyl)-4-O-(4,6-O-benzylidene-β-D-galactopyranosyl)-6-O-benzyl-2-deoxy-β-D-glucopyranoside (compound 45)

Compound 44 (200 mg) was treated with 20 mL of sodium methoxide in methanol. After 3 hours, t.l.c. (toluene-ethyl acetate, 1:1) indicated the disappearance of the starting material and the appearance of a slower moving spot. The solution was neutralized with amberlite resin IR-120 H$^+$ and the solvent evaporated under reduced pressure to give a quantitative yield of crude compound 45. The product was purified on silica gel using toluene-ethyl acetate (2:1) as eluant. $^1$H-n.m.r. (CDCl$_3$): δ 7.15–7.55 (aromatic, 25 H), 5.62 (d, 1 H,NH), 5.58 (s, 1 H, CH-benzylidene), 5.06(d, 1 H, J$_{1'',2''}$ 7.0 Hz, H-1''), 4.95 (d, 1 H, J$_{1',2'}$ 3.8 Hz, H-1') 4.85 (d, 1 H, J$_{1,2}$=9.0 Hz, H-1) 3.62 (s, 3 H, COOCH$_3$) 1.0(d, 2 H, Fuc-CH$_3$).

EXAMPLE 11—Synthesis of 8-methoxycarbonyloctyl 2-acetamido-3-O-(α-L-fucopyranosyl)-4-O-(3-O-sulphate-β-D-galactopyranosyl)-2-deoxy-β-D-glucopyranoside (compound 47)

Diol (100 mg—compound 45) was dissolved in 5 mL dry dimethylformamide. Pyridine:sulfur trioxide complex (120 mg) was added to the solution and the reaction mixture stirred at room temperature for 1 hour. The reaction was followed by t.l.c. to monitor the disappearance of the diol (R$_f$=0.28 in EtOAc: MeOH 80:20). Solvent was evaporated to dryness and taken up in 50 mL of methanol then treated with Na$^+$ resin to convert it to the sodium salt. Purification by column chromatography on silica gel gave 65 mg of compound 46 which was immediately hydrogenated with 10% Pd(OH)$_2$ on carbon to give 35 mg of compound 47. $^{13}$C-n.m.r. (D$_2$O): δ 103.94(C-1, Gal), 103.44(C1, GlcNAc), 101.07(C-1, Fuc), 82.7(C-3, Gal), 63.83(C-6, Gal), 62.2(C6, GlcNAc), 54.55(C-N, GlcNAc), 17.75(C6-Fuc).

EXAMPLE 12—Synthesis of 2-O-benzoyl-4,6-O-benzylidene-3-O-chloroacetyl-α-D-galactopyranosyl bromide (compound 33)

Compound 31, benzyl 4,6-O-benzylidene-2-O-benzoyl-3-chloroacetyl-β-D-thiogalactopyranoside (8.87 g) was dissolved in 100 mL of dichloromethane, cooled to 0° C. and treated with a solution of bromine (2.7 g) in 10 mL of dichloromethane. After 15 minutes, 1.7 g of tetraethylammonium bromide was added to the mixture and the mixture stirred for 2 to 3 hours at room temperature (followed by t.l.c. on silica gel). A small quantity of cyclohexene was added to quench excess bromine and the reaction mixture was quenched into cold saturate sodium bicarbonate solution, washed with water, dried, and the volume of the solution reduced to 30 mL so as to provide a dichloromethane solution of compound 33. This solution was used directly in the synthesis of compound 38.

EXAMPLE 13—Synthesis of 8-methoxycarbonyloctyl 2-acetamido-4-O-(2'-O-benzoyl-4',6'-O-benzylidene-3'-O-chloroacetyl-β-D-galactopyranosyl)-6-O-benzyl-2-deoxy-3-O-p-methoxybenzyl-β-D-glucopyranoside (compound 37)

A solution of the compound 7 (5.0 g, 0.9 mmol) and compound 33 (1.4 to 1.5 equivalents—from example 12) and 2,6-di-t-butyl-4-methyl pyridine (1.78 g, 1.0 mmol) in 50 mL of dichloromethane and 20 g of molecular sieves (4 Å) was stirred at room temperature for 30 minutes, and then cooled to −50° C. under nitrogen. A dry solution of silver triflate (3.3 g, 1.5 mL) in toluene (10 mL) was added to the stirred mixture. The mixture was warmed to −15° C. over two hours and kept at −15° C. for an additional 5 hours, then allowed to warm to room temperature and stirred overnight. 1 mL of pyridine and 100 mL of dichloromethane were added to the mixture and it was filtered over celite, the filtrate was washed with aqueous sodium bicarbonate (100 mL) and then with water (100 mL), aqueous hydrogen chloride (0.5N, 100 mL) and water (100 mL), then concentrated in vacuo. Purification of the crude mixture on column chromatography with silica gel as adsorbent eluted with hexane:ethyl acetate (1:1) gave 5.2 g of pure compound 37. $^1$H-n.m.r. (CDCl$_3$): δ 5.85(d, 1 H, NH), 5.62(t, 1 H, J$_{2',3'}$ 10.8 Hz, H-2'), 5.52(s, 1H-CH-benzylidene), 5.08 (dd, 1 H, J$_{3',4'}$ 4 Hz, H-3'), 4.85 (d, 1 H, J$_{1',2'}$ 11.0 Hz, H-1'), 4.68 (d, 1 H, J$_{1,2}$ 9.0 Hz, H-1), 3.72 and 3.64 (2 s, 6 H, OCH$_3$ and COOCH$_3$); $^{13}$C-n.m.r.: 159.0(aromatic c-p-methoxyl) 165.15 (c=0, chloroacetyl), 167.12 (c-0, acetyl), 174.2(c=0, COOCH$_3$), 99.64(c-1), 100.26(c-1'), 101.0(PhCH).

Compound 37 was then treated with DDQ in the same manner as Example 8 to give compound 38 in near quantitative yields.

EXAMPLE 14—Synthesis of 8-methoxycarbonyloctyl 2-acetamido-3-O-(2,3,4-tri-O-benzyl-α-L-fucopyranosyl)-4-O-(2-O-benzoyl-4,6-O-benzylidene-3-O-chloroacetyl-β-D-galactopyranosyl)-6-O-benzyl-2-deoxy-β-D-glucopyranoside (compound 39)

Thiofucoside 20 (4 g) was stirred in dry dichloromethane (50 mL) and bromine (0.60 g) was added. The mixture was cooled to −20° C. The conversion to the bromide was complete in 1 hour and the reaction mixture was washed with cold aqueous sodium bicarbonate, dried and concentrated to 10 mL and syringed into a flask containing the alcohol 38 (2.97 g, 3.56 mmol), CuBr$_2$ (2.39 g), tetraethylammonium bromide (2.24 g), molecular sieves 4 Å (4 g) in dimethylformamide (1 mL) in dry dichloromethane (75 mL). The mixture was stirred at room temperature for 48 hours after which the t.l.c. showed the disappearance of the alcohol 38 and a faster moving spot (Rf 0.56—toluene:ethyl acetate 2:1). After the usual work up, the crude mixture was purified by column chromatography to give compound 39 (4.2 g, about 80% yield). $^1$H-n.m.r. (CDCl$_3$): δ 7.1–8.0 (m,aromatic-30 H), 5.58, 5.61 (m, 2 H, NH and CH-benzylidene, overlapping), 5.56 (d, 1 H, J$_{1'',2''}$ 7.0 Hz, H-1''), 4.98 (d, 1 H, J$_{1,2}$ 8.0 Hz, H-1), 4.95 (d, 1 H, J$_{1',2'}$ 3.8 Hz, H-1'), 3.65 (s, 3 H, COOCH$_3$) and 1.1 (d, 3 H, CH$_3$-Fuc).

Compound 39 is then dechloroacetylated by treatment with thiourea and the compound is sulphated with sulfur trioxide/pyridine complex in dimethylformamide at 0° C. for 2 hours to provide for compound 41. The blocking groups on compound 41 are then removed by conventional techniques to provide for compound 47.

EXAMPLE 15—Synthesis of 2-deoxy-2-phthalimido-1,3,4,6-tetra-O-acetyl-β-D-glucopyranoside (compound 1)

(D+) Glucosamine hydrochloride (100 g, 0.46 mol) was added to a solution of sodium methoxide in methanol which was prepared from equimolar amount of sodium metal in methanol (0.5 L). The resultant mixture was treated with equimolar equivalent of phthalic anhydride and triethylamine (80 mL). The mixture was then stirred for 2 hours, filtered and the solid was dried in vacuum for 12 hours. The dry solid was dissolved in pyridine (300 mL) and treated with acetic anhydride (200 mL, 2.1 mol). The mixture was then stirred at room temperature for 48 hours and quenched in an ice-water mixture, and the resultant precipitate was filtered, concentrated and crystallized from diethylether to 98.3 g (45%) of the title compound. $^1$H-n.m.r. (CDCl$_3$): δ 7.75 (m, 4 H, aromatic), 6.45 (d, 1 H, H-1, J$_{1,2}$ 9.0 Hz), 5.85 (t, 1 H), 5.15 (t, 1 H), 4.4 (t, 1 H), 4.3 (q, 1 H), 4.1 (q, 1 H), 4.00 (m, 1 H), 2.05, 2.00, 1.95, 1.80 (4 s, 12 H, 4 Ac). $^{13}$C-n.m.r. (CDCl$_3$) δ 89.7 (C-1), 72.6, 70.5, 68.3 (3C, C-3, C-4, C-5), 61.45 (C-6), 53.42 (C-2).

EXAMPLE 16—Synthesis of 2-deoxy-2-phthalamido-3,4,6-tri-O-acetyl-β-D-glucopyranosyl bromide (compound 12)

2-deoxy-2-phthalamido-1,3,4,6-tetra-O-acetyl-β-D-glucopyranoside (20 g, 41.9 mmol) was treated with hydrogen bromide solution in acetic acid (30%, 200 mL) and stirred at room temperature for 2 hrs. The mixture was then poured into an ice water mixture and extracted with dicloromethane. The extract was washed with NaHCO$_3$ solution and water followed by MgSO$_4$ drying. The mixture is filtered, dried and concentrated in vacuo to give compound 12 as a dry syrup (compound 12)

EXAMPLE 17—Synthesis of Ethyl 2-deoxy-2-phthalimido-3,4,6-tri-O-acetyl-β-D-glucopyranoside (compound 13)

2-Deoxy-2-phthalamido-3,4,6-tri-O-acetyl-β-D-glucopyranosyl bromide (compound 12) from example 16 was taken up in dry ethanol and treated directly with dry ethanol (200 mL), mercuric cyanide (13.7 g, 55 mmol) and stirred at room temperature for 48 hr. The mixture was then filtered and concentrated. The residue was taken up in 200 mL of dichloromethane and washed with a solution of 10% potassium iodide, 5% sodium bicarbonate, water, dried over MgSO$_4$ and concentrated to a syrup.

EXAMPLE 18—Synthesis of Ethyl 2-deoxy-2-phthalimido-β-D-glucopyranoside (Compound 14)

Ethyl 2-deoxy-2-phthalamido-3,4,6-tri-O-acetyl-β-D-glucopyranoside (compound 13) from example 17 was taken up in 100 mL of dry methanol and treated with 100 mg of sodium metal. The solution was stirred at room temperature for 24 hours and then neutralized with Amberlite [R-120 (H+)] resin, filtered, and evaporated to dryness in vacuo. This compound was used in the preparation of compound 15 and compound 66.

EXAMPLE 19—Synthesis of Ethyl 2-deoxy-2-phthalimido-6-O-benzyl-β-D-glucopyranoside (Compound 15)

Compound 14 (2.1 g, 6.23 mmol) was taken up in 100 mL of toluene. To it was added bis(tributyl tin) oxide (2.22 mL, 4.35 mmol) and tetrabutylammonium bromide (0.983 g, 3.05 mmol). The mixture was heated at 150° C. for 4 hours and then toluene (50 mL) was distilled off from the mixture. The reaction mixture was cooled to room temperature and benzyl bromide (2.17 mL, 18.27 mmol) was added and the reaction heated to 110° C. for 36 hours. Toluene was evaporated and the residue taken up in ethyl acetate (22 mL), washed successively with aqueous sodium bicarbonate, saturated sodium chloride solution and water. The organic layer was dried and evaporated to dryness to give a crude solid. Purification by column chromatography on silica gel gave a crystalline solid 15 (1.4 g, 70%). $^1$H-n.m.r.(CDCl$_3$) δ 7.3–8.1 (9 H, aromatic), 4.5 (dd, 2 H, CH$_2$Ph), 5.18 (d, 1 H, J$_{1,2}$ 10.0 Hz, H-1), 4.36 (dd, 1 H, H-3), 4.25 (dd, H, J$_{2,1}$ 10.0 Hz, J$_{2,3}$ 8.0 Hz, H-2) and 1.0 (t, 3 H, CH$_3$).

EXAMPLE 20—Synthesis of Ethyl 6-O-benzyl-2-deoxy-2-phthalimido-3-O-(2,3,4,-tri-O-benzyl-α-L-fucopyranosyl)-4-O-(2,3,4,6-tetra-O-acetyl-β-D-galactopyranosyl)-β-D-glucopyranoside (Compound 49)

To a stirred solution of compound 15 (2.49, 5.71 mmol) in dry dichloromethane (50 mL) was added dry CaSO$_4$ (7.5 g), silver triflate (0.73 g, 2.8 mmol) and silver carbonate (7.0 g, 25.7 mmol) and the reaction mixture cooled to −50° C. 2,3,4,6-tetraacetyl-1-α-bromogalactose (3.5 g, 8.5 mmol) in dry dichloromethane (15 mL) was added dropwise through a dropping funnel. The reaction mixture was warmed to −30° C. and stirred for 48 hours and then methanol (5 mL) was added to cease the reaction and the mixture allowed to warm to room temperature. After filtration through a celite pad and the filtrate was washed with aqueous bicarbonate and 5% EDTA solution. Evaporation of the solvent in vacuo gave a reddish brown syrup which was chromatographed on silica with toluene: acetone:MeOH (20:3:1) as eluant to give compound 48 (Rf 0.528) as the major compound.

Thiofucoside 20 (1.5 g, 2.8 mmol) was stirred in dry dichloromethane (50 mL) cooled to −20° C. and bromine (0.40 g) was added. The conversion to bromide was complete in 1 hour and the reaction mixture was washed with cold aqueous bicarbonate, dried and concentrated to 50 ml and syringed into a flask containing compound 48 (1 g, 1.4 mmol), HgBr$_2$ (1.08 g, 3 mmol), molecular sieves 4 Å (2 g) and tetraethylammonium bromide (1 g) in dry dichloromethane (50 mL). The mixture was stirred at room temperature for 48 hours. T.l.c. showed a faster moving spot. The reaction mixture was filtered through celite, and the filtrate washed with water, 5% EDTA, saturated aqueous sodium bicarbonate, water, then dried over sodium sulphate, filtered and evaporated to dryness in vacuo. Purification of the crude product by silica gel chromatography gave the title compound 49 (1.2 g, 70%, Rf 0.669 in toluene; acetone; MeOH 20:3:1).

$^1$H-n.m.r. (CDCl$_3$): δ 7.00–7.8 (aromatic 24 H) 5.35(d,1H, J$_{1,2}$ 9.0 Hz, H-1), 5.15 (d, 1 H, J$_{1,2}$ 3.8 Hz, H-1-Fuc), 4.35(dd, 1 H, J$_{2',3'}$ 10.0 Hz, H-3') 2.1(s, 3 H, acetyl CH$_3$) 1.95(s, 6 H, acetyl CH$_3$), 1.90(S, 3 H, acetyl CH$_3$), 1.1(t, 3 H, CH$_3$), and 0.6 (d, 3 H, CH$_3$-Fuc). $^{13}$C-n.m.r.: δ 168, 170 (C=O, phthalimido and acetyl), 101.0 (C-1, Gal), 100.0(C-1, GlcNPhth) 97.7(C-1-Fuc), 20.6(CH$_2$—CH$_3$) and 15.98 (C-6-Fuc).

EXAMPLE 21—Synthesis of Ethyl 2-acetamido-6-O-acetyl-3-O-benzyl-2-deoxy-β-D-glucopyranoside A solution of compound 90 (described below-2 g, 4.68 mmol) in aqueous acetic acid (80%, 150 mL) was heated at 80° C. for 2 hours. The mixture then was evaporated and the resultant solid was dried over P$_2$O$_5$ in high vacuum. The dry solid was selectively acetylated with acetyl chloride (0.33 mL, 4.7 mmol) and pyridine (10 mL) in dichloromethane (100 mL) at 10° C. to 5° C. The mixture was then diluted with dichloromethane (50 mL), washed with aqueous NaHCO$_3$, dried over MgSO$_4$ and evaporated. The residue was chromatographed on a silica gel column using ETOAc: hexanes, 3:1 (v:v) as eluant to give 0.82 g (46%) of the title compound: $^1$H-n.m.r. (300 MHz, CDCl$_3$): δ7.3(m, 5 H, aromatic), 5.67(bs, 1 H, NH), 4.86(d, 1 H, H-1), 4.75(m, 2 H), 4.48(q, 1 H), 4.27(d, 1 H), 4.1(t, 1 H), 3.85(m, 1 H), 3.5(m, 3 H), 3.16(m, 1 H), 2.70(bs, 1 H, OH), 2.1(s, 3 H, Ac), 1.9(s, 3 H, Ac), 1.18(t, 3 H, CH$_3$), $^{13}$C-n.m.r. (CDCl$_3$): δ 99.45(C-1), 79.85, 74.5(CH$_2$ph), 73.7, 71.09, 65.25 (C-6), 63.36(CH$_2$—), 57.7(C-2), 23.6 (Ac), 20.86(Ac), 15.06 (CH$_3$).

EXAMPLE 22—Synthesis of Ethyl 6-O-acetyl-3-O-benzyl-2-deoxy-2-phthalimido-β-D-glucopyranoside (compound 69)

A solution of ethyl 2-deoxy-2-phthalimido-β-D-glucopyranoside (compound 14) from Example 18 was taken up in dry acetonitrile (100 mL) and treated with benzaldehyde dimethylacetal (9.6 g) and a catalytic amount of p-toluenesulphonic acid (100 mg). The mixture was stirred for 17 hours at room temperature and then neutralized to pH 7 with triethylamine. The mixture was evaporated and crystallized from hot hexanes to give 12.7 grams of ethyl 4,6-O-benzylidene-2-deoxy-2-phthalimido-β-D-glucopyranoside compound 66.

Compound 66 (10 g) was dissolved in dry dimethylformamide (DMF) at −5° C. and treated with 1.1 g (46.6 mol) sodium hydride and benzyl bromide (5.46 mL, 22 mmol). The mixture was stirred at 0° C. for 2 hours and then treated slowly with 20 mL methanol then slowly brought to room temperature and treated with HCl (1N) to pH 7 and then extracted three times with dichloromethane. The organic layer was dried over anhydrous magnesium sulfate then filtered, concentrated to dryness and taken up in hot ethanol to give 7.2 g of compound 67. Compound 67 (5.43 g, 10.50 mmol) in aqueous acetic acid (80%, 200 mL) was heated at 80° C. for 2 hours. The mixture was evaporated and the resultant solid was dried over $P_2O_5$ in high vacuum. The dry solid was selectively acetylated with acetyl chloride (0.8 mL, 11.0 mmol) and pyridine (10 mL) in dichloromethane (200 mL) at −10° C. to 0° C. The mixture was then diluted with dichloromethane (10 mL), washed with aqueous $NaHCO_3$, dried over $MgSO_4$ and evaporated. The residue was chromatographed on a silica gel column using EtOAc:hexane, 1:2 (v:v) as eluant to give 3.5 g (71%) of the compound 69: $^1$H-n.m.r. (300 MHz, $CDCl_3$): δ 7.7(m, 4 H, aromatic), 7.0(m, 5 H, aromatic), 5.16(d, 1 H, H-1), 4.7(d, 1 H), 4.5(m, 2 H), 4.2(m, 3 H), 3.8(m, 1 H), 3.6(m, 2 H), 3.45(m, 1 H), 2.9(bs, 1 H, OH), 2.1(s, 3 H, Ac), 1.95(t, 3H, $CH_3$). $^{13}$C-n.m.r. ($CDCl_3$): δ 98.09(C-1), 78.45, 74.5, 73.9, 71.7, 65.1, 63.1, 55.5, 20.87 (Ac), 14.92 ($CH_3$).

EXAMPLE 23—Synthesis of Ethyl 6-O-acetyl-3-benzyl-2-deoxy-2-phthalimido-4-O-(2,3,4,6-tetra-O-acetyl-β-D-galactosyl)-β-D-glucopyranoside (compound 70)

To a stirred solution of compound 69 (80 mg, 0.17 mmol) in dichloromethane (10 mL) containing molecular sieves (3 A, 1 g), 2,6-di-tert-butyl-4-methylpyridine (45 mg, 0.22 mmol) and silver triflate (57 mg, 0.22 mmol) was added, at −30° C. under nitrogen, 2,3,4,6-tetra-O-acetyl-α-D-galactosyl bromide in dichloromethane (5 mL). The mixture was stirred at this temperature for 1 hour and then warmed up to 5° C. over 2 hours. The mixture was then diluted with dichloromethane (10 mL), filtered and the insoluble material was washed with dichloromethane (5 mL). The combined filtrates were washed with saturated aqueous sodium hydrogen carbonate and water, dried over $MgSO_4$, and concentrated. The residue was chromatographed on a silica gel column using ethyl acetate: hexanes, 1:2 (v:v) as eluant to give 120 mg (80%) of the title compound: $^1$H-n.m.r. (300 MHz, $CDCl_3$): δ 7.68, 6.96(2 m, 9 H, aromatic), 5.3(m, 2 H), 5.13(d, 1 H, H-1', $J_{1',2'}$ 8.0 Hz), 4.99(q, 1 H), 4.82(d, 1 H), 4.62(d, 1 H, H-1, $J_{1,2}$ 7.7 Hz), 4.54(d, 1 H), 4.42(d, 1 H), 4.3(q, 1 H), 4.15(m, 2 H), 3.99(m, 2 H), 3.87(m, 2 H), 3.72(m, 2 H), 3.46(m, 1H), 2.15, 2.12, 2.09, 2.00, 1.98(5 s, 15 H, 5XAc), 1.00(t, 3 H, $CH_3$). $^{13}$C-n.m.r. ($CDCl_3$): δ 101.2, 97.8(C-1, C-1'), 14.85($CH_3$).

The 2-amine of Compound 67 above can be regenerated by contacting this compound with hydrazine acetate and then acetylated with acetic anhydride/pyridine or other acetylating agents to provide for a saccharide (compound 90)

EXAMPLE 24—Synthesis of Ethyl 2-acetamido-6-O-acetyl-2-deoxy-4-O-(2,3,4,6-tetra-O-acetyl-β-D-galactosyl)-3-O-(2,3,4-tri-O-benzyl-α-L-fucosyl)-β-D-glucopyranoside To a stirred solution of the disaccharide 90 (80 mg, 0.129 mmol) in dichloromethane (2 mL) containing molecular sieves (3 A, 1 g), tetraethylammonium bromide (41 mg, 0.195 mmol), dimethylformamide (0.1 mL) and diisopropylethylamine (0.087 mL, 0.5 mmol) was added, at room temperature under nitrogen, a solution of 2,3,4-tri-O-benzylfucosyl bromide (130 mg, 0.26 mmol—as per Example 14) in dichloromethane (2 mL). The mixture was stirred at room temperature under nitrogen for 72 hours and then filtered, and the insoluble material was washed with dichloromethane (10 mL). The combined filtrates were washed with saturated aqueous sodium hydrogen carbonate and water, dried over $MgSO_4$, and concentrated. The residue was chromatographed on a silica gel column using ethyl acetate:hexanes, 3:1 (v:v) as eluant to give 115 mg (90%) of the title trisaccharide: $^1$H-n.m.r. (300 MHz, $CDCl_3$): δ 7.30(m, 15 H, aromatic), 6.00(d, 1 H, NH, J 8.0 Hz), 5.38(d, 1 H, H-1 Fuc, $J_{1,2}$ 3.3 Hz), 5.14(d, 1 H, H-1 Glc, $J_{1,2}$ 7.8 Hz), 5.1(m, 1 H), 4.98(m, 2 H), 4.80(m, 6 H), 4.40(m, 2 H), 4.33(q, 1 H), 4.1(m, 5 H), 3.77(m, 7 H), 3.48(m, 1 H). 2.09, 2.07, 2.01, 2.00, 1.97(5XAc, 15 H), 1.80(s, 3 H, NAc), 1.18(d, 3 H, H-6 Fuc, $J_{5,6}$ 6.6 Hz), 1.087(t, 3 H, $CH_3$ofEt). $^{13}$C-n.m.r. ($CDCl_3$): δ 99.87 (C-1 Gal), 99.19(C-1 Glc), 97.18(C-1 Fuc), 16.67(C-6 Fuc), 14.79($CH_3$ofEt).

Examples 25–30 illustrate the synthesis of modified sialyl Lewis$^x$ and sialyl Lewis$^A$ structures as depicted in FIGS. 27 to 32. Sialyl Lewis$^A$ contains a core type I structure whereas sialyl Lewis$^x$ contains a core type II structure.

General methods used in Examples 25–30 as well as methods for preparation of the sialyltransferase and the fucosyltransferase used in these examples are set forth below:

General Methods

Pre-coated plates of silica gel (Merck, 60-$F_{254}$) were used for analytical t.l.c. and spots were detected by charring after spraying with a 5% solution of sulfuric acid in ethanol. Silica gel 60 (Merck, 230–400 mesh) was used for column chromatography. Iatrobeads were from Iatron (Order No. 6RS-8060). Millex-GV filters (0.22 μm) were from Millipore. $C_{18}$ Sep-Pak cartridges and bulk $C_{18}$ silica gel were from Waters Associates.

Commercial reagents were used in chemical reactions and solvents were purified and dried according to usual procedures. Unless otherwise noted, the reaction mixtures were processed by dilution with dichloromethane and washing with a dilute solution of sodium bicarbonate followed by water. After drying over magnesium sulfate, the solvents were removed by evaporation under vacuum with a bath temperature of 35° C. or lower when necessary.

$^1$H-n.m.r. were recorded at 300 MHz or 500 MHz with either tetramethylsilane in $CDCl_3$ or acetone set at 2.225 in $D_2O$ as internal standards, at ambient temperature, unless otherwise noted. The chemical shifts and coupling constants (observed splitting) were reported as if they were first order, and only partial n.m.r. data are reported. $^{13}$C-n.m.r. spectra were recorded at 75.5 MHz with tetramethylsilane in $CDCl_3$ or dioxane set at 67.4 in $D_2O$ as reference.

Frozen rat livers were from Pel-Freeze Biologicals. Sepharose 6B, Dowex 1-X8 were from Pharmacia, CDP and CMP-Neu5Ac were from Sigma. GDP-fucose was obtained by chemical synthesis as described below. All other chemicals were of analytical grade and of commercial origin.

Preparative Example A—Preparation of βGal(1→¾)βGlcNAc α(2→3)sialyltransferase

The βGal(1→¾)βGlcNAc α(2→3)sialyltransferase [(EC 2.4.99.5)—sometimes referred to as "α(2→3)ST"] and the βGal(1→4)βGlcNAc α(2→6)sialyltransferase [(EC 2.4.99.1)—sometimes referred to as "α(2→6)ST" were extracted from rat liver (600 g) using Triton CF-54 (Sigma) according to Weinstein et al.[74] The enzymes from the Triton extract were partially purified and concentrated on Cibacron Blue F3GA-Sepharose by a reported modification[77] of Sticher et al.'s process.[75] The detergent extract (3 L, 3.5 mg protein/ML) was loaded onto a column (8×20 cm) of Cibacron Blue F3GA (Serva) linked to Sepharose 6B (prepared according to Dean and Watson[76]) equilibrated in 10 mM sodium cacodylate (pH 6.5), 0.15M NaCl, 25% glycerol, 0.1% Triton CF-54 (buffer A) in two portions, with a wash step in between with buffer A. The column was washed with the same buffer until no further protein was eluted, and was then eluted with buffer A containing 2.0M NaCl. Active fractions containing sialytransferases were pooled, concentrated by ultrafiltration on an Amicon PM 30 membrane and dialyzed against 200 volumes of buffer A. The α(2→3)ST was separated from the α(2→6)ST and purified by affinity chromatography on a matrix (Le$^c$-Sepharose) obtained by covalently linking the hapten βGal(1→3)βGlcNAcO(CH$_2$)$_8$COOH disclosed by Mazid et al.[77] to activated Sepharose described by Matsumoto[78] using art recognized techniques involving the N-succinimidyl ester of the hapten. The sialytransferases, partially purified by the above dye chromatography, containing ~160 mU of α(2→3)ST and 2.4 U of α(2→6)ST (about 860 mg protein) were diluted with an equal volume of buffer A containing 2.5 mM CDP at a flow rate of 5 mL/hour. The column was washed with the equilibrating buffer to remove any loosely bound protein. Enzyme activity determination indicted that the α(2→3)ST adsorbed strongly to the column during application and subsequent wash steps, while the bulk of the inert protein and the α(2→6)ST eluted unretarded. The α(2→3)ST was then eluted from the column with buffer A containing 0.2M lactose. Fractions (2 mL each) containing the α(2→3)ST were pooled and concentrated to a small column (~1 mL) on an Amicon PM 30 membrane. The concentrate was dialyzed against 200 volumes of 50 mM sodium cacodylate (pH 6.5), 0.25M NaCl, 50% glycerol, 0.1% Triton CF-54 and stored at −20° C. This preparation, 82,000-fold purified to a specific activity of 2.7 U/mg protein, was devoid of α(2→6)ST activity when preparative sialylation using βGal(1→4) βGlcNAc-O-(CH$_2$)$_8$COOCH$_3$ (compound 22a) as the acceptor[9] was carried out and the product analyzed by $^1$H-n.m.r. spectroscopy and by t.l.c.

Preparative Example B—Preparation of the βGal(1→¾) βGlcNAc α(1→¾)fucosyltransferase from Human Milk (EC 2.4.1.65)

The enzyme was purified from human milk obtained from Lewis$^{a+b-}$ donors, according to the methodology using affinity chromatography on GDP-hexanolamine Sepharose described by Palcic et al.[25].

EXAMPLE 25—Synthesis of the starting materials: Synthesis of Acceptors: Compounds 120b, 120c, 122b, 122c, 122d (FIG. 29A)

A. Preparation of 8-Methoxycarbonyl 2,3,4,6-tetra O-acetyl-β-D-galactopyranosyl-(1→3)-O-2-azido-2-deoxy-β-D-glucopyranoside (compound 119) and 8-methoxycarbonyl 2,3,4,6-tetra-O-acetyl-β-D-galactopyranosyl-(1→4)-O-2-azido-2-deoxy-β-D-glucopyranoside (compound 121).

A solution of trimethylsilyltrifluoromethanesulfonate (0.460 g, 1.94 mmol) in dry methylene chloride (5 mL) was syringed dropwise to a mixture of compound 117[12] (1.20 g, 1.94 mmol), compound 118 (0.757 g, 1.94 mmol) and molecular sieves 4 Å (2 g) in dichloromethane stirred at 22° C. After 2 h, the reaction was stopped by addition of triethylamine, the mixture filtered and worked up as usual. The recovered material was chromatographed on silica gel (150 g) using a 3:1 mixture of hexanes and ethyl acetate as eluant providing a mixture of the β(1→3) and the β(1→4) disaccharide (1.10 g, 60%) which could not be separated at this stage.

Tetraethylammonium chloride (0.196 g, 1.18 mmol) and anhydrous potassium fluoride (0.299 g, 5.15 mmol) were added to a solution of the mixture of the above disaccharides (0.460 g, 0.487 mmol) in dry acetonitrile (10 mL). After 24 hours at 22° C., acetic acid (1–5 mL) was added and the solvents were evaporated in vacuo. The residue was dissolved in chloroform (20 mL), washed with a dilute solution of sodium bicarbonate followed by water. The recovered crude material was chromatographed on silica gel (36 g) using a 1:1 mixture of ethyl acetate and hexane as eluant providing the (1→4) disaccharide 121 (157 mg, 46%) and the (1→3) disaccharide 119 (96 mg, 28%).

Disaccharide 121: $[α]_D^{20}$+6.9° (c 1.0, CHCl$_3$) $^1$H-n.m.r. (CDCl$_3$) 5.381 (d, 1 H, J$_{3',4',3,5}$ Hz, H-4'), 5.222(dd, 1 H, J$_{1',2'}$ 8.0 Hz, J$_{2',3'}$ 10.0 Hz,H-2'), 5.014 (dd, 1 H, H-3'), 4.628(d, 1 H, H-1'), 4.257[m, incl. H-1 (d, J$_{1,2}$ 8.0 Hz)], 3.420–3.640 [m, incl. CO$_2$CH$_3$(s, 3.650)], 2.227(t,2 H, J 7.5Hz, CH$_2$CO$_2$), 2.150, 2.100 (two), 1.950(3 s, 12 H, 4 OAc), 1.600(m, 4 H, methylenes), 1.300(m, 8 H, methylenes);

Disaccharide 119: $[α]_D^{20}$+7.8° (c 1, CHCl$_3$) $^1$H-n.m.r. (CDCl$_3$) 5.359 (d,1 H, J$_{3',4'}$ 3.2 Hz), 5.225(dd, 1H, J$_{1',2'}$ 8.0, J$_{2',3'}$ 10 Hz, H-2'), 5.013 (dd, 1 H, H-3'), 4.524 (d, 1 H, H-1'), 4.300 (d, J$_{1,2}$ 8.0 Hz, H-1), 3.628(s, 3 H, CO$_2$CH$_3$), 2.230 (t, 2 H, J 7.5 Hz, CH$_2$CO$_2$), 2.150, 2.080, 2.000, 1.920 (4 s, 12 H, 4 OAc), 1.600(m, 4H, methylenes), 1.300(m, 8H, methylenes).

For identification purposes both disaccharides were peracetylated in a mixture of pyridine and acetic anhydride.

Peracetylated derivative of 121: 5.314(dd, 1H, J$_{3',4'}$ 3.5, J$_{4',5'}$, <1 Hz,H-4'), 5.047(dd, 1 H, J$_{1',2'}$ 8.0, J$_{2',3'}$ 10.0 Hz, H-2'), 4.870–4.970[m,2H, incl. H-3, 4.923(dd, J$_{2',3'}$ ~J$_{3',4'}$ 10.0 Hz) and H-3'(4.903, dd)], 4.420[m, 2 H, incl. H-1'(d)], 4.300(d, J$_{1,2}$ 8.0 Hz, H-1), 3.627[m, incl. CO$_2$CH$_3$(s, 3.627)], 3.335(dd, 1 H, H-2), 2.230(t,J 7.5 Hz, CH$_2$CO$_2$) 2.080, 2.070, 2.050, 2.010, 1.980, 1.936(5 s, 18 H, 6 OAc), 1.570(m, 4 H, methylenes), 1.210(m, 8 H, methylenes).

Peracetylated derivative of compound 119: 5.120(dd, 1 H, J$_{3',4'}$ 3.5, J$_{4',5'}$ 1.0 Hz, H-4'), 5.080 (dd, 1 H, J$_{1',2'}$ 7.8, J$_{2',3'}$ 10.0 Hz, H-2'), 4.980 (dd, 1 H, H-3'), 4.875(dd, 1 H, J$_{3,4}$~J$_{4,5}$~10.0 Hz, H-4), 4.715(d, 1 H, H-1'), 4.257(d, 1 H, J$_{1,2}$ 8.0 Hz, H-1), 3.627(s, 3 H, CO$_2$CH$_3$), 3.320(dd, 1 H, J$_{2,3}$ 10.0 Hz, H-2), 2.230(t, J 7.5 Hz, CH$_2$CO$_2$), 2.080, 2.050, 2.020, 2.010, 1.970, (6 s, 18 H, 6 OAc), 1.600(m, 4 H, methylenes), 1.250(m, 8 H, methylenes).

B. Preparation of 8-Methoxycarbonyloctyl β-D-galactopyranosyl-(1-3)-O-2-azido-2-deoxy-β-D-glucopyranoside (compound 120b)

A catalytic amount of a dilute solution of sodium methoxide in methanol was added to a solution of compound 119 (0.045 g, 0.064 mmol) in methanol (2 mL). After 5 hours at 22° C., neutralization with Dowex 50W X8 (H$^+$ form) and filtration, the solvent was evaporated in vacuo providing the pure 120b (30 mg, 88%); $[α]_D^{20}$−11.7° (c 0.65, H$_2$O) $^1$H-n.m.r. (CD$_3$OD,DOH: 4.80): δ 4.45(d, 1 H, J 7.0 Hz) and 4.34(d, 1 H, J 7.5 Hz): H-1 and H-1', 3.61(s, CO$_2$CH$_3$), 2.27(t, 2 H, J 7.5 Hz, CH$_2$CO$_2$), 1.58(m, 4 H) and 1.30 (m, 8 H): methylenes.

C. Preparation of 8-Methoxycarbonyloctyl β-D-galactopyranosyl-(1→3)-O-2-amino-2-deoxy-β-D-glucopyranoside (compound 120c)

Compound 120b (0.018 g, 0.034 mmol) was hydrogenated in the presence of 5% palladium on carbon (5 mg) in methanol (2 mL) at atmospheric pressure for 6 hours. After filtration through Celite, the solvent was evaporated and the residue chromatographed on Iatrobeads (2 g) using a mixture of chloroform and methanol as the eluant providing the pure compound 120c; $[α]^{20}_D$−4.2° (c 0.48 H$_2$O); $^1$H-n.m.r (D$_2$O, DOH at 4.80): δ 4.56 and 4.48(2 d, 1 H each, J 7.5 Hz): H-1 and H-1', 3.70(s, CO$_2$CH$_3$) 2.90(~t, 1 H, J 9.5 Hz, H-2) 2.39(t, 2 H, J 7.5 Hz, CH$_2$CO$_2$), 1.62(m, 4 H) and 1.35 (m, 8 H): methylenes.

D. Preparation of 8-Methoxycarbonyloctyl β-D-galactopyranosyl-(1→4)-O-2-azido-2-deoxy-β-D-glucopyranoside (compound 122b)

A catalytic amount of a dilute solution of sodium methoxide in methanol was added to a solution of compound 121 (0.027 g, 0.38 mmol) in methanol (2 mL). After 5 hours at 22° C., neutralization with Dowex 50W X8 (H$^+$ form) and filtration, the solvent was evaporated in vacuo. The residue was chromatographed on Iatrobeads using a 65:35 mixture of chloroform and methanol as eluant to give compound 122b (0.019 g, 92%); $[\alpha]^{20}_D$ –12.4° (c 0.73 $CH_3OH$); $^1$H-n.m.r. ($CD_3OD$, DOH at 4.80): δ 4.32(d, 1 H, J 7.5 Hz) and 4.30(d,1H, J 8.0 Hz): H-1 and H-1', 3.60(s, $CO_2CH_3$), 3.13(dd, $J_{1,2}$ 8.0 $J_{2,3}$ 10.0 Hz, H-2) 2.27(t, 2 H, J 7.5 Hz, $CH_2CO_2$), 1.56(m, 4 H) and 1.29(m, 8 H): methylenes.

E. Preparation of 8-Methoxycarbonyloctyl β-D-galactopyranosyl-(1-4)-O-2-amino-2-deoxy-β-D-glucopyranoside (compound 122c)

Compound 122b (0.016 g, 0.29 mmol) was hydrogenated in the presence of 5% palladium on carbon (10 mg) in methanol (5 mL) for 5 hours at 22° C. After filtration through Celite, the solvent was evaporated and the residue chromatographed on Iatrobeads (0.25 g) using a 8:2 mixture of chloroform and methanol as eluant providing the pure 122c (0.013 g, 86%). $[\alpha]^{20}_D$ 2.8° (c 0.42, $H_2O$).

F. Preparation of 8-Methoxycarbonyloctyl β-D-galactopyranosyl-(1→4)-O-2-deoxy-2-propionamido-β-D-glucopyranoside (compound 122d)

Compound 121 (0.017 g, 0.032 mmol) was hydrogenated in the presence of 5% palladium on carbon (5 mg) in methanol (8 mL) at atmospheric pressure for 8 hours. After filtration through Celite and evaporation of the solvent, the residue was dissolved in dry methanol (3 mL) containing some triethylamine (0.150 mL). Propionic anhydride (0.150 mL) was added and the mixture was stirred for 4 hours at 22° C. after which the solvents were evaporated to dryness. The residue was acetylated in a 2:1 mixture of pyridine and acetic anhydride (4 mL) at 22° C. for 18 hours. After addition of methanol, the mixture was worked up as usual and after evaporation of the solvents, the residue was chromatographed on silica gel using a 1:1 mixture of ethyl acetate and hexane as eluant providing the pure hexa-O-acetate of compound 122d; $^1$H-n.m.r. ($CDCl_3$): 5.50(d, 1 H, J 9.5 Hz, NH), 5.32(~d, $J_{3',4'}$ 3.5 Hz, H-4'), 5.07(m, 2 H, H-2' and H-3), 4.93(dd, 1 H, $J_{2',3'}$ 10.0 Hz, H-3'), 4.45(m, 3 H, incl. H-1 and H-1'), 3.63(s, $CO_2CH_3$), 2.257(t, 2 H, J 7.5, $CH_2CO_2$), 2.137(dq, J 1.0 and 7.5 Hz, $NHCH_2$), 2.11, 2.07, 2.02 (three), 1.93(4 s, 12 H, 6 OAc), 1.540(m, 4 H) and 1.25(m, 8 H): methylenes, 1.09 (t, 2 H, $NHCH_2CH_3$).

The above disaccharide was de-O-acetylated in dry methanol (1 mL) containing a catalytic amount of a solution of sodium methoxide. After neutralization with Dowex 50W X8 (H$^+$ form) resin and filtration, evaporation of the solvents left the pure 122d; $[\alpha]^{20}_D$ –18.0° (c 0.43, $CH_3OH$); $^1$H-n.m.r. ($CD_3OD$, DOH at 4.80): δ 4.36(d, 1 H, J 8.0 Hz) and 4.33(d, 1 H, J 7.5 Hz): H-1 and H-1', 3.60(s, $CO_2CH_3$), 2.26(t, 2 H, J 7.5 Hz, $CH_2CO_2$), 2.18(q, 2 H, J 7.5 Hz, $NHCOCH_2$), 1.51(m, 4 H) and 1.26(m, 8 H): methylenes, 1.09(t, 3 H, $NHCOCH_2CH_3$).

EXAMPLE 26—Synthesis of Sialylated Trisaccharides (Compounds 111b, 111c, and 111d, FIG. 27A)

Preparation of 8-methoxycarbonyloctyl (5-acetamido-3, 5-dideoxy-D-glycero-α-D-galacto-2-nonulopyranosylonic acid)-(2→3)-O-(β-D-galactopyranosyl)-(1→4)-O-(2-azido-2-deoxy-β-D-glucopyranoside (Trisaccharide 111b)

Known[12] trisaccharide 104 (60.8 mg, 0.05 mmol) is hydrogenated in ethyl acetate (1.5 mL) at 22° C. in the presence of 5% palladium on carbon for 1 hour to obtain the intermediate free acid (sialic acid). $[\alpha]_D^{20}$ –18.6° (c, 0.3, chloroform). This product is de-O-acetylated using a catalytic amount of sodium methoxide in methanol for 16 hours at 22° C. and the recovered material is chromatographed on BioGel P2 providing trisaccharide 111b (10.4 mg, 55%), $[\alpha]_D^{20}$ –6.5° (c,0.17, water). $^1$H-n.m.r. data are reported below.

B. Preparation of 8-Methoxycarbonyloctyl (benzyl-5-acetamido-4,7,8,9-tetra-O-acetyl-3,5-dideoxy-D-glycero-α-D-galacto-2-nonulopyranosylonate)-(2→3)-O-(2,4,6-tri-O-acetyl-β-D-galacto-pyranosyl)-(1→4)-O-(6-O-acetyl-2-amino-2-deoxy-β-D-glucopyranoside) (trisaccharide 109)

Hydrogen sulfide is bubbled through a solution of trisaccharide 104 (400 mg, 0.32 mmol) in a mixture of pyridine (32 mL), water (4.8 mL) and triethylamine (1.3 mL). After 16 hours at 22° C., the mixture is evaporated to dryness and co-evaporated with toluene to give a crude trisaccharide (430 g). Some of this material (85.9 mg, 0.07 mmol) is chromatographed (10:1, toluene:ethanol) providing 109 (55 mg, 70%). $[\alpha]_D$+25.9° (c,0.22, chloroform); $^1$H-n.m.r. ($CDCl_3$): δ 7.25–7.45 (m, 5 H, aromatics), 5.480(m, H-8", overlapping with 5.42(d, J 12.5 Hz, benzylic), 5.340(dd, 1 H, $J_{6",7"}$ 2.5, $J_{7",8"}$ 8.5 Hz, H-7"), 5.052(m, incl. benzylic (d) and H-2' dd($J_{1',2'}$ 8.0, $J_{2',3'}$10.0 Hz) 5.000(dd, 1 H, $J_{3',4'}$ 3.5 Hz, H-4'), 4.904(d, 1 H, J 10.0 Hz, NH), 4.860(ddd, 1 H, $J_{3"eq,4"}$ 4.5, $J_{3"ax,4"}$ 12.5, $J_{4",5"}$ 11.0 Hz, H-4"), 4.640[m, 2 H, incl., H-1' and H-3'), 3.660(s, 3 H, $OCH_3$), 2.780(dd, $J_{1,2}$~$J_{2,3}$ 8.5 Hz H-2), 2.604(dd, 1 H, $J_{3"eq,3"ax}$ 13.0 Hz, H-3"), 2.300(t,J 7.5 Hz, $CH_2CO_2$), 2.260, 2.170, 2.115, 2.080(three), 2.050, 1.985, 1.830(7 s,27 H, 8 OAc, 1 NAc), 1.670 (t, 1 H, J H-3eq), 1.600(m, 6 H, methylenes), 1.240(m, 8 H, methylenes).

C. Preparation of 8-Methoxycarbonyloctyl (5-acetamido-3,5-dideoxy-D-glycero-α-D-galacto-2-nonulopyranosylonic acid)-(2→3)-O-(β-D-galactopyranosyl)-(1→4)-O-(2-amino-2-deoxy-β-D-glucopyranoside (trisaccharide 111c)

A solution of the pure 109 (53 mg, 0.04 mmol) is hydrogenated in methanol for 1 hour at 22° C. in the presence of 5% palladium on carbon. Filtration of the catalyst and evaporation of the methanol provides the sialic acid intermediate (44 mg), $[\alpha]_D$+11.3° (c,0.22,water). This compound is de-O-acetylated using a catalytic amount of sodium methoxide in methanol for 24 hours at 22° C. Evaporation of the solution obtained after neutralization with acetic acid left a material which is purified by chromatography on BioGel P2 to provide for trisaccharide 111c (29.5 mg, 99%), $[\alpha]_D$–5.5° (c, 0.22, water). $^1$H-n.m.r. data are reported below.

D. Preparation of 8-Methoxycarbonyloctyl (benzyl-5-acetamido-4,7,8,9-tetra-O-acetyl-3,5-dideoxy-D-glycero-α-D-galacto-2-nonulopyranosylonate)-(2→3)-O-(2,4,6-tri-O-acetyl-β-D-galacto-pyranosyl)-(1→4)-O-(6-O-acetyl-2-deoxy-2-N-propionamido-β-D-glucopyranoside) (trisaccharide 110)

The crude amino compound 109 (98 mg, 0.08 mmol) is N-propionylated by adding propionic anhydride dropwise over 10 min to a solution of the crude amino trisaccharide 109 in a mixture of pyridine and water (about a 10:1 ratio of pyridine to water). The mixture is stirred overnight at 22° C., evaporated in vacuo and co-evaporated with toluene leaving a residue which is chromatographed (100:10, toluene:ethanol) providing trisaccharide 110 (74.4 mg, 71%). $[\alpha]_D$+10.3° (c,0.17, chloroform); $^1$H-n.m.r. ($CDCl_3$): δ 7.400 (m, 5 H, aromatics), 5.543(d, 1 H, J 7.5 Hz, NH), 5.480(m, 1 H, H-8"), overlapping with 5.440(d,1 H, J 12.5 Hz, benzylic), 5.341 (dd, 1 H, $J_{6",7"}$ 2.5, $J_{7",8"}$ 8.5 Hz, H-7"), 4.490–5.100[m, 3 H, incl. benzylics (5.051, d, J 12.5 Hz), H-2'(5.038, dd, $J_{1',2'}$ 8.09 $J_{2',3'}$ 10.0 Hz), 4.859(ddd, 1 H, $J_{3"eq,4"}$ 4.6, $J_{3"ax,4"}$ 12.5, $J_{4",5"}$ 10.5 Hz, H-4"), 4.610–4.69 [m, 2 H, incl., H-1'(d) and H-3'(dd)], 3.580–3.700[m, 2 H, incl., $OCH_3$(s, 3.668)], 2.602(dd, 1 H, $J_{3"eq,3"ax}$12.5 Hz, H-3"eq), 2.150–2.330 [m, 10 H, incl., $CH_2CO_2$(t, J 7.5 Hz), $NHCOCH_2$(q, J 7.5 Hz) and acetyls (2.260, 2,180, 2 s)], 2.088(four), 2.068, 1.987, 1.838(4 s, 21 H, acetyls), 1.662(t, 1 H, H-3"ax), 1.570(m, 6 H, methylenes), 1.240(m, 8 H, methylenes), 1.130(t, 3 H, $CH_2CH_3$).

E. Preparation of 8-methoxycarbonyloctyl (5-acetamido-3,5-dideoxy-D-glycero-α-D-galacto-2-nonulopyranosylonic acid)-(2→3)-O-(β-D-galactopyranosyl)-(1→4)-O-(2-deoxy-2-N-propionamido-β-D-glucopyranoside. (111d)

Trisaccharide 110 (71 mg, 0.055 mmol) is hydrogenated in the same manner as indicated in the synthesis of trisaccharide 111c to obtain the intermediate product (64 mg, 97%), $[\alpha]_D$–22.6° (c, 0.23, chloroform). This material was de-O-acetylated as usual and the recovered material chromatographed on BioGel P2giving 111d (39 mg, 83%), $[\alpha]_D$–8.5° (c, 0.2, water). $^1$H-n.m.r. data are reported below.

EXAMPLE 27—Synthesis of Sialylated Trisaccharides (Compounds 107b, 107c, and 107d, FIG. 27B)

A. Preparation of 8-methoxycarbonyloctyl (5-acetamido-3,5-dideoxy-D-glycero-α-D-galacto-2-nonulopyranosylonic acid)-(2→3)-O-(β-D-galactopyranosyl)-(1→3)-O-(2-azido-2-deoxy-β-D-glucopyranoside (Trisaccharide 107b)

Known[12] trisaccharide 103 (60.8 mg, 0.05 mmol) was hydrogenated in ethyl acetate (1.5 mL) at 22° C. in the presence of 5% palladium on carbon (60 mg) for 1 hour to obtain the intermediate free acid (sialic acid) (57.6 mg, 98.8%), $[\alpha]_D^{20}$–14.7° (c, 0.18, chloroform); i.r. (chloroform): 2120 cm$^{-1}$ ($N_3$). This intermediate was de-O-acetylated by using a catalytic amount of sodium methoxide in methanol for 16 hours at 22° C. After neutralization with BioRex-70 (BioRad) weak acid resin (H$^+$ form) and evaporation of the filtrate, the residue was chromatographed on BioGel P2 providing trisaccharide 107b (36.6 mg, 88%), $[\alpha]_D$–10.1° (C,0.32, water). $^1$H-n.m.r. data are reported below.

B. Preparation of 8-methoxycarbonyloctyl (benzyl-5-acetamido-4,7,8,9-tetra-O-acetyl-3,5-dideoxy-D-glycero-β-D-galacto-2-nonulopyranosylonate)-(2→3)-O-(2,4,6-tri-O-acetyl-β-D-galactopyranosyl)-(1→3)-O-(6-O-acetyl-2-amino-2-deoxy-β-D-glucopyranoside) (trisaccharide 105)

Hydrogen sulfide was bubbled through a solution of trisaccharide 103 (500 mg, 0.4 mmol) in a mixture of pyridine (40 mL), water (6 mL) and triethylamine (1.5 mL). After 16 hours at 22° C., the mixture was evaporated to dryness and co-evaporated with toluene to give a crude product (450 mg). Some of this material (105 mg) was chromatographed (10:1, toluene-ethanol) providing tetrasaccharide 105 (86 mg, 75%), $[\alpha]_D^{20}$–21.1° (c,0.02, chloroform). $^1$H-n.m.r. (CDCl$_3$): δ 7.32–7.45(m, 5 H, aromatics), 5.484(ddd, 1 H, $J_{7",8"}$8.5, $J_{8",9"a}$ 2.5, $J_{8",9"b}$ 5.5 Hz,H-8"), 5.418(d, 1 H, J 12.2 Hz, benzylic), 5.291(dd, 1 H, $J_{6",7"}$ 2.7 Hz, H-7"), 5.080(dd, 1 H, $J_{1',2'}$ 8.0, $J_{2',3'}$ 10.0 Hz, H-2'), 5.022(d, 1 H, J 12.2 Hz, benzylic), 4.980(bd, 1 H, $J_{3',4'}$ 3.5 Hz, H-4'), 4.890 (d, 1 H, $J_{5",NH}$ 10.5 Hz, NH), 4.829 (ddd,1 H, $J_{3"eq,4"}$4.5, $J_{3"ax,4"}$12.5, $J_{4",5"}$ 10.5 Hz,H-4"), 4.739 (d, 1 H, $J_{1',2'}$ 8.0 Hz, H-1'), 4.670(dd, 1 H, $J_{2',3'}$ 10.3, $J_{3',4'}$ 3.5 Hz, H-3'), 3.635(s, 3 H, OCH$_3$), 2.851(dd, 1 H, $J_{1,2}$ 8.5, $J_{2,3}$ 9.5 Hz, H-2), 2.586(dd, 1 H, $J_{3"ax,3"eq}$ 13.0 Hz, H-3"eq), 2.265(t, 1 H, 7.5 Hz, CH$_2$CO$_2$), 2.222, 2.150, 2.060, 2.050, 2.045, 2.040, 2.018, 1.958, 1.805(9 s, 3 H each, 8 OAc, 1 NHAc), 1.650(t, 1 H, H-3"ax), 1.564(m, 6 H, methylenes), 1.300(m, 8 H, methylenes).

C. Preparation of 8-methoxycarbonyloctyl (5-acetamido-3,5-dideoxy-D-glycero-α-D-galacto-2-nonulopyranosylonic acid)-(2→3)-O-(β-D-galactopyranosyl)-(1→3)-O-(2-amino-2-deoxy-β-D-glucopyranoside (tetrasaccharide 107c)

A solution of pure trisaccharide 105 (82 mg, 0.07 mmol) in methanol (1 mL) was hydrogenated for 1 hour at 22° C. in the presence of 5% palladium on carbon (82 mg). Filtration of the catalyst and evaporation left the intermediate (76 mg), $[\alpha]_D^{20}$+60° (c,0.4, chloroform). This compound (72 mg, 0.06 mmol) was de-O-acetylated by using a catalytic amount of sodium methoxide in methanol (3 mL) for 24 hours at 22° C. Evaporation of the solution obtained after neutralization with acetic acid left a material which was purified by chromatography on BioGel P2providing trisaccharide 107c (45.5 mg) 88%, $[\alpha]_D$–6.3° (c,0.35, water). $^1$H-n.m.r. data are reported below.

D. Preparation of 8-Methoxycarbonyloctyl (benzyl-5-acetamido-4,7,8,9-tetra-O-acetyl-3,5-dideoxy-D-glycero-α-D-galacto-2-nonulopyranosylonate)-(2→3)-O-(2,4,6-tri-O-acetyl-β-D-galactopyranosyl)-(1→3)-O-(6-O-acetyl-2-deoxy-2-N-propionamido-β-D-glucopyranoside) (trisaccharide 106)

Propionic anhydride (0.5 mL) was added dropwise in 10 min to a solution of the crude amino trisaccharide 105 (140 mg, 0.11 mmol) in a mixture of pyridine (9.5 mL) and water 0.9 mL). The mixture was stirred overnight at 22° C., evaporated in vacuo and co-evaporated with toluene leaving a residue which was chromatographed (100:10, toluene:ethanol) providing trisaccharide 106 (110 mg, 72%) which contained a small amount of the 4-O-propionylated trisaccharide. $^1$H-n.m.r. (CDCl$_3$): δ 7.310–7.450(m, 5 H, aromatics), 5.812(d, 1 H, J 8.0 Hz, NH), 5.45[m, incl., H-8" and benzylic (d, J 12.5 Hz)], 5.280(dd), $J_{6",7"}$ 2.7, $J_{7",8"}$ 8.5 Hz, H-7"), 5.300[m, incl. benzylic (d)], 3.630(s, 3 H, OCH$_3$), 2.578(dd, 1 H, $J_{3"eq,4}$ 4.5, $J_{3"eq,3"ax}$ 13.0 Hz, H-3"eq), 2.262(t, 2 H, J 7.5 Hz, CH$_2$CO$_2$), 2.200(q, NHCOCH$_2$), 2.147, 2.060, 2.045 (five), 1.955, 1.800(5 s, 27 H, 8 OAc, 1 NAc), 1.630(t, 1 H, $J_{3"ax,4"}$ 13.0 Hz, H-3"), 1.570(m, 6 H, methylenes), 1.240(m, 8 H, methylenes), 1.130(t, 7.5 Hz, COCH$_2$CH$_3$).

E. Preparation of 8-methoxycarbonyloctyl (5-acetamido-3,5-dideoxy-D-glycero-α-D-galacto-2-nonulopyranosylonic acid)-(2→3)-O-β-D-galactopyranosyl-(1→3)-O-(2-deoxy-2-N-propionamido-(β-D-glucopyranoside (trisaccharide 107d)

Trisaccharide 106 (105 mg, 0.082 mmol) was deprotected using the same procedure as indicated in the synthesis of 107c. Chromatography on BioGel P2 provided the pure 107d (60.8 mg, 95%), $[\alpha]_D^{20}$–16.6° (c,0.32, water). $^1$H-n.m.r. data are reported below.

EXAMPLE 28—Preparative Fucosylation i. Synthesis of GDP-Fucose.

A. Preparation of Bis(tetra-n-butylammonium) hydrogen phosphate

Tetra-n-butylammonium hydroxide (40% aq. w/w, about 150 g) was added dropwise to a solution of phosphoric acid (85% aq, w/w, 18 g, 0.155 mmol) in water (150 mL) until the pH reached 7. Water was then evaporated in vacuo to give a syrup which was co-evaporated with dry acetonitrile (2×400 mL) followed by dry toluene (2×400 mL). The resulting white solid (75 g) was dried in vacuo and stored over phosphorus pentoxide under vacuum until used.

B. Preparation of β-L-Fucopyranosyl-1-phosphate

A solution of bis(tetra-n-butylammonium) hydrogen phosphate (58 g, 127.8 mmol) in dry acetonitrile (300 mL) was stirred at room temperature under nitrogen in the presence of molecular sieves (4 A, 20 g) for about one hour. A solution of tri-O-acetyl fucosyl-1-bromide (freshly prepared from 31 g, 93 mmol of L-fucose tetraacetate in the manner of Nunez et al.[80]) in dry toluene (100 mL) was added dropwise in about 0.5 hour to the above solution, cooled at 0° C. After one more hour at 0° C., the mixture was brought to room temperature and stirred for 3 hour. T.l.c. (1:1 toluene:ethyl acetate) indicated a main spot on the base line and several faster moving smaller spots.

The mixture was filtered over a pad of Celite (which was further washed with acetonitrile) and the solvents evaporated in vacuo to give a red syrup. This material was dissolved in water (400 mL) and extracted with ethyl acetate (250 mL, twice). The aqueous layer was then evaporated in vacuo leaving a yellowish syrup to which a solution of ammonium hydroxide (25% aq., 200 mL) was added. The mixture was stirred at room temperature for 3 hours after which t.l.c. (65:35:8 chloroform:methanol:water) indicated a baseline spot. The solvent was evaporated in vacuo to give a yellowish syrup which was diluted with water (400 mL). The pH of this solution was checked and brought to 7, if necessary, by addition of a small amount of hydrochloric acid. The solution was slowly absorbed onto a column of ion exchange resin Dowex 2×8 [200–400 mesh, 5×45 cm, bicarbonate form which had been prepared by sequential washing of the resin with methanol (800 mL), water (1200 mL), ammonium bicarbonate (1M, 1600 mL) and water (1200 mL)]. Water (1000 mL) was then run through the column followed by a solution of ammonium bicarbonate (0.5M, 2.3 mL/minute, overnight). The eluate was collected in fractions (15 mL) and the product detected by charring after spotting on a t.l.c. plate. Fractions 20 to 57 were pooled and evaporated in vacuo leaving a white solid which was further co-evaporated with water (3×300 mL) and freeze drying of the last 50 mL and then drying of the residue with a vacuum pump to give β-L-fucopyransyl-1-phosphate (9.5 g, 40%) as a 12:1 mixture of β and α anomers containing some ammonium acetate identified by a singlet at δ=1.940 in the $^1$H-n.m.r. spectrum. This product was slowly run through a column of Dowex 5×8 resin (100–200 mesh, triethylammonium form) and eluted with water to provide the bis-triethylammonium salt of β-L-fucopyransyl-1-phosphate as a sticky gum after freeze drying of the eluate. $^1$H-n.m.r. δ:4.840 (dd, $J_{1,2}=J_{1,P}$=7.5 Hz, H-1), 3.82 (q, 1 H, $J_{5,6}$ 6.5 Hz, H-5), 3.750 (dd, 1 H, $J_{3,4}$ 3.5, $J_{4,5}$ 1.0 Hz, H-4), 3.679 (dd, 1 H, $J_{2,3}$ 10.0 Hz, H-3), 3.520 (dd, 1 H, H-2), 1.940 (s, acetate), 1.26 (d, H-6). Integral of the signals at 3.20 (q, J 7.4 Hz, NCH$_2$) and 1.280 and 1.260 (NCH$_2$CH$_3$ and H-6) indicates that the product is the bis-triethylammonium salt which may loose some triethylamine upon extensive drying. $^{13}$C-n.m.r. δ:98.3 (d, $J_{C,1P}$ 3.4 Hz, C-1), 72.8 (d, $J_{C,2P}$ 7.5 Hz, C-2), 16.4(C-6); $^{31}$P-nmr δ: +2.6(s).

β-L-fucopyransyl-1-phosphate appears to slowly degrade upon prolonged storage (1+ days) in water at 22° C. and, accordingly, the material should not be left, handled or stored as an aqueous solution at 22° C. or higher temperatures. In the present case, this material was kept at −18° C. and dried in vacuo over phosphorus pentoxide prior to being used in the next step.

C. Preparation of Guanosine 5'-(β-1-fucopyranosyl)-diphosphate

Guanosine 5'-(β-1-fucopyranosyl)-diphosphate was prepared from β-L-fucopyranosyl-1-phosphate using two different art recognized procedures as set forth below:

PROCEDURE #1

β-L-fucopyranosyl-1-phosphate and guanosine 5'-monophosphomorpholidate (4-morpholine-N,N'-dicyclohexylcarboxamidine salt, available from Sigma, St. Louis, Mo., "GMP-morpholidate") were reacted as described in a recent modification[79,81] of Nunez's original procedure[80]. Accordingly, tri-n-octylamine (0.800 g, available from Aldrich Chemical Company, Milwaukee, Wis.) was added to a mixture of β-L-fucopyranosyl-1-phosphate (triethylammonium salt, 1.00 g, about 2.20 mmol) in dry pyridine (10 mL) under nitrogen the solvent removed in vacuo. The process was repeated three times with care to allow only dry air to enter the flask. GMP morpholidate (2.4 g, about 3.30 mmol) was dissolved in a 1:1 mixture of dry dimethylformamide and pyridine (10 mL). The solvents were evaporated in vacuo and the procedure repeated three times as above. The residue was dissolved in the same mixture of solvents (20 mL) and the solution added to the reaction flask accompanied by crushed molecular sieves (4 A, 2 g). The mixture was stirred at room temperature under nitrogen. T.l.c. (3:5:2 25% aq. ammonium hydroxide, isopropanol and water) showed spots corresponding to the starting GMP-morpholidate (Rf~0.8, U.V.), guanosine 5'-(β-1-fucopyranosyl)-diphosphate (Rf~0.5, U.V. and charring), followed by the tailing spot of the starting fucose-1-phosphate (Rf~0.44, charring). Additional U.V. active minor spots were also present. After stirring for 4 days at room temperature, the yellowish mixture was co-evaporated in vacuo with toluene and the yellowish residue further dried overnight at the vacuum pump leaving a thick residue (2.43 g). Water (10 mL) was then added into the flask to give a yellow cloudy solution which was added on top of a column of AG 50W-X12 (from Biorad) resin (100–200 mesh, 25×1.5 cm, Na$^+$ form). The product eluted with water after the void volume. The fractions which were active, both by U.V. and charring after spotting on a t.l.c. plate, were recovered and the solution freeze-dried overnight in vacuo providing a crude material (1.96 g).

This residue was dissolved in water (10 mL overall) and slowly absorbed onto a column of hydrophobic C$_{18}$ silica gel (Waters, 2.5×30 cm) which had been conditioned by washing with water, methanol and water (250 mL each). Water was then run through the column (0.4 mL/min) and the eluate collected in fractions (0.8 mL) which were checked by t.l.c. (3:5:2 25% aq. ammonium hydroxide, isopropanol and water). β-L-fucopyranosyl-1-phosphate, (Rf~0.54, charring) was eluted in fractions 29 to 45. A product showing a strongly U.V. active spot (Rf~0.51) eluted mainly in fractions 46 to 65. Other minor U.V. active spots of higher or lower Rf were observed. Fractions 59 to 86, which contained guanosine 5'-(β-1-fucopyranosyl)diphosphate (Rf~0.62), also showed a narrow U.V. active spot (Rf~0.57). Fractions 59 to 86 were pooled and freeze-dried overnight providing 0.353 g of material enriched in guanosine 5'-(β-1-fucopyranosyl)diphosphate. $^1$H-n.m.r. indicated that this material was contaminated by a small amount of impurities giving signals at δ=4.12 and δ=5.05.

Fractions 29 to 45 and 47 to 57 were separately pooled and freeze-dried providing recovered β-L-fucopyranosyl-1-phosphate (0.264 g and 0.223 g, respectively, in which the second fraction contains some impurities). Occasionally, pooling of appropriate fractions provided some amount of guanosine 5'-(β-1-fucopyranosyl)-diphosphate in good purity ($^1$H-n.m.r.). Generally, all the material enriched in guanosine 5'-(β-1-fucopyranosyl)-diphosphate was dissolved in a minimum amount of water and run on the same column which had been regenerated by washing with large amounts of methanol followed by water. The fractions containing the purified guanosine 5'-(β-1-fucopyranosyl)-diphosphate (t.l.c.) were pooled and freezed dried in vacuo leaving a white fluffy material (187 mg, 16%). $^1$H-n.m.r. was identical to the previously reported data[67].

PROCEDURE #2

β-L-fucopyranosyl-1-phosphate and guanosine 5'-monophosphomorpholidate (4-morpholine-N,N'-dicyclohexyl-carboxamidine salt—"GMP-morpholidate") were reacted in dry pyridine as indicated in the original procedure of Nunez, et al[80]. Accordingly, the β-L-fucopyranosyl-1-phosphate (triethylammonium salt, 0.528 g, about 1.18 mmol) was dissolved in dry pyridine (20 mL) and the solvent removed in vacuo. The process was repeated three times with care to allow only dry air to enter the flask. GMP-morpholidate (1.2 g, 1.65 mmol) and pyridine (20 mL) were added into the reaction flask, the solvent evaporated in vacuo and the process repeated three times as above. Pyridine (20 mL) was added to the final residue and the heterogeneous mixture was stirred for 3 to 4 days at room temperature under nitrogen. An insoluble mass was formed which had to be occasionally broken down by sonication.

The reaction was followed by t.l.c. and worked up as indicated in the first procedure to provide the GDP-fucose (120 mg, 16%).

ii. Enzymatic Conditions

βGal(1→¾)βGlcNAc(1→¾) fucosyltransferase was purified from human milk according to the methodology using affinity chromatography on GDP-hexanolamine Sepharose described by Palcic et al.[25] The enzymatic reactions were carried out at 37° C. in a plastic tube using a sodium cacodylate buffer (100 mM, pH 6.5), $MnCl_2$ (10 mM), ATP (1.6 mM) $NaN_3$ (1.6 mM). The final reaction mixture was diluted with $H_2O$ (5 mL) and applied onto $C_{18}$ Sep-Pak cartridges as reported[25]. After washing with $H_2O$ (30 mL) the products were eluted with $CH_3OH$ and the solvents evaporated. The residue was dissolved in a 65:35:5 mixture of $CHCl_3$, $CH_3OH$, and $H_2O$ and applied on a small column of Iatrobeads (0.200 to 0.500 g). After washing with the same solvent mixture, the products were eluted with a 65:35:8 and/or 60:40:10 mixtures of the same solvents. The appropriate fractions (t.l.c.) were pooled, the solvents evaporated in vacuo, the residue run through a small column of AG 50W X8 ($Na^+$ form) (BioRad) in $H_2O$ and the products recovered after freeze drying in vacuo. $^1H$-n.m.r. data of the tetrasaccharides are reported below:

iii. Fucosylation Reactions

A. Preparation of 8-Methoxycarbonyloctyl(5-acetamido-3,5-di-deoxy-D glycero-α-D-galacto-2-nonulopyranosylonic acid)-(2-3)-O-β-D-galactopyranosyl-(1-4)-O-[α-L-fucopyranosyl-(1-3)-O]-(2-azido-2-deoxy-β-D-glucopyranoside) (tetrasaccharide 112b)

Trisaccharide 111b (7.7 mg), GDP-fucose (18 mg), the fucosyltransferase (20 mU) and calf intestine alkaline phosphatase (10 U) were incubated for 72 hours in the buffer (2 mL). Isolation and purification provided 12b (2.84 mg).

B. Preparation of 8-Methoxycarbonyloctyl(5-acetamido-3,5-di-deoxy-D-glycero-α-D-galacto-2-nonulopyranosylonic acid)-(2-3)-O-β-D-galacto-pyranosyl-(1-4)-O-[α-L-fucopyranosyl-(1-3)-O]-(2-amino-2-deoxy-β-D-glucopyranoside) (tetrasaccharide 112c)

Trisaccharide 111c (8.4 mg), GDP-fucose (18 mg), the fucosyltransferase (20 mU) and calf intestine alkaline phosphatase (10 U) were incubated for 67 hours in the buffer (2 mL). Isolation and purification provided 112c (2.46 mg).

C. Preparation of 8-Methoxycarbonyloctyl(5-acetamido-3,5-di-deoxy-D-glycero-α-D-galacto-2-nonulopyranosylonic acid)-(2-3)-O-β-D-galacto-pyranosyl-(1-4)-O-[α-L-fucopyranosyl-(1-3)-O]-(2-N-propionamido-2-deoxy-β-D-glucopyranoside) (tetrasaccharide 112d)

Trisaccharide 111d (8.3 mg), GDP-fucose (18 mg), the fucosyltransferase (18 mU) and calf intestine alkaline phosphatase (10 U) were incubated for 72 hours in the buffer (2 mL). Isolation and purification provided 112d (6.17 mg).

D. Preparation of 8-methoxycarbonyloctyl (5-acetamido-3,5-di-deoxy-D-glycero-α-D-galacto-2-nonulopyranosylonic acid)-(2→3)-O-β-D-galactopyranosyl-(1→3)-O-[α-L-fucopyranosyl-(1→4)-O]-(2-azido-2-deoxy-β-D-glucopyranoside) (Tetrasaccharide 108b)

The trisaccharide 107b (8.7 mg), GDP-fucose (18 mg), the fucosyltransferase (18 mU) and calf intestine alkaline phosphatase (10 U) were incubated for 68 hours in the buffer (2 mL). Isolation and purification provided tetrasaccharide 108b (4.42 mg).

E. Preparation of 8-Methoxycarbonyloctyl (5-acetamido-3,5-di-deoxy-D-glycero-α-D-galacto-2-nonulopyranosylonic acid)-(2→3)-O-β-D-galacto-pyranosyl-(1→3)-O-[α-L-fucopyranosyl-(1→4)-O]-(2-amino-2-deoxy-β-D-glucopyranoside) (tetrasaccharide 108c)

The trisaccharide 107c (9.5 mg), GDP-fucose (18 mg), the fucosyltransferase (18 mU) and calf intestine alkaline phosphatase (10 U) were incubated for 60 hours in the buffer (2.8 mL). Isolation and purification provided for tetrasaccharide 108c (4.94 mg).

F. Preparation of 8-methoxycarbonyloctyl(5-acetamido-3,5-di-deoxy-D-glycero-α-D-galacto-2-nonulopyranosylonic acid)-(2→3)-O-β-D-galacto-pyranosyl-(1→3)-O-[α-L-fucopyranosyl-(1→4)-O]-(2-N-propionamido-2-deoxy-β-D-glucopyranoside) (tetrasaccharide 108d)

Trisaccharide 107d (8.4 mg), GDP-fucose (18 mg), the fucosyltransferase (19.4 mU) and calf intestine alkaline phosphatase (10 U) were incubated for 72 hours in the buffer (2 mL). Isolation and purification provided for tetrasaccharide 108d (5.81 mg).

Table A provides $^1H$-n.m.r. data for compounds 111b, 111c, 111d, 112b, 112c, and 112d; whereas Table B provides $^1H$-n.m.r. data for compounds 107b, 107c, 107d, 108b, 108c, and 108d.

TABLE A

Selected $^1H$-n.m.r. data for compounds: 111b,111c,111d,112b,112c,112d[a,b].

| Sugar Unit | Hydrogen | Chemical Shifts (J in Hz) | | | | | |
|---|---|---|---|---|---|---|---|
| | | 111b | 111c | 111d | 112b | 112c | 112d |
| β-GlcR[2] | 1 | 4.565°(8.0) | 4.715(8.5) | 4.552°(8.0) | 4.597(8.2) | 4.543(7.8) | 4.523°(7.5) |
| | 2 | 3.314(8.5; 10.0) | 3.007(~9.0) | — | 3.45 | 3.065(~9.0) | 3.88 |
| | $COCH_2$ | — | — | 2.291(7.5) | — | — | 2.287(7.5) |
| | $COCH_2CH_3$ | — | — | 1.123 | — | — | 1.120 |
| a-Fuc | 1 | — | — | — | 5.398(4.0) | 5.126(2.4) | 5.100(3.7) |
| | 2 | — | — | — | 3.76 | 3.83 | 3.66 |
| | 5 | — | — | — | 4.826(6.5) | 4.734(6.5) | 4.820(6.7) |
| | 6 | — | — | — | 1.165 | 1.195 | 1.166 |

TABLE A-continued

Selected $^1$H-n.m.r. data for compounds: 111b,111c,111d,112b,112c,112d$^{a,b}$.

| Sugar Unit | Hydrogen | 111b | 111c | 111d | 112b | 112c | 112d |
|---|---|---|---|---|---|---|---|
| β-Gal | 1 | 4.531$^c$(8.0) | 4.542(8.0) | 4.528$^c$(8.0) | 4.503(7.6) | 4.614(8.0) | 4.523$^c$(7.7) |
|  | 2 | — | — | — | 3.50 | 3.56 | 3.51 |
|  | 3 | 4.108(3.0; 10.0) | 4.113(3.0; 10.0) | 4.113(3.0; 10.0) | 4.081(3.0; 10.0) | 4.095(3.0; 10.0) | 4.083(3.0; 10.0) |
|  | 4 | — | 3.955 | 3.956 | 3.93 | — | 3.92 |
| α-Neu5Ac | 3eq | 2.755(4.5; 12.6) | 2.760(4.5; 12.6) | 2.757(4.5; 12.5) | 2.76(4.4; 12.5) | 2.769(4.5; 12.5) | 2.764(4.5; 12.5) |
|  | 3ax | 1.795(12.0) | 1.795(12.0) | 1.797(12.0) | 1.795(12.0) | 1.796(12.2) | 1.793(12.3) |
|  | 4 | — | — | — | 3.67 | 3.68 | 3.70 |
|  | NHAc | 2.029 | 2.031 | 2.031 | 2.029 | 2.030 | 2.025 |
|  | CH$_2$CO$_2$ | 2.385(7.5) | 2.387(7.5) | 2.384(7.5) | 2.387(7.5) | 2.386(7.5) | 2.384(7.5) |
|  | CO$_2$CH$_3$ | 3.686 | 3.686 | 3.686 | 3.687 | 3.686 | 3.687 |

$^a$in D$_2$O, with acetone set at 2.225.
$^b$11b, 11c, 11d: 300 MHz; 12b, 12c, 12d: 500 MHz,
$^c$interchangeable

TABLE B

Selected $^1$H-n.m.r. data for compounds: 107b, 7c, 7d, 8b, 8c, 8d$^{a,b}$.

| Sugar Unit | Hydrogen | 107b R$^2$ = N$_3$ | 107c R$^2$ = NH$_2$ | 107d R$^2$ = NHPr | 108b R$^2$ = N$_3$ | 108c R$^1$ = NH$_2$ | 108d R$^2$ = NHPr |
|---|---|---|---|---|---|---|---|
| β-GlcR$^2$ | 1 | 4.550(8.2) | 4.707(8.3) | 4.567$^c$(7.2) | 4.553(8.2) | 4.746 | 4.563(8.5) |
|  | 2 | — | 3.176(9.0; 9.5) | — | 3.47(9.0) | 3.03(9.0; 10.0) | 3.83 |
|  | COCH$_2$ | — | — | 2.285(7.5) | — | — | 2.295(7.5) |
|  | COCH$_2$CH$_3$ | — | — | 1.131 | — | — | 1.158 |
| α-Fuc | 1 | — | — | — | 4.987(3.5) | 5.077(3.7) | 5.005(3.5) |
|  | 2 | — | — | — | 3.76 | 3.78 | 3.78 |
|  | 5 | — | — | — | 4.885(6.7) | 4.80$^d$ | 4.856(6.5) |
|  | 6 | — | — | — | 1.179(6.5) | 1.183(6.5) | 1.173 |
| β-Gal | 1 | 4.717 | 4.658(8.0) | 4.485$^c$(7.6) | 4.846(7.7) | 4.647 | 4.518(7.7) |
|  | 2 | — | — | — | 3.54 | 3.67 | 3.51 |
|  | 3 | 4.130(2.7; 10.0) | 4.124(3.0; 10.0) | 4.070(3.0; 10.0) | 4.106(2.5; 9.8) | 4.118(2.7; 9.7) | 4.028(3.0; 10.0) |
|  | 4 | — | 3.948 | 3.955(1.0) | 3.93 | 3.94 | 3.90 |
| α-Neu5Ac | 3eg | 2.765(4.5; 12.5) | 2.771(4.5; 12.6) | 2.753(4.7; 12.5) | 2.773(4.4; 12.5) | 2.774(4.5; 12.5) | 2.762(4.5; 12.5) |
|  | 3ax | 1.814(12.2) | 1.782(12.0) | 1.775(12.2) | 1.814(12.0) | 1.785(12.0) | 1.764(12.0) |
|  | 4 | — | — | — | 3.67 | — | 3.68 |
|  | NHAc | 2.032 | 2.031 | 2.026 | 2.033 | 2.032 | 2.029 |
|  | CH$_2$CO$_2$ | 2.387(7.5) | 2.388(7.5) | 2.390(7.5) | 2.392(7.5) | 2.314(7.5) | 2.389(7.5) |
|  | CO$_2$CH$_3$ | 3.686 | 3.687 | 3.687 | 3.686 | — | 3.686 |

$^a$is D$_2$O, with acetone set at 2.225,
$^b$7b, 7c, 7d: 300 MHz; 8b, 8c, 8d: 500 MHz,
$^c$interchangeable,
$^d$overlapped.

EXAMPLE 29—Synthesis of Acceptor 114a

A. Preparation of 8-Methoxycarbonyloctyl β-D-galactopyranosyl-(1→3)-O-2-acetamido-6-bromo-2,6-dideoxy-β-D-glucopyranoside (compound 114a)

A mixture of the compound 113$^{50}$ (0.061 g, 0.075 mmol), barium carbonate (0.020 g, 0.1 mmol) and N-bromosuccinimide (0.016 g, 0.09 mmol) in carbon tetrachloride (2 mL) was refluxed for 2 hours as indicated[82]. After the appropriate work up, the recovered crude material was chromatographed on silica gel (6 g) using a 1:1 mixture of hexanes and ethyl acetate as eluant providing the pure bromo derivative (36 mg, 54%).

Some of this material (0.019 g, 0.021 mmol) in dry methanol was de-O-acetylated using a catalytic amount of sodium methoxide for 3 hours at 22° C. After neutralization with Dowex 50W X8 (H$^+$ form) and filtration, the solvents were evaporated in vacuo and the residue chromatographed on Iatrobeads (2 g) using a 10:1 mixture of chloroform and methanol as eluant providing a pure disaccharide (0.012 g, 99%), which was poorly soluble in water. This material was saponified using a 0.25N solution of sodium hydroxide for 1 hour at 22° C. After neutralization with Dowex 50W X8 (H$^+$ form) and filtration, the solution was freeze dried in vacuo providing the disaccharide 114a; $[\alpha]^{20}_D$–11.4° (c 0.12, H$_2$O).

As noted above, the oligosaccharide glycosides related to blood group determinants can be administered to a mammalian patient as part of a liposome. The following example sets forth one method for preparing such liposomes.

EXAMPLE 30—SYNTHESIS OF AGGREGATES CONTAINING SIALYL LEWIS$^x$ ANALOGUES

Aggregates such as liposomes and micelles can be prepared so as to incorporate oligosaccharide glycosides related to blood group determinants having a type I or a type II core structure. Specifically, incorporation of such an oligosaccharide glycoside into such aggregates requires that the aglycon moiety be sufficiently hydrophobic to be incorporated into such aggregates. It is contemplated that such hydrophobic aglycons can include the —(CH$_2$)$_x$COOCH$_3$ (x≥2) which has been extended by various moieties such as naphthyl, substituted naphthyl, octyl, and the like which would improve the ability to incorporate the saccharide into the aggregate.

In such aggregates, the hydrophobic aglycon group of the oligosaccharide glycoside becomes partitioned in the lipid portion of the aggregate whereas the oligosaccharide group is generally partitioned in the aqueous phase.

Methods of preparing such aggregates are well known in the art. See, for instance, U.S. Pat. No. 4,522,803 which is incorporated herein by reference.

Examples 31–43 illustrate the synthesis of modified sialyl Lewis$^x$ and sialyl Lewis$^a$ structures as depicted in FIGS. 33 to 43.

General methods used in Examples 31–43 as well as methods are as follows:

General Methods

In one or more of Examples 31–43, pre-coated plates of silica gel (Merck, 60-$F_{254}$) were used for analytical t.l.c. and spots were detected by charring after spraying with a 5% solution of sulfuric acid in ethanol. Silica gel 60 (Merck, 40–63 μm) was used for column chromatography. Iatrobeads were from Iatron (Order No. 6RS-8060). Millex-GV filters (0.22 μm) were from Millipore. $C_{18}$ Sep-Pak cartridges and bulk $C_{18}$ silica gel were from Waters Associates.

Commercial reagents were used in chemical reactions and solvents were purified and dried according to usual procedures. Unless otherwise noted, the reaction mixtures were processed by dilution with dichloromethane and washing with a dilute solution of sodium bicarbonate followed by water. After drying over magnesium sulfate, the solvents were removed by evaporation under vacuum with a bath temperature of 35° C. or lower when necessary.

$^1$H-n.m.r. were recorded at 300 MHz (Bruker AM-300) with either tetramethylsilane in CDCl$_3$ or acetone set at 2.225 in D$_2$O as internal standards, at ambient temperature, unless otherwise noted. The chemical shifts and coupling constants (observed splittings) were reported as if they were first order, and only partial n.m.r. data are reported. $^{13}$C-n.m.r. spectra were recorded at 75.5 MHz with tetramethylsilane in CDCl$_3$ or dioxane set at 67.4 in D$_2$O as reference.

A. SYNTHESIS OF DERIVATIVES OF Neu5Ac

Unless otherwise noted, derivatives of Neu5Ac have been prepared following known procedures with suitable substitution of starting materials where necessary. The following derivatives have been prepared by a convenient modification of procedures reported in the literature: 9-N$_3$-Neu5Ac 201b, $^{53}$ Neu5Pr (5-propionamido) 201f, 7-d-Neu5Ac 201d$^{83}$ and the C8-Neu5Ac 201i$^{84}$.

FIGS. 33A and 33B illustrate a general synthetic scheme used for the synthesis of derivatives of Neu5Ac. Compounds referred to by underlined Arabic numerals in Examples 31–34 below are depicted Table I and in FIGS. 33A and B.

EXAMPLE 31—Synthesis of 5-acetamido-9-azido-3,5,9-trideoxy-D-glycero-D-galacto-2-nonulopyranosylonic acid (9-N$_3$-Neu5Ac) 201b Glycosyl chloride 238 (2.83 g, 5.57 mmol) in dry dichloromethane (13 mL) was added to the mixture of benzyl alcohol (5.0 mL, 48.2 mmol), molecular sieves 4 A (18.5 g, crushed), dry silver carbonate (4.2 g, 15.2 mmol) in dichloromethane (8 mL). The mixture was stirred in the dark for 4 days, diluted with dichloromethane (50 mL) and filtered through Celite. After usual work up, the residue was chromatographed on silica gel using a 3:2 mixture of hexanes and ethyl acetate as eluant. The product was then eluted with a 4:5 mixture of the same solvents giving (1.96 g, 60%) of pure material and 0.33 g (10%) of material containing a small amount of impurities. $^1$H-n.m.r.: 5.436 (ddd, 1 H, $J_{7,8}$ 8.5, $J_{8,9'}$ 2.5, $J_{8,9}$ 5.5 Hz, H-8), 5.317 (dd, 1 H, $J_{6,7}$ 1.8 Hz, H-7), 5.110 (d, 1 H, $J_{5,NH}$ 9.5 Hz, NH), 4.849 (ddd, 1 H, $J_{3ax,4}$ 12.0, $J_{3eq,4}$ 4.5, $J_{4,5}$ 9.5 Hz, H-4), 4.788 and 4.397 (AB, 2 H, $J_{gem}$ 12.0 Hz, benzylics), 3.642 (s, CO$_2$CH$_3$), 2.629 (dd, 1 H, $J_{3eq,3ax}$ 12.5 Hz, H-3eq), 2.140, 2.113, 2.017, 1.997, 1.857, (5 s, 15 H, 4 OAc, 1 NAc), 1.986 (dd, 1 H, H-3ax).

The above material (1.5 g, 2.58 mmol) was de-O-acetylated in dry methanol (20 mL) containing a catalytic amount of sodium methoxide for 5 hours at 22° C. After de-ionization with Dowex 50×8 (H$^+$ form), the solvent was evaporated leaving the product 239 (1.0 g, 94%) which was used in the next step; $^1$H-n.m.r. (CDCl3): 4.815 and 4.619 (AB, 2 H, $J_{gem}$ 11.5 Hz, benzylics), 3.802 (s, CO$_2$CH$_3$), 3.582 (dd, 1 H, $J_{5,6}$ 9.0, $J_{6,7}$ 0.5 Hz, H-6), 2.752 (dd, 1 H, $J_{3eq,3ax}$ 12.5, $J_{3eq,4}$ 4.5 Hz, H-3eq), 2.039 (s, 3 H, N Ac), 1.861 (dd, 1 H, $J_{3ax,4}$ 11.0 Hz, H-3ax).

A solution of para-toluenesulfonyl chloride (0.125 g, 0.65 mmol) in pyridine (0.1 mL) was syringed into a solution 239 (0.248 g, 0.60 mmol), 4-dimethylaminopyridine (0.01 g) in pyridine (1.1 mL) at 0° C. After stirring for 4 hours at 0° C., methanol (0.10 mL) was added and the mixture was co-evaporated with dry toluene. The residue was quickly chromatographed on silica gel using acetonitrile as eluant giving the tosylate (0.21 g, 62%) still containing some impurities. Sodium azide (0.19 g, 2.92 mmol) was added to a solution of this material (0.21 g, 0.37 mmol) in dimethylformamide (0.5 mL). The mixture was stirred at 65° C. for 18 hours after which it was filtered through Celite and the solvent evaporated in vacuo. The residue was chromatographed on silica gel using a 6:1 mixture of ethyl acetate and acetonitrile as eluant giving the product 240 (0.136 g, 85%); i.r.u $cm^{-1}$ 2110 (N$_3$); $^1$H-n.m.r.: 5.775 (d, 1 H, $J_{5,NH}$ 9.0 Hz, NH), 4.816 and 4.470 (AB, 2 H, $J_{gem}$ 11.5 Hz, benzylics), 3.738 (s, CO$_2$CH$_3$), 2.871 (dd, 1 H, $J_{3eq,4}$ 4.8, $J_{3eq,3ax}$ 13.0 Hz, H-3eq), 2.086 (s, 3 H, NAc), 1.964 (dd, 1 H, $J_{3ax,4}$ 11.5 Hz, H-3ax).

The above compound 240 (0.105 g, 0.24 mmol) was left for 3 hours at 22° C. in 0.25N sodium hydroxide (2 mL). After bringing the pH to 6 by addition of Dowex 50×8 (H$^+$ form) followed by filtration, the material, recovered after freeze drying, was chromatographed on Iatrobeads using a 65:35:5 mixture of chloroform, methanol and water as eluant. The appropriate fractions gave the product (0.087 g, 86%). This compound (0.100 g, 0.235 mmol) was heated at 80° C. for 6 hours in 0.025N hydrochloric acid (3 mL). The solution was neutralized with sodium hydroxide and then freeze dried. The product was chromatographed on Iatrobeads (0.60 g) using a 65:35:5 mixture of chloroform, methanol and water giving 201b (0.067 g, 85%); $^1$H-n.m.r.: 4.106–3.895 (m, 5 H), 3.639 (dd, 1 H, $J_{8,9}$ 3.0, $J_{9,9'}$ 13.0 Hz, H-9), 3.528 (dd, 1 H, $J_{8',9'}$ 6.0 Hz, H-9"), 2.249 (dd, 1 H, $J_{3eq,4}$ 4.5, $J_{3eq,3ax}$ 12.5 Hz, H-3eq), 2.090 (s, 3 H, NAc), 1.852 (dd, 1 H, $J_{3ax,4}$ 11.0 Hz, H-3ax).

EXAMPLE 32—Synthesis of 5-propionamido-3,5-dideoxy-D-glycero-D-galacto-2-nonulopyranosylonic acid (Neu5Pr) 201f A solution of 239 (0.075 g, 0.18 mmol) in 2N sodium hydroxide (1 mL) was left for 0.5 hours at 22° C. followed by 7 hours at 95° C. The pH was then adjusted to 7.5 by addition of IR-C50 resin (H$^+$ form). The filtrate obtained after filtration of the resin was evaporated in vacuo and the residue dried over phosphorous pentoxide.

Propionic anhydride (0.12 mL, 0.94 mmol) was then syringed into a suspension of the above product in a mixture of dry methanol (1.5 mL) and triethylamine (0.2 mL) which was stirred at 0° C. After 3 hours, more propionic anhydride (0.025 mL, 0.195 mmol) was added and the mixture stirred for 2 more hours at 0° C. The mixture was co-evaporated with methanol, and a solution of the residue in water (2 mL) was passed through Dowex 50×8 (H$^+$ form, 6 g). The recovered fractions were evaporated in vacuo and the residue chromatographed on Iatrobeads (5 g) using a 3:1 mixture of chloroform and methanol as eluant giving 241 (0.0646 g, 86.5%); $^1$H-n.m.r.: 4.800, 4.578 (AB, 2 H, $J_{gem}$ 11.0 Hz, benzylics), 3.580 (dd, 1 H, $J_{5,6}$ 9.0, $J_{6,7}$ 1.0 Hz, H-6) 2.776 (dd, 1 H, $J_{3eq,4}$ 4.5, $J_{3eq,3ax}$ 12.5 Hz, H-3eq), 2.316 (q, 2 H, J 7.5 Hz, CH$_2$CO), 1.762 (dd, 1 H, $J_{3ax,4}$ 12.0 Hz), 1.129 (t, 3 H, CH$_3$).

A solution of the above benzyl glycoside (0.115 g, 0.278 mmol) in water (5 mL) was hydrogenated in the presence of 5% palladium on charcoal (10 mg) at atmospheric pressure and 22° C. for 5 hours. The eluate obtained after filtration through Celite followed by Millipore filter, was freeze dried leaving compound 201f (0.074 g, 82.5%); $^1$H-n.m.r.: 3.72–4.10 (m, H-4, -5,-7,-8,-9), 3.614 (dd, 1 H, $J_{8,9a}$ 6.5, $J_{9a,9b}$ 11.75 Hz, H-9a), 3.530 (dd, 1 H, $J_{5,6}$ 9.0 $J_{6,7}$ 1.0 Hz, H-6), 2.250–2.400 [m, 2 H incl. CH$_2$CO (q, 2.315, J 7.5 Hz) and H-3eq (dd, $J_{3eq,3ax}$ 11.5 Hz, $J_{3eq,4}$ 4.5 Hz)], 1.880 (t, 1 H, $J_{3ax,3eq}$ 11.5 Hz, H-3ax), 1.130 (t, 3 H, CH$_3$).

EXAMPLE 33—Synthesis of 5-acetamido-3,5-dideoxy-D-galacto-2-octulosonic acid (C8-Neu5Ac) 1i The synthesis of 201i from 239 essentially follows the published procedure of Hasegawa et al.[84] but using a different starting material than the reported one. In particular, a suspension of 239 (0.52 g, 0.125 mmol) in 2,2-dimethoxypropane (3 mL) was stirred for 1.5 hours at 22° C. in the presence of paratoluenesulfonic acid (0.5 mg). After neutralization with some triethylamine, the mixture was evaporated and the residue chromatographed on silica gel using a 16:1 mixture of chloroform and methanol giving 242 (0.049 g, 88%).

242 (0.054 g, 0.185 mmol) was acetylated in a 2:1 mixture of acetic anhydride (1 mL) and pyridine kept at 50° C. for 5 hours. After the usual work up, the residue was chromatographed on silica gel using ethyl acetate as eluant giving the acetylated product (0.091 g, 92%); $^1$H-n.m.r.: 5.420 (dd, 1 H, $J_{6,7}$ 1.5, $J_{7,8}$ 3.5 Hz, H-7), 5.196 (d, 1 H, $J_{5,NH}$ 9.0 Hz, NH), 5.009 (ddd, 1 H, $J_{4,3ax}$ 13.0, $J_{4,3eq}$ 5.0, $J_{4,5}$ 10.0 Hz, H-4), 4.797 and 4.498 (AB, 2 H, $J_{gem}$ 11.5 Hz, benzylics), 3.776 (s, 3 H, CO$_2$CH$_3$), 2.724 (dd, 1 H, $J_{3ax,3eq}$ 13.0 Hz, H-3eq), 2.151, 2.032, 1.895 (3 s, 9 H, 2 OAc, 1 NAc), 2.032 (t, 1 H, H-3ax), 1.363 and 1.350 (2 s, 6 H, methyls).

The above product (0.091 g, 0.169 mmol) was heated for 4 hours at 40° C. in 70% aqueous acetic acid. The mixture was co-evaporated with toluene in vacuo. The dry residue was dissolved in dry methanol and stirred for 2 hours at 22° C. in the presence of sodium metaperiodate (0.059 g, 0.275 mmol). The mixture was filtered through a pad of Celite which was washed with methanol. The combined filtrate was stirred at 0° C. for 25 minutes in the presence of sodium borohydride (0.036 g, 0.95 mmol). The mixture was then stirred at 0° C. with some acetic acid (0.2 mL), after which the solvents were evaporated leaving a residue which was dried in vacuo for 15 minutes and then acetylated in a 5:1 mixture of pyridine and acetic anhydride (6 mL) for 20 hours at 22° C. The residue recovered after the usual work up was chromatographed on silica gel using ethyl acetate as eluant to give a product which still contained some non-separable impurities. The dry material (0.074 g, still containing some impurities) was dissolved in dry methanol (5 mL) and stirred at room temperature for 3 hours in the presence of sodium (3 mg). After de-ionization with Dowex 50×8 (H$^+$ form) and filtration, the solvent was evaporated in vacuo and the residue chromatographed on silica gel using a 15:1 mixture of chloroform and methanol to give a pure product 244 (0.047 g, 78%); $^1$H-n.m.r.: (CD$_3$OD): 4.724 and 4.416 (AB, 2 H, $J_{gem}$ 11.5 Hz, benzylics), 3.671 (s, 3 H, CO$_2$CH$_3$), 3.456 (dd, 1 H, $J_{5,6}$ 9.5, $J_{6,7}$ 1.0 Hz, H-6), 2.642 (dd, 1 H, $J_{3eq,4}$ 4.5, $J_{3eq,3ax}$ 12.5 Hz, H-3eq), 1.938 (s, 3 H, NAc), 1.699 (t, 1 H, $J_{3ax,4}$ 12.5 Hz, H-3ax).

The above material (0.022 g, 0.057 mmol) was stirred in 0.25N sodium hydroxide (2 mL) for 5 hours at 22° C., the solution was neutralized with Dowex 50×8 (H$^+$ form) and the filtrate was freeze dried to give a white solid (0.019 g, 90%). This product was dissolved in water (2 mL) and hydrogenated for 3 hours at 22° C. in the presence of 5% palladium on charcoal (4 mg). The mixture was first filtered through Celite and then through a Millipore filter. The filtrate was freeze dried leaving the desired product 201i (13.3 mg, 94%); $^1$H-n.m.r.: 3.462–4.093 (m,6 H), 2.287 (dd, 1 H, $J_{3eq,4}$ 4.5, $J_{3eq,3ax}$ 12.5 Hz, H-3eq), 2.052 (s, 3 H, NAc), 1.853 (t, 1 H, $J_{3eq,4}$ 12.5 Hz, H-3ax).

EXAMPLE 34—Synthesis of 5-acetamido-3,5,7-trideoxy-β-D-galacto-2-nonulopyranosylonic acid (7-d-Neu5Ac) 201d The synthesis of 201d essentially follows the published procedure of Zbiral et al.[37] but using a different starting material. In particular, imidazole (0.13 g, 1.93 mmol) and tert-butyldimethylsilyl chloride (0.135 g, 0.89 mmol) were added to a solution of 242 (0.11 g, 0.19 mmol) in dimethylformamide (2 mL). After 4 hours at room temperature, the solvent was removed in vacuo, the residue dissolved in chloroform and worked up as usual. Chromatography of the product on silica gel using a 1:1 mixture of ethyl acetate and hexane provided the monosilylated derivative (0.101 g, 92%): [α]$_D$=–2.66 (c. 0.6, chloroform); $^1$H-n.m.r.: 5.195 (d, 1 H, $J_{5,NH}$ 7 Hz, NH), 4.853 and 4.603 (AB, 2 H, $J_{gem}$ 11.5 Hz, benzylics), 3.736 (s, CO$_2$CH$_3$), 2.692 (dd, 1 H, $J_{3eq,4}$ 4.5, $J_{3eq,3ax}$ 13.0 Hz, H-3eq), 2.022 (s, 3 H, NAc), 1.884 (dd, 1 H, $J_{3ax,4}$ 11.0 Hz, H-3ax), 1.405, 1.375 (2 s, 6 H, methyls), 0.868 (s, 9 H, t-butyl), 0.093 and 0.084 (2 s, 6 H, methyls).

Sec-butyl lithium (1.3M in cyclohexane, 0.65 mL, 0.85 mmol) followed by carbon disulfide (1.25 mL, 20.8 mmol) were added dropwise to a solution of the above compound (0.437 g, 0.77 mmol) in dry tetrayhdrofuran (20 mL) at –30° C. After stirring at –25° C. for 0.5 hours, methyl iodide (1.6 mL, 25.6 mmol) was slowly warmed up to room temperature. After evaporation, the residue was chromatographed on silica gel using a 4:1 mixture of hexanes and ethyl acetate as eluant providing the xanthate (0.327 g, 65%): [α]$_D$ 93.9 (c. 0.655, chloroform); $^1$H-n.m.r.: 6.388 (dd, 1 H $J_{6,7}$ 1.0, $J_{7,8}$ 2.5 Hz, H-7), 5.610 (d, 1 H, $J_{5,NH}$ 7.0 Hz, NH), 4.778, 4.466 (AB, 2 H, $J_{gem}$ 11.5 Hz, benzylics), 3.778 (s, CO$_2$CH$_3$), 2.662 (dd, 1 H, $J_{3eq,4}$ 4.5, $J_{3eq,3ax}$ 12.5 Hz, H-3eq), 2.584 (s, 3 H, OCH$_3$), 1.883 (s, 3 H, NAc), 1.693 (dd, 1 H, $J_{3ax,4}$ 11.5 Hz, H-3ax), 1.315 (s, 6 H, methyls) 0.825 (9 H, t-butyl), 0.025, 0.092 (2 s, 6 H, methyls).

Azobisisobutyronitrile (0.004 g) and tri-n-butyltin hydride (0.5 mL, 1.86 mmol) were added to a solution of the above xanthate (0.32 g, 0.48 mmol) in dry toluene (3 mL). After heating at 100° C. for 7 hours, the solvents were co-evaporated with dry toluene, and the residue chromatographed on silica gel using a 3:2 and then 1:1 mixtures of hexane and ethyl acetate as eluant to give the 7-deoxy product (0.260 g, 70%); $^1$H-n.m.r.: 5.334 (d, 1 H, $J_{5,NH}$ 7.0 Hz, NH), 4.740, 4.455 (AB, 2 H, $J_{gem}$ 11.6 Hz, benzylics), 3.690 (s, $CO_2CH_3$), 2.628 (dd, 1 H, $J_{3eq,4}$ 4.2, $J_{3eq,3ax}$ 12.9 Hz, H-3eq), 1.914 (s, 3 H, NAc), 1.805 (dd, 1 H, $J_{3ax,4}$ 10.9 Hz, H-3ax), 1.718 and 1.597 (m, 2 H, H-7 and H-7'), 1.325 (s, 6 H, methyls), 0.804 (9 H, t-butyl), 0.010, 0.009 (2 s, 6 H, methyls). The above compound (0.260 g, 0.47 mmol) was heated at 75° C. in 70% acetic acid for 7.5 hours. After co-evaporation with toluene, the residue was chromatographed on silica gel using a 10:1 mixture of chloroform and methanol giving 243 (0.157 g, 84%); $^1$H-n.m.r.: 4.860 and 4.655 (AB, 2 H, $J_{gem}$ 11.5 Hz, benzylics), 3.834 (s, $CO_2CH_3$), 2.806 (dd, 1 H, $J_{3eq,4}$ 4.5, $J_{3eq,3ax}$ 12.5 Hz, H-3eq), 2.069 (s, 3 H, NAc), 1.881 (dd, 1 H, $J_{3ax,4}$ 12.5 Hz, H-3ax), 1.698 (m, 2 H, H-7 and H-7').

Compound 243 (0.157 g, 0.396 mmol) was kept in 0.25N sodium hydroxide (6 mL) at room temperature for 5 hours. After neutralization with Dowex 50W X8 ($H^+$ form) and filtration, the product (0.149 g, 97%) was recovered after lyophilization of the solution. This product (0.146 g, 0.38 mmol) was hydrogenated in water (5 mL) for 5 hours at room temperature in the presence of 5% palladium on charcoal (0.010 g). The mixture was filtered through Celite and through a Millex-GV (0.22 μm) filter. The filtrate was freeze dried to provide 201d (0.105 g, 94%); $^1$H-n.m.r.: as reported by Christian[56].

Table 1 below summarizes the derivatives of Neu5Ac prepared.

TABLE I

Sialic Acid Derivatives

| Compound No. | R1 | R2 | R3 | R4 | R5 | R6 | R7 | R8 | R9 |
|---|---|---|---|---|---|---|---|---|---|
| 201a | H | H | OH | NHAc | H | OH | OH | H | $CH_2OH$ |
| 201b | " | " | " | " | " | " | " | " | $CH_2N_3$ |
| 201c | " | " | " | " | " | " | " | " | $CH_3$ |
| 201d | " | " | " | " | " | H | " | " | $CH_2OH$ |
| 201e | " | " | " | " | OH | H | " | " | " |
| 201f | " | " | " | $NHCOCH_2CH_3$ | H | OH | " | " | " |
| 201g | " | " | " | OH | " | " | " | " | " |
| 201h | " | " | " | $NHCOCH_2OH$ | " | " | " | " | " |
| 201i | " | " | " | NHAc | " | " | " | " | H |

Sialyl Moieties obtained by chemical modification of sialylated oligosaccharides:

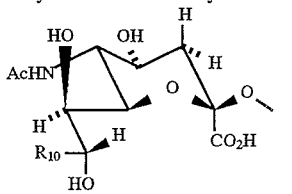

1j $R_{10} = CH_2NH_2$
1k $R_{10} = CH_2NHAc$

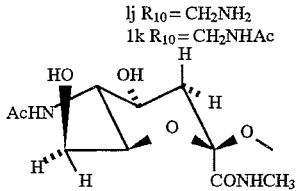

1l

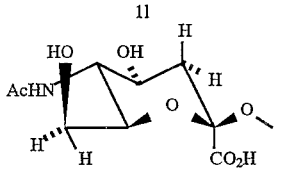

1m

B. SYNTHESIS OF CMP DERIVATIVES OF Neu5Ac AND ANALOGUES THEREOF

EXAMPLE 35—Synthesis of the CMP-derivatives of Neu5Ac

CMP-sialic acid synthase was extracted from calf brain and partially purified at 4° C. by a slight modification of the original procedure of Higa et al.[52] Routinely, ~200 g of brain tissue were homogenized in a Cuisinart blender (three 30 second bursts with 1 minute intervals) with 400 mL of 25 mM Tris/HCl, pH 7.5, 10 mM magnesium chloride, 10 mM sodium chloride, 2.5 mM dithioerythritol, 0.5 mM phenylmethylsulfonyl fluoride. The homogenate was stirred for 1 hour and then centrifuged at 23,000×g for 15 minutes. The supernatant was decanted and the pellets were extracted once again with 200 mL of the same buffer as above. The supernatants were combined and centrifuged at 28,000×g for 15 minutes. The supernatant was filtered through glass wool to give the crude extract (515 mL, 4.7 mg protein/mL, ~90 U of enzyme).

After adjusting salt concentration to 0.4M with solid potassium chloride, the crude extract was stirred and solid ammonium sulfate was added to 35% saturation (208 g/L) over a period of 15 minutes. The solution was stirred for an additional 15 minutes, kept on ice for 1 hour and centrifuged at 28,000×g for 30 minutes. The precipitate was discarded and the supernatant was stirred and adjusted to 60% saturation by the addition of solid ammonium sulfate (163 g/L) over 15 minutes. After an additional 15 minutes of stirring, the suspension was left on ice overnight and then centrifuged as above. The resultant pellets were washed with 150 mL of 60% ammonium sulfate solution to remove the co-precipitates. The washed pellets contain 70–80 U of enzyme with a specific activity of 0.08 U/mg protein. The enzyme was assayed as described by Kean et al.[85], with one unit of enzymatic activity defined as one µmol of product formed per minute at 37° C.

The enzyme present in the pellet could be stored for several weeks in the cold room. Before using the enzyme for synthesis, the pellets were suspended in a minimal volume of 50 mM Tris/HCl, pH 9.0, 35 mM magnesium chloride, 3 mM 2-mercaptoethanol (activation buffer) and dialyzed overnight against 100 volumes of the same buffer. The dialyzed enzyme was centrifuged at 9,000×g for 10 min. The supernatant containing more than 90% of the enzyme activity was used directly for the synthesis.

The CMP-derivatives of sialic acid analogues were synthesized as noted above and purified by a modification of the reported procedures of Higa et al.[52] and Gross et al.[86] For example, 7-d-Neu5Ac 201d (Table 1, 20 mg, 69 µmol) was activated by using 15 U of the above dialyzed enzyme for 5–6 hours at 37° C. in 12 mL of the activation buffer in the presence of four fold excess of cytidine triphosphate. When appropriate, the conversion of the sialic acid analogues was estimated by the usual thiobarbituric acid assay for sialic acid after reduction with sodium borohydride as per Kean et al.[85] The product was extracted with cold acetone as per Gross et al.[86] After evaporation of the acetone in vacuo (at ~15° C.), the concentrated solution was applied to a column of Bio-Gel P-2 (2.5×91 cm) equilibrated and eluted with 10 mM ammonium hydroxide at 4° C. with a flow rate of 60 mL/hour. Fractions (1 mL) were assayed for cytidine by absorbance at 273 nm, and the fractions corresponding to the first peak were pooled, concentrated in vacuo and the residue was freeze-dried leaving the CMP-7-d-Neu5Ac (201d, 30 mg, ~94%). This material showed a very small amount of impurities by $^1$H-n.m.r. (Table 2) and was used directly for the reaction with sialyltransferases. In some cases (202e, 202q, 202h), $^1$H-n.m.r. spectra showed that the CMP-derivatives contained some of the unreacted sialic acid.

Table 2A below illustrates the CMP-derivatives of analogues of Neu5Ac prepared from the analogues of Neu5Ac set forth in Table 1 above, and partial $^1$H-n.m.r. data concerning these compounds are set forth in Table 2B.

TABLE 2A $^1$H-n.m.r. Data and Reaction Data for CMP-sialic Acid Derivatives

| Sialic Acid Analogue | CMP-Derivative | Conversion[2] (%) | Ribose H-1(d) | Cytidine H-5(d) | Cytidine H-6(d) | R-4 | H-3eq(dd) | H-3ax(ddd) | Other |
|---|---|---|---|---|---|---|---|---|---|
| 201b | 202b | 70 | 5.98 | 6.12 | 7.97 | NHAc2.05(s) | 2.48 (4.0; 13.5) | 1.64(6.0; 13.0; 13.5) | — |
| 201c | 202c | 90 | 5.98 | 6.19 | 8.05 | NHAc2.05(s) | 2.48 (4.2; 13.0) | 1.64(6.0; 12.0; 13.0) | H-9 1.23(d, 6.5) |
| 201d | 202d | NA | 5.99 | 6.15 | 8.03 | NHAc2.05(s) | 2.52 (4.5; 13.5) | 1.65 (5.7; 12.5; 13.0) | H-7 1.60 (m) |
| 201e | 202e | 70 | 5.98 | 6.13 | 7.98 | NHAc2.05(s) | 2.53 (4.5; 13.2) | 1.70 (12.0; 13.2) | — |
| 201f | 202f | 62 | 5.97 | 6.12 | 7.98 | NHCOCH$_2$CH$_3$[3] | 2.48 (4.0; 13.0) | 1.65 (6.0; 12.0; 13.0) | — |
| 201g | 202g[4] | 35 | 5.99 | 6.13 | 7.98 | OH | 2.44 | 1.60 | — |
| 201h | 202h | 44 | 5.98 | 6.11 | 7.96 | NHCOCH$_2$OH 4.12(s) | 2.49 (4.7; 12.5) | 1.65 (5.6; 12.5; 13.0) | — |
| 201i | 202i | 94 | 5.97 | 6.11 | 7.97 | NHAc205(s) | 2.48 (4.0; 13.2) | 1.64 (5.6; 12.5; 13.0) | — |

[1] in D$_2$O with DOH set at 4.80.
[2] thiobartiburic assay
[3] 2.31 (q, 7.5 Hz, CH$_2$); 1.33 (t, CH$_3$)
[4] coupling constants not accurately obtained due to poor resolution.

TABLE 2B

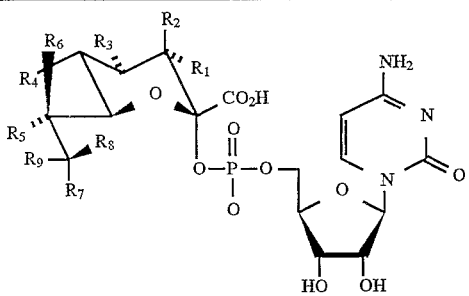

| | | | CMP-Sialic Acid Derivatives | | | | | | Compound |
|---|---|---|---|---|---|---|---|---|---|
| R1 | R2 | R3 | R4 | R5 | R6 | R7 | R8 | R9 | No. |
| H | H | OH | NHAc | H | OH | OH | H | $CH_2OH$ | 202a |
| " | " | " | " | " | " | " | " | $CH_2N_3$ | 202b |
| " | " | " | " | " | " | " | " | $CH_3$ | 202c |
| " | " | " | " | " | H | " | " | $CH_2OH$ | 202d |
| " | " | " | " | OH | H | " | " | " | 202e |
| " | " | " | $NHCOCH_2CH_3$ | H | OH | " | " | " | 202f |
| " | " | " | OH | " | " | " | " | " | 202g |
| " | " | " | $NHCOCH_2OH$ | " | " | " | " | " | 202h |
| " | " | " | NHAc | " | " | " | " | H | 202i |

C. SYNTHESIS OF OLIGOSACCHARIDE GLYCOSIDES

Examples 36–37 illustrate the synthesis of oligosaccharide glycosides. The structure of 203b to 207a are illustrated in FIG. 34. Oligosaccharide glycosides 204b, 205b, 205f, 206a, and 207a were synthesized according to the procedures of Lemieux et al.[87], Lemieux et al.[88], Paulsen et al.[89], Sabesan et al.[90], and Lemieux et al.[91], respectively.

Oligosaccharide glycosides 204d and 205d were synthesized following the procedure reported for the synthesis of oligosaccharide glycosides 204b and 205b but by replacing the 8-methoxycarbonyloctyl by methanol.

Oligosaccharide glycosides 205e and 205g were synthesized according to the procedures of Paulsen et al.[89] and Alais et al.[92] but replacing the methanol by 8-methoxycarbonyloctanol. In all cases, the oligosaccharide glycosides were purified by chromatography on Iatrobeads with the appropriate solvent mixtures and the recovered materials chromatographed on BioGel P2or Sephadex LH20 and eluted with water. The recovered materials were lyophilized from water and the products further dried in vacuo over phosphorus pentoxide.

EXAMPLE 36—Synthesis of 9-Hydroxynonyl 2-acetamido-2-deoxy-[β-D-galactopyranosyl-(1-3)-O-]-β-D-glucopyranoside 204a Sodium acetate (0.200 g) and sodium borohydride (0.060 g) were added to a solution of the disaccharide 204b (0.100 g, 0.189 mmol) in a 10:1 mixture of water and methanol (20 mL) cooled at +4° C. After 24 hours, more sodium borohydride (0.020 g) was added to the reaction mixture maintained at +4° C. After 48 hours at the same temperature, the pH was brought to 5–6 by addition of acetic acid. The solution was then co-evaporated with an excess of methanol. The residue was dissolved in water (10 mL) and run through a column of $C_{18}$ silica gel which was further washed with water. After elution with methanol, the solvent was evaporated in vacuo. The residue was dissolved in a 10:1 mixture of water and methanol and the pH brought to 13–14 by addition of 1N sodium hydroxide. The mixture was left at room temperature until t.l.c. (65:35:5-chloroform, methanol and water) indicated the disappearance of the unreacted starting material 204b. The mixture was then neutralized by addition of Dowex 50×8 (H⁺ form) and the resin filtered off. The resulting solution was run through a column of AG 1×8 (formate form). The eluate was freeze dried and the residue was run through Sephadex LH 20 using a 1:1 mixture of water and ethanol. The appropriate fractions were pooled and concentrated to give 204a (0.060 g, 65%); $^1$H-n.m.r. (D₂O): 4.545 (d, 1 H, $J_{1,2}$ 8.0 Hz, H-1), 4.430 (d, 1 H, $J_{1',2'}$, 7.5 Hz, H-1'), 2.025 (s, 3 H, NAc), 1.543 (m, 4 H), and 1.304 (m, 10 H): methylenes; $^{13}$C-n.m.r. (D₂O): 175.3 (Ac), 104.36 (C-1'), 101.72 (C-1), 67.72, 61.85, 61.60 (three $CH_2OH$).

EXAMPLE 37—9-Hydroxynonyl 2-acetamido-2-deoxy-[β-D-galactopyranosyl-(1-4)-O-]-β-D-glucopyranoside 205a Oligosaccharide glycoside 205a was prepared from 205b as indicated above (60%); $^1$H-n.m.r. (D2O): 4.520 (d, 1 H, $J_{1,2}$ 7.5 Hz, H-1), 4.473 (d, 1 H, $J_{1',2'}$ 7.6 Hz, H-1'), 2.033 (s, 3 H, NAc), 1.543 (m, 4 H) and 1.302 (m,10H):methylenes; $^{13}$C-n.m.r. (D2O): 175.23 (Ac), 103.71 and 101.88 (C-1 and C-1'), 60.93, 61.85 and 62.71 (three $CH_2OH$).

EXAMPLE 38—Synthesis of 5-Allyloxypentyl 2-acetamido-2-deoxy-[β-D-galactopyranosyl-(1-3)-O-]-β-D-glucopyranoside 204c The synthetic schemes for this example and Example 39 are set forth in FIG. 35.

A. Synthesis of Allyloxy-5-pentanol 229

Allyl bromide (2.5 mL, 0.029 mol) was added dropwise to the mixture of 1,5-pentanediol (3 g, 0.029 mol) and sodium hydride (1.2 g, 80% dispersion in oil) in dry dimethylformamide. Stirring was continued overnight at room temperature. T.l.c. (2:1-toluene and ethyl acetate) still indicated the presence of some unreacted pentanediol. The unreacted sodium hydride was destroyed by addition of methanol. The mixture was concentrated to 50 mL by evaporation in vacuo. After dilution with methylene chloride (150 mL), the solvents were washed with water (three times), dried over magnesium sulfate and evaporated in vacuo. The residue was chromatographed on silica gel using a 2:1 mixture of toluene and ethyl acetate as eluant. The appropriate fractions gave compound 229 (0.931 g, 30%). $^1$H-n.m.r. (CDCl₃): 5.83 (m, 1 H, —CH=), 5.20 (m, 2 H, =CH$_2$), 3.95 (dd, 1 H, J=5.5 and 1.0 Hz, allylics), 3.66 and 3.46 (two t, 2 H each, J=6.5 Hz, O—CH$_2$), 1.64 (m, 4 H) and 1.44 (m, 2 H): methylenes); $^{13}$C-n.m.r. (CDCl$_3$): 134.7 and 116.6 (ethylenics), 71.6, 70.1 (CH$_2$—O—CH$_2$), 62.1 (CH$_2$OH) 32.2, 29.2 and 22.2 (methylenes).

B. Synthesis of 5-Allyloxypentyl 2-deoxy-2-phthalimido-β-D-glucopyranoside 232

A solution of 3,4,6-tri-O-acetyl-2-deoxy-2-phthalimido-D-glucopyranosyl bromide 230 (5.0 g, 10.0 mmol) in dichloromethane (5 mL) was added dropwise to a mixture of the alcohol 229 (1.33 mL, 10 mmol), silver trifluoromethanesulphonate (2.57 g, 10.0 mmol) and collidine (1.23 mL, 9.0 mmol) in dichloromethane (10 mL) at −70° C. After stirring for 3 hours at −70°, t.l.c. (2:1-toluene and ethyl acetate) indicated that the starting bromide and the reaction product had the same Rf. After addition of some triethylamine, the reaction mixture was diluted with dichloromethane and worked up as usual. The syrupy residue was chromatographed on silica gel using a 5:1 mixture of toluene and ethyl acetate providing compound 231 (4.0 g, 71%). $^1$H-n.m.r. (CDCl$_3$): 5.80 (m, 2 H, —CH= and H-3), 5.36 (d, 1 H, J$_{1,2}$ 8.5 Hz, H-1), 5.18 (m, 3 H, =CH$_2$ and H-4), 2.13, 2.06, 1.87 (3 s, 3 H each, 3 OAc), 1.40 (2 H) and 1.15 (m, 4 H): methylenes. A 0.2M solution of sodium methoxide in methanol (0.500 mL) was added dropwise to a solution of compound 231 (4.00 g, 7.1 mmol) in dry methanol (30 mL) cooled at 0° C. The mixture was stirred at 0° C. for 2 hours until t.l.c. (10:1-chloroform and methanol) indicated the disappearance of the starting material. The reaction mixture was de-ionized with Dowex 50 (H$^+$ form, dry) at 0° C. Filtration and evaporation of the solvent left a residue which was purified by chromatography on silica gel using a 100:5 mixture of chloroform and methanol as eluant providing compound 232 (2.36 g, 76%). $^1$H-n.m.r. (CDCl$_3$): 7.70 and 7.80 (m, 4 H, aromatics), 5.82 (m, 1 H, —CH=), 5.17 (m, 3 H, =CH$_2$ and H-1), 1.38 and 1.10 (m, 6 H, methylenes); $^{13}$C-n.m.r. (CDCl$_3$): 134.9 and 116.6 (ethylenics), 98.3 (C-1), 56.6 (C-2).

C. Synthesis of 5-Allyloxypentyl 4,6-O-benzylidene-2-deoxy-2-phthalimido-β-D-glucopyranoside 233

Paratoluenesulfonic acid monohydrate (0.025 g) was added to a solution of 232 (1.0 g, 2.3 mmol) and α,α-dimethoxytoluene (0.690 mL, 4.6 mmol) in dry dimethylformamide. After stirring for 2 hours at 40° C., t.l.c. (10:1-chloroform and methanol) indicated the completion of the reaction. After addition of a small amount of triethylamine, most of the solvent was evaporated in vacuo and the residue diluted with dichloromethane and worked up as usual. After evaporation of the solvents, the residue was chromatographed on silica gel using a 9:1 mixture of toluene and ethyl acetate giving compound 233 (1.36 g, 90.1%). [α]$_D^{20}$+24.1 (c 0.5 chloroform); $^1$H-n.m.r. (CDCl$_3$): 7.15–7.90 (m, 9 H, aromatics), 5.83 (m, 1 H, —CH=), 5.56 (s, 1 H, benzylidene), 5.10–5.37 [m, 3 H, =CH$_2$ and H-1 (5.25, d, J$_{1,2}$ 8.5 Hz)], 1.40 (m, 2 H) and 1.17 (m, 4 H): methylenes.

D. Synthesis of 5-Allyloxypentyl 4,6-O-benzylidene-2-deoxy-[2,3,4,6-tetra-O-acetyl-β-D-galactopyranosyl-(1-3)-O-]-2-phthalimido-β-D-glucopyranoside 235

A solution of trimethylsilyltrifluoromethanesulfonate (0.1 mL of a solution made from 0.050 mL of the reagent in 1.0 mL of dichloromethane) was syringed into a mixture of compound 233 (1.20 g, 2.29 mmol), 2,3,4,6-tetra-O-acetyl-α-D-galactopyranosyl acetimidate 234 (1.70 g, 3.50 mmol) and molecular sieves (0.500 g, crushed in a 1:1 mixture of toluene and dichloromethane (30 mL) cooled to −20° C. The mixture was stirred at −20° C. for 0.5 hours and slowly brought to 0° C. in 1 hour. T.l.c. (1:1 hexane and ethyl acetate) indicated the completion of the reaction. Some triethylamine was added and after dilution with methylene chloride and filtration, the solvents were worked up in the usual manner. After evaporation, the residue was applied on a column of silica gel by using toluene and elution was then continued with a 2:1 mixture of hexane and ethyl acetate. The appropriate fractions gave the disaccharide 235 (1.63 g, 74%). [α]$_D^{20}$+4.1 (c, 0.5, CHCl$_3$); $^1$H-n.m.r. (CDCl$_3$): 7.40–8.00 (m, 9 H, aromatics), 5.85 (m, 1 H, —CH=), 5.58 (s, 1 H, benzylidene), 5.07–5.25 (m, 4 H, incl. =CH$_2$, H-4' and H-1), 5.00 (dd, 1 H, J$_{1',2'}$ 8.0, J$_{2',3'}$ 10.0 Hz, H-2'), 2.11, 1.90, 1.85, 1.58 (4 s, 12 H, 4 OAc), 1.37 and 1.12 (m, 6 H, methylenes); $^{13}$C-n.m.r. (CDCl$_3$): 134.6 and 117.0 (ethylenics), 102.1, 101.2, 99.4 (benzylidene, C-1 and C-1').

E. Synthesis of 5-Allyloxypentyl 2-deoxy-[2,3,4,6-tetra-O-acetyl-β-D-galactopyranosyl-(1-3)-O-]-2-phthalimido-β-D-glucopyranoside 236

A solution of the disaccharide 235 (1.63 g, 1.91 mmol) in 90% aqueous acetic acid (10 mL) was heated at 70° C. for 1 hour at which time t.l.c. (100:5-chloroform and methanol) indicated the completion of the reaction. Co-evaporation with an excess of toluene left a residue which was chromatographed on silica gel using a 100:2 mixture of chloroform and methanol as eluant giving compound 236 (1.12 g, 76%) [α]$_D^{20}$+9.3 (C, 0.55 CHCl$_3$); $^1$H-n.m.r (CDCl$_3$): 7.70–7.95 (m, 4 H, aromatics), 5.82 (m, 1 H, —CH=), 5.33 (dd, 1 H, J$_{3',4'}$ 3.5, J$_{4',5'}$ 1.0 Hz, H-4'), 5.10–5.27 (m, 3 H, incl. =CH$_2$ and H-2'), 5.07 (d, 1 H, J$_{1,2}$ 8.5 Hz, H-1), 4.84 (dd, 1 H, J$_{2',3'}$ 10.0 Hz, H-3'), 2.10, 2.08, 1.90 (3 s, 9 H, 3 OAc), 1.05–1.47 (m, 9 H, incl. 1 OAc). $^{13}$C-n.m.r. (CDCl$_3$): 100.3 and 97.5 C-1 and C-1'. Anal.calcd: C, 56.88; H, 6.17; N, 1.83. Found: C, 55.59; H, 6.20; N, 1.84.

F. Synthesis of 5-Allyloxypentyl 2-acetamido-2-deoxy-[β-D-galactopyranosyl-(1-3)-O-]-β-D-glucopyranoside 204c Sodium borohydride (0.690 g, 18 mmol) was added to the disaccharide 236 (0.700 g, 0.91 mmol) in a 5:1 mixture of isopropanol and water (20 mL). The mixture was stirred for 24 hours at room temperature after which t.l.c. (65:35:5, chloroform, methanol and water) showed the disappearance of the starting material. After addition of acetic acid (8.2 mL) the mixture was heated for 3 hours at 100° C. The mixture was co-evaporated with an excess of toluene and the dried residue acetylated in a 3:2 mixture of pyridine and acetic anhydride (5 mL) in the presence of dimethylaminopyridine for 24 hours at 22° C. After addition of some methanol, the mixture was diluted with dichloromethane worked up as usual leaving a residue which was co-evaporated with some toluene. The final syrup was chromatographed on silica gel using a 100:2 mixture of chloroform and methanol giving the peracetylated disaccharide (0.500 g, 71%). $^1$H-n.m.r. (CDCl3): 5.90 (m, 1 H, —CH=), 5.77 (d, 1 H, J$_{2,NH}$ 7.5 Hz, NH), 5.37 (dd, 1 H, J$_{3',4'}$ 3.5, J$_{4',5'}$ 1.0 Hz, H-4'), 5.15–5.23 (m, 2 H, =CH$_2$), 1.95–2.18 (7 s, 21 H, 6 OAc, 1 NAc), 1.58 (m, 4 H) and 1.41 (m, 2 H): methylenes.

A 0.5N solution of sodium methoxide (0.300 mL) was syringed into a solution of the above compound (0.500 g, 0.623 mmol) in dry methanol (20 mL). After stirring overnight at room temperature, the mixture was de-ionized with Dowex 50 (H$^+$ form, dried) and evaporated in vacuo. The residue was dissolved in methanol and coated on Celite (3 g) by evaporation of the solvent. The Celite was then applied on top of a column of Iatrobeads (30 g) and the product eluted with a 65:25:1 mixture of chloroform, methanol and water giving the disaccharide 204c (0.266 g, 80%); [α]$_D^{20}$−0.164 (c.1, water); $^1$H-n.m.r. (D2O): 5.95 (m, 1 H, —CH=), 5.30 (m, 2 H, =CH$_2$), 4.548 (d, 1 H, J$_{1,2}$ 7.7 Hz, H-1), 4.426 (d, 1 H, J$_{1',2'}$ 7.7 Hz, H-1'), 4.031 (dd, 1 H, J 1.0, 11.5 Hz, allylics), 2.023 (s, 3 H, NAc), 1.58 (m, 4 H) and 1.38 (m, 2 H): methylenes; $^{13}$C-n.m.r. (D$_2$O): 175.24 (carbonyl), 134.70 and 119.05 (ethylenics), 104.33 (C-1'), 101.68 (C-1), 55.42 (C-2).

EXAMPLE 39—Synthesis of 5-Allyloxypentyl 2-acetamido-2-deoxy-β-D-glucopyranoside 237

The starting material 232 (0.300 g, 0.689 mmol) was deprotected as indicated previously for compound 236. The crude material recovered after peracetylation was chromatographed on silica gel using a 1:1 mixture of hexane and ethyl acetate which gave the peracetylated derivative (0.180 g, 55%), [α]$_D^{20}$ +11.5 (c, 0.7, chloroform); $^1$H-n.m.r. (CDCl3): 5.90 (m, 1 H, —CH=), 5.64 (d, 1 H, J$_{2,NH}$ 8.5 Hz, NH), 4.68 (d, 1 H, J$_{1,2}$ 7.5 Hz, H-1), 1.95, 2.03 (two), 2.05 (3 s, 12 H, 3 OAc, 1 NAc), 1.58 (m, 4 H) and 1.41 (m, 2 H): methylenes. Anal.calcd.: C, 55.8; H, 7.5; N, 2.05. Found: C, 55.82; H, 7.53; N, 2.98.

This material was de-O-acetylated in methanol (5 mL) to which a 0.5N solution of sodium methoxide in methanol (0.100 mL) was added. After overnight at room temperature, the mixture was de-ionized with IR-C50 resin (H$^+$ form, dry) and the solvents evaporated. The residue was run through Iatrobeads using a 7:1 mixture of chloroform and methanol giving the pure 237 (0.103 g, 80%), [α]$_D^{20}$ −0.17 (c.1, water); $^1$H-n.m.r. (D$_2$O): 5.85 (m, 1 H, —CH=), 5.29 (m, 2 H, —CH=), 4.50 (d, 1 H, J$_{1,2}$ 8.5 Hz, H-1), 4.03 (d, 2 H, J 6.0 Hz, allylics), 2.033 (s, 3 H, NAc), 1.58 (m, 4 H) and 1.36 (m, 2 H): methylenes; $^{13}$C-n.m.r. (D$_2$O): 175.2 (carbonyl), 134.7 and 119.1 (ethylenes), 101.9 (C-1), 61.6 (C-6), 56.4 (C-2), 29.1, 23.0 and 22.6 (methylenes).

D. TRANSFER OF SIALIC ACIDS AND OTHER SUGARS TO OLIGOSACCHARIDE STRUCTURES

EXAMPLE 40—Transfer of Sialic Acids and other Sugars to Oligosaccharide Structures via Glycosyltransferases This example demonstrates the enzymatic transfer of Neu5Ac, analoguss thereof (collectively "sialic acids"), and other sugars onto oligosaccharide glycoside structures via glycosyltransferases. FIGS. 36, 37, 38, 39, and 40 illustrate these transfers and provide structures for the prepared compounds identified by an underlined arabic numeral. In Examples 40a–40e, preparative sialylation and fucosylation were performed as follows:

i. Preparative sialylation

Sialic acids, activated as their CMP-derivatives (as set forth in Examples 31–35 above), were transferred onto synthetic oligosaccharide structures containing βGal(1-3)βGlcNAc-, βGal(1-4)βGlcNAc-, βGal(1-3)βGalNAc-, and βGal(1-4)βGlc- terminal sequences by using three mammalian sialyltransferases (Examples 40a–e). The βGal(1-¾)βGlcNAc-α(2-3)sialyltransferase (EC 2.4.99.5) and the βGal(1-4)βGlcNAc-α(2-6)sialyltransferase (EC 2.4.99.1) from rat liver were purified to homogeneity by affinity chromatography according to the procedure of Mazid et al.[77], which is incorporated herein by reference on a matrix obtained by covalently linking the hapten βGal(1-3)βGlcNAcO(CH$_2$)$_8$CO$_2$H[87] to activated Sepharose by methods known in the art. The βGal(1-3)αGalNAc-α(2-3)sialyltransferase (EC 2.4.99.4) was purchased from Genzyme Corporation, Norwalk, Conn.

In all preparative sialylation reactions, the acceptor oligosaccharide (5–20 mg) was incubated with the selected CMP-sialic acids (5–20 mg) in the presence of the appropriate sialyltransferase (10–50 mU) and calf intestinal alkaline phosphatase (Boehringer Mannheim, Mannheim, Germany) as in the procedure of Unverzagt et al.[93] for 37° C. for 24–48 hours in 50 mM sodium cacodylate pH 6.5, 0.5% Triton CF-54, 1 mg/mL BSA ("sialyl transfer buffer"). For example, the sialyloligosaccharide 7-d-αNeu5Ac(2-6)βGal(1-4)βGlcNAc-0-(CH$_2$)$_8$—COOCH$_3$ (213d, 4.4 mg) was synthesized by incubation of βGal(1-4)βGlcNAc-0-(CH$_2$)$_8$—COOCH$_3$ (205b, 4.6 mg) and CMP-7-d-Neu5Ac (202d, 15.6 mg) in the presence of βGal(1-4)βGlcNAc-α(2-6)sialyltransferase (51 mU) and calf intestinal alkaline phosphatase (2.4 U) for 28 hours at 37° C. in 2.5 mL of the sialyl transfer buffer (see Examples 1–5). After completion, the reaction mixture was diluted to 10 mL and passed onto three Sep-Pak C$_{18}$ cartridges, conditioned as suggested by the manufacturer. Each cartridge was washed with water (4×5 mL) and then with methanol (3×5 mL). The methanol eluate was evaporated to dryness in vacuo and the residue was dissolved in a 65:35:3 mixture of chloroform, methanol and water (0.5 mL-solvent I) and applied on to a small column of Iatrobeads (500 mg) equilibrated in the same solvent. The column was successively eluted with solvent I followed by a 65:35:5 mixture of chloroform, methanol and water (solvent II) and then by a 65:35:8 mixture of chloroform, methanol and water (solvent III). The appropriate fractions (30 drops) containing the product, as identified by t.l.c. on silica gel plates (with a 65:35:8 mixture of chloroform, methanol and 0.2% calcium chloride solution as eluent), were pooled together and concentrated to dryness in vacuo. The residue was run through a small column of AG 50W-X8 (Na$^+$ form), the eluate freeze-dried and the recovered product characterized by $^1$H-n.m.r. which, in all cases, indicated good purity.

ii. Preparative Fucosylation

Sialylated analogues of the type I and II oligosaccharides can be further fucosylated by the human milk βGlcNAcα(1-¾)fucosyltransferase. The enzyme was purified from human milk according to the methodology using affinity chromatography on GDP-hexanolamine Sepharose described by Palcic et al.[25] The synthesis and purification of the fucosylated oligosaccharides was carried out by a modification of the procedures of Palcic et al.[25] For example, the fucosylated structure 9-N$_3$-αNeu5Ac(2-3)βGal(1-3)-[α-L-Fuc(1-4)]-βGlcNAc-0-(CH$_2$)$_8$—CH$_2$OH 217b was synthesized by incubating GDP-fucose (2.5 mg) and 9-N$_3$-αNeu5AC(2-3)βGal(1-3)βGlcNAc-0-(CH$_2$)$_8$—CH$_2$OH 208b (1.7 mg) with affinity purified βGlcNAcα(1-¾) fucosyltransferase (4.6 mU) in 1.3 mL of 100 mM sodium cacodylate (pH 6.5), 10 mM manganese chloride, 1.6 mM ATP, 1.6 mM sodium azide. After 27 hours at 37° C., 2.5 mg of GDP-fucose and 2.3 mU of the fucosyltransferase were added to the reaction mixture, which was kept at 37° C. for an additional 21 hours. The product was isolated as described above for the sialylation reaction. T.l.c. of the crude material (as above) indicated that the fucosylation was almost complete. After purification and chromatography on AG 50W X8 (Na$^+$ form), $^1$H-n.m.r. of the product 217b (1.0 mg) indicated a very good purity (Table 5). In some cases where the fucosyltransferase was not highly purified, partial hydrolysis of the methyl ester of the linking arm occurred.

EXAMPLES 40a–40e are as follows:

Example 40a: This example refers to the transfer of modified sialic acids such as 201a–g to the 3-OH of a terminal βGal of acceptors possessing a βGal(1-3)βGlcNAc- (Lewis$^c$ or Type I) terminal structure such as 204a and 204b by a sialyltransferase such as the βGal(1-¾)βGlcNAcα(2-3)sialyltransferase from rat liver following the experimental procedure reported above. The $^1$H-n.m.r. data of the reaction products, which were purified as indicated previously, are reported (Tables 3 and 4).

Example 40b: This example refers to the transfer of modified sialic acids such as 201b and 201c to the 3-OH of the terminal βGal of acceptors possessing a βGal(1-4)βGlcNAc- (LacNAc or Type II) terminal structure such as 205a, b, d–g by a sialyltransferase such as that used in 40a. In some cases, dimethylsulfoxide (5% volume) may be added to solubilize the acceptor. The $^1$H-n.m.r. data of the reaction products, which were purified as indicated previously, is reported (Tables 6 and 8). The reaction mixture was worked up in the manner described previously.

Example 40c: This example refers to the transfer of modified sialic acids such as 201c to the 3-OH structure of the terminal βGal of acceptors possessing a βGal(1-4)βGlc- (lactose) terminal structure such as 206a by a sialyltransferase such as that used in Example 40a following the same experimental procedure. The $^1$H-n.m.r. data of the reaction products, which were purified as indicated previously, is reported (Table 6).

Example 40d: This example refers to the transfer of modified sialic acids such as 201b–h to the 6-OH of the terminal βGal of acceptors possessing a βGal(1-4)βGlcNAc- (LacNAc or Type II) terminal unit such as 205b, d–g by a sialyltransferase such as the βGal(1-4)βGlcNAcα(2-6)sialyltransferase reported previously. The $^1$H-n.m.r. data of the reaction products, which were purified as indicated previously, is reported (Tables 7 and 8).

Example 40e: This example refers to the transfer of modified sialic acids such as 201c to the 3-OH of the terminal βGal of acceptors possessing a βGal(1-3)αGalNAc- ("T") terminal unit such as 207a by a sialyltransferase such as the βGal(1-3)βGalNAcα(2-3)sialyltransferase (Genzyme) following the experimental procedure reported previously. The $^1$H-n.m.r. data of the reaction products, which were purified as indicated previously, is reported (Table 9).

TABLE 3

$^1$H-n.m.r. Data of Sialyloligosaccharides Obtained by Transfer of Sialic Acids on the Acceptor 204a by the βGal(1-3/4)βGlcNAc α(2-3) Sialyltransferase, and by Chemical Modification

| | | Sialic Acid | | | | βGal | | |
| --- | --- | --- | --- | --- | --- | --- | --- | --- |
| Sialic Acid | Reaction Product | H-3eq(dd) ($J_{3eq,3ax}$; $J_{3eq,4}$) | H-3ax(t) ($J_{3ax,4}$) | R4 | Other | H-1(d) ($J_{1,2}$) | H-3(dd) ($J_{2,3}$; $J_{3,4}$) | H-4 (d) |
| 201b | 208b | 2.756 (12.5; 4.6) | 1.775 (12.5) | NHAc | — | 4.485 (7.7) | 4.065 (10.0; 3.1) | |
| 201c | 208c | 2.756 (12.0; 4.0) | 1.771 (12.0) | NHAc | H-9 1.254 (d, 6.3) | 4.473 (8.0) | 4.058 (9.7; 3.5) | — |
| 201d | 208d | 2.720 (12.5; 3.5) | 1.800 (12.0) | NHAc | H-7(1) (m) | 4.500 (7.6) | 4.080 (9.7; 3.0) | 3.945 |
| 201f | 208f | 2.763 (12.5; 4.5) | 1.785 | NHCOCH$_2$CH$_3$: 2.295(q, 7.7), 1.114(t) | — | 4.496 (7.5) | 4.083 | (10.0; 3.5) |
| 201j | 208j | 2.742 (12.0; 4.2) | 1.810 (12.2) | NHAc | (2) | 4.510 (7.5) | 4.076 (9.7; 3.0) | 3.982 |
| 201k | 208k | 2.755 (12.0; 4.5) | 1.792 (12.0) | NHAc | — | 4.494 (7.7) | 4.072 (9.8; 3.3) | |
| 201m | 208m | 2.698 (12.0; 4.0) | 1.757 (12.0) | NHAc | — | 4.497 (7.6) | 4.085 (9.7; 3.1) | 3.980 |

| | | βGlcNAc | | | | |
| --- | --- | --- | --- | --- | --- | --- |
| Sialic Acid | Reaction Product | H-1(d) ($J_{1,2}$) | NHAc | CO$_2$CH$_3$ (s) | (CH$_2$)$_s$ (two m) | CH$_2$CO$_2$ (t, J=7.5) |
| 201b | 208b | 4.556 (8.1) | 2.034 (two) | NA | 1.546; 1.308 | NA |
| 201c | 208c | 4.558 (7.5) | 2.028; 2.034 | " | 1.542; 1.304 | " |
| 201d | 208d | 4.552 (7.7) | 2.022; 2.018 | " | 1.548; 1.305 | " |
| 201f | 208f | 4.555 (7.5) | 2.026 (one) | " | 1.548; 1.305 | " |
| 201j | 208j | 4.562 (7.7) | 2.032 (two) | " | 1.547; 1.309 | " |
| 201k | 208k | 4.552 (7.8) | 2.020; 2.032 (three) | " | 1.546; 1.308 | " |
| 201m | 208m | 4.553 (7.8) | 2.024 (two) | " | 1.541; 1.306 | " |

$^1$overlapping signals 1.500–1.730
$^2$H-9a: 3.110 (dd, 2.8, 13.2); H-9b: 2.792 (dd,8.3, 13.2)

TABLE 4

$^1$H-n.m.r. Data of Sialyloligosaccharides Obtained by Transfer of Sialic Acids on the Acceptor 204b by the βGal (1-3/4)βGlcNAc α(2-3) Sialyltransferase

| Sialic Acid | Reaction Product | Sialic Acid | | | | βGal | | |
|---|---|---|---|---|---|---|---|---|
| | | H-3eq(dd) ($J_{3eq,3ax}$; $J_{3eq,4}$) | H-3ax(t) ($J_{3ax,4}$) | R4 | Other | H-1(d) ($J_{1,2}$) | H-3(dd) ($J_{2,3}$; $J_{3,4}$) | H-4 |
| 201c | 209c | 2.756 (12.5; 4.5) | 1.769 (12.5) | NHAc | H-9 1.252 (d, 6.3) | 4.469 (7.9) | 4.057 (9.7; 3.0) | |
| 201e | 209e | 2.740 (12.5; 4.5) | 1.779 (12.2) | NHAc | 4.017(dd) | 4.500 (7.7) | 4.125 (9.7; 3.0) | |
| 201g | 209g | 2.710 (12.0; 4.2) | 1.726 (12.2) | HO | — | 4.481 (7.7) | 4.064 (10.0; 3.0) | |
| 201i | 209i | 2.705 (12.5; 4.5) | 1.768 (12.0) | NHAc | — | 4.494 (7.7) | 4.050 (10.0; 3.0) | |

| | | Sialic Acid | Reaction Product | βGlcNAc H-1(d) ($J_{1,2}$) | NHAc | $CO_2CH_3$ (s) | $(CH_2)_s$ (two m) | $CH_2CO_2$ (t, J=7.5) |
|---|---|---|---|---|---|---|---|---|
| | | 201c | 209c | 4.551 (8.1) | 2.030 (two) | 3.687 | 1.567; 1.299 | 2.390 |
| | | 201e | 209e | 4.552 (7.7) | 2.047; 1.996 | 3.689 | 1.560; 1.299 | 2.390 |
| | | 201g | 209g | 4.540 (7.7) | 2.023 (one) | 3.689 | — | 2.390 |
| | | 201i | 209i | 4.559 (8.0) | 2.035 (two) | 3.685 | 1.560; 1.290 | 2.389 |

TABLE 5

$^1$H-n.m.r. Data of Sialyl Lewis$^a$ (CA19-9, 217) and of Sialyl Lewis$^x$ 218 Structures

| Sialic Acid | Reaction Product | Sialic Acid | | | | βGal | | | βGlcNAc |
|---|---|---|---|---|---|---|---|---|---|
| | | H-3eq(dd) ($J_{3eq,3ax}$; $J_{3eq,4}$) | H-3ax(t) ($J_{3ax,4}$) | R4 | Other | H-1(d) ($J_{1,2}$) | H-3(dd) ($J_{2,3}$; $J_{3,4}$) | H-4(d) | H-1(d) ($J_{1,2}$) |
| 201b | 217b | 2.767 (12.5; 4.5) | 1.757 (12.2) | NHAc | — | 4.520(1) (7.7) | (2) | (2) | 4.536(1) (8.5) |
| 201k | 217k | 2.770 (12.5; 4.5) | 1.755 (12.0) | NHAc | H-9a(dd) 3.270 (13.5; 7.5) | 4.530(1) (8.0) | (2) | (2) | 4.530(1) (8.0) |
| 201m | 217m | 2.709 (21.0; 4.4) | 1.749 (12.0) | NHAc | — | 4.528(1) (8.8) | (2) | (2) | 4.558(1) (7.7) |
| 201c | 218c | 2.757 (12.5; 4.5) | 1.782 (12.4) | NHAc | H-9, 1.273 (d, 6.5) | 4.514(1) (7.5) | 4.027 (3.0; 10.8) | (2) | 4.520(1) (7.5) |
| 201l | 218l | 2.770(2) (4.1) | 1.918 (12.5) | NHAc | $CONHCH_3$ (3) | 4.518(1) (7.5) | 4.027 (3.0; 10.8) | (2) | 4.529(1) (7.5) |

| | | αFuc | | | | | | | |
|---|---|---|---|---|---|---|---|---|---|
| | | Sialic Acid | Reaction Product | H-1(d) ($J_{1,2}$) | H-5(q) ($J_{5,6}$) | H-6(d) ($J_{5,6}$) | NHAc | $CO_2CH_3$ (s) | $(CH_2)_s$ (two m) | $CH_2CO_2$ (t, J=7.5) |
| | | 201b | 217b | 5.010 (3.6) | 4.870 (6.5) | 1.169 (6.5) | 2.059; 2.031 | NA | 1.546; 1.308 | NA |
| | | 201k | 217k | 5.010 (3.5) | (2) | 1.170 (6.5) | 2.025 (three) | NA | 1.570; 1.300 | NA |
| | | 201m | 217m | 5.011 (6.5) | (2) | 1.175 (6.5) | 2.049; 2.023 | NA | 1.540; 1.304 | NA |
| | | 201c | 218c | 5.100 (3.8) | (2) | 1.165 (6.5) | 2.028; 2.014 | 3.688 | 1.550; 1.300 | 2.385 |
| | | 201l | 218l | 5.100 (3.8) | (2) | 1.169 (6.5) | 2.035; 2.015 | NA(3) | 1.545; 1.285 | $CH_2CONH$ 2.225 |

$^1$interchangeable
$^2$overlapping with other signals
$^3CH_3NHCO$(2.708 and 2.797, two s)

TABLE 6

$^1$H-n.m.r. Data of Sialyloligosaccharides Obtained by Transfer of Sialic Acids on the Acceptors 205a, 205b and 206a by the βGal (1-3/4)βGlcNAc α(2-3) Sialyltransferase

| Sialic Acid | Acceptor | Reaction Product | Sialic Acid | | | | βGal | | |
|---|---|---|---|---|---|---|---|---|---|
| | | | H-3eq(dd) ($J_{3eq,3ax}$; $J_{3eq,4}$) | H-3ax(t) ($J_{3ax,4}$) | R4 | Other | H-1(d) ($J_{1,2}$) | H-3(dd) ($J_{2,3}$; $J_{3,4}$) | H-4 |
| 201b | 205a | 210b | 2.758 (12.5; 4.4) | 1.790 (12.0) | NHAc | — | 4.540 (8.0) | 4.099 (9.5; 3.0) | (2) |
| 201c | 205b | 211c | 2.749 (12.5; 4.5) | 1.794 (12.1) | NHAc | H9 1.219(d, 6.6) | 4.540 (7.7) | 4.099 (10.0; 3.1) | (2) |
| 201a | 206a | 214a | 2.760 (12.5; 4.7) | 1.798 (12.0) | NHAc | — | 4.529(1) (8.0) | 4.113 (10.0; 3.0) | |
| 201c | 206a | 214c | 2.752 (12.5; 4.3) | 1.795 (12.5) | NHAc | H-9 1.268(d, 6.5) | 4.517(1) (8.0) | 4.100 (10.0; 2.8) | (2) |

| Sialic Acid | Acceptor | Reaction Product | βGlcNAc or βGlc H-1(d) ($J_{1,2}$) | NHAc | $CO_2CH_3$ (s) | $(CH_2)_s$ (two m) | $CH_2CO_2$ (t, J=7.5) |
|---|---|---|---|---|---|---|---|
| 201b | 205a | 210b | 4.520 (7.0) | 2.030; 2.034 | NA | 1.570; 1.310 | NA |
| 201c | 205b | 211c | 4.513 (7.7) | 2.029 (two) | 3.685 | 1.560; 1.297 | 2.389 |
| 201a | 206a | 214a | 4.475(1) (8.0) | 2.030 (one) | 3.687 | 1.609; 1.314 | 2.387 |
| 201c | 206a | 214c | 4.478(1) (8.2) | 2.029 (one) | 3.685 | 1.600; 1.312 | 2.378 |

(1)interchangeable
(2)overlapping with other signals

TABLE 7

$^1$H-n.m.r. Data of Sialyloligosaccharides Obtained by Transfer of Sialic Acids on the Acceptor 205b by the βGal(1-4)βGlcNAc α(2-6) Sialyltransferase

| Sialic Acid | Reaction Product | Sialic Acid | | | | β Gal H-1(d) ($J_{1,2}$) | βGlcNAc H-1(d) ($J_{1,2}$) | NHAc | $CO_2CH_3$ (s) | $(CH_2)_s$ (two m) | $CH_2CO_2$ (t, J=7.5) |
|---|---|---|---|---|---|---|---|---|---|---|---|
| | | H-3eq(dd) ($J_{3eq,3ax}$; $J_{3eq,4}$) | H-3ax(t) ($J_{3ax,4}$) | R4 | Other | | | | | | |
| 201b | 213b | 2.660 (12.2; 4.5) | 1.706 (12.0) | NHAc | — | 4.442 (7.8) | 4.550 (8.0) | 2.033; 2.054 | 3.680 | 1.550; 1.289 | 2.388 |
| 201c | 213c | 2.665 (12.5; 4.5) | 1.708 (12.0) | NHAc | H-9 1.266 (d, 6.3) | 4.446 (7.7) | 4.549 (7.7) | 2.029; 2.055 | 3.680 | 1.556; 1.300 | 2.389 |
| 201d | 213d | 2.676 (12.4; 4.0) | (1) | NHAc | H-7(m) (1) | 4.455 (7.6) | 4.549 (7.1) | 2.048; 2.022 | 3.688 | (1) 1.302 | 2.307 |
| 201e | 213e | 2.654 (12.1; 4.4) | 1.718 (12.0) | NHAc | — | 4.441 (7.7) | 4.551 (8.1) | 1.992; 2.059 | 3.691 | 1.560; 1.305 | 2.390 |
| 201f | 213f | 2.672 (12.5; 4.5) | 1.715 (12.0) | $NHCOCH_2CH_3$; 2.294(q, 7.6); | — | 4.447 (7.5) | 4.554 (7.6) | 2.055 (one) | 3.685 | 1.554; 1.299 | 2.389 |
| 201g | 213g | 2.623 (13.0; 4.0) | 1.660 (12.0) | HO | — | 4.435 (7.5) | 4.545 (7.5) | 2.056 (one) | 3.688 | 1.560; 1.300 | 2.390 |
| 201h | 213h | 2.688 (12.7; 4.9) | 1.730 (12.0) | $NHCOCH_2OH$: 4.115 (s) | — | 4.450 (8.1) | 4.553 (7.7) | 2.055 (one) | 3.680 | 1.558; 1.305 | 2.787 |

(1)overlapping signals 1.500–1.730

TABLE 8

¹H-n.m.r. Data of Sialyloligosaccharides Obtained by Transfer of Sialic Acids on the Acceptor 205q by the
βGal(1-3/4)βGlcNAc α(2-3) Sialyltransferase (I) and the βGal(1-4)βGlcNAc α(2-6) Sialyltransferase (II)

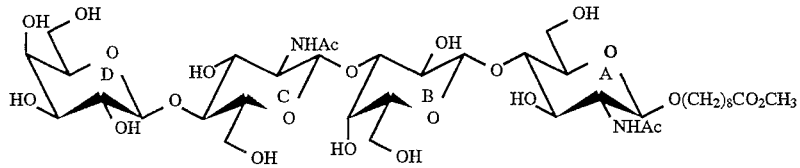

| Acceptor | | | | | | | 5g | | | | | |
|---|---|---|---|---|---|---|---|---|---|---|---|---|
| Sialic | En- | Reaction | | Sialic Acid | | H-1 (C) | H-3 (D) | H-1 (A,B,D) | | | CO₂CH₃ | CH₂CO₂ |
| Acid | zyme | Product | H-3eq(dd) | H-3ax(t) | Other | (d) | (dd) | (d) | H-4 (B) | NHAc | (s) | t, J = 7.5 |
| 201a | I | 212a | 2.755 (4.5; 12.0 Hz) | 1.795 (12.0 Hz) | — | 4.695 (8.0 Hz) | 4.112 (3.0; 10.0 Hz) | 4.552; 4.513; 4.455 (8.0; 7.5; 8.0 Hz) | 4.152 (2.7 Hz) | 2.020 (three) | 3.695 | 2.382 |
| 201a | II | 214a | 2.670 (4.5; 12.0 Hz) | 1.720 (12.1 Hz) | — | (1) | NA | 4.485; 4.460; (three, 7.5 Hz) | 4.155 (2.7 Hz) | 2.018 2.050 (three) | 3.685 | 2.389 |
| 201g | II | 214g | 2.623 (4.5; 13.0 Hz) | 1.658 (12.5 Hz) | — | (1) | NA | 4.515; 4.464; 4.439 (7.5 Hz) | 4.156 (2.7 Hz) | 2.027 2.057 (two) | 3.690 | 2.387 |

(1) overlapping with other signals

TABLE 9

¹H-n.m.r. Data of Sialyloligosaccharides Obtained by Transfer of Sialic Acids on the Acceptor
207a by the βGal(1-3)αGalNAc α(2-3) Sialyltransferase

| | | Sialic Acid | | | | βGal | | |
|---|---|---|---|---|---|---|---|---|
| Sialic Acid | Reaction Product | H-3eq(dd) ($J_{3eq,3ax}$; $J_{3eq,4}$) | H-3ax(t) ($J_{3ax,4}$) | R4 | Other | H-1(d) ($J_{1,2}$) | H-3(dd) ($J_{2,3}$; $J_{3,4}$) | H-4 ($J_{4,5}$) |
| 201c | 216c | 2.749 (11.9, 5.0) | 1.777 (12.3) | NHAc | H9, 1.259 (d, 6.6) | 4.538 (8.09) | (1) | (1) |

| | | βGalNAc | | | | | | |
|---|---|---|---|---|---|---|---|---|
| Sialic Acid | Reaction Product | H-1(d) ($J_{1,2}$) | H-2(dd) ($J_{2,3}$) | H-4(d) ($J_{3,4}$) | NHAc | CO₂CH₃ (s) | (CH₂)ₙ (two m) | CH₂CO₂ (t, J=7.5) |
| 201c | 216c | 4.905 (3.60) | 4.278 (11.0) | 4.233 (3.5) | 2.029 (two) | 3.689 | 1.560; 1.300 | 2.388 |

¹overlapping with other signals

E. PREPARATION OF ANALOGUES OF OLIGOSACCHARIDE GLYCOSIDES BY CHEMICAL MODIFICATION OF THE COMPLETED OLIGOSACCHARIDE GLYCOSIDE STRUCTURE

Examples 41–43 below describe the synthesis of analogues of oligosaccharide glycosides by the chemical modification of the completed oligosaccharide glycoside structure (prepared by either enzymatic or chemical means). FIGS. 41–43 illustrate the reaction schemes involved in the preparation of these analogues and provide structures for the prepared analogues which are identified by an underlined arabic numeral.

EXAMPLE 41—Synthesis of 9-Hydroxynonyl (5-acetamido-3,5-dideoxy-β-L-arabino-2-heptulopyranosylonic acid)-(2-3)-O-β-D-galactopyranosyl-(1-3)-O-[α-L-fucopyranosyl-(1-4)-O-]-2-acetamido-2-deoxy-β-D-glucopyranoside 217m The starting trisaccharide 208a (1.3 mg) was stirred for 24 hours at +4° C. in 1.7 mL of a solution 0.05M in sodium acetate and 0.010M in sodium periodate. The excess of sodium periodate was then destroyed by addition of some ethylene glycol. Sodium borohydride (20 mg) was then added and the stirring was continued for 24 hours at 4° C. The pH of the reaction mixture was then brought to 6 by addition of acetic acid and the solvents were co-evaporated with methanol. The residue was dissolved in water (1 mL) and run through a Sep-Pak cartridge which was further washed with water followed by methanol. The methanol eluate was evaporated and the residue chromatographed on Iatrobeads (200 mg) using a 65:35:5 mixture of chloroform, methanol and water as eluant. The appropriate fractions were pooled and evaporated leaving the product 208m (1 mg); ¹H-n.m.r.: see Table 3 above.

Trisaccharide 208m was enzymatically fucosylated following the procedure reported in Example 10 and the product purified in the same manner. T.l.c. of the recovered crude material indicated that the transformation of 208m was almost complete. Purification gave 217m (0.5 mg); $^1$H-n.m.r.: see Table 5 above.

EXAMPLE 42—Synthesis of 9-Hydroxynonyl (5,9-diacetamido-3,5,9-tri-deoxy-α-D-glycero-D-galacto-2-nonulo-pyranosylonic acid)-(2-3)-O-β-D-galactopyranosyl-(1-3)-O-[α-L-fucopyranosyl-(1-4)-O-]-2-acetamido-2-deoxy-β-D-glucopyranoside 217k A solution of the trisaccharide 208b (1 mg) in water (0.5 mL) was hydrogenated at 22° C. at atmospheric pressure in the presence of Lindlar catalyst (1.0 mg, Aldrich Chemical Company, Milwaukee, Wis.) for 15 minutes T.l.c. (65:35:8-chloroform, methanol and 0.2% calcium chloride), indicated a complete transformation. The mixture was filtered through Celite and the solid extensively washed with water. The filtrate was concentrated, filtered through Millipore filter and the eluate freeze dried leaving the trisaccharide 208j; $^1$H-n.m.r.: see Table 3 above.

Acetic anhydride (about 0.2 mg) in methanol (10 μL) was added to a solution of 208j (about 1 mg) in a 1:1 solution of 0.002N sodium hydroxide and methanol (0.300 mL) at 0° C. T.l.c. (solvent as above) indicated a complete reaction and the solvents were then evaporated. The residue was dissolved in water (2 mL) and applied to a Sep-Pak cartridge. The cartridge was washed with water and the product eluted with methanol giving the trisaccharide 208k (about 1 mg); $^1$H-n.m.r.: see Table 3 above.

Trisaccharide 208k was enzymatically fucosylated following the procedure reported in Example 10 and the product purified in the same manner. T.l.c. of the recovered crude material indicated that the transformation of 208k was almost complete. Purification gave 217k (about 0.5 mg); $^1$H-n.m.r.: see Table 5 above.

EXAMPLE 43—Synthesis of 8-N-methylamidooctyl (5-acetamido-3,5-dideoxy-α-D-glycerogalacto-2-nonulopyranosylonic acid N-methylamide)-(2-3)-O-β-D-galactopyranosyl-(1-3)-O-[α-L-fucopyranosyl-(1-4)-O-]-2-acetamido-2-deoxy-β-D-glucopyranoside 218l Tetrasaccharide 218a (0.003 g) was applied on Dowex 50×8 (Na$^+$ form) resin and eluted with water. The appropriate fractions, were freeze-dried, followed by further drying over phosphorous pentoxide. Methyl iodide (0.050 mL) was added to the residue dissolved in dimethyl sulfoxide. After stirring in the dark for 20 hours, the solution was evaporated in vacuo, diluted with water (11 mL) and applied to a Sep-Pak C$_{18}$ cartridge. After washing with water (10 mL), the product was eluted with methanol. Evaporation of the appropriate fractions left a residue which was chromatographed on Iatrobeads (0.5 g) using a 65:35:5 mixture of chloroform: methanol:water providing the methyl ester of compound 218a (0.025 g): $^1$H-n.m.r.: 5.099 (d, 1 H, J$_{1,2}$ 3.75 Hz, H-1 αFUC), 4.517 (d, 2 H, J$_{1,2}$ 7.5 Hz, H-1 βGal and βGlcNAc), 3.866 and 3.683 (2 s, CO$_2$CH$_3$), 2.781 (dd, 1 H, J$_{3ax,3eq}$ 12.5 Hz, J$_{3eq,4}$ 4.5 Hz, H-3eq Neu5Ac), 2.032 and 2.018 (2 s, 6 H, 2 NAc), 1.913 (dd, 1 H, J$_{3ax,4}$ 12.5 Hz, H-3ax Neu5Ac), 1.160 (d, 3 H, J$_{5,6}$ 6.5 Hz, H-6 αFuc).

This material was heated at 50° C. in a 40% solution of N-methylamine (1 mL) for 3.5 hours. After evaporation in vacuo, the residue was dissolved in water (1 mL) and applied on a Sep-Pak cartridge which was further washed with water. After elution of the product with methanol, the solvent was evaporated and the residue freeze-dried from water providing 218l (0.0025 g); $^1$H-n.m.r.: (Table 5).

SYNTHESIS OF MONOFUCOSYLATED OLIGOSACCHARIDES TERMINATING IN DI-N-ACETYLLACTOSAMINYL STRUCTURES

Examples 44–51 below are presented for the purpose of illustrating different methods for synthesizing an oligosaccharide glycoside related to blood group determinants having a type II core structure, i.e., CD65, which is a sialyl Lewis$^x$ derivative having a βGal(1→4)βGlcNAc-OR disaccharide glycoside attached to the reducing sugar of the sialyl Lewis$^x$. See further Kashem, et al.[10], and U.S Ser. No. 07/771,259, filed Oct. 2, 1991, entitled "Methods for the Synthesis of Monofucosylated Oligosaccharides Terminating in Di-N-acetyllactosaminyl Structures," both of which are incorporated herein by reference.

The following examples illustrate the preparation of Compounds 305a and 305b which preparation is illustrated in FIG. 44. The synthetic pathway in Examples 44–51 utilized the following general methods:

General Methods: All organic solvents used were redistilled reagent grade. Pre-coated silica gel plates (60-F254, E. Merck, Darmstadt) were run in 65:35:5, 65:35:8 and/or 60:40:10 mixtures of CHCl$_3$, CH$_3$OH, and 0.2% CaCl$_2$ solution, and detection was by charring after spraying with a 5% solution of sulphuric acid (H$_2$SO$_4$) in ethanol. Sep-Pak C$_{18}$ cartridges (Waters Associates, Milford, Mass.) were conditioned as indicated by the supplier. Iatrobeads (6RS-8060) were from Iatron Laboratories, Tokyo, Japan and the AG 50W X8 ion exchange resin was purchased from BioRad, Richmond, Calif. CMP-Neu5Ac was purchased from Sigma Chemical Company (St. Louis, Mo.) and GDP-fucose was obtained by chemical synthesis.[42] βGal(1-4)βGlcNAc(1-3)βGal(1-4)βGlcNAc-OR was obtained by following the procedures of Alais et al[92] with the appropriate substitution of the aglycon. Evaporation of organic solvents was done at 20°–25° C. using a rotary evaporator connected to a water aspirator. $^1$H-n.m.r. spectra have been run on at 300 and 500 MHz using internal acetone (δ=2.225) as reference and samples were freeze dried twice from D$_2$O and dissolved in 99.99% D$_2$O. The spectra of compounds obtained as 8-methoxycarbonyloctyl glycosides all show a singlet at δ=3.686 (CO$_2$CH$_3$) and a triplet at δ=2.387 (7.5 Hz, CH$_2$CO$_2$). The spectra of compounds obtained as the 8-carboxyoctyl glycosides differ from the respective 8-methoxycarbonyloctyl glycosides by the absence of the singlet due to CO$_2$CH$_3$ and the presence of a triplet at δ=2.314 (t, 7.5 Hz) for CH$_2$CO$_2$H.

In Examples 44 to 51 below, preparative sialylation was conducted as follows:

The rat liver βGal(1→¾)βGlcNAc α(2-3) sialyltransferase (EC 2.4.99.5) was purified by affinity chromatography according to the procedure of Mazid, et al.[77] but using a matrix obtained by covalently linking the hapten βGal(1→3)βGlcNAcO(CH$_2$)$_8$CO$_2$H[87] activated as in its N-succinimidyl ester to epichlorohydrin activated Sepharose.[78]

The βGal(1→4)βGlcNAc α(2→6)sialyltransferase contained in the flow-through of the above affinity-column, was further chromatographed on CDP-hexanolamine Sepharose as reported.[74]

The enzymatic sialylations were carried out at 37° C. in a plastic tube using a sodium cacodylate buffer (50 mM, pH 6.5) containing Triton CF-54 (0.5%), BSA (1 mg/mL) and calf intestine alkaline phosphatase.[66,93] The final reaction mixtures were diluted with H$_2$O and applied onto C$_{18}$ Sep-Pak cartridges as reported.[25] After washing with H$_2$O, the products were eluted with CH$_3$OH and the solvents evaporated. The residue was dissolved in a 65:35:5 mixture of CHCl$_3$, CH$_3$OH and H$_2$O and applied on a small column of Iatrobeads (0.200 to 0.500 g). After washing with the same solvent mixture, the products were eluted with a 65:35:8 and/or 65:40:10 mixtures of the same solvents. The appropriate fractions (t.l.c.) were pooled, the solvents evaporated in vacuo, the residue run through a small column of AG 50W X8 (Na⁺ form) in H$_2$O and the products recovered after freeze drying in vacuo. In all cases, the 8-methoxycarbonyloctyl glycosides were separated from the corresponding 8-carboxyoctyl glycosides.

In examples 44 to 51 below, preparative fucosylation was conducted as follows:

The βGlcNAc α(1→¾)fucosyltranferase (EC 2.4.1.65) was purified from human milk, as reported.[25] The enzymatic reactions were carried out at 37° C. in a plastic tube using a sodium cacodylate buffer (100 mM, pH 6.5), MnCl$_2$ (10 mM), ATP (1.6 mM), NaN$_3$ (1.6 mM). The reaction products were isolated and purified as indicated above.

EXAMPLE 44—Preparation of 8-Methoxycarbonyloctyl (5-Acetamido-3,5-dideoxy-α-D-glycero-D-galacto-2-nonulopyranosylonic acid)-(2-6)-O-β-D-galactopyranosyl-(1-4)-O-2-acetamido-2-deoxy-glucopyranosyl-(1-3)-O-β-D-galactopyranosyl-(1-4)-O-2-acetamido-2-deoxyglucopyranoside (302a)

Compound 301a (6.5 mg), CMP-Neu5Ac (17 mg), βGal (1-4)βGlcNAc α(2-6)sialyltransferase (50 mU) and alkaline phosphatase (15 U) were incubated for 48 hours in 2.5 mL of the above buffer. Isolation and purification provided 302a (3.0 mg).

EXAMPLE 45—Preparation of 8-Methoxycarbonyloctyl (5-Acetamido-3,5-dideoxy-α-D-glycero-D-galacto-2-nonulopyranosylonic acid)-(2-6)-O-β-D-galacto-pyranosyl-(1-4)-O-2-acetamido-2-deoxy-glucopyranosyl-(1-3)-O-β-D-galactopyranosyl-(1-4)-O-[α-L-fucopyranosyl-(1-3)-O-]2-acetamido-2-deoxy-glucopyranoside (303a) and the 8-carboxyoctyl glycoside (303b)

Compound 302a (3.0 mg), GDP-fucose (5 mg), βGlcNAc α(1-¾)fucosyltransferase (10 mU) were incubated for 68 hours in the buffer (1.3 mL). Isolation and purification provided 303a (1.2 mg) and 303b (0.5 mg).

EXAMPLE 46—Preparation of 8-Methoxycarbonyloctyl β-D-galactopyranosyl-(1-4)-O-2-acetamido-2-deoxy-β-D-glucopyranosyl-(1-3)-O-β-D-galactopyranosyl-(1-4)-O-[α-L-fucopyranosyl-(1-3)-O-]2-acetamido-2-deoxy-β-D-glucopyranoside (304a) and the 8-carboxyoctyl glycoside (304b)

Compounds 303a and 303b (1.7 mg) were incubated with Clostridium Perfringens neuraminidase immobilized on agarose (Sigma Chemical Company, 1 U) in a buffer of sodium cacodylate (50 mM, pH 5.2, 2 mL) at 37° C. After 24 hours the mixture was diluted with water (10 mL) and filtered through Amicon PM-10 membrane. The flow-through and washings were lyophilized and the residue dissolved in water (3 mL) and applied to two C$_{18}$ cartridge. Each cartridge was washed with water (10 mL) prior to elution with methanol (20 mL). After evaporation of the solvent, the residue was chromatographed on Iatrobeads (210 mg) as indicated above giving (304a, 0.8 mg) and 304b (0.7 mg). 304b was dissolved in dry methanol and treated with diazomethane until t.l.c. indicated the complete conversion into 304a.

EXAMPLE 47—Preparation of 8-Methoxycarbonyloctyl (5-Acetamido-3,5-dideoxy-α-D-glycero-D-galacto-2-nonulopyranosylonic acid)-(2-3)-O-β-D-galactopyranosyl-(1-4)-O-2-acetamido-2-deoxy-β-D-glucopyranosyl-(1-3)-O-β-D-galactopyranosyl-(1-4)-O-[α-L-fucopyranosyl-(1-3)-)-]2-acetamido-2-deoxy-β-D-glucopyranoside (305a) and the 8-carboxyoctyl glycoside (305b)

Compound 304a (1.5 mg), CMP-Neu5Ac (8 mg), βGal (1-¾)βGlcNAc α(2-3)sialyltransferase (17 mU), alkaline phosphatase (5 U), were incubated for 40 hours in the sialylation buffer (1.5 mL). Isolation and purification provided 305a (0.7 mg) and 305b (0.55 mg).

EXAMPLE 48—Preparation of 8-Methoxycarbonyloctyl (5-Acetamido-3,5-dideoxy-α-D-glycero-D-galacto-2-nonulopyranosylonic acid)-(2-3)-O-β-D-galactopyranosyl-(1-4)-O-2-acetamido-2-deoxy-β-D-glucopyranosyl-(1-3)-O-β-D-galactopyranosyl-(1-4)-O-2-acetamido-2-deoxyglucopyranoside(306)

Compound 301a (5 mg), CMP-Neu5Ac (15 mg), βGal (1→¾)βGlcNAc α(2-3)sialyltransferase (46 mU), and alkaline phosphatase (15 U) were incubated in the sialylation buffer (2.5 mL) for 48 hours. Isolation and purification of the product gave 306a (2.5 mg).

EXAMPLE 49—Preparation of 8-Methoxycarbonyloctyl (5-Acetamido-3,5-dideoxy-α-D-glycero-D-galacto-2-nonulopyranosylonic acid)-(2-3)-O-β-D-galactopyranosyl-(1-4)-O-[α-L-fucopyranosyl-(1-3)-O-]2-acetamido-2-deoxyglucopyranosyl-(1-3)-O-β-D-galactopyranosyl-(1-4)-O-[α-L-fucopyranosyl-(1-3)-O-]2-acetamido-2-deoxy-glucopyranoside (307a)

Compound 306a (2.5 mg), GDP-fucose (8 mg) and the βGlcNAc α(1→¾)fucosyltransferase (19 mU) were incubated in the enzymatic buffer (2.0 mL) for 48 h. Isolation and purification of the product give 307b (1.7 mg).

¹H-NMR data for the compounds prepared in Examples 44 to 49 above are set forth below:

| | | ¹H-n.m.r. Structural Parameters | | | | | | |
|---|---|---|---|---|---|---|---|---|
| Sugar Unit | Hydrogen | 301a | 302a | 303a | 304a | 305a | 306a | 307a |
| βGlcNAc | 1(d) | 4.516(8.2) | 4.516(7.5) | 4.522(8.0) | 4.525 (7.8) | 4.525(8.0) | 4.516(7.5) | 4.527(7.8) |
| βGal | 1(d) | 4.457*(7.8) | 4.455*(7.8) | 4.439(7.8) | 4.436 (7.7) | 4.435(8.0) | 4.457(7.7) | 4.434(7.7) |
|  | 4(d) | 4.157(3.0) | 4.417(3.2) | 4.095(3.0) | 4.098 (3.2) | 4.098(3.0) | 4.156(3.2) | 4.092(3.2) |
| βGlcNAc | 1(d) | 4.698(8.2) | 4.728(7.7) | 4.722(7.7) | 4.703 (7.7) | 4.692(8.0) | 4.696(8.0) | 4.696(8.3) |
| βGal | 1(d) | 4.479*(7.8) | 4.462*(7.8) | 4.455(8.0) | 4.480 (7.7) | 4.457(7.7) | 4.555(8.0) | 4.527(7.8) |
|  | 3(dd) |  |  |  |  | 4.114(3.0, 10.0) | 4.114(3.0, 9.8) | 4.082(3.0, 10.0) |
| αFuc | 1(d) |  |  | 5.094(3.7) | 5.096 (3.8) | 5.094(3.8) |  | 5.127, 5.093 (3.8) |
|  | 5(q) |  |  | 4.814(6.5) | 4.814 (6.5) | 4.814(6.5) |  |  |
|  | 6(d) |  |  | 1.150 | 4.814 (6.5) 1.152 | 1.150 |  | 4.822, 4.818 (6.5) 1.170, 1.144 |

$^1$H-n.m.r. Structural Parameters

| Sugar Unit | Hydrogen | 301a | 302a | 303a | 304a | 305a | 306a | 307a |
|---|---|---|---|---|---|---|---|---|
| αNeu5Ac(2-3) | $3_{ax}$(dd) |  |  |  |  | 2.756(4.5, 13.0) 1.796(12.0) | 2.758(4.5, 12.5) 1.796(12.2) | 2.762(4.5, 12.7) 1.792(12.0) |
|  | $3_{eq}$(t) |  |  |  |  |  |  |  |
| αNeu5Ac(2-6) | $3_{ax}$(dd) |  | 2.670(4.5, 12.5) 1.720(12.0) | 2.666(4.5, 12.5) 1.718(12.0) |  |  |  |  |
|  | $3_{eq}$(t) |  |  |  |  |  |  |  |
| NAc | (s) | 2.028 2.033 | 2.027(two) 2.055 | 2.021, 2.026 2.043 | 2.027 2.032 | 2.024 (three) | 2.030 (three) | 2.012, 2.018 2.028 |
| $CH_2CO_3$ | (t) | 2.388(7.5) | 2.387(7.5) | 2.387(7.5) | 2.386 (7.5) | 2.386(7.5) | 2.387(7.5) | 2.314(7.5) |
| $CO_2R$ |  | $CH_3$ 3.685 | $CH_3$ 3.686 | $CH_3$ 3.686 | $CH_3$ 3.68 | $CH_3$ 3.686 | $CH_3$ 3.684 | H |

*interchangeable

The following Examples 50 and 51 illustrate alternative methods for preparing for compounds of Formula I.

In these examples, during the chemical synthesis, unless otherwise specially indicated, the work up generally included extraction with dichloromethane followed by the normal sequential washings of the organic phase with water, a dilute solution of sodium carbonate and water. The organic solvent were then dried over magnesium sulfate, the solid filtered and the solvent evaporated in vacuo as indicated.

Evaporation of organic solvents was done at 20°–25° C. using a rotary evaporator connected to a water aspirator. $^1$H-n.m.r. spectra were run at 300 MHz using internal acetone ($\delta$=2.225) as reference and samples were freeze dried twice from $D_2O$ and dissolved in 99.99% $D_2O$. The spectra of compounds obtained as 8-methoxycarbonyloctyl all show a singlet at $\delta$=3.686 ($CO_2CH_3$) and a triplet at $\delta$=2.387 (7.5 Hz, $CH_2CO_2$). The spectra of compounds obtained as the 8-carboxyoctyl glycosides differ from the respective 8-methoxycarbonyloctyl glycosides by the absence of the singlet due to $CO_2CH_3$ and the presence of a triplet at $\delta$=2.314 (t, 7.5 Hz) for $CH_2CO_2H$.

Preparative Enzymatic Galactosylation

The bovine milk βGlcNAc β(1→4) galactosyltransferase (EC 2.4.1.22, specific activity 6.5 units/mg of protein) and UDP-Gal were obtained from Sigma. The enzymatic reactions were carried out at 37° C. in a plastic tube using a sodium cacodylate buffer (100 mM, pH 7.5) containing 20 mM manganese dichloride. The reaction products were purified as indicated above in the case of the preparative sialylation.

In some cases, depending upon the enzymatic preparation, it may happen that the terminal methyl ester of the aglycone is hydrolyzed. As a result, the final products may possibly be isolated as saccharides possessing the aglycone terminated by a methyl ester or a free acid group. These two saccharides are separated during the step of the chromatography on Iatrobeads as indicated above. The two forms of the aglycone of the saccharide are identified by $^1$H-n.m.r.

EXAMPLE 51—Synthesis of Compound 319

A. Synthesis of 8-Methoxycarbonyloctyl (2,3,4,6-tetra-O-acetyl-β-D-galactopyranosyl)-(1-4)-O-3,6-di-O-acetyl-2-deoxy-2-phthalimido-β-D-glucopyranoside (Compound 312)

A solution of trimethylsilyltrifluoromethanesulfonate (0.504 mL, 2.6 mmol) in dichloromethane (4 mL) was added to the mixture of the disaccharide donor 311[92] (2.0 g, 2.6 mmol), drierite (4.0 g, crushed) and 8-methoxycarbonyloctanol (1.9 g, 10.0 mmol) in dichloromethane (30 mL) at 4° C. After stirring for 0.5 h at 4° C., the mixture was slowly warmed up to room temperature for 1 h. After cooling to 4° C., a second portion of the catalyst (0.250 mL, 1.3 mmol) in dichloromethane (2 mL) was added. After slowly warming up and stirring at room temperature for 1 h, the reaction was stopped by addition of triethylamine. After filtration, the crude product recovered after the usual work up was dried in vacuo, and acetylated in a 2:1 mixture of pyridine and acetic anhydride. After addition of methanol, the mixture was worked up as usual, and the solvents co-evaporated with an excess of toluene. The residue was chromatographed on silica gel using a 2:1 mixture of toluene and ethyl acetate providing compound 312 (1.40 g, 60%). $^1$H-n.m.r. ($CDCl_3$): δ 7.90–7.70(m, 4H, aromatics), 5.75(dd, 1 H, $J_{2,3}$ 10.5 $J_{3,4}$ 3.5 Hz, H-3), 5.34(m, 2 H, incl. H-1 and H-4'), 5.15(dd, 1 H, $J_{1',2'}$ 8.0, $H_{2',3'}$ 10.5 Hz, H-2'), 4.97(dd, 1 H, H-3'), 3.67(s, 3 H, $CO_2CH_3$), 2.25(t, 2 H, J 7.5 Hz, $CH_2CO_2$), 2.19–1.94(6 s, 18 H, 6 OAc), 1.45 (m, 4 H) and 1.08(m, 8 H): methylenes.

B. Synthesis of Compound 315—8-Methoxycarbonyloctyl (2,6-di-O-acetyl-3,4-O-isopropylidene-β-D-galactopyranosyl)-(1-4)-O-(3,6-di-O-acetyl-2-deoxy-2-phthalimido-β-D-glucopyranoside (315)

A 1M solution of sodium methoxide in methanol (0.200 mL) was added to a solution of compound 312 (1.40 g, 1.65 mmol) in methanol (40 mL) cooled at 4° C. After 1.5 h at 4° C., the solution was deionized using IRC-50 resin ($H^+$ form). The resin was filtered, the solvent evaporated and the product dried in vacuo (1.0 g, 94%).

A solution of the above material (0.776 g, 1.2 mmol) and paratoluene sulfonic acid monohydrate (60 mg) in dry acetone (60 mL) was refluxed for 3 h. After neutralization with triethylamine, the solvent was evaporated and the residue chromatographed on silica gel using a 100:1 mixture of ethyl acetate and methanol providing compound 314 (0.575 g, 70%); $^1$H-n.m.r. ($CD_3OD$, DOH at 4.80): 7.80–7.60(m, 4H, aromatics), 5.10(d, 1 H, $J_{1,2}$ 8.0 Hz, H-1), 4.38(m, 2 H, H-1 and H-3), 3.70(s, 3 H, $CO_2CH_3$), 2.31(t, J 7.5 Hz, $CH_2CO_2$), 1.65–1.00[m, incl. 1.57 and 1.45 (2 s, $C(CH_3)_2$]. Further elution provided the 4,6-isopropylidene derivative (0.200 g, 24%).

Compound 314 (0.515 g, 0.84 mmol) was acetylated in a 2:1 mixture of pyridine and acetic anhydride for 24 h at 22°. After addition of methanol and the usual work up, the solvents were co-evaporated with an excess of toluene and the residue chromatographed on silica gel using a 100:3 mixture of chloroform and methanol providing compound 315 (0.646 g, 90%); $[\alpha]_D$+13.8° (c, 1 chloroform); $^1$H-n.m.r. ($CDCl_3$); δ 7.90–7.70(m, 4 H, aromatics), 5.74($J_{1,2}$ 8.5, $J_{2,3}$ 10.5 Hz, H-3), 5.34(d, 1 H $J_{1,2}$ 8.5 Hz, H-1), 4.88(dd, 1 H, $J_{1',2'}$ ~$J_{2',3'}$, 6.5 Hz, H-2'), 3.67(s, 3 H, $CO_2CH_3$), 2.23(t, J 7.5 Hz, $CH_2CO_2$), 2.14, 2.13, 2.10, 1.91(4 s, 12 H, 4 OAc), 1.30–1.54[m, incl. 1.53 and 1.32(2 s, $C(CH_3)_2$].

C. Synthesis of Compound 316—8-Methoxycarbonyloctyl (2,6-di-O-acetyl-β-D-galactopyranosyl)-(1-4)-O-3,6-di-O-acetyl-2-deoxy-2-phthalimido-β-D-glucopyranosyl Compound 315 (0.575 g, 0.68 mmol) in 90% acetic acid (12 mL) was heated at 80° C. for 2 hours. After dilution with dichloromethane, the solvent was washed with water, a solution of sodium bicarbonate and water. After drying over magnesium sulfate, the solvents were evaporated in vacuo, and the residue chromatographed on silica gel providing compound 316 (0.452 g, 82%); $[\alpha]_D$+12.1 (c, 1.03 chloroform).

D. Synthesis of Compound 318—8-Methoxycarbonyloctyl (3,4,6-tri-O-acetyl-2-deoxy-2-phthalimido-β-D-glucopyranosyl)-(1-3)-O-(2,6-di-O-acetyl-β-D-galactopyranosyl)-(1-4)-O-3,6-di-O-acetyl-2-deoxy-2-phthalimido-β-D-glucopyranoside (318)

Trimethylsilyltrifluoromethanesulfonate (0.036 mL, 0.060 mmol) in methylene chloride (0.5 mL) was added to a solution of compound 316 (0.100 g, 0.123 mmol) in methylene chloride (5 mL). A solution of the imidate 17 (0.102 g, 0.185 mmol) in methylene chloride (4 mL) was slowly added to the above solution cooled at −70°. The mixture was further stirred at that temperature for 0.5 h. An additional portion of the catalyst (0.018 mL, 0.030 mmol) in methylene chloride (0.5 mL) was further added. After 0.5 h at −70°, the reaction was stopped by addition of triethylamine, and the mixture worked up as usual. The recovered residue was chromatographed on silica gel using a 100:2 mixture of chloroform and methanol providing compound 318 (0.120 g, 80%); $^1$H-n.m.r. (CDCl$_3$): δ 7.95–7.60 (m, 8 H, aromatics), 5.74(dd, 1 H, $J_{2'',3''}$ 10.5 $J_{3'',4''}$ 9.0 Hz, H-3"), 5.61(dd, 1 H, $J_{2,3}$ 10.5, $J_{3,4}$ 8.5 Hz, H-3), 5.48(d, 1 H, $J_{1'',2''}$ 8.5 Hz, H-1"), 5.27(d, 1 H, $J_{1,2}$ 8.5 Hz, H-1), 5.14(dd, 1 H, $J_{4'',5''}$ 10.0 Hz, H-4"), 4.90(dd, 1 H, $J_{2',3'}$ 8.0 $J_{3',4'}$ 10.0 Hz, H-2'), 3.68(s, CO$_2$CH$_3$), 2.22(t, J 7.5 Hz, CH$_2$CO$_2$), 2.12(two), 2.10, 2.04, 1.86, 1.85, 1.56(6 s, 21 H, 7 OAc), 1.40(m, 4 H), and 1.20(m, 8 H): methylenes.

E. Synthesis of Compound 319—8-Methoxycarbonyloctyl (2-acetamido-2-deoxy-β-D-glucopyranosyl)-(1-3)-O-(β-D-galactopyranosyl)-(1-4)-O-2-acetamido-2-deoxy-6-D-glucopyranoside Hydrazine acetate (1.27 g, 13.8 mmol) was added to compound 318 (0.120 g, 0.098 mmol) in anhydrous ethanol (15 mL). The mixture was refluxed for 18 h. The solvents were then co-evaporated with an excess of toluene. After drying in vacuo, the residue was acetylated in a 2:1 mixture of pyridine and acetic anhydride for 48 h. After quenching the excess of acetic anhydride with some methanol, the reaction mixture was worked up as usual. The recovered solvents were evaporated in vacuo and the residue co-evaporated with an excess of toluene. The residue was chromatographed on silica gel using a 100:9 mixture of chloroform and methanol as eluant provided the peracetylated trisaccharide intermediate. This material was de-O-acetylated in anhydrous methanol (5 mL) in the presence of 0.2M sodium methoxide in methanol (0.200 mL). After overnight at 22° C., deionization with Dowex 50×8 and filtration, the solvent was evaporated in vacuo. The recovered product was chromatographed on BioGel P-2 and eluted with a 1:1 mixture of water and ethanol which provided the pure trisaccharide 319 (0.044 g, 60%); $[\alpha]_D$−4.8° (c, 0.48, water); $^1$H-n.m.r. (D$_2$O): data provided below.

EXAMPLE 51—Synthesis of 8-Methoxycarbonyloctyl (5-acetamido-3,5-dideoxy-α-D-glycero-D-galacto-2-nonulopyranosylonic acid)-(2-3)-O-(β-D-galactopyranosyl)-(1-4)-O-(2-acetamido-2-deoxy-β-D-glucopyranosyl)-(1-3)-O-(β-D-galactopyranosyl)-(1-4)-O-[α-L-fucopyranosyl-(1-3)-O]-2-acetamido-2-deoxy-β-D-glucopyranoside (322) (Compound 322—the CD-65/VIM-2 Saccharide)

A. Synthesis of Compound 320—8-Methoxycarbonyloctyl (2-acetamido-2-deoxy-β-D-glucopyranosyl)-(1-3)-O-(β-D-galactopyranosyl)-(1-4)-O-[α-L-fucopyranosyl-(1-3)-O]-2-acetamido-2-deoxy-β-D-glucopyranoside Compound 319 (15 mg), GDP-fucose (33 mg) and the βGlcNAc α(1-¾)fucosyltransferase (56 mU) were incubated for 72 hours in the buffer (4 mL) as indicated above. Isolation and purification provided the compound 320 (14.0 mg). $^1$H-n.m.r. data is set forth below.

B. Synthesis of Compound 321—8-Methoxycarbonyloctyl (β-D-galactopyranosyl)-(1-4)-O-(2-acetamido-2-deoxy-β-D-glucopyranosyl)-(1-3)-O-(β-D-galactopyranosyl)-(1-4)-O-[α-L-fucopyranosyl-(1-3)-O]-2-acetamido-2-deoxy-β-D-glucopyranoside Compound 320 (14.0 mg), UDP-Gal (25 mg), βGlcNAc β(1-4) galactosyltransferase (14.5 U, Sigma) were incubated for 48 hours in the buffer described above (3.2 mL). Isolation and purification provided compound 321 (13.2 mg). $^1$H-n.m.r. data is set forth below.

C. Synthesis of Compound 322—8-Methoxycarbonyloctyl (5-acetamido-3,5-dideoxy-α-D-glycero-D-galacto-2-nonulopyranosylonic acid)-(2-3)-O-(β-D-galactopyranosyl)-(1-4)-O-(2-acetamido-2-deoxy-β-D-glucopyranosyl)-(1-3)-O-(β-D-galacto-pyranosyl)-(1-4)-O-[α-L-fucopyranosyl-(1-3)-O]-2-acetamido-2-deoxy-β-D-glucopyranoside Compound 322 was synthesized from compound 321 as indicated above[10].

$^1$H-n.m.r. data for compounds 319, 320, 321, and 322 are set forth below.

In addition to the above methodology, FIGS. 45, 46A & B, and 48A & B illustrate alternative methods to prepare some of the above compounds, to prepare alternative structures and to prepare extended chains.

| | $^1$H-n.m.r. Structural Parameters | | | |
|---|---|---|---|---|
| Sugar Unit | Hydrogen | 319[a,b] | 320[a,b] | 321[a,b] | 322[a,b] |
| βGlcNAc(A) | 1(d) | 4.50[c](7.5) | 4.52(7.5) | 4.52(8.0) | 4.53(8.0) |
| βGal(B) | 1(d) | 4.45[c](8.0) | 4.43(7.0) | 4.43(7.5) | 4.43(8.0) |
| | 4(d) | 4.15(3.0) | 4.09(3.5) | 4.10(3.2) | 4.10(3.0) |
| βGlcNAc(C) | 1(d) | 4.66(8.5) | 4.67(8.5) | 4.70(7.8) | 4.69(8.0) |
| βGal(D) | 1(d) | | | 4.48(7.8) | 4.46(7.7) |
| | 3(d) | | | | |
| αFuc | 1(d) | | 5.09(4.0) | 5.10(3.8) | 5.09(3.8) |
| | 5(q) | | 4.81(6.5) | 4.81(6.5) | 4.81(6.5) |
| | 6(d) | | 1.14 | 1.15 | 1.15 |

| | ¹H-n.m.r. Structural Parameters | | | |
|---|---|---|---|---|
| Sugar Unit | Hydrogen | 319[a,b] | 320[a,b] | 321[a,b] | 322[a,b] |
| αNeu5Ac | 3_ax(dd) | | | | 2.76(4.5, 13.0) |
| | 3_eq(t) | | | | 1.79(12.0) |
| NHAc | s | 2.02, 2.01 | 2.02, 2.01 | 2.03, 2.02 | 2.02(three) |
| CH₂CO₂ | t | 2.38(7.5) | 2.38(7.5) | 2.38(7.5) | 2.38(7.5) |
| CO₂CH₃ | s | 3.68 | 3.69 | 3.69 | 3.69 |

[a]9, 10, 11 and 12 show multiplets around 1.49–1.63(4H) and 1.30(8H): methylenes
[b]J in Hz
[c]interchangeable Examples 52–53 below are offered to illustrate the synthesis of 2-sulfated and 3-sulfated Lewis$^C$-OR derivatives and the synthesis of 3-sulfated and LacNAc-OR. Such compounds and further derivatives thereof are described in detail in U.S. patent application Ser. No. 07/988,254, filed on Dec. 9, 1992 which application is incorporated herein by reference in its entirety.

In the following examples, unless indicated otherwise, R=—(CH₂)₈CO₂CH₃

EXAMPLE 52—Synthesis of 8-Methoxycarbonyloctyl-3-O-(4,6-O-benzylidene-3-O-sulfo-β-D-galactopyranosyl)-2-acetamido-4,6-O-benzylidene-2-deoxy-β-D-glucopyranoside The title compound was prepared by first generating 8-methoxycarbonyloctyl 3-O-(2,3-di-O-benzoyl-4,6-O-benzylidene-β-D-galactopyrnosyl)-2-acetamido-4,6-O-benzylidene-2-deoxy-β-D-glucopyranoside which, in turn, was generated by coupling the 8-methoxycarbonyloctyl 2-acetamido-4,6-O-benzylidene-2-deoxy-β-D-glucopyranoside and compound 32, the synthesis of which is exemplified in example 2 above. The 8-methoxycarbonyloctyl 2-acetamido-4,6-O-benzylidene-2-deoxy-β-D-glucopyranoside can be prepared by reacting N-acetylglucosamine-OR (e.g., compound 4 in FIG. 1) with about 1.5 equivalents of C₆H₅CH(OCH₃)₂ in an acidic (p-toluene sulfonic acid) acetonitrile or dimethylformamide (DMF) medium at from about 0° to about 50° C. over 6–48 hours to provide for the 4,6-O-protected benzylidene compound.

Coupling of compound 32 with the 8-methoxycarbonyloctyl 2-acetamido-4,6-O-benzylidine-2-deoxy-β-D-glucopyranoside ("compound A") can be achieved by first combining about 1 equivalent of N-iodosuccinimide with about 1 equivalent of trifluoromethanesulfonic acid in methylene chloride containing molecular sieves which remove any water present. The reaction mixture is cooled to −50° C. and then compound A is added followed by the addition of approximately, 1 to 1.1 equivalents of compound 32 (based on compound A). When large amounts of trifluoromethanesulfonic acid are employed, the reaction is preferably cooled to −50° C. prior to the addition of the trifluoromethanesulfonic acid.

The reaction is allowed to equilibrate to about −20° to 0° C. over about 1–3 hours. The reaction solution is then quenched by cooling to −50° followed by the addition of triethylamine until neutral pH is reached. The solution is filtered through Celite and then washed with a saturated sodium bicarbonate solution and water. The organic layer was dried and stripped in vacuo to provide for 8-methoxycarbonyloctyl 3-O-(2,3-di-O-benzoyl-4,6-O-benzylidene-β-D-galactopyranosyl)-2-acetamido-4,6-O-benzylidine-2-deoxy-β-D-glucopyranoside ("compound B").

The benzoyl groups on compound B can be removed under Zemplen conditions (NaOMe/MeOH) to provide for 8-methoxycarbonyloctyl 3-O-(4,6-O-benzylidene-β-D-galactopyranosyl)-2-acetamido-4,6-O-benzylidene-2-deoxy-β-D-glucopyranoside ("compound C").

Compound C (1 gram, 1.37 mmol) was dissolved in dry dimethylformamide (5.0 mL) and sulfur trioxidepyridine complex (267.1 mg, 1.64 mmol) was added at −30° C. The resulting solution was stirred at −30° C. for 5 hours and then 15 hours at 0° C. Excess reagent was destroyed by the addition of methanol (2 mL). The The reaction mixture was converted into sodium salt by passage through Dowex 50-X8 (Na+) resin in methanol. Evaporation and co-evaporation with toluene left a while solid which was purified by chromatography on silica gel using dichloromethane-methanol-pyridine (9:1:0.1) as eluant to provide the title compound as a white solid. This material was converted into sodium salt by passage through Dowex 50-X8 (Na+) resin in methanol to give the title compound (850 mg, 74.6%).

EXAMPLE 53—Synthesis of 8-Methoxycarbonyloctyl 3-O-(3-O-sulfo-β-D-galactopyranosyl)-2-acetamido-2-deoxy-β-D-glucopyranoside The product of Example 52 (800 mg, 0.96 mmol) was dissolved in methanol (10 mL) containing 5% palladium on carbon (800 mg) and was stirred under hydrogen (1 atmosphere) for 5 hours at room temperature. Catalyst was removed by filtration, washed with methanol (500 mL) and the solvent was evaporated to dryness. The residue was then purified by chromatography on silica gel using dichloromethane-methanol-water-pyridine (80:20:2:0.2) as eluant. The title compound (488 mg, 77.5%) was obtained as a white solid after BioGel P-2 (200–400 mesh) filtration and conversion into its sodium salt. 1H.n.m.r. (D₂O) δ: 4.520–4.570 [m, 2 h, incl. H-1(d, 4.550, J₁,₂ 8.0 Hz and H1'(d, 4.542, J₁',₂' 7.7 Hz)], 4.277–4.343 [m, 2 H, incl. H-3'(dd, 4.310, J₂,₃ 10.0 Hz, J₃,₄ 3.5 Hz) and H-4'(4.296)], 3.687(s, 3 H, OCH₃), 2.388(t, 2 H, J7.5 Hz, CH₂COO), 2.025(s, 3 H, NHAc), 1.570(m,4 H) and 1.30(m, 8 H).

The 2,3-disulfate of Example 53 was prepared in a similar manner except that sulfation was conducted with 6 equivalents of sulfur trioxide/pyridine complex and the reaction was conducted at room temperature for 24 hours. The resulting product was a mixture of 2-, 3-sulfate and predominantly 2,3-disulfate. The mixture was purified by chromatography in the manner described and ion exchange of the resulting product provided for the 2,3-disulfate of Lewis$^C$-OR as the disodium salt.

The 2-sulfate of Lewis$^C$-OR was prepared from compound C by benzoylation under conditions described above. The resulting product contained predominantly the 3-benzoyl group on the galactose unit and a small amount of the 2-benzoyl and 2,3-dibenzoyl derivatives. The products were separated by chromatography on silica gel to provide for both the 2-benzoyl and the 3-benzoyl derivatives as pure products.

The 3-benzoyl derivative was sulfated in the manner described above and then deprotected to provide for the 2'-sulfo-Lewis$^C$-OR which upon ion exchange as described above provided for the sodium salt of this product.

The 3'-sulfo-LacNAc derivative was prepared from compound 42 (prepared in Example 7) wherein the dibenzoyl groups are removed via Zemplen conditions (sodium methoxide/methanol) and then sulfated under the conditions described above to provide for 3'-sulfo-Lewis$^C$-OR.

In the following examples, enzymatic fucosylation was conducted as follow:

Ezymatic Fucosylation

βGal(1-¾)βGalcNAc(1-¾) fucosyltransferase was purified from human milk according to the methodology using affinity chromatography on GDP-hexanolamine Sepharose described by Palcic et al.[22] The cloned fucosyltransferases, Fuc TIII and Fuc T IV, immobilized on rabbit IgG-sepharose (Sigma) were provided by Glycomed, Alameda, Calif. The enzyamatic reactions were carried out at room temperature or 37° C. in a plastic tube using a sodium cacodylate buffer (100 mM, pH 6.5), MnCl$_2$ (10 mM), ATP (1.6 mM) NaN$_3$ (1.6 mM). The final reaction mixture was diluted with H$_2$O (5 mL) and applied onto C$_{18}$ Sep-Pak cartridges as reported[22]. After washing with H$_2$O (30 mL) the products were eluted with CH$_3$OH and the solvents evaporated. The residue was dissolved in a 65:35:5 mixture of CHCl$_3$, CH$_3$OH and H$_2$O and applied on a small column of Iatrobeads (0.200 to 0.500 g). After washing with the same solvent mixture, the products were eluted with a 65:35:8 and/or 60:40:10 mixtures of the same solvents. The appropriate fractions (t.l.c.) were pooled, the solvents evaporated in vacuo, the residue run through a small column of AG 50Wx8 (Na form) (BioRad) in H$_2$O and the products recovered after freeze drying in vacuo.

iii. Fucosylation Reactions

A. Preparation of fucosylated derivative of the sodium salt of the 3-sulfo-Lewis$^C$-OR (3-sulfo-βGal(1-3)-[α-L-Fuc(1-4)]-βGlcNAc-OR)

The product prepared in Example 53 above (19.2 mg) GDP-fucose (17.2 mg), milk βGal(1-¾)βGalcNAc(1-¾) fucosyltransferase (25 mL) and calf intestine alkaline phosphatase (20 U) were incubated for 68 hours in the buffer (3.5 mL) at 37° C. Isolation and purification provided the title compound (10.8 mg).

B. Preparation of fucosylated derivative of the sodium salt of the 2-sulfo-Lewis$^C$-OR (2-sulfo-βGal(1-3)-[α-L-Fuc(1-4)]-βGlcNAc-OR)

The 2-sulfo-Lewis$^C$-OR compound, described above, (9.5 mg), GDP-fucose (9.5 mg), cloned fucosyltransferase FucT-III (75 μL of beads) and calf intestine alkaline phosphatase (20 U) were incubated for 72 hours in the buffer (2.0 mL) at room temperature. Isolation and purification provided the title compound (5.8 mg).

C. Preparation of fucosylated derivative of the sodium salt of the 3-sulfo-LacNAc-OR (3-sulfo-βGal(1-4)-[α-L-Fuc(1-3)]-βGlcNAc-OR)

The 3-sulfo-LacNAc-OR compound, described above (6.8 mg), GDP-fucose (6.8 mg), cloned fucosyltransferase Fuc T-IV (50 mL beads) and calf intestine alkaline phosphatase (20 U) were incubated for 72 hours in the buffer (2.0 mL) at room temperature. Isolation and purification provided the title compound.

What is claimed is:

1. A method for reducing inflammation in a mammal arising from initiation of a mammal's secondary immune response due to antigen exposure which method comprises administering to said mammal an inflammation reducing effective amount of an oligosaccharide glycoside related to blood group determinants having a type I or type II core structure wherein said oligosaccharide glycoside has from 2 to 6 saccharide units and has either a core type I disaccharide structure of βGal(1-3)βGlcNAc—OR or a core type II disaccharide structure of βGal(1-4)βGlcNAc—OR wherein R is an aglycon having from 1 to 10 carbon atoms, or said oligosaccharide glycoside is an analog of said type I or type II disaccharide wherein the —NHAc group at the 2-position of the βGlcNAc saccharide unit is replaced with a substituent selected from the group consisting of —N$_3$, —NH$_2$, or —C(O)CH$_2$CH$_3$ provided that if said oligosaccharide glycoside has only 2 saccharide units then said oligosaccharide has at least one substituent which carries a charge at physiological pH which substituent is selected from the group consisting of a sulfate group, a phosphate group and a carboxyl group at either the 2, 3, or 6 position of the galactose unit, wherein said administration is after initiation of the mammal's secondary immune response to the antigen exposure but at or prior to one-half that period of time required for maximal inflammatory response to the antigen exposure.

2. A method according to claim 1 wherein said oligosaccharide glycoside is administered at least 0.5 hours after initiation of said mammal's immune response.

3. A method according to claim 1 wherein said oligosaccharide glycoside is administered parenterally.

4. The method according to claim 1 wherein R is —(CH$_2$)$_8$CO$_2$CH$_3$.

* * * * *